United States Patent
Ara et al.

(10) Patent No.: US 6,613,454 B2
(45) Date of Patent: Sep. 2, 2003

(54) ORGANIC EL DEVICE

(75) Inventors: Kensuke Ara, Tokyo (JP); Tetsushi Inoue, Tokyo (JP); Tetsuji Fujita, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 09/838,260

(22) Filed: Apr. 20, 2001

(65) Prior Publication Data

US 2003/0027016 A1 Feb. 6, 2003

(30) Foreign Application Priority Data

Apr. 21, 2000 (JP) .......................... 2000-121724
Apr. 19, 2001 (JP) .......................... 2001-121664

(51) Int. Cl.$^7$ .............................. H05B 33/14
(52) U.S. Cl. ................ 428/690; 428/917; 313/504; 313/506
(58) Field of Search ................ 428/690, 917; 313/504, 506

(56) References Cited

U.S. PATENT DOCUMENTS

| | | | | |
|---|---|---|---|---|
| 3,557,233 A | * | 1/1971 | Zweig et al. | 260/668 |
| 3,729,426 A | * | 4/1973 | Zweig et al. | 252/188.3 |
| 6,203,933 B1 | | 3/2001 | Nakaya et al. | |
| 6,358,633 B1 | * | 3/2002 | Sano et al. | 428/690 |

FOREIGN PATENT DOCUMENTS

| | | | |
|---|---|---|---|
| JP | 4-335087 | | 11/1992 |
| JP | 07-065958 A | * | 3/1995 |
| JP | 10-189247 | | 7/1998 |
| JP | 10-189248 | | 7/1998 |
| JP | 10-294177 | | 11/1998 |
| JP | 10-330295 | | 12/1998 |
| JP | 10-340783 | | 12/1998 |
| JP | 11-012205 | | 1/1999 |
| JP | 11-097178 | | 4/1999 |
| JP | 11-149987 | | 6/1999 |
| JP | 11-233261 | | 8/1999 |
| JP | 2000-7594 | | 1/2000 |
| JP | 2000-026324 | | 1/2000 |
| JP | 2000-026325 | | 1/2000 |
| JP | 2000-034234 | | 2/2000 |
| JP | 2000-048958 | | 2/2000 |
| JP | 2000-086549 | | 3/2000 |
| JP | 2000-133457 | | 5/2000 |
| JP | 2000-159697 | | 6/2000 |
| JP | 2000-178212 | | 6/2000 |
| JP | 2000-186054 | | 7/2000 |

OTHER PUBLICATIONS

J. D. Debad, et al., J. Am. Chem.. Soc., vol. 118, No. 10, pp. 2374–2379, "Dibenzotetraphenylperiflanthene: Synthesis, Photophysical Properties, and Electrogenerated Chemiluminescence", 1996.

* cited by examiner

Primary Examiner—Cynthia H. Kelly
Assistant Examiner—Dawn Garrett
(74) Attorney, Agent, or Firm—Oblon, Spivak, McClelland, Maier & Neustadt, P.C.

(57) ABSTRACT

In an organic EL device comprising organic layers between a pair of electrodes participating in at least a light emitting function, at least one organic layer contains an organic compound selected from naphthacene, tetraaryldiamine, anthracene and quinoxaline derivatives as a host material and an organic compound having a specific skeleton, typically diindeno[1,2,3-cd:1',2',3'-lm]perylene derivative as a dopant. The device is capable of light emission to a satisfactory luminance, especially in a long wavelength region, and with a chromatic purity sufficient for use in full color displays, and had a sufficient durability to sustain such improved light emission performance over a long time.

27 Claims, 2 Drawing Sheets

ORGANIC EL DEVICE

BACKGROUND OF THE INVENTION

1. Field of the Invention

This invention relates to an organic electroluminescent (EL) device, and more particularly, to a compound for use in a device of the type wherein an electric field is applied across a thin film of an organic compound to emit light.

2. Background Art

Organic electroluminescent (EL) devices include a thin film containing a luminescent organic compound interleaved between an electron injecting electrode and a hole injecting electrode. Electrons and holes are injected into the thin film where they are recombined to create excitons. Light is emitted by utilizing luminescence (phosphorescence or fluorescence) upon deactivation of excitons.

The organic EL devices are characterized by plane light emission at a high luminance of about 100 to 10,000 cd/m² with a voltage of about 10 volts and light emission in a spectrum from blue to red color by a simple choice of the type of fluorescent material.

Doping is one technique for producing light emission of any desired color from organic EL devices. It was reported in Jpn. J. Appl. Phys., 10, 527 (1971) to change emission color from blue to green by doping anthracene crystals with a minor level of tetracene. With respect to organic thin film EL devices having a multilayer structure, it was reported in JP-A 63-264692 to incorporate in a host material having a light emitting function a minor amount of a fluorescent dye capable of emitting light different from that of the host material in response to light emission from the host material as a dopant to form a light emitting layer, thereby changing the color of light emission from green to orange or red.

With respect to long wavelength light emission of yellow to red, known light emitting materials or dopant materials include laser dyes capable of red oscillation (EPO 281381), compounds capable of exciplex emission (JP-A 2-255788), perylene compounds (JP-A 3-791), coumarin compounds (JP-A 3-792), dicyanomethylene compounds (JP-A 3-162481), thioxanthene compounds (JP-A 3-177486), mixtures of a conjugated polymer and an electron transporting compound (JP-A 6-73374), squalirium compounds (JP-A 6-93257), oxadiazole compounds (JP-A 6-136359), oxynate derivatives (JP-A 6-145146), and pyrene compounds (JP-A 6-240246).

It is reported in J. Am. Chem. Soc., 118, 2374–2379, 1996, that benzofluoranthene derivatives have a very high fluorescent quantum yield. JP-A 10-330295 and JP-A 11-233261 disclose organic EL devices having a light emitting layer in which a variety of host materials are doped with dibenzo[f,f']diindeno[1,2,3-cd:1',2',3'-lm]perylene derivatives derived from benzofluoranthene.

Other light emitting materials disclosed heretofore include condensed polycyclic aromatic compounds (JP-A 5-32966 and 5-214334). Also dopant materials proposed heretofore include various condensed polycyclic aromatic compounds (JP-A 5-258859).

However, when these materials are used as the dopant, EL devices often fail to allow dopant molecules to exert their own fluorescence due to the interaction between dopants or between the dopant and the host.

Therefore, with respect to organic EL devices of the type in which a host material is doped with a fluorescent dye, a choice of host material is an important and difficult task in order for the device to produce high efficiency light emission. Currently available organic EL devices fail to reach a practically acceptable level of emission efficiency although fluorescent dyes having a high fluorescent quantum yield are used as the dopant.

When organic EL devices are fabricated using the doping technique, the energy transfer from host molecules in the excited state to the dopant is not 100%, and often not only the dopant, but also the host material emit light. Especially in the case of red light emitting devices, the chromatic purity is often exacerbated by faint light emission of the host material since the host material emits light in a wavelength region of higher visibility than the dopant. Further improvements in properties pertaining to the luminous lifetime and durability are needed, with the target placed on practical application.

SUMMARY OF THE INVENTION

An object of the invention is to provide an organic EL device capable of light emission to a satisfactory luminance, especially in a long wavelength region, and with a chromatic purity sufficient for use in full color displays, and having a sufficient durability to sustain such improved light emission performance over a long time.

The above and other objects are achieved by the invention which is defined below.

[1] An organic EL device comprising one or more organic layers between a pair of electrodes participating in at least a light emitting function, at least one of the organic layers containing at least one of organic compounds having basic skeletons of the following formulas (I) to (IV) and at least one organic compound having a skeleton of the following formula (V) at the same time:

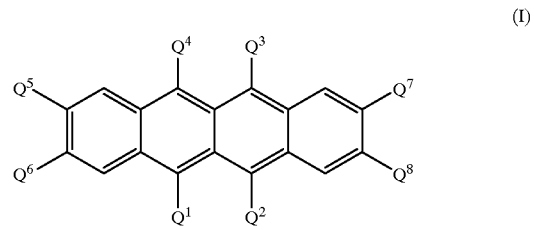

(I)

wherein $Q^1$ to $Q^8$ are independently hydrogen or substituted or unsubstituted alkyl, aryl, amino, heterocyclic or alkenyl radicals,

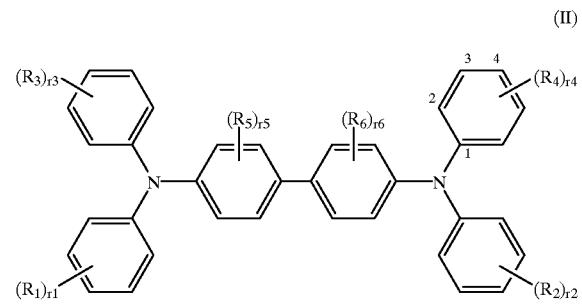

(II)

wherein $R_1$, $R_2$, $R_3$ and $R_4$ are independently aryl, fluorene, carbazolyl, alkyl, alkoxy, aryloxy, amino or halogen radicals, at least one of $R_1$, $R_2$, $R_3$ and $R_4$ is aryl, r1, r2, r3 and r4 each are 0 or an integer of 1 to 5, with the proviso that r1, r2, r3 and r4 are not 0 at the same time, $R_5$ and $R_6$ are independently alkyl, alkoxy, amino, aryl or halogen radicals and may be the same or different, r5 and r6 each are 0 or an integer of 1 to 4,

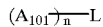  (III)

wherein $A_{101}$ is a monophenylanthryl or diphenylanthryl radical and may be the same or different, L is hydrogen, a single bond or an n-valent linkage, and n is an integer of 1 to 4,

  (IV)

wherein Q is a pyrazinyl radical having fused thereto a six-membered aromatic ring containing 0 to 2 nitrogen atoms and may be the same or different, n is 2 or 3, and $L_{101}$ is a single bond or n-valent radical,

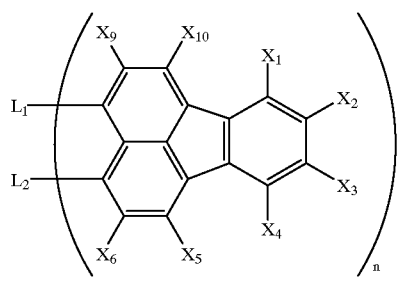 (V)

wherein $X_1$ to $X_{10}$, $L_1$ and $L_2$ are independently hydrogen, halogen atoms, straight, branched or cyclic alkyl radicals which may have substituents, straight, branched or cyclic alkoxy radicals which may have substituents, straight, branched or cyclic alkylthio radicals which may have substituents, straight, branched or cyclic alkenyl radicals which may have substituents, straight, branched or cyclic alkenyloxy radicals which may have substituents, straight, branched or cyclic alkenylthio radicals which may have substituents, substituted or unsubstituted aralkyl radicals, substituted or unsubstituted aralkyloxy radicals, substituted or unsubstituted aralkylthio radicals, substituted or unsubstituted aryl radicals, substituted or unsubstituted aryloxy radicals, substituted or unsubstituted arylthio radicals, substituted or unsubstituted amino radicals, cyano, hydroxyl, —COOR$^1$ radicals (wherein $R^1$ is hydrogen, a substituted or unsubstituted straight, branched or cyclic alkyl radical, a substituted or unsubstituted straight, branched or cyclic alkenyl radical, a substituted or unsubstituted aralkyl radical or a substituted or unsubstituted aryl radical), —COR$^2$ radicals (wherein $R^2$ is hydrogen, a substituted or unsubstituted straight, branched or cyclic alkyl radical, a substituted or unsubstituted straight, branched or cyclic alkenyl radical, a substituted or unsubstituted aralkyl radical, a substituted or unsubstituted aryl radical or an amino radical), or —OCOR$^3$ radicals (wherein $R^3$ is a substituted or unsubstituted straight, branched or cyclic alkyl radical, a substituted or unsubstituted straight, branched or cyclic alkenyl radical, a substituted or unsubstituted aralkyl radical, or a substituted or unsubstituted aryl radical), or at least two adjoining radicals selected from $X_1$ to $X_{10}$, $L_1$ and $L_2$ may bond or fuse together to form a substituted or unsubstituted carbocyclic aliphatic ring, aromatic ring or fused aromatic ring with the carbon atoms to which they are attached, or $L_1$ and $L_2$ each may be a single bond. n is 1 or 2.

[2] The organic EL device of [1] wherein the at least one of the organic layers contains a host material and a dopant,
said host material comprises at least one compound selected from the organic compounds having basic skeletons of the formulas (I) to (IV) and
said dopant comprises at least one compound selected from the organic compounds having a skeleton of the formula (V).

[3] The organic EL device of [1] or [2] wherein in formula (V), at least two adjoining radicals selected from $X_1$ to $X_{10}$, $L_1$ and $L_2$ bond or fuse together to form a substituted or unsubstituted carbocyclic aliphatic ring, aromatic ring or fused aromatic ring with the carbon atoms to which they are attached.

[4] The organic EL device of any one of [1] to [3] wherein the compound of formula (V) is a compound of the following formula (VI):

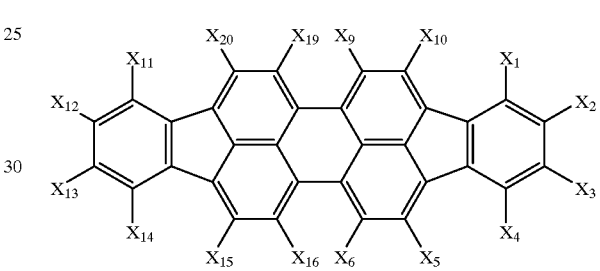 (VI)

wherein $X_1$ to $X_6$, $X_9$, $X_{10}$, $X_{11}$ to $X_{16}$, $X_{19}$ and $X_{20}$ are independently hydrogen, halogen atoms, straight, branched or cyclic alkyl radicals which may have substituents, straight, branched or cyclic alkoxy radicals which may have substituents, straight, branched or cyclic alkylthio radicals which may have substituents, straight, branched or cyclic alkenyl radicals which may have substituents, straight, branched or cyclic alkenyloxy radicals which may have substituents, straight, branched or cyclic alkenylthio radicals which may have substituents, substituted or unsubstituted aralkyl radicals, substituted or unsubstituted aralkyloxy radicals, substituted or unsubstituted aralkylthio radicals, substituted or unsubstituted aryl radicals, substituted or unsubstituted aryloxy radicals, substituted or unsubstituted arylthio radicals, substituted or unsubstituted arylalkenyl radicals, substituted or unsubstituted alkenylaryl radicals, substituted or unsubstituted amino radicals, cyano, hydroxyl, —COOR$^1$ radicals (wherein $R^1$ is hydrogen, a substituted or unsubstituted straight, branched or cyclic alkyl radical, a substituted or unsubstituted straight, branched or cyclic alkenyl radical, a substituted or unsubstituted aralkyl radical or a substituted or unsubstituted aryl radical), —COR$^2$ radicals (wherein $R^2$ is hydrogen, a substituted or unsubstituted straight, branched or cyclic alkyl radical, a substituted or unsubstituted straight, branched or cyclic alkenyl radical, a substituted or unsubstituted aralkyl radical, a substituted or unsubstituted aryl radical or an amino radical), or —OCOR$^3$ radicals (wherein $R^3$ is a substituted or unsubstituted straight, branched or cyclic alkyl radical, a substituted or unsubstituted straight, branched or cyclic alkenyl radical, a substituted or unsubstituted aralkyl radical, or a substituted or unsubstituted aryl radical), or at least two adjoining radicals selected from $X_1$ to $X_{20}$ may bond together to form a substituted or unsubstituted carbocyclic aliphatic ring, aromatic ring or fused aromatic ring with the carbon atoms to which they are attached.

[5] The organic EL device of [4] wherein the compound of formula (VI) is a compound of the following formula (VI'):

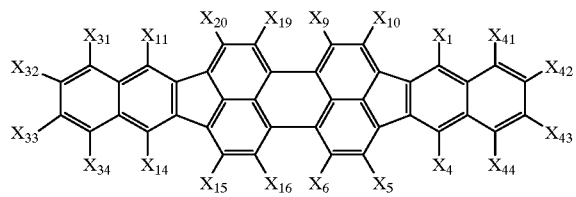

(VI')

wherein $X_1$ to $X_{44}$ are as defined for $X_1$ to $X_{20}$ in formula (VI).

[6] The organic EL device of [4] or [5] wherein $X_1$ to $X_{20}$ in formula (VI) and $X_1$ to $X_{44}$ in formula (VI') are independently substituted or unsubstituted aryl, alkyl, alkenyl, alkoxy or aryloxy radicals.

[7] The organic EL device of any one of [4] to [6] wherein at least one of $X_1$ to $X_{20}$ in formula (VI) and $X_1$ to $X_{44}$ in formula (VI') is an ortho-substituted phenyl radical. [8] The organic EL device of any one of [4] to [7] wherein in formula (VI) or (VI'), either one or both of $X_1$ and $X_4$ and/or either one or both of $X_{11}$ and $X_{14}$ are ortho-substituted phenyl radicals.

[9] The organic EL device of any one of [1] to [8] wherein said at least one of the organic layers contains at least one organic compound having a basic skeleton of the formula (I).

[10] The organic EL device of any one of [1] to [9] wherein said at least one of the organic layers contains at least one organic compound having a basic skeleton of the formula (I) and at least one organic compound having a basic skeleton of the formula (II) at the same time.

[11] The organic EL device of any one of [4] to [10] wherein at least one of the organic compounds has a vibration structure in both an excitation spectrum and a fluorescence spectrum.

[12] The organic EL device of any one of [4] to [11] wherein at least one of the organic compounds has a Stokes shift of up to 0.1 eV.

[13] The organic EL device of any one of [4] to [12] wherein the host material in a light emitting layer has a greater electron affinity than an electron transporting layer and/or a hole transporting layer.

[14] The organic EL device of any one of [1] to [13] wherein the organic compound having a basic skeleton of the formula (I) is one wherein at least two of $Q^1$ to $Q^8$ are substituted or unsubstituted aryl radicals.

[15] The organic EL device of [14] wherein the organic compound having a basic skeleton of the formula (I) is one wherein at least six of $Q^1$ to $Q^8$ are substituted or unsubstituted aryl radicals.

[16] The organic EL device of [14] or [15] wherein the organic compound having a basic skeleton of the formula (I) is one wherein at least two of $Q^1$, $Q^2$, $Q^3$ and $Q^4$ are substituted or unsubstituted aryl radicals.

[17] The organic EL device of any one of [14] to [16] wherein the organic compound having a basic skeleton of the formula (I) is one wherein at least four of $Q^1$, $Q^2$, $Q^3$ and $Q^4$ are substituted or unsubstituted aryl radicals.

[18] The organic EL device of any one of [14] to [17] wherein at least two of the aryl radicals represented by $Q^1$, $Q^2$, $Q^3$ and $Q^4$ have aryl radicals substituted thereon.

[19] The organic EL device of any one of [2] to [18] wherein the at least one of the organic layers contains 80 to 99.9% by weight of the host material.

[20] An organic EL device wherein at least one of organic layers contains at least one organic compound having a basic skeleton of the formula (I) as set forth in [16] and at least one organic compound having a basic skeleton of the formula (IV').

[21] The organic EL device of any one of [1] to [20], further comprising at least one hole injecting and transporting layer.

[22] The organic EL device of any one of [1] to [21], further comprising at least one electron injecting and transporting layer.

[23] An organic EL device comprising one or more organic layers between a pair of electrodes participating in at least a light emitting function, wherein the one or more organic layers contain organic compounds, at least one of which has a vibration structure in both an excitation spectrum and a fluorescence spectrum.

[24] An organic EL device comprising one or more organic layers between a pair of electrodes participating in at least a light emitting function, wherein the one or more organic layers contain organic compounds, at least one of which has a Stokes shift of up to 0.1 eV.

[25] The organic EL device of [24] wherein a host material in a light emitting layer has a greater electron affinity than an electron transporting layer and/or a hole transporting layer.

DESCRIPTION OF THE PREFERRED EMBODIMENT

Figure 1:
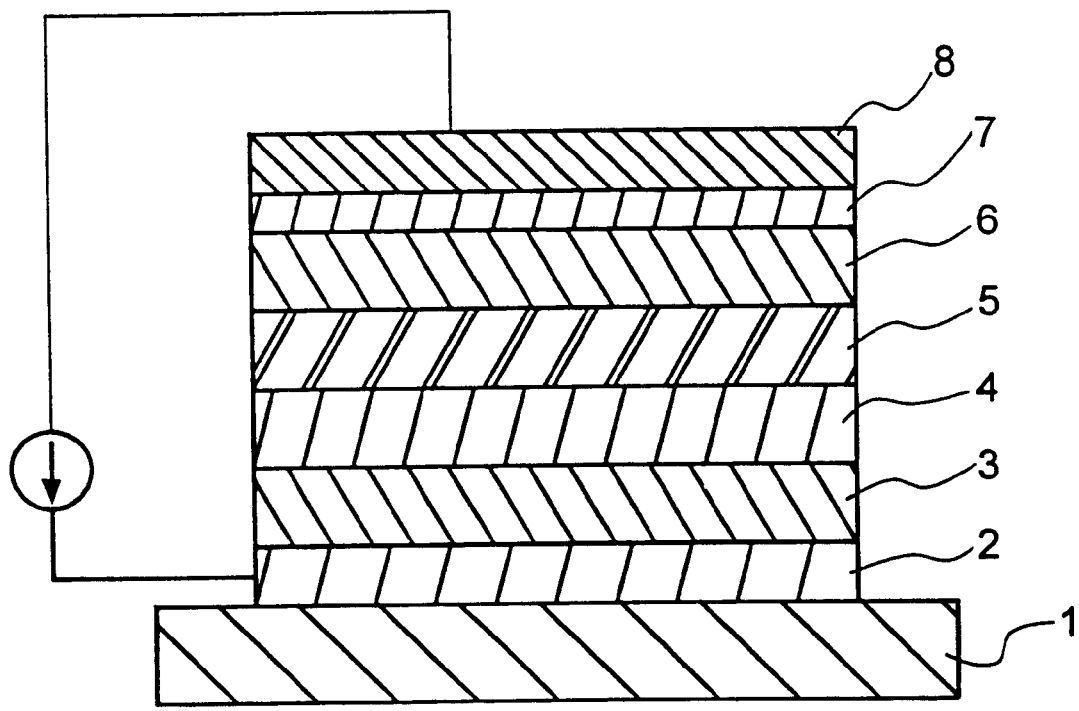
FIG. 1 is a schematic cross-sectional view showing the basic construction of an organic EL device according to the invention.

According to the invention, an organic EL device having a high luminous efficiency and a long lifetime is obtained by combining an organic compound of formula (V) or (VI) with at least one of organic compounds of formulas (I) to (IV), especially by combining an organic compound of formula (V) or (VI) as a dopant with an organic compound of formula (I) as a host material. First the organic compounds useful as the host material are described in detail.

Host Materials

Naphthacene Compounds

One class of organic compounds useful as the host material according to the invention have a basic skeleton of the following formula (I).

In the device of the invention, the use of the naphthacene derivative, preferably as the host material, helps induce strong light emission from the dopant.

Naphthacene derivatives belong to a class of preferable organic compounds, especially effective as the host material, among others. For example, the fluorescence intensity of a film of a naphthacene derivative of host material in example 1 doped with 1 wt % of a dibenzo[f,f']diindeno[1,2,3-cd:1',2',3'-lm]perylene derivative of dopant material in Example 1, as measured on photoexcitation, is about 2 times the fluorescence intensities of films of other organic compounds (e.g., Alq3) as the host.

The reason why such intense fluorescence is produced is presumably that the combination of a naphthacene derivative with the above dopant is an ideal combination that avoids interaction such as formation of an exciplex, and bipolar interaction between the respective molecules maintains a high intensity of fluorescence.

In the event of a red dopant, since the energy gap of a naphthacene derivative is relatively approximate to that of the dopant, an energy transfer phenomenon due to emission resorption takes place as well as energy transfer by electron exchange. This accounts for a high fluorescence intensity as well.

The combination with the above host material minimizes the concentration quenching of the dopant, which also accounts for a high fluorescence intensity.

In an exemplary organic EL device which was fabricated using the above doped film as a light emitting layer, a luminance of at least 600 cd/m² at maximum was obtained at a current density of 10 mA/cm² and a drive voltage as low as about 6 V. When operated at a current density of about 600 mA/cm², the device consistently produced a luminance of greater than about 20,000 cd/m². As compared with other organic compounds (e.g., Alq3) serving as the host, this provides a luminous efficiency greater by a factor of about 4 when assessed in terms of current efficiency, and because of possible driving at a lower voltage, a luminous efficiency greater by a factor of about 5 when assessed in terms of power efficiency. In the event of doping with a red dopant as in the above example, entailing the high efficiency of energy transfer from the host to the dopant, the device is characterized by a high chromatic purity in that only the dopant produces light emission, with little light emission from the host being observable.

It is believed that such a very high luminous efficiency exerted when organic EL devices are fabricated is due to the effects of an improved recombination probability of carriers in the light emitting layer and a singlet excitation state that the dopant forms as a result of energy transfer from the triplet excitation state of naphthacene, as well as the above-mentioned mechanism of providing a high fluorescence intensity.

As opposed to conventional organic EL devices whose drive voltage is increased by carrier trapping of the dopant, the inventive organic EL device using the above-mentioned light emitting layer has a very low drive voltage, because the order of carrier trapping of the dopant is low and high efficiency light emission is accomplished by the above-mentioned mechanism. Another accomplished by the above-mentioned mechanism. Another probable reason is the ease of injection of carriers into the light emitting layer.

Since the naphthacene derivative is very stable and highly durable against carrier injection, the device fabricated using the above host-dopant combination has a very long lifetime. For example, an organic EL device having a light emitting layer of a compound of formula (VII') doped with 1 wt % of a dibenzo[f,f']diindeno[1,2,3-cd:1',2',3'-lm]perylene derivative of dopant material in Example 1 is highly durable as demonstrated by its ability to sustain a luminance of at least 2,400 cd/m² over a period of 1,000 hours or longer, with an attenuation of less than about 1%, when driven at 50 mA/cm².

In organic EL devices as mentioned above, the dopant concentration ensuring a chromatic purity and maximum efficiency is about 1% by weight although dopant concentrations of about 2 or 3% by weight lead to devices which are practically acceptable albeit a drop of less than about 10%.

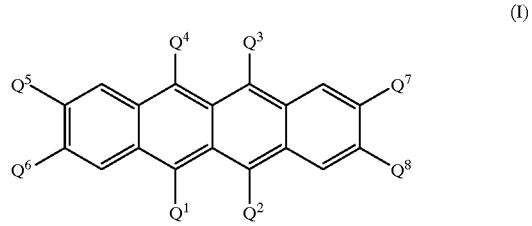

(I)

In formula (I), $Q^1$ to $Q^4$ are independently selected from among hydrogen and substituted or unsubstituted alkyl, aryl, amino, heterocyclic and alkenyl radicals. Preferred are aryl, amino, heterocyclic and alkenyl radicals. It is also desirable that $Q^2$ and $Q^3$ are these preferred radicals and $Q^1$ and $Q^4$ are hydrogen.

The aryl radicals represented by $Q^1$ to $Q^4$ may be monocyclic or polycyclic, inclusive of fused rings and a collection of rings. Those aryl radicals having 6 to 30 carbon atoms in total are preferred and they may have substituents. Preferred examples of the aryl radical include phenyl, o-, m- and p-tolyl, pyrenyl, perylenyl, coronenyl, 1- and 2-naphthyl, anthryl, o-, m- and p-biphenylyl, terphenyl and phenanthryl.

The amino radicals represented by $Q^1$ to $Q^4$ may be selected from among alkylamino, arylamino, aralkylamino and analogous radicals. They preferably have aliphatic radicals having 1 to 6 carbon atoms in total and/or aromatic carbocyclic radicals having 1 to 4 rings. Illustrative examples include dimethylamino, diethylamino, dibutylamino, diphenylamino, ditolylamino, bisdiphenylylamino, and bisnaphthylamino radicals.

The heterocyclic radicals represented by $Q^1$ to $Q^4$ include 5- or 6-membered ring aromatic heterocyclic radicals containing O, N or S as a hetero atom, and fused polycyclic aromatic heterocyclic radicals having 2 to 20 carbon atoms. Examples of the aromatic heterocyclic radicals and fused polycyclic aromatic heterocyclic radicals include thienyl, furyl, pyrolyl, pyridyl, quinolyl, and quinoxalyl radicals.

The alkenyl radicals represented by $Q^1$ to $Q^4$ are preferably those having a phenyl group as at least one substituent, such as 1- and 2-phenylalkenyl, 1,2- and 2,2-diphenylalkenyl, and 1,2,2-triphenylalkenyl although unsubstituted alkenyl radicals are acceptable.

When $Q^1$ to $Q^4$ are substituted radicals, at least two of the substituents are preferably aryl, amino, heterocyclic, alkenyl or aryloxy groups. These aryl, amino, heterocyclic and alkenyl groups are as illustrated above for $Q^1$ to $Q^4$. The aryloxy groups to substitute on $Q^1$ to $Q^4$ are preferably those of aryl groups having 6 to 18 carbon atoms in total, for example, o-, m- and p-phenoxy. At least two of these substituents may form a fused ring. Also, these substituents may be further substituted ones, in which preferred substituents are as described above.

When $Q^1$ to $Q^4$ have substituents, it is preferred that at least two of the substituents have the above-described substituents. The position of substitution is not particularly limited and may be a meta, para or ortho position. $Q^1$ and $Q^4$, and $Q^2$ and $Q^3$ in the respective pairs are preferably identical although they may be different.

$Q^5$ to $Q^8$ are independently selected from among hydrogen and substituted or unsubstituted alkyl, aryl, amino, heterocyclic and alkenyl radicals.

The alkyl radicals represented by $Q^5$ to $Q^8$ are preferably those of 1 to 6 carbon atoms, which may be straight or branched. Preferred examples of the alkyl radical include methyl, ethyl, n- and i-propyl, n-, i-, sec- and tert-butyl, n-, i-, neo- and tert-pentyl.

The aryl, amino and alkenyl radicals represented by $Q^5$ to $Q^8$ are as illustrated above for $Q^1$ to $Q^4$. $Q^5$ and $Q^6$, and $Q^7$ and $Q^8$ in the respective pairs are preferably identical although they may be different.

It is preferred that rubrene of formula (I) wherein all $Q^1$ to $Q^4$ are phenyl and all $Q^5$ to $Q^8$ are hydrogen be excluded.

The naphthacene derivative contained in the light emitting layer should preferably have a basic skeleton of the following formula (VII).

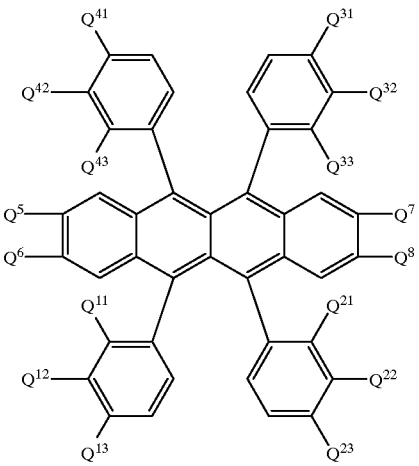

(VII)

In formula (VII), $Q^{11}$ to $Q^{13}$, $Q^{21}$ to $Q^{23}$, $Q^{31}$ to $Q^{33}$ and $Q^{41}$ to $Q^{43}$ are hydrogen, aryl, amino, heterocyclic, aryloxy or alkenyl radicals. Preferably the Q's in at least one of these sets are radicals having substituents selected from among aryl, amino, heterocyclic and aryloxy groups. Two or more of these Q's may form a fused ring.

Preferred examples of the aryl, amino, heterocyclic and aryloxy radicals are as exemplified above for $Q^1$ to $Q^4$. Preferably $Q^{11}$ to $Q^{13}$ and $Q^{41}$ to $Q^{43}$, and $Q^{21}$ to $Q^{23}$ and $Q^{31}$ to $Q^{33}$ in the respective paired sets are identical although they may be different.

The amino groups substituting on $Q^{11}$ to $Q^{13}$, $Q^{21}$ to $Q^{23}$, $Q^{31}$ to $Q^{33}$ and $Q^{41}$ to $Q^{43}$ may be selected from among alkylamino, arylamino, aralkylamino and analogous groups. They preferably have aliphatic groups having 1 to 6 carbon atoms in total and/or aromatic carbocyclic groups having 1 to 4 rings. Illustrative examples include dimethylamino, diethylamino, dibutylamino, diphenylamino, ditolylamino, and bisbiphenylylamino groups.

Examples of the fused ring include indene, naphthalene, anthracene, phenanthrene, quinoline, isoquinoline, quinoxaline, phenazine, acridine, indole, carbazole, phenoxazine, phenothiazine, benzothiazole, benzothiophene, benzofuran, acridone, benzimidazole, coumarin, and flavone.

Of the naphthacene derivatives used herein, those of the following formula (VII') are preferred because devices are given a longer lifetime.

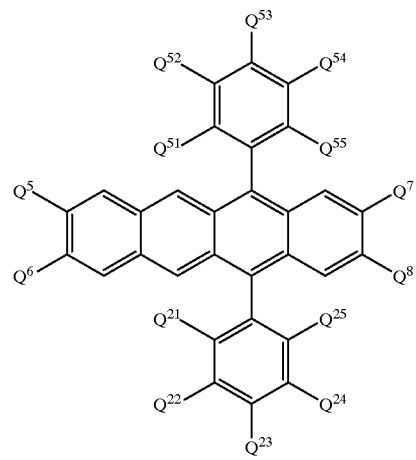

(VII')

In formula (VII'), $Q^{51}$ to $Q^{55}$ and $Q^{21}$ to $Q^{25}$ are the same as $Q^{11}$ in formula (VII).

Illustrative examples of the preferred naphthacene derivatives used herein are given below as IB-1 to IB-189. The substituents $Q^1$ to $Q^8$ are denoted as $Q^{10}$ to $Q^{80}$.

TABLE 1

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IB-1 | —⌬ | —⌬—⌬ | —⌬—⌬ | —⌬ | H | H | H | H |
| IB-2 | —⌬ | —⌬—⌬ | —⌬—⌬ | —⌬ | H | H | H | H |

TABLE 1-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-3 | phenyl | 2-biphenylyl | 2-biphenylyl | phenyl | H | H | H | H |
| IB-4 | phenyl | 2,4-diphenylphenyl-biphenyl | 2,4-diphenylphenyl-biphenyl | phenyl | H | H | H | H |
| IB-5 | phenyl | 3,4-diphenylphenyl-biphenyl | 3,4-diphenylphenyl-biphenyl | phenyl | H | H | H | H |
| IB-6 | phenyl | 3,5-diphenylphenyl | 3,5-diphenylphenyl | phenyl | H | H | H | H |
| IB-7 | phenyl | 2,4,6-triphenylphenyl-biphenyl | 2,4,6-triphenylphenyl-biphenyl | phenyl | H | H | H | H |
| IB-8 | phenyl | 2,3,4-triphenylphenyl-biphenyl | 2,3,4-triphenylphenyl-biphenyl | phenyl | H | H | H | H |

TABLE 2

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-9 | phenyl | 2-methyl-4,4'-biphenyl with phenyl at 3-position (terphenyl branched) | 2-methyl-4,4'-biphenyl with phenyl at 3-position (terphenyl branched) | phenyl | H | H | H | H |
| IB-10 | phenyl | 2-methyl-1,3-diphenylbenzene | 2-methyl-1,3-diphenylbenzene | phenyl | H | H | H | H |
| IB-11 | phenyl | 2-methyl-1,4,5-triphenylbenzene | 2-methyl-1,4,5-triphenylbenzene | phenyl | H | H | H | H |
| IB-12 | phenyl | 2-methyl-1,3,4-triphenylbenzene | 2-methyl-1,3,4-triphenylbenzene | phenyl | H | H | H | H |
| IB-13 | phenyl | 4-(naphthalen-2-yl)phenyl | 4-(naphthalen-2-yl)phenyl | phenyl | H | H | H | H |

TABLE 2-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-14 | phenyl | 3-(2-naphthyl)phenyl | 3-(2-naphthyl)phenyl | phenyl | H | H | H | H |
| IB-15 | phenyl | 2-(2-naphthyl)phenyl | 2-(2-naphthyl)phenyl | phenyl | H | H | H | H |
| IB-16 | phenyl | 4-(1-naphthyl)phenyl | 4-(1-naphthyl)phenyl | phenyl | H | H | H | H |

TABLE 3

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-17 | phenyl | 3-(1-naphthyl)phenyl | 3-(1-naphthyl)phenyl | phenyl | H | H | H | H |
| IB-18 | phenyl | 2-(1-naphthyl)phenyl | 2-(1-naphthyl)phenyl | phenyl | H | H | H | H |
| IB-19 | 2-naphthyl | 4-biphenyl | 4-biphenyl | 2-naphthyl | H | H | H | H |
| IB-20 | 2-naphthyl | 3-biphenyl | 3-biphenyl | 2-naphthyl | H | H | H | H |

TABLE 3-continued

| Compound No. | Q$^{10}$ | Q$^{20}$ | Q$^{30}$ | Q$^{40}$ | Q$^{50}$ | Q$^{60}$ | Q$^{70}$ | Q$^{80}$ |
|---|---|---|---|---|---|---|---|---|
| IB-21 | [2-naphthyl] | [2-methylbiphenyl] | [2-methylbiphenyl] | [2-naphthyl] | H | H | H | H |
| IB-22 | [2-naphthyl] | [methyl-biphenyl-phenyl substituted phenyl] | [methyl-biphenyl-phenyl substituted phenyl] | [2-naphthyl] | H | H | H | H |
| IB-23 | [2-naphthyl] | [methyl-biphenyl-phenyl substituted phenyl] | [methyl-biphenyl-phenyl substituted phenyl] | [2-naphthyl] | H | H | H | H |
| IB-24 | [2-naphthyl] | [3,5-diphenylphenyl] | [3,5-diphenylphenyl] | [2-naphthyl] | H | H | H | H |

TABLE 4

| Compound No. | Q$^{10}$ | Q$^{20}$ | Q$^{30}$ | Q$^{40}$ | Q$^{50}$ | Q$^{60}$ | Q$^{70}$ | Q$^{80}$ |
|---|---|---|---|---|---|---|---|---|
| IB-25 | [2-naphthyl] | [tetraphenyl-substituted phenyl] | [tetraphenyl-substituted phenyl] | [2-naphthyl] | H | H | H | H |

TABLE 4-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-26 | | | | | H | H | H | H |
| IB-27 | | | | | H | H | H | H |
| IB-28 | | | | | H | H | H | H |
| IB-29 | | | | | H | H | H | H |
| IB-30 | | | | | H | H | H | H |
| IB-31 | | | | | H | H | H | H |
| IB-32 | | | | | H | H | H | H |

TABLE 5
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-33 | 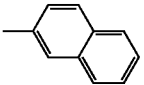 | 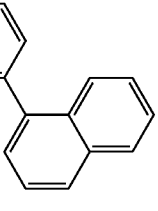 | 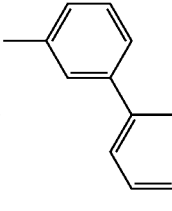 | 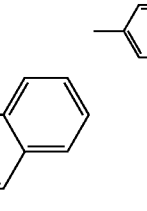 | H | H | H | H |
| IB-34 | 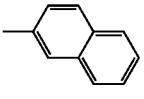 | 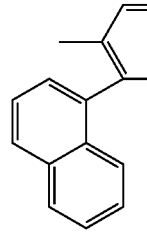 | 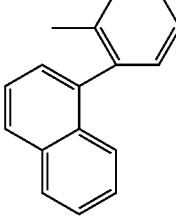 | 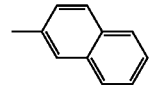 | H | H | H | H |
| IB-35 | 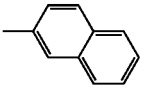 | 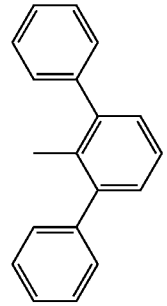 | 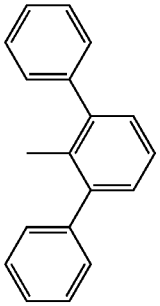 | 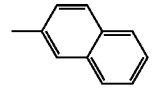 | H | H | H | H |
| IB-36 | 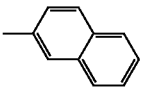 | 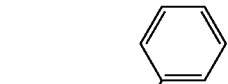 |  | 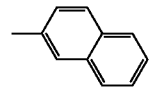 | H | H | H | H |
| IB-37 | 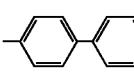 | 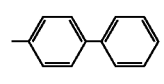 | 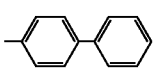 | 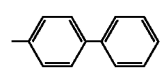 | H | H | H | H |
| IB-38 | 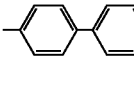 | 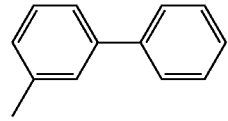 | 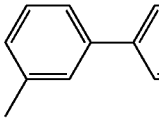 | 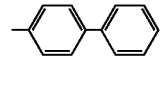 | H | H | H | H |
| IB-39 | 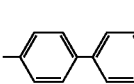 | 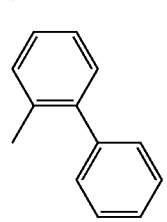 |  | 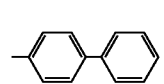 | H | H | H | H |

TABLE 5-continued

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IB-40 | biphenyl | terphenyl-phenyl branched | terphenyl-phenyl branched | biphenyl | H | H | H | H |

TABLE 6

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IB-41 | biphenyl | methyl-phenyl-phenyl substituted | methyl-phenyl-phenyl substituted | biphenyl | H | H | H | H |
| IB-42 | biphenyl | 3,5-diphenylphenyl | 3,5-diphenylphenyl | biphenyl | H | H | H | H |
| IB-43 | biphenyl | tetraphenyl branched | tetraphenyl branched | biphenyl | H | H | H | H |
| IB-44 | biphenyl | triphenyl branched | triphenyl branched | biphenyl | H | H | H | H |

TABLE 6-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-45 | 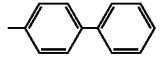 |  |  | 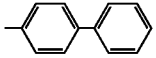 | H | H | H | H |
| IB-46 | 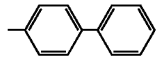 |  |  | 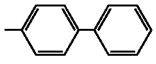 | H | H | H | H |
| IB-47 | 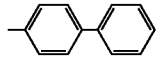 |  |  | 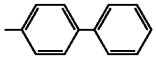 | H | H | H | H |

TABLE 7

| Compound No. | Substituent | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IB-48 | 4-biphenylyl | 3-(2-naphthyl)phenyl | 3-(2-naphthyl)phenyl | 4-biphenylyl | H | H | H | H |
| IB-49 | 4-biphenylyl | 2-(2-methylphenyl)naphthyl | 2-(2-methylphenyl)naphthyl | 4-biphenylyl | H | H | H | H |
| IB-50 | 4-biphenylyl | 1-(4-methylphenyl)naphthyl | 1-(4-methylphenyl)naphthyl | 4-biphenylyl | H | H | H | H |

TABLE 7-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-51 |  |  | 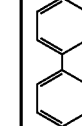 | 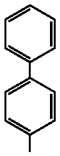 | H | H | H | H |
| IB-52 |  |  | 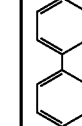 |  | H | H | H | H |
| IB-53 | 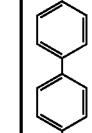 | 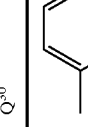 | 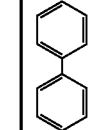 | 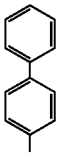 | H | H | H | H |

TABLE 7-continued

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IB-54 | 4-biphenyl | 2-methyl-4-phenyl-biphenyl | 2-methyl-4-phenyl-biphenyl | 4-biphenyl | H | H | H | H |
| IB-55 | 4-tolyl | 4-(anthracen-2-yl)-tolyl | 4-(anthracen-2-yl)-tolyl | 4-tolyl | H | H | H | H |

TABLE 8
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-56 | 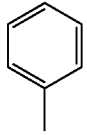 |  | 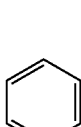 | 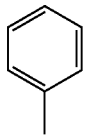 | H | H | H | H |
| IB-57 | 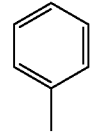 |  | 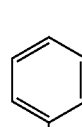 | 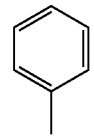 | H | H | H | H |
| IB-58 | 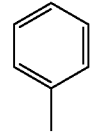 |  | 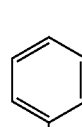 | 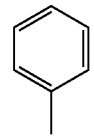 | H | H | H | H |

TABLE 8-continued
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-59 | 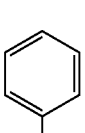 |  | 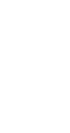 | 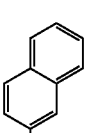 | H | H | H | H |
| IB-60 |  |  |  |  | H | H | H | H |
| IB-61 | 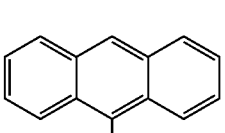 | 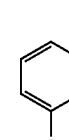 |  |  | H | H | H | H |
| IB-62 |  |  |  |  | H | H | H | H |

TABLE 9
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-63 |  |  |  |  | H | H | H | H |
| IB-64 |  |  |  |  | H | H | H | H |
| IB-65 |  |  |  |  | H | H | H | H |
| IB-66 |  | | | | H | H | H | H |

TABLE 9-continued
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-67 | 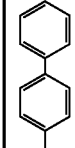 |  | 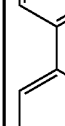 |  | H | H | H | H |
| IB-68 | 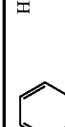 | 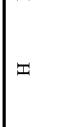 |  | 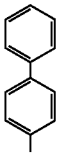 | H | H | H | H |
| IB-69 |  | 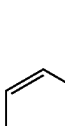 |  | 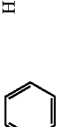 | H | H | H | H |

TABLE 10

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-70 | biphenyl | phenyl-anthracenyl | phenyl-anthracenyl | biphenyl | H | H | H | H |
| IB-71 | biphenyl | anthracenyl-phenyl | anthracenyl-phenyl | biphenyl | H | H | H | H |
| IB-72 | biphenyl | phenyl-O-phenyl | phenyl-O-phenyl | biphenyl | H | H | H | H |
| IB-73 | phenyl | naphthyl (2-) | naphthyl (2-) | phenyl | H | H | H | H |
| IB-74 | phenyl | naphthyl (1-) | naphthyl (1-) | phenyl | H | H | H | H |
| IB-75 | phenyl | naphthyl-phenyl | naphthyl-phenyl | phenyl | H | H | H | H |
| IB-76 | phenyl | naphthyl-phenyl | naphthyl-phenyl | phenyl | H | H | H | H |
| IB-77 | phenyl | anthracenyl | anthracenyl | phenyl | H | H | H | H |

TABLE 11
| Compound No. | Q10 | Q20 | Q30 | Q40 | Q50 | Q60 | Q70 | Q80 |
|---|---|---|---|---|---|---|---|---|
| IB-78 | 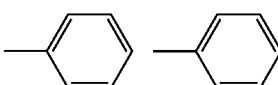 | 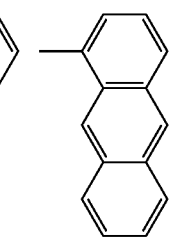 | 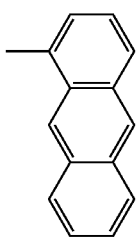 | 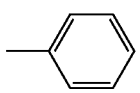 | H | H | H | H |
| IB-79 | 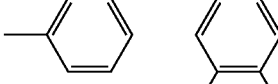 | 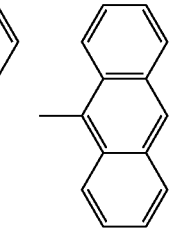 | 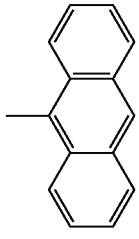 | 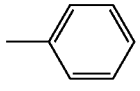 | H | H | H | H |
| IB-80 | 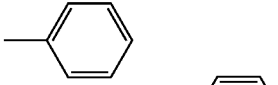 | 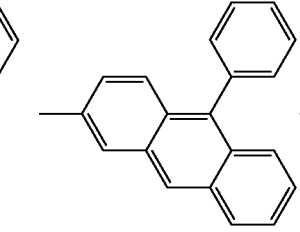 | 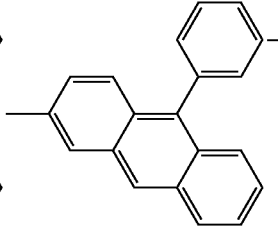 | | H | H | H | H |
| IB-81 | 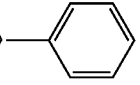 | 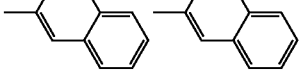 | 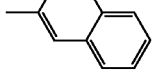 | 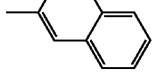 | H | H | H | H |
| IB-82 | 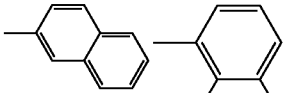 | 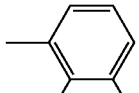 | 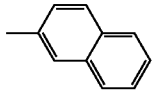 | 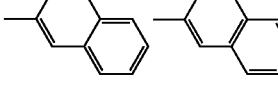 | H | H | H | H |
| IB-83 | 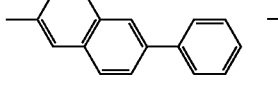 | 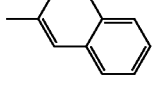 |  | 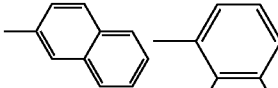 | H | H | H | H |
| IB-84 | 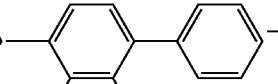 | 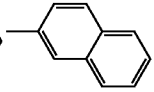 | 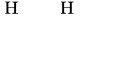 | 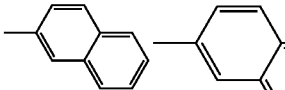 | H | H | H | H |
| IB-85 | 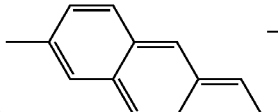 | 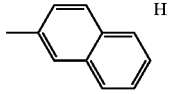 | 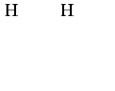 | | H | H | H | H |

TABLE 12

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-86 | naphthyl | anthracenyl | anthracenyl | naphthyl | H | H | H | H |
| IB-87 | naphthyl | anthracenyl | anthracenyl | naphthyl | H | H | H | H |
| IB-88 | naphthyl | phenyl-anthracenyl | phenyl-anthracenyl-naphthyl | | H | H | H | H |
| IB-89 | biphenyl-naphthyl | naphthyl | | biphenyl | H | H | H | H |
| IB-90 | biphenyl | naphthyl | naphthyl | biphenyl | H | H | H | H |
| IB-91 | biphenyl | naphthyl-phenyl | naphthyl-phenyl | biphenyl | H | H | H | H |
| IB-92 | biphenyl | naphthyl-phenyl | naphthyl-phenyl | biphenyl | H | H | H | H |
| IB-93 | biphenyl | anthracenyl | anthracenyl | biphenyl | H | H | H | H |

TABLE 13

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-94 | biphenyl | 1-anthryl | 1-anthryl | biphenyl | H | H | H | H |
| IB-95 | biphenyl | 9-anthryl (10-substituted) | 9-anthryl (10-substituted) | biphenyl | H | H | H | H |
| IB-96 | biphenyl | 10-phenyl-2-anthryl | 10-phenyl-2-anthryl | biphenyl | H | H | H | H |
| IB-97 | phenyl | 10-(4-(10-phenyl-9-anthryl)phenyl)-9-anthryl | 10-(4-(10-phenyl-9-anthryl)phenyl)-9-anthryl | phenyl | H | H | H | H |
| IB-98 | 2-naphthyl | 10-(4-(10-phenyl-9-anthryl)phenyl)-9-anthryl | 10-(4-(10-phenyl-9-anthryl)phenyl)-9-anthryl | 2-naphthyl | H | H | H | H |
| IB-99 | biphenyl | 10-(4-(10-phenyl-9-anthryl)phenyl)-9-anthryl | 10-(4-(10-phenyl-9-anthryl)phenyl)-9-anthryl | biphenyl | H | H | H | H |

TABLE 13-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-100 | 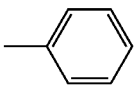 | 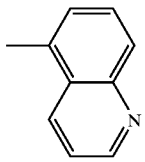 | 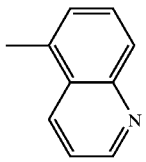 | 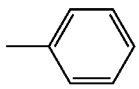 | H | H | H | H |
TABLE 14
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-101 | 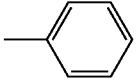 | 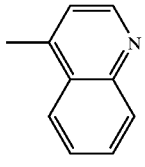 | 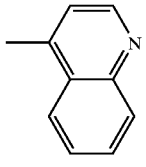 | 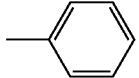 | H | H | H | H |
| IB-102 | 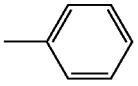 | 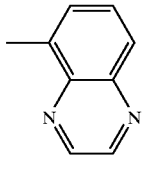 | 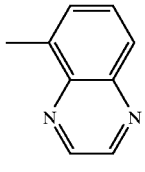 | 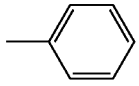 | H | H | H | H |
| IB-103 | 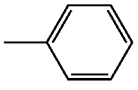 | 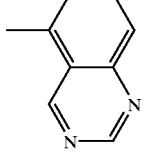 | 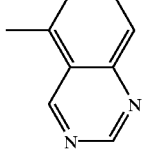 | 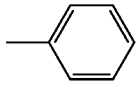 | H | H | H | H |
| IB-104 | 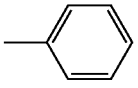 | 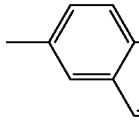 | 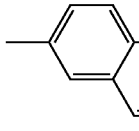 | 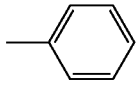 | H | H | H | H |
| IB-105 | 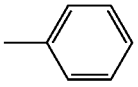 | 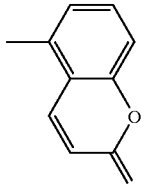 | 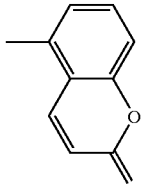 | 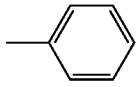 | H | H | H | H |
| IB-106 | 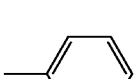 | 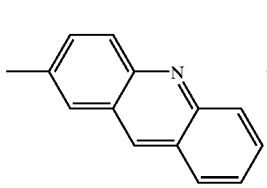 | 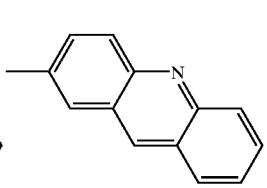 | 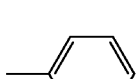 | H | H | H | H |

TABLE 14-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-107 | 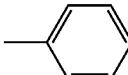 | 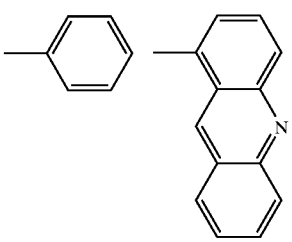 | 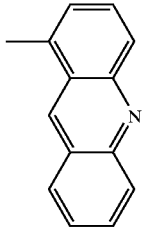 | 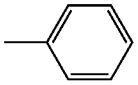 | H | H | H | H |
| IB-108 | 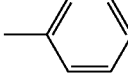 | 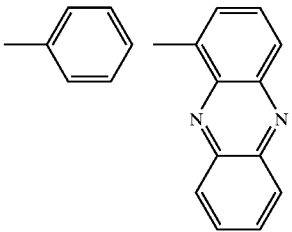 | 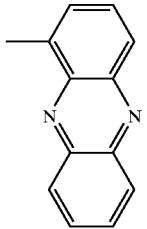 | 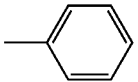 | H | H | H | H |
TABLE 15
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-109 | 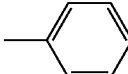 | 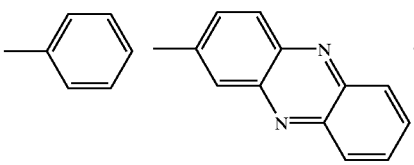 | 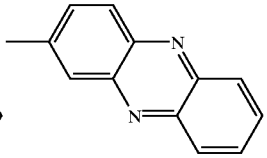 | 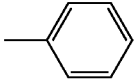 | H | H | H | H |
| IB-110 | 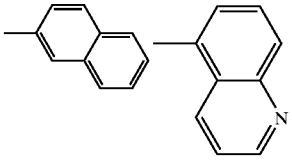 | 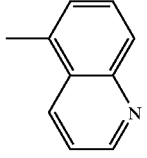 | 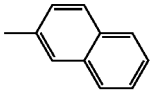 | 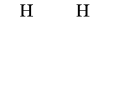 | H | H | H | H |
| IB-111 | 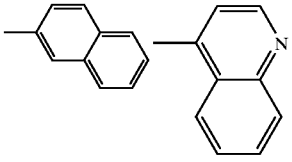 | 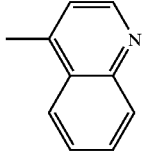 | 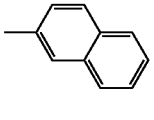 | 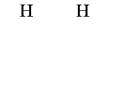 | H | H | H | H |
| IB-112 | 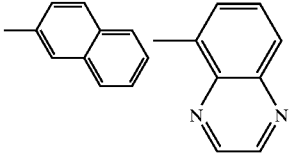 | 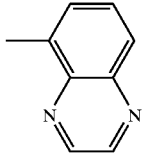 | 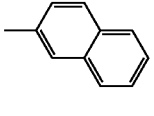 | 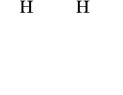 | H | H | H | H |

TABLE 15-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-113 | 2-naphthyl | quinazolin-5-yl | quinazolin-5-yl | 2-naphthyl | H | H | H | H |
| IB-114 | 2-naphthyl | 2H-chromen-2-one-6-yl | 2H-chromen-2-one-6-yl | 2-naphthyl | H | H | H | H |
| IB-115 | 2-naphthyl | 2H-chromen-2-one-5-yl | 2H-chromen-2-one-5-yl | 2-naphthyl | H | H | H | H |
| IB-116 | 2-naphthyl | acridin-3-yl | acridin-3-yl | 2-naphthyl | H | H | H | H |

TABLE 16

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-117 | 2-naphthyl | acridin-4-yl | acridin-4-yl | 2-naphthyl | H | H | H | H |
| IB-118 | 2-naphthyl | phenazin-1-yl | phenazin-1-yl | 2-naphthyl | H | H | H | H |

TABLE 16-continued

SUBSTITUENT

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-119 | naphthyl | phenazinyl | phenazinyl | naphthyl | H | H | H | H |
| IB-120 | biphenyl | quinolin-5-yl | quinolin-5-yl | biphenyl | H | H | H | H |
| IB-121 | biphenyl | quinolin-4-yl | quinolin-4-yl | biphenyl | H | H | H | H |
| IB-122 | biphenyl | quinoxalin-5-yl | quinoxalin-5-yl | biphenyl | H | H | H | H |
| IB-123 | biphenyl | quinazolin-5-yl | quinazolin-5-yl | biphenyl | H | H | H | H |
| IB-124 | biphenyl | coumarin-6-yl | coumarin-6-yl | biphenyl | H | H | H | H |

TABLE 17

SUBSTITUENT

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-125 | biphenyl | coumarin-5-yl | coumarin-5-yl | biphenyl | H | H | H | H |

TABLE 17-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-126 | biphenyl | acridinyl | acridinyl | biphenyl | H | H | H | H |
| IB-127 | biphenyl | acridinyl | acridinyl | biphenyl | H | H | H | H |
| IB-128 | biphenyl | phenazinyl | phenazinyl | biphenyl | H | H | H | H |
| IB-129 | biphenyl | phenazinyl | phenazinyl | biphenyl | H | H | H | H |
| IB-130 | naphthyl | p-terphenyl | p-terphenyl | naphthyl | H | H | H | H |
| IB-131 | naphthyl | m,p-terphenyl | m,p-terphenyl | naphthyl | H | H | H | H |
| IB-132 | naphthyl | pyridyl-phenyl-phenyl | pyridyl-phenyl-phenyl | naphthyl | H | H | H | H |

TABLE 18

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IB-133 | naphthyl | biphenyl(4) | biphenyl(4) | naphthyl | H | H | H | H |
| IB-134 | naphthyl | biphenyl(3) | biphenyl(3) | naphthyl | H | H | H | H |
| IB-135 | naphthyl | biphenyl(2) | biphenyl(2) | naphthyl | H | H | H | H |
| IB-136 | biphenyl(4) | biphenyl(4) | biphenyl(4) | biphenyl(4) | H | H | H | H |
| IB-137 | biphenyl(3) | biphenyl(3) | biphenyl(3) | biphenyl(3) | H | H | H | H |
| IB-138 | biphenyl(2) | biphenyl(2) | biphenyl(2) | biphenyl(2) | H | H | H | H |
| IB-139 | terphenyl(4) | terphenyl(4) | terphenyl(4) | terphenyl(4) | H | H | H | H |
| IB-140 | terphenyl(3) | terphenyl(3) | terphenyl(3) | terphenyl(3) | H | H | H | H |
| IB-141 | terphenyl(2) | terphenyl(2) | terphenyl(2) | terphenyl(2) | H | H | H | H |

TABLE 19

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-142 | phenyl | 2-methyl-1,3-diphenylphenyl | 2-methyl-1,3-diphenylphenyl | phenyl | phenyl | phenyl | H | H |
| IB-143 | phenyl | 2-methyl-1,3-diphenylphenyl | 2-methyl-1,3-diphenylphenyl | phenyl | $CH_3$ | $CH_3$ | H | H |

TABLE 19-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-144 | Ph | terphenyl | terphenyl | Ph | Ph | Ph | Ph | Ph |
| IB-145 | Ph | Ph | Ph | Ph | Ph | Ph | H | H |
| IB-146 | Ph | biphenyl | biphenyl | Ph | Ph | Ph | H | H |

TABLE 19-continued

[Structure: tetracene/naphthacene core with substituents R10, R20, R30, R40, R50, R60, R70, R80]

| Compound No. | Q10 | Q20 | Q30 | Q40 | Q50 | Q60 | Q70 | Q80 |
|---|---|---|---|---|---|---|---|---|
| IB-147 | phenyl | 2-methylbiphenyl | 2-methylbiphenyl | phenyl | phenyl | phenyl | H | H |
| IB-148 | phenyl | 2-methyl-m-terphenyl | 2-methyl-m-terphenyl | phenyl | CH$_3$ | CH$_3$ | CH$_3$ | CH$_3$ |
| IB-149 | phenyl | 2-methyl-m-terphenyl | 2-methyl-m-terphenyl | phenyl | phenyl | phenyl | CH$_3$ | CH$_3$ |

TABLE 19-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-150 | 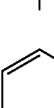 |  | 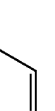 | 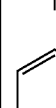 |  |  |  |  |
| IB-151 | 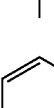 |  | 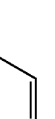 | 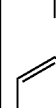 |  |  |  |  |
| IB-152 | 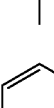 |  | 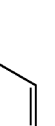 | 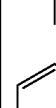 |  |  |  |  |

TABLE 20
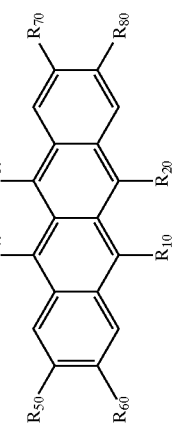
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-153 | 4-methylbiphenyl | 2-methyl-1,3-diphenylbenzene | 2-methyl-1,3-diphenylbenzene | 4-methylbiphenyl | H | H | H | H |
| IB-154 | 4-methylbiphenyl | 2-methyl-1,3-diphenylbenzene | 2-methyl-1,3-diphenylbenzene | 4-methylbiphenyl | toluene | toluene | H | H |

TABLE 20-continued

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-155 | 4-biphenylyl | 2,6-diphenylphenyl | 2,6-diphenylphenyl | 4-biphenylyl | CH₃ | CH₃ | H | H |
| IB-156 | 4-biphenylyl | 2,6-diphenylphenyl | 2,6-diphenylphenyl | 4-biphenylyl | phenyl | phenyl | phenyl | phenyl |

TABLE 20-continued

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-157 | 4-methylbiphenyl | o-tolyl | o-tolyl | biphenyl | o-tolyl | o-tolyl | o-tolyl | H |
| IB-158 | 4-methylbiphenyl | biphenyl | 4-methylbiphenyl | 4-methylbiphenyl | biphenyl | o-tolyl | o-tolyl | H |
| IB-159 | 4-methylbiphenyl | 2-methylbiphenyl | 2-methylbiphenyl | 4-methylbiphenyl | biphenyl | o-tolyl | o-tolyl | H |

TABLE 20-continued

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-160 | 4-methylbiphenyl | 2,6-diphenyltolyl | 2,6-diphenyltolyl | 4-methylbiphenyl | $CH_3$ | $CH_3$ | $CH_3$ | $CH_3$ |
| IB-161 | 4-methylbiphenyl | 2,6-diphenyltolyl | 2,6-diphenyltolyl | 4-methylbiphenyl | tolyl | tolyl | $CH_3$ | $CH_3$ |

TABLE 21

Structure: naphthacene (tetracene) core with substituents $R_{10}$, $R_{20}$ (on central ring), $R_{30}$, $R_{40}$ (on central ring top), $R_{50}$, $R_{60}$ (left outer ring), $R_{70}$, $R_{90}$ (right outer ring).

SUBSTITUENT

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IB-162 | phenyl | biphenyl-4-yl | biphenyl-4-yl | phenyl | $CH_3$ | $CH_3$ | H | H |
| IB-163 | phenyl | 2-biphenylyl | 2-biphenylyl | phenyl | $CH_3$ | $CH_3$ | H | H |
| IB-164 | $CH_3$ | biphenyl-4-yl | biphenyl-4-yl | $CH_3$ | H | H | H | H |
| IB-165 | $CH_3$ | 2-biphenylyl | 2-biphenylyl | $CH_3$ | H | H | H | H |
| IB-166 | $CH_3$ | 3-phenylbiphenyl-4-yl | 3-phenylbiphenyl-4-yl | $CH_3$ | H | H | H | H |
| IB-167 | $CH_3$ | p-terphenyl-4-yl | p-terphenyl-4-yl | $CH_3$ | H | H | H | H |
| IB-168 | H | biphenyl-4-yl | biphenyl-4-yl | H | $CH_3$ | $CH_3$ | H | H |
| IB-169 | H | 3-phenylbiphenyl-4-yl | 3-phenylbiphenyl-4-yl | H | $CH_3$ | $CH_3$ | H | H |

TABLE 21-continued

[Structure: tetracene core with substituents R40, R30 (top center), R50, R70 (upper outer), R60, R90 (lower outer), R10, R20 (bottom center)]

SUBSTITUENT

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-170 | H | 2-methylbiphenyl | 2-methylbiphenyl | H | CH₃ | CH₃ | H | H |

TABLE 22

[Structure: tetracene core with substituents R40, R30, R50, R70, R60, R90, R10, R20]

SUBSTITUENT

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-171 | H | p-terphenyl | p-terphenyl | H | CH₃ | CH₃ | H | H |
| IB-172 | H | biphenyl | biphenyl | H | CH₃ | CH₃ | CH₃ | CH₃ |
| IB-173 | H | 2-methylbiphenyl | 2-methylbiphenyl | H | CH₃ | CH₃ | CH₃ | CH₃ |
| IB-174 | H | 3-phenylbiphenyl (methyl-substituted) | 3-phenylbiphenyl (methyl-substituted) | H | CH₃ | CH₃ | CH₃ | CH₃ |
| IB-175 | H | p-quaterphenyl | p-quaterphenyl | H | CH₃ | CH₃ | CH₃ | CH₃ |

TABLE 23

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-176 | phenyl | biphenyl | biphenyl | phenyl | CH₃ | CH₃ | H | H |
| IB-177 | phenyl | 2-phenylphenyl | 2-phenylphenyl | phenyl | CH₃ | CH₃ | H | H |
| IB-178 | CH₃ | biphenyl | biphenyl | CH₃ | H | H | H | H |
| IB-179 | CH₃ | 2-phenylphenyl | 2-phenylphenyl | CH₃ | H | H | H | H |
| IB-180 | CH₃ | 3-phenyl-biphenyl | 3-phenyl-biphenyl | CH₃ | H | H | H | H |
| IB-181 | CH₃ | terphenyl | terphenyl | CH₃ | H | H | H | H |

TABLE 24

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IB-182 | H | | biphenyl | H | CH₃ | CH₃ | H | H |
| IB-183 | H | | 3-phenyl-biphenyl | H | CH₃ | CH₃ | H | H |
| IB-184 | H | | 2-phenylphenyl | H | CH₃ | CH₃ | H | H |

TABLE 24-continued

| Compound No. | Q10 | Q20 | Q30 | Q40 | Q50 | Q60 | Q70 | Q80 |
|---|---|---|---|---|---|---|---|---|
| IB-185 | H | 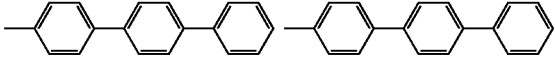 | 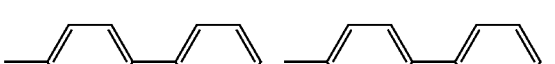 | H | CH₃ | CH₃ | H | H |
| IB-186 | H |  |  | H | CH₃ | CH₃ | CH₃ | CH₃ |
| IB-187 | H | 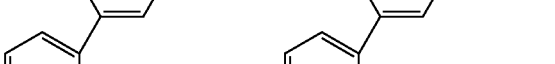 | 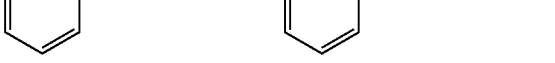 | H | CH₃ | CH₃ | CH₃ | CH₃ |
| IB-188 | H |  | 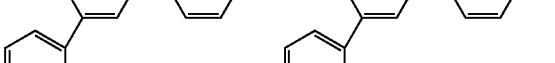 | H | CH₃ | CH₃ | CH₃ | CH₃ |
| IB-189 | H | 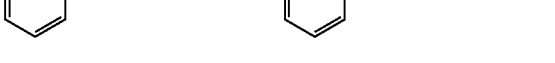 | 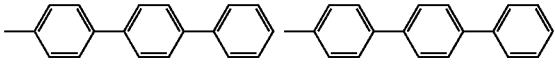 | H | CH₃ | CH₃ | CH₃ | CH₃ |

Other illustrative examples of the preferred naphthacene derivatives used herein are given below as IIB-1 to IIB-32 and IIIB-1 to IIIB-36. The substituents $Q^1$ to $Q^8$ are denoted as $Q^{10}$ to $Q^{80}$.

TABLE 25

| Compound No. | Q10 | Q20 | Q30 | Q40 | Q50 | Q60 | Q70 | Q80 |
|---|---|---|---|---|---|---|---|---|
| IIB-1 | 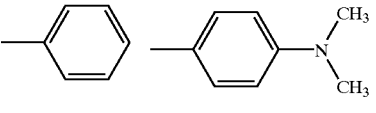 | 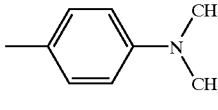 | 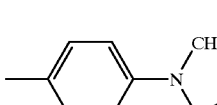 | 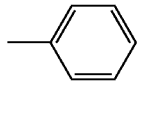 | H | H | H | H |
| IIB-2 | 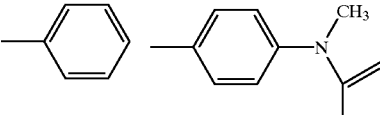 | 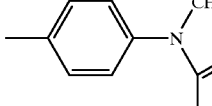 | 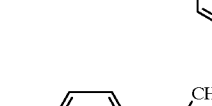 | 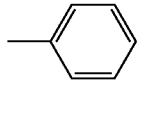 | H | H | H | H |
| IIB-3 | 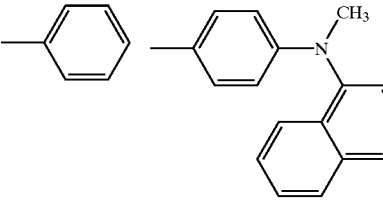 | 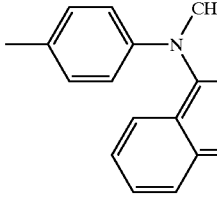 |  | 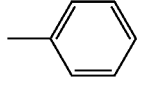 | H | H | H | H |

TABLE 25-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IIB-4 | phenyl | 4-(N-methyl-N-(2-naphthyl)amino)phenyl | 4-(N-methyl-N-(2-naphthyl)amino)phenyl | phenyl | H | H | H | H |
| IIB-5 | phenyl | 4-(N-methyl-N-(2-anthryl)amino)phenyl | 4-(N-methyl-N-(2-anthryl)amino)phenyl | phenyl | H | H | H | H |
| IIB-6 | 2-naphthyl | 4-(N,N-dimethylamino)phenyl | 4-(N,N-dimethylamino)phenyl | 2-naphthyl | H | H | H | H |
| IIB-7 | 2-naphthyl | 4-(N-methyl-N-(1-naphthyl)amino)phenyl | 4-(N-methyl-N-(1-naphthyl)amino)phenyl | 2-naphthyl | H | H | H | H |
| IIB-8 | 2-naphthyl | 4-(N-methyl-N-(2-naphthyl)amino)phenyl | 4-(N-methyl-N-(2-naphthyl)amino)phenyl | 2-naphthyl | H | H | H | H |

TABLE 26

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IIB-9 | 2-naphthyl | N(CH₃)(p-tolyl)(2-anthryl) | N(CH₃)(p-tolyl)(2-anthryl) | 2-naphthyl | H | H | H | H |
| IIB-10 | 4-biphenyl | N(CH₃)(p-tolyl)(CH₃) | N(CH₃)(p-tolyl)(CH₃) | 4-biphenyl | H | H | H | H |
| IIB-11 | 4-biphenyl | N(CH₃)(p-tolyl)(1-naphthyl) | N(CH₃)(p-tolyl)(1-naphthyl) | 4-biphenyl | H | H | H | H |
| IIB-12 | 4-biphenyl | N(CH₃)(p-tolyl)(2-naphthyl) | N(CH₃)(p-tolyl)(2-naphthyl) | 4-biphenyl | H | H | H | H |

TABLE 26-continued

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IIB-13 | biphenyl-tolyl | N(CH₃)(tolyl)(anthracenyl) | N(CH₃)(tolyl)(anthracenyl) | biphenyl-tolyl | H | H | H | H |
| IIB-14 | phenyl | N(phenyl)(phenyl)(tolyl) | N(phenyl)(phenyl)(tolyl) | phenyl | H | H | H | H |
| IIB-15 | phenyl | N(phenyl)(tolyl-CH₃)(tolyl) | N(phenyl)(tolyl-CH₃)(tolyl) | phenyl | H | H | H | H |

TABLE 27

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IIB-16 | —phenyl | | —C₆H₄-N(phenyl)(naphthyl) | —C₆H₄-N(phenyl)(naphthyl) | —phenyl | H | H | H | H |
| IIB-17 | —phenyl | | —C₆H₄-N(di-naphthyl) | —C₆H₄-N(di-naphthyl) | —phenyl | H | H | H | H |
| IIB-18 | —phenyl | | —C₆H₄-N(phenyl)(quinolinyl) | —C₆H₄-N(phenyl)(quinolinyl) | —phenyl | H | H | H | H |
| IIB-19 | —phenyl | | —C₆H₄-N(di-quinolinyl) | —C₆H₄-N(di-quinolinyl) | —phenyl | H | H | H | H |
| IIB-20 | —naphthyl | | —C₆H₄-N(diphenyl) | —C₆H₄-N(diphenyl) | —naphthyl | H | H | H | H |

TABLE 27-continued
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IIB-21 | 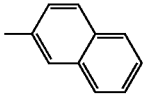 | 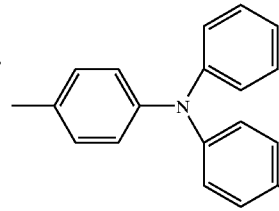 | 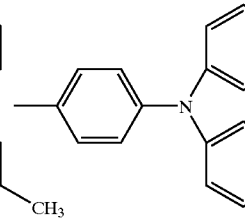 | 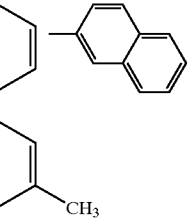 | H | H | H | H |
TABLE 28
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IIB-22 | 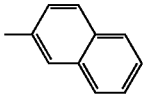 | 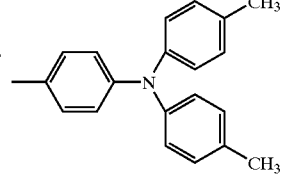 | 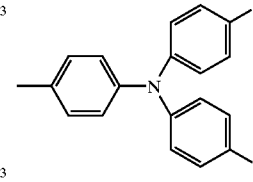 | 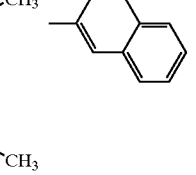 | H | H | H | H |
| IIB-23 | 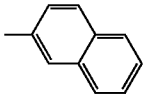 | 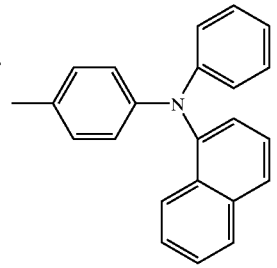 | 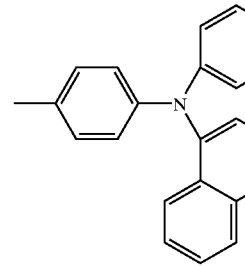 | 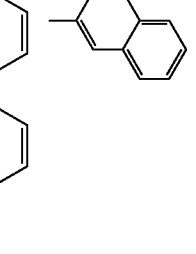 | H | H | H | H |
| IIB-24 | 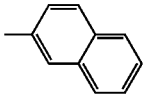 | 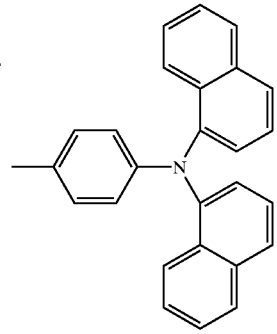 | 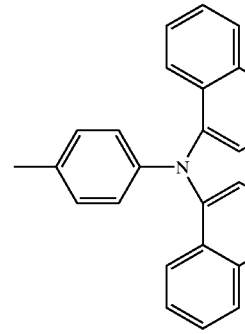 | 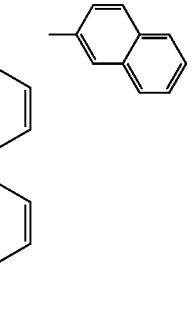 | H | H | H | H |

TABLE 28-continued
| Compound No. | Q10 | Q20 | Q30 | Q40 | Q50 | Q60 | Q70 | Q80 |
|---|---|---|---|---|---|---|---|---|
| IIB-25 | 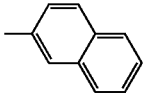 | | 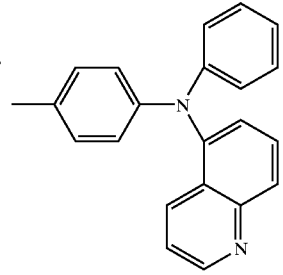 | 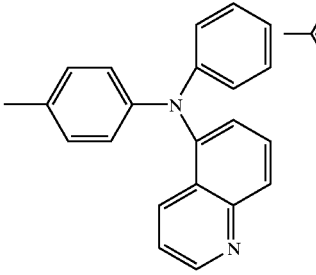 |  | H | H | H | H |
| IIB-26 | 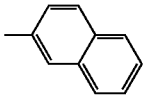 | | 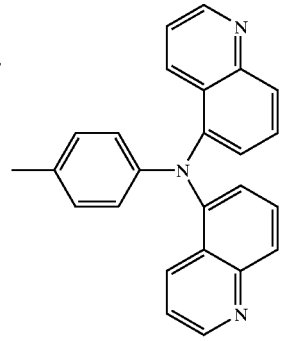 | 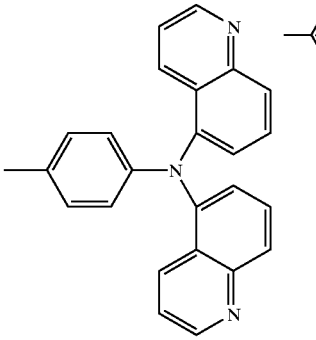 |  | H | H | H | H |

TABLE 29
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IIB-27 | 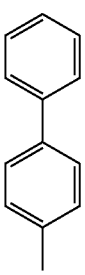 | 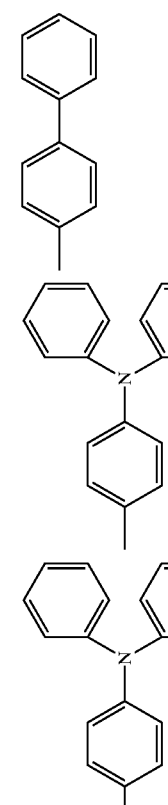 | 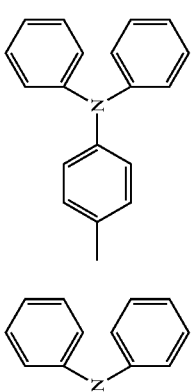 | 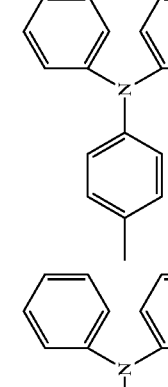 | H | H | H | H |
| IIB-28 | 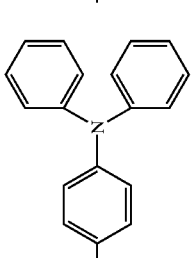 | 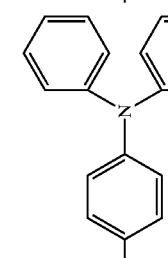 | 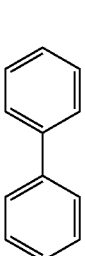 | 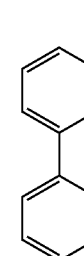 | H | H | H | H |
| IIB-29 |  |  | | | H | H | H | H |

TABLE 29-continued

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IIB-30 | 4-biphenyl | N(1-naphthyl)(1-naphthyl)(p-tolyl) | N(1-naphthyl)(1-naphthyl)(p-tolyl) | 4-biphenyl | H | H | H | H |
| IIB-31 | 4-biphenyl | N(phenyl)(quinolinyl)(p-tolyl) | N(phenyl)(quinolinyl)(p-tolyl) | 4-biphenyl | H | H | H | H |
| IIB-32 | 4-biphenyl | N(quinolinyl)(quinolinyl)(p-tolyl) | N(quinolinyl)(quinolinyl)(p-tolyl) | 4-biphenyl | H | H | H | H |

TABLE 30

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IIIB-1 | phenyl | styryl | styryl | phenyl | H | H | H | H |
| IIIB-2 | phenyl | 2-phenylstyryl | 2-phenylstyryl | phenyl | H | H | H | H |
| IIIB-3 | phenyl | 2,2-diphenylvinyl-phenyl | 2,2-diphenylvinyl-phenyl | phenyl | H | H | H | H |
| IIIB-4 | phenyl | 1,2,2-triphenylvinyl-phenyl | 1,2,2-triphenylvinyl-phenyl | phenyl | H | H | H | H |
| IIIB-5 | phenyl | 4-phenyl-1,3-butadienyl-phenyl | 4-phenyl-1,3-butadienyl-phenyl | phenyl | H | H | H | H |
| IIIB-6 | phenyl | 4-vinylstyryl-phenyl | 4-vinylstyryl-phenyl | phenyl | H | H | H | H |

TABLE 31

| Compound No. | Q$^{10}$ | Q$^{20}$ | Q$^{30}$ |
|---|---|---|---|
| IIIB-7 | 2-naphthyl | 4-(2-phenylethenyl)phenyl | 4-(2-phenylethenyl)phenyl |
| IIIB-8 | 2-naphthyl | 4-(2,2-diphenylethenyl)phenyl (mono-phenyl on β) | 4-(2,2-diphenylethenyl)phenyl (mono-phenyl on β) |
| IIIB-9 | 2-naphthyl | 4-(2,2-diphenylethenyl)phenyl | 4-(2,2-diphenylethenyl)phenyl |
| IIIB-10 | 2-naphthyl | 4-(1,2,2-triphenylethenyl)phenyl | 4-(1,2,2-triphenylethenyl)phenyl |
| IIIB-11 | 2-naphthyl | 4-(4-phenyl-1,3-butadienyl)phenyl | 4-(4-phenyl-1,3-butadienyl)phenyl |
| IIIB-12 | 2-naphthyl | 4-[4-(ethenyl)styryl]phenyl | 4-[4-(ethenyl)styryl]phenyl |

TABLE 31-continued

| Compound No. | Q⁴⁰ | Q⁵⁰ | Q⁶⁰ | Q⁷⁰ | Q⁸⁰ |
|---|---|---|---|---|---|
| IIIB-7 | (naphthyl) | H | H | H | H |
| IIIB-8 | (naphthyl) | H | H | H | H |
| IIIB-9 | (naphthyl) | H | H | H | H |
| IIIB-10 | (naphthyl) | H | H | H | H |
| IIIB-11 | (naphthyl) | H | H | H | H |
| IIIB-12 | (naphthyl) | H | H | H | H |

TABLE 32

| Compound No. | Q¹⁰ | Q²⁰ | Q³⁰ |
|---|---|---|---|
| IIIB-13 | biphenyl | phenyl-CH=CH₂ | phenyl-CH=CH₂ |
| IIIB-14 | biphenyl | phenyl-CH=CH-phenyl | phenyl-CH=CH-phenyl |
| IIIB-15 | biphenyl | phenyl-C(=C(phenyl)(phenyl)) | phenyl-C(=C(phenyl)(phenyl)) |

TABLE 32-continued
| Compound No. | Q⁴⁰ | Q⁵⁰ | Q⁶⁰ | Q⁷⁰ | Q⁸⁰ |
|---|---|---|---|---|---|
| IIIB-16 |  | | | | |
| IIIB-17 |  | | | | |
| IIIB-18 |  | | | | |
| Compound No. | Q⁴⁰ | Q⁵⁰ | Q⁶⁰ | Q⁷⁰ | Q⁸⁰ |
|---|---|---|---|---|---|
| IIIB-13 |  | H | H | H | H |
| IIIB-14 |  | H | H | H | H |
| IIIB-15 |  | H | H | H | H |
| IIIB-16 |  | H | H | H | H |

TABLE 32-continued
| | | | | | | |
|---|---|---|---|---|---|---|
| IIIB-17 | 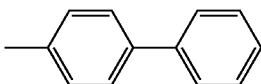 | H | H | H | H |
| IIIB-18 | 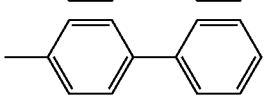 | H | H | H | H |
TABLE 33
| | SUBSTITUENT | | | |
|---|---|---|---|---|
| Compound No. | $Q^{10}$ | $Q^{20}$ | $Q^{30}$ | $Q^{40}$ |
| IIIB-19 | 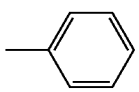 | 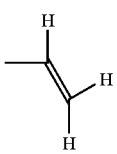 | 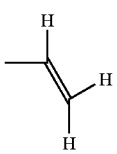 | 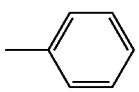 |
| IIIB-20 | 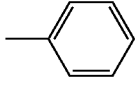 | 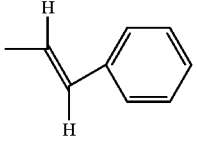 | 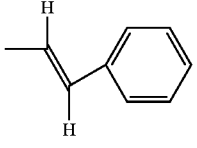 | 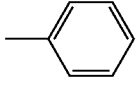 |
| IIIB-21 | 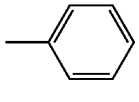 | 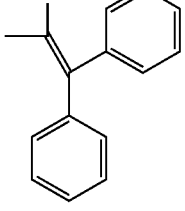 | 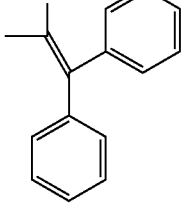 | 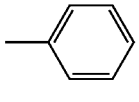 |
| IIIB-22 | 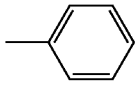 | 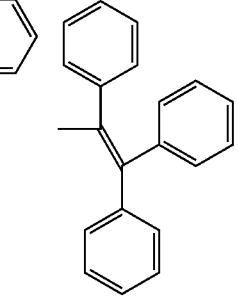 | 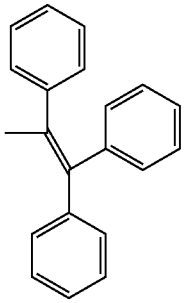 | 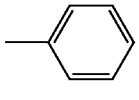 |
| IIIB-23 | 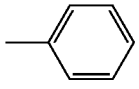 | 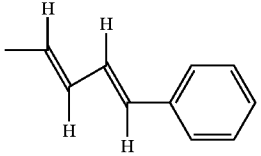 | 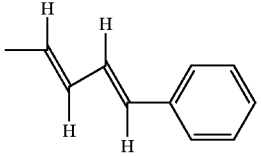 | 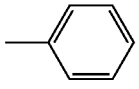 |
| IIIB-24 | 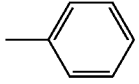 | 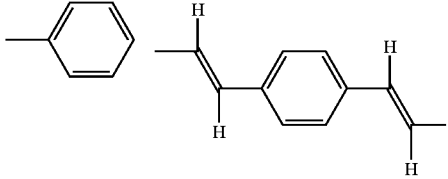 | 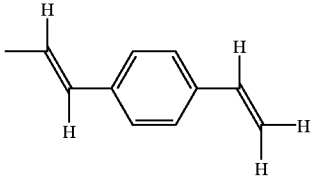 | 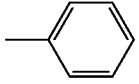 |

TABLE 33-continued

| Compound No. | Q⁵⁰ | Q⁶⁰ | Q⁷⁰ | Q⁸⁰ |
|---|---|---|---|---|
| IIIB-19 | H | H | H | H |
| IIIB-20 | H | H | H | H |
| IIIB-21 | H | H | H | H |
| IIIB-22 | H | H | H | H |
| IIIB-23 | H | H | H | H |
| IIIB-24 | H | H | H | H |

TABLE 34

Compound No. Q¹⁰, Q²⁰, Q³⁰, Q⁴⁰

IIIB-25, IIIB-26, IIIB-27, IIIB-28, IIIB-29, IIIB-30

TABLE 34-continued

| Compound No. | SUBSTITUENT | | | |
|---|---|---|---|---|
| | $Q^{50}$ | $Q^{60}$ | $Q^{70}$ | $Q^{80}$ |
| IIIB-25 | H | H | H | H |
| IIIB-26 | H | H | H | H |
| IIIB-27 | H | H | H | H |
| IIIB-28 | H | H | H | H |
| IIIB-29 | H | H | H | H |
| IIIB-30 | H | H | H | H |

TABLE 35

| Compound No. | SUBSTITUENT | | |
|---|---|---|---|
| | $Q^{10}$ | $Q^{20}$ | $Q^{30}$ |
| IIIB-31 | | | |
| IIIB-32 | | | |
| IIIB-33 | | | |
| IIIB-34 | | | |
| IIIB-35 | | | |
| IIIB-36 | | | |

TABLE 35-continued

| Compound No. | Q⁴⁰ | Q⁵⁰ | Q⁶⁰ | Q⁷⁰ | Q⁸⁰ |
|---|---|---|---|---|---|
| IIIB-31 | biphenyl | H | H | H | H |
| IIIB-32 | biphenyl | H | H | H | H |
| IIIB-33 | biphenyl | H | H | H | H |
| IIIB-34 | biphenyl | H | H | H | H |
| IIIB-35 | biphenyl | H | H | H | H |
| IIIB-36 | biphenyl | H | H | H | H |

Further illustrative examples of the preferred naphthacene derivatives used herein are given below as IVB-1 to IVB-206 and VB-1 to VB-142. The substituents $Q^1$ to $Q^8$ are denoted as $Q^{10}$ to $Q^{80}$.

TABLE 36

| Compound No. | Q¹⁰ | Q²⁰ | Q³⁰ |
|---|---|---|---|
| IVB-1 | 4-methylphenyl | 4-methylphenyl | phenyl |
| IVB-2 | 4-methoxyphenyl | 4-methoxyphenyl | phenyl |
| IVB-3 | 4-(2-phenylethenyl)phenyl | 4-(2-phenylethenyl)phenyl | phenyl |
| IVB-4 | diphenylamino | diphenylamino | phenyl |

TABLE 36-continued
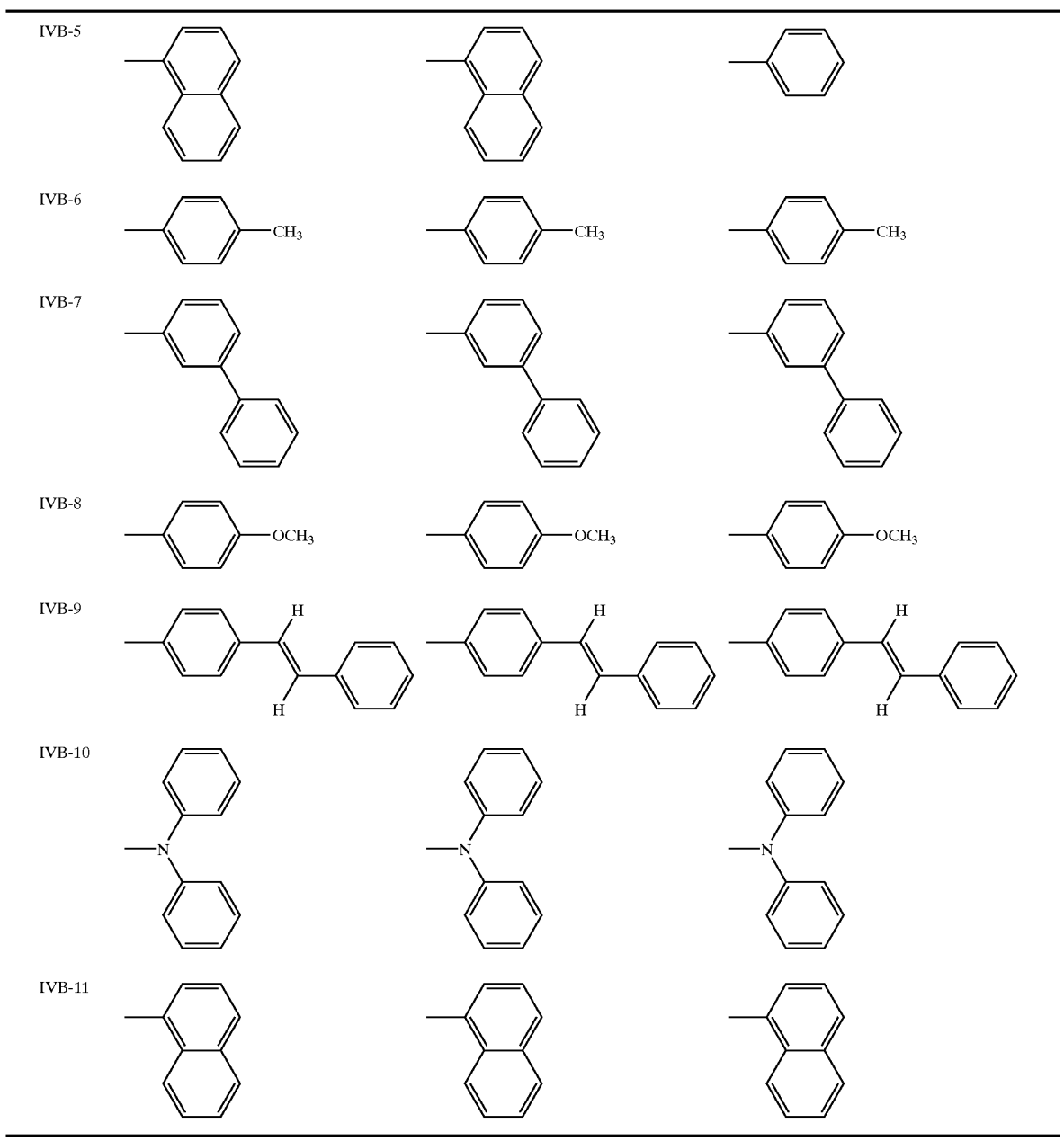

TABLE 36-continued
| Compound No. | Structure | | | | |
|---|---|---|---|---|---|
| IVB-4 | 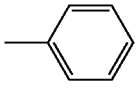 | CH₃ | CH₃ | H | H |
| IVB-5 | 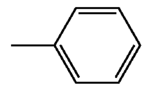 | CH₃ | CH₃ | H | H |
| IVB-6 | 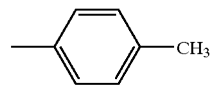 | CH₃ | CH₃ | CH₃ | CH₃ |
| IVB-7 | 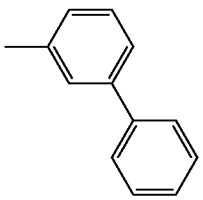 | CH₃ | CH₃ | CH₃ | CH₃ |
| IVB-8 | 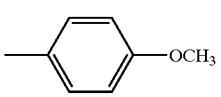 | CH₃ | CH₃ | CH₃ | CH₃ |
| IVB-9 | 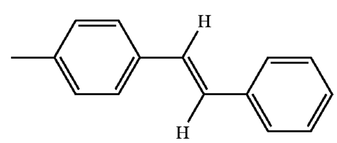 | CH₃ | CH₃ | CH₃ | CH₃ |
| IVB-10 | 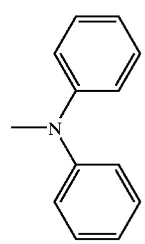 | CH₃ | CH₃ | CH₃ | CH₃ |
| IVB-11 | 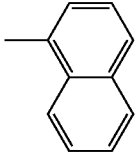 | CH₃ | CH₃ | CH₃ | CH₃ |
TABLE 37
| | SUBSTITUENT | | | | | |
|---|---|---|---|---|---|---|
| Compound No. | $Q^{10}$ | $Q^{20}$ | $Q^{30}$ | $Q^{40}$ | $Q^{50}$ | $Q^{60}$ |
| IVB-12 | 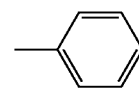 | 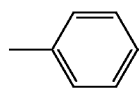 | 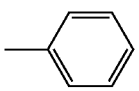 | 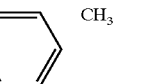 | CH₃ | CH₃ |

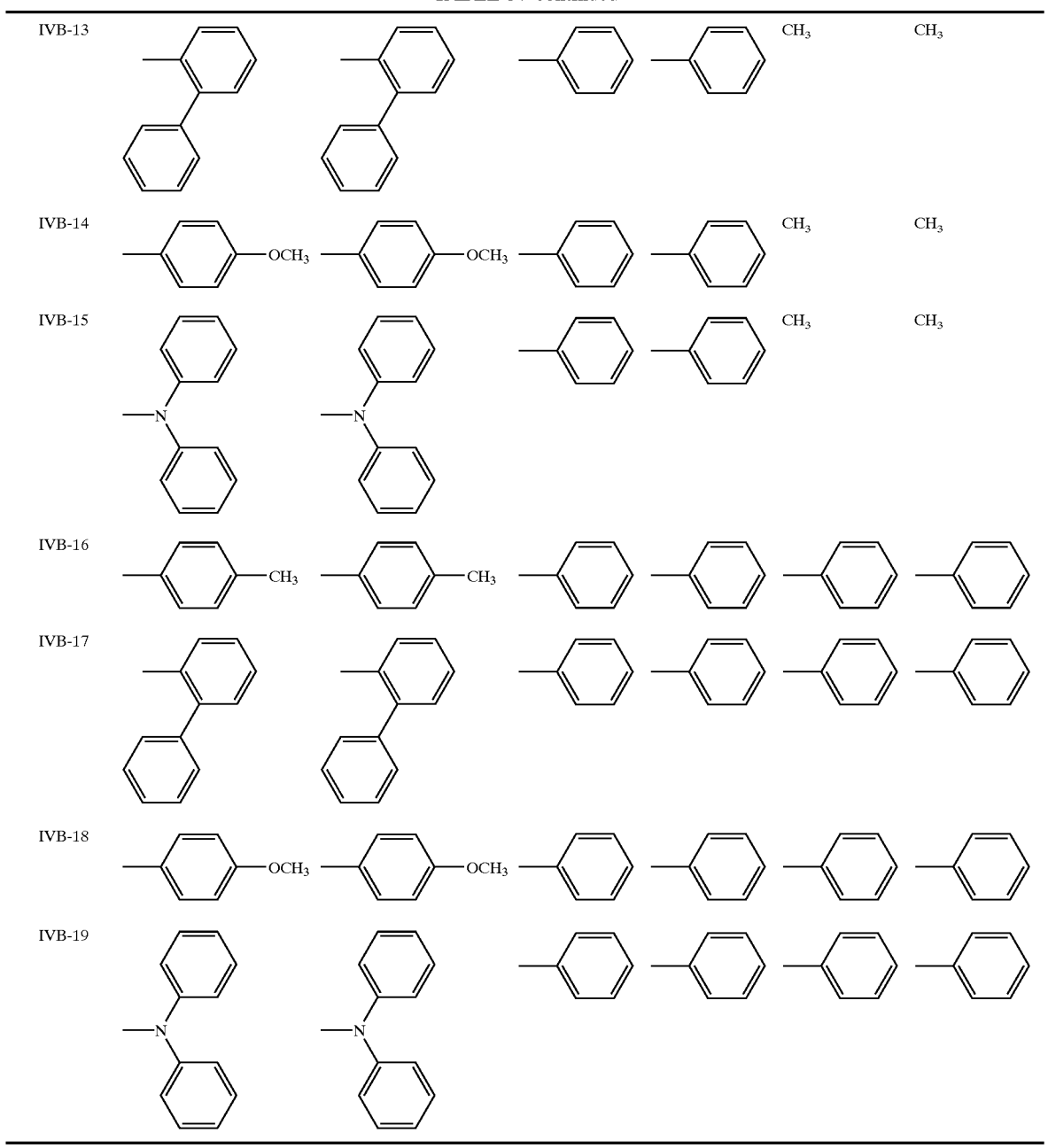

TABLE 37-continued
| | | |
|---|---|---|
| IVB-18 |  |  |
| IVB-19 | 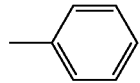 | 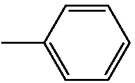 |
TABLE 38
| Compound No. | SUBSTITUENT | | | | |
|---|---|---|---|---|---|
| | $Q^{10}$ | $Q^{20}$ | $Q^{30}$ | $Q^{40}$ | $Q^{50}$ |
| IVB-20 | 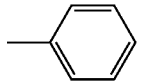 | 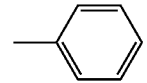 | 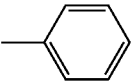 | 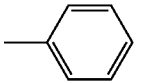 | 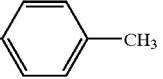 |
| IVB-21 | 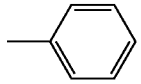 | 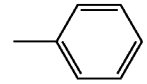 | 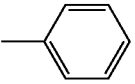 | 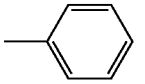 | 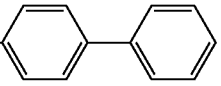 |
| IVB-22 | 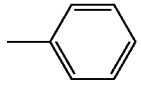 | 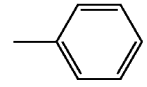 | 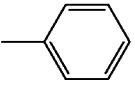 | 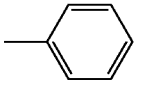 | 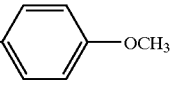 |
| IVB-23 | 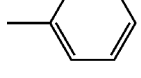 | 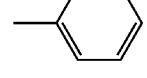 | 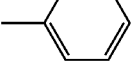 | 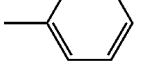 | 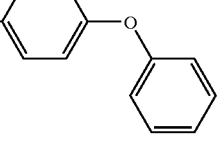 |
| IVB-24 | 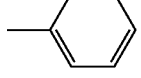 | 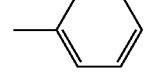 | 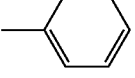 | 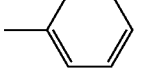 | 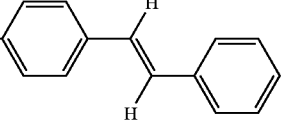 |
| IVB-25 | 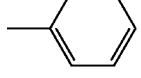 | 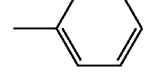 | 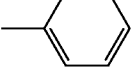 | 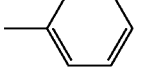 | 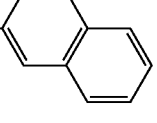 |
| IVB-26 | 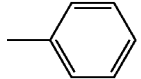 | 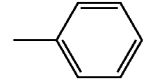 | 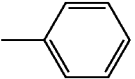 | 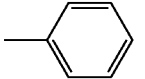 | 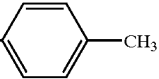 |
| IVB-27 | 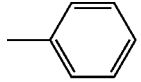 | 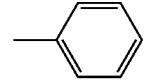 | 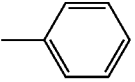 | 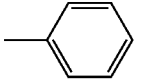 | 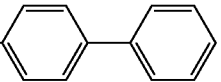 |
| IVB-28 | 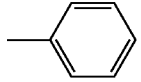 | 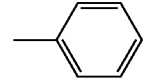 | 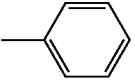 | 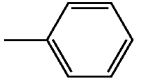 | 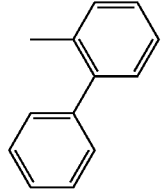 |

TABLE 38-continued

| Compound No. | | | | | |
|---|---|---|---|---|---|
| IVB-29 | phenyl | phenyl | phenyl | phenyl | 4-methoxyphenyl |
| IVB-30 | phenyl | phenyl | phenyl | phenyl | 4-phenoxyphenyl |
| IVB-31 | phenyl | phenyl | phenyl | phenyl | 4-(trans-styryl)phenyl |
| IVB-32 | phenyl | phenyl | phenyl | phenyl | 1-naphthyl |

| | SUBSTITUENT | | |
|---|---|---|---|
| Compound No. | $Q^{60}$ | $Q^{70}$ | $Q^{80}$ |
| IVB-20 | 4-methylphenyl | 4-methylphenyl | 4-methylphenyl |
| IVB-21 | 4-biphenylyl | 4-biphenylyl | 4-biphenylyl |
| IVB-22 | 4-methoxyphenyl | 4-methoxyphenyl | 4-methoxyphenyl |
| IVB-23 | 4-phenoxyphenyl | 4-phenoxyphenyl | 4-phenoxyphenyl |
| IVB-24 | 4-(trans-styryl)phenyl | 4-(trans-styryl)phenyl | 4-(trans-styryl)phenyl |
| IVB-25 | 2-naphthyl | phenyl | phenyl |
| IVB-26 | 4-methylphenyl | phenyl | phenyl |

TABLE 38-continued
| Compound No. | Q10 | Q20 | Q30 |
|---|---|---|---|
| IVB-27 | 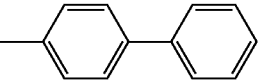 | 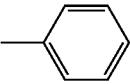 | 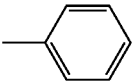 |
| IVB-28 | 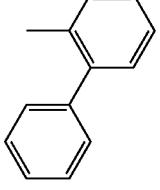 | 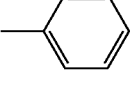 | 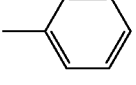 |
| IVB-29 | 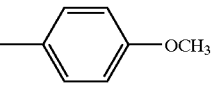 | 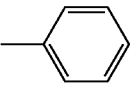 | 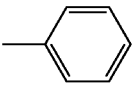 |
| IVB-30 | 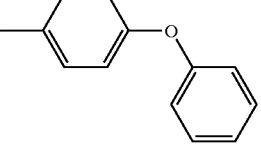 | 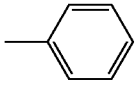 | 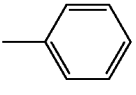 |
| IVB-31 | 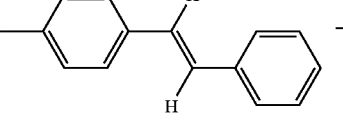 | 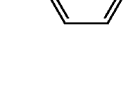 | 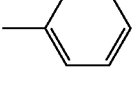 |
| IVB-32 | 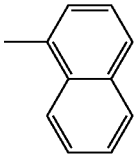 | 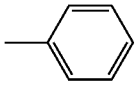 | 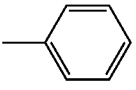 |
TABLE 39
| Compound No. | SUBSTITUENT | | |
|---|---|---|---|
| | Q10 | Q20 | Q30 |
| IVB-33 | 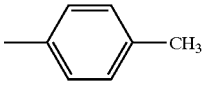 | 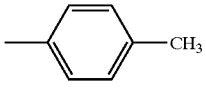 | 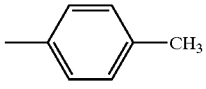 |
| IVB-34 | 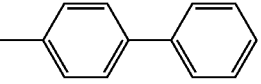 | 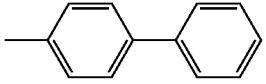 | 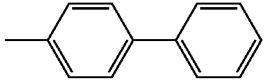 |
| IVB-35 | 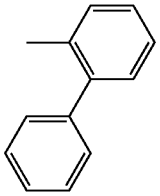 | 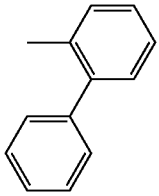 | 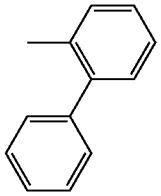 |
| IVB-36 | 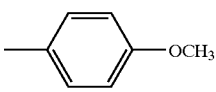 | 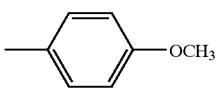 | 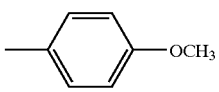 |

TABLE 39-continued
| | | | | | |
|---|---|---|---|---|---|
| IVB-37 | 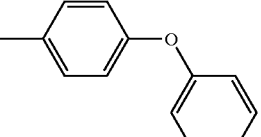 | | 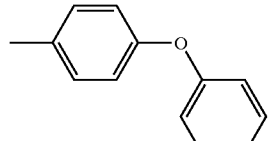 | | 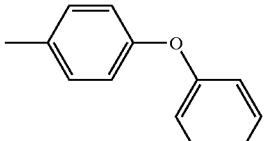 |
| IVB-38 | 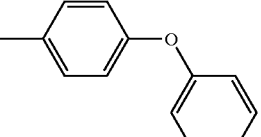 | | 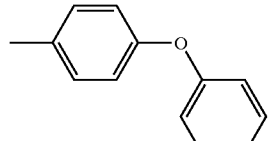 | | 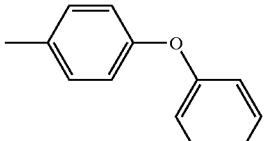 |
| IVB-39 | 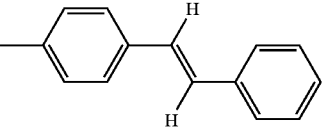 | | 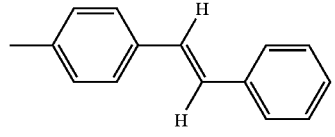 | | 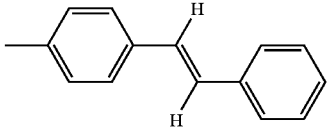 |
| IVB-40 | 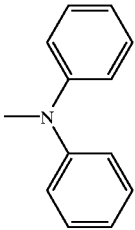 | | 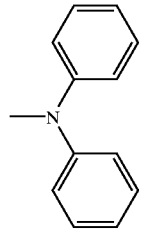 | | 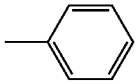 |
| IVB-41 | 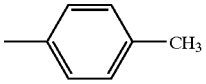 | |  | | 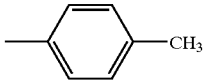 |
| IVB-42 | 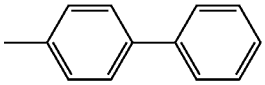 | | 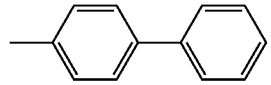 | | 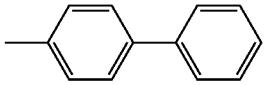 |
| IVB-43 | 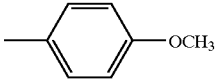 | | 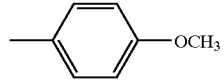 | | 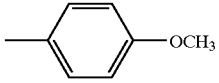 |
| IVB-44 | 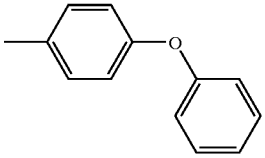 | | 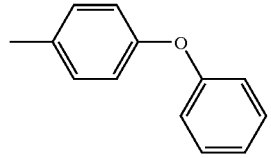 | | 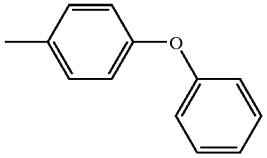 |
| IVB-45 | 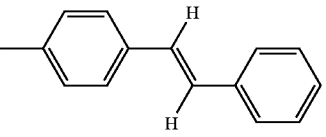 | | 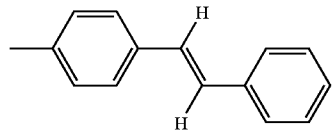 | | 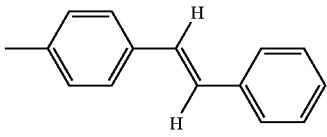 |
SUBSTITUENT
| Compound No. | $Q^{40}$ | $Q^{50}$ | $Q^{60}$ | $Q^{70}$ | $Q^{80}$ |
|---|---|---|---|---|---|
| IVB-33 | 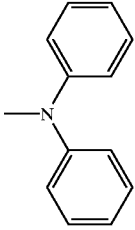 | 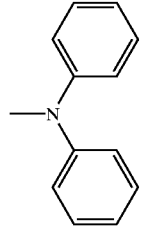 | 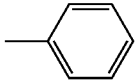 | 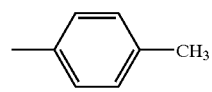 | 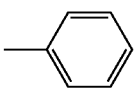 |

TABLE 39-continued
| | | | | | |
|---|---|---|---|---|---|
| IVB-34 | 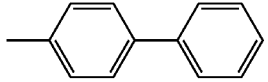 | 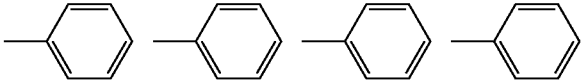 | | | |
| IVB-35 | 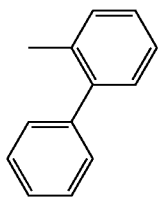 | 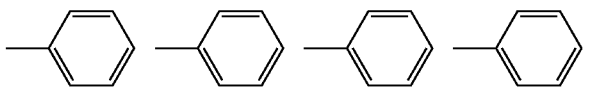 | | | |
| IVB-36 | 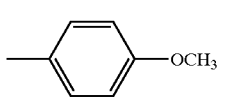 |  | | | |
| IVB-37 |  |  | | | |
| IVB-38 |  |  | | | |
| IVB-39 |  |  | | | |
| IVB-40 |  |  | | H | H |
| IVB-41 | 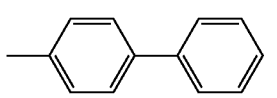 | 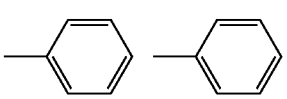 | | H | H |
| IVB-42 | 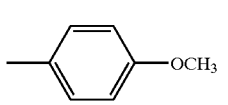 | 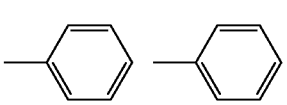 | | H | H |
| IVB-43 | 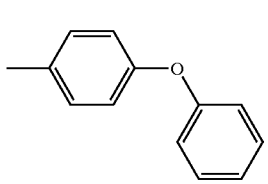 | 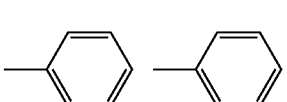 | | H | H |
| IVB-44 | 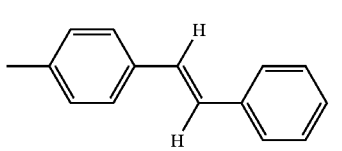 | 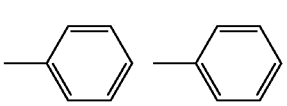 | | H | H |
| IVB-45 | 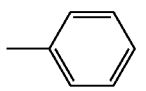 | 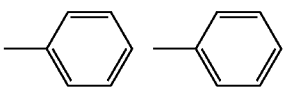 | | H | H |

TABLE 40
| Compound No. | Q¹⁰ | Q²⁰ | Q³⁰ |
|---|---|---|---|
| IVB-46 | 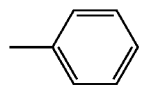 | 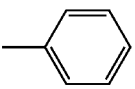 | 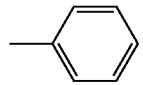 |
| IVB-47 | 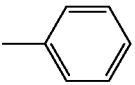 | 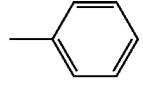 | 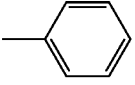 |
| IVB-48 | 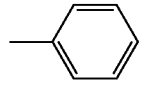 | 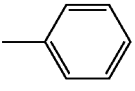 | 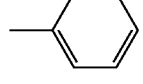 |
| IVB-48 | 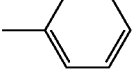 | 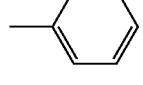 | 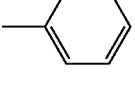 |
| IVB-49 | 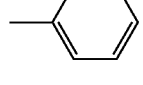 | 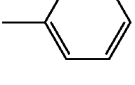 | 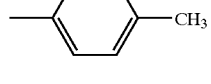 |
| IVB-50 | 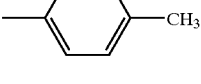 | 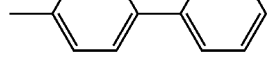 | 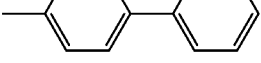 |
| IVB-51 | 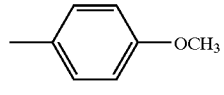 | 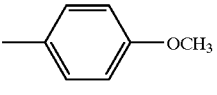 | 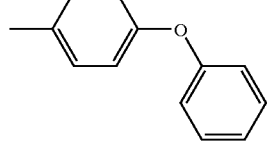 |
| IVB-52 | 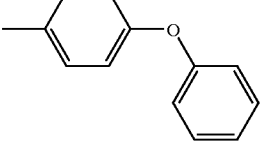 | 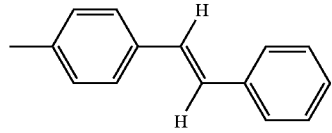 | 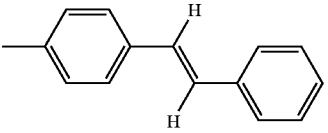 |
| IVB-53 | | | |
| IVB-54 | | | |
| IVB-55 | | | |
| IVB-56 | | | |

TABLE 40-continued
| Compound No. | | | |
|---|---|---|---|
| IVB-57 | 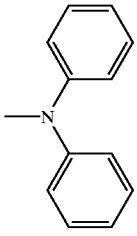 | 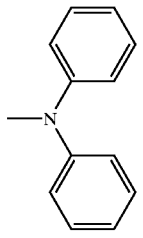 | 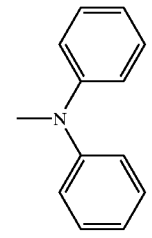 |
| IVB-58 | 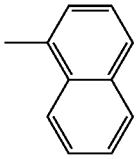 | 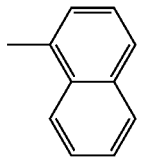 | 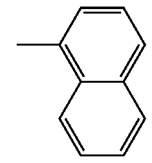 |
| | SUBSTITUENT | | |
|---|---|---|---|
| Compound No. | $Q^{40}$ | $Q^{50}$ | $Q^{60}$ |
| IVB-46 | 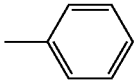 | 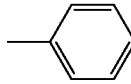 | 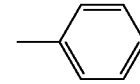 |
| IVB-47 | 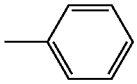 | 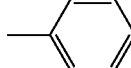 | 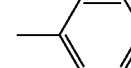 |
| IVB-48 | 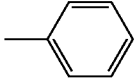 | 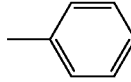 | 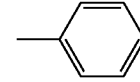 |
| IVB-49 | 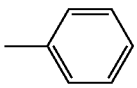 | 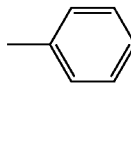 | 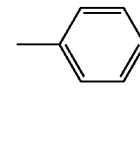 |
| IVB-50 | 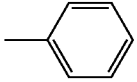 | 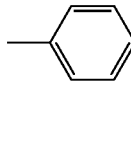 | 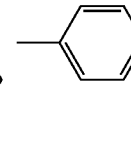 |
| IVB-51 | 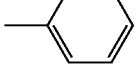 | 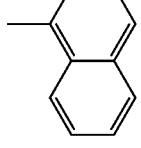 | 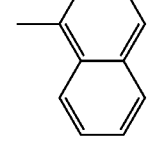 |
| IVB-52 | 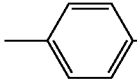 | $CH_3$ | $CH_3$ |
| IVB-53 | 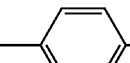 | $CH_3$ | $CH_3$ |
| IVB-54 | 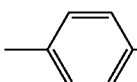 | $CH_3$ | $CH_3$ |

TABLE 40-continued
| | | | |
|---|---|---|---|
| IVB-55 | 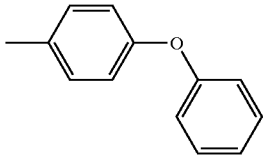 | $CH_3$ | $CH_3$ |
| IVB-56 | 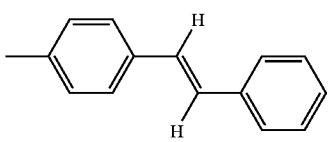 | $CH_3$ | $CH_3$ |
| IVB-57 | 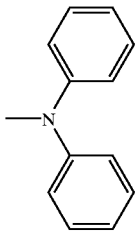 | $CH_3$ | $CH_3$ |
| IVB-58 | 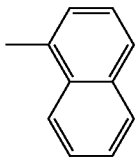 | $CH_3$ | $CH_3$ |
| | SUBSTITUENT | |
|---|---|---|
| Compound No. | $Q^{70}$ | $Q^{80}$ |
| IVB-46 | H | H |
| IVB-47 | H | H |
| IVB-48 | H | H |
| IVB-49 | H | H |
| IVB-50 | H | H |
| IVB-51 | H | H |
| IVB-52 | H | H |
| IVB-53 | H | H |
| IVB-54 | H | H |
| IVB-55 | H | H |
| IVB-56 | H | H |
| IVB-57 | H | H |
| IVB-58 | H | H |

TABLE 41
| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-59 |  |  |  |  | $CH_3$ | $CH_3$ | H | H |
| IVB-60 |  |  |  |  | $CH_3$ | $CH_3$ | H | H |
| IVB-61 |  |  |  |  | $CH_3$ | $CH_3$ | H | H |
| IVB-62 |  |  |  |  | $CH_3$ | $CH_3$ | H | H |
| IVB-63 |  |  |  |  | $CH_3$ | $CH_3$ | H | H |
| IVB-64 |  |  |  |  | $CH_3$ | $CH_3$ | H | H |

TABLE 41-continued
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-65 | 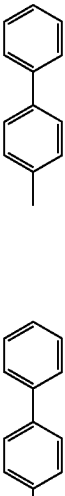 | 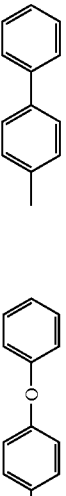 |  |  | CH$_3$ | CH$_3$ | H | H |
| IVB-66 |  |  |  |  | CH$_3$ | CH$_3$ | H | H |
| IVB-67 |  |  |  | 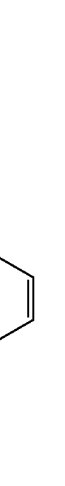 | CH$_3$ | CH$_3$ | H | H |
| IVB-68 |  |  |  |  | CH$_3$ | CH$_3$ | H | H |
| IVB-69 |  |  |  | 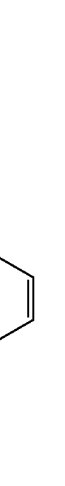 | CH$_3$ | CH$_3$ | H | H |

TABLE 42
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IVB-70 |  | 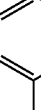 | 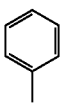 |  | CH₃ | CH₃ | H | H |
| IVB-71 |  |  | 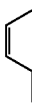 |  | CH₃ | CH₃ | H | H |
| IVB-72 |  |  | 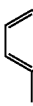 |  | CH₃ | CH₃ | H | H |
| IVB-73 |  | 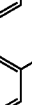 | 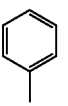 |  | CH₃ | CH₃ | H | H |
| IVB-74 |  |  |  |  | CH₃ | CH₃ | H | H |

TABLE 42-continued

| Compound No. | SUBSTITUENT | | | | | | |
|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-75 | biphenyl | terphenyl | terphenyl | biphenyl | $CH_3$ | $CH_3$ | H | H |
| IVB-76 | terphenyl | terphenyl | terphenyl | terphenyl | $CH_3$ | $CH_3$ | H | H |
| IVB-77 | terphenyl | terphenyl | terphenyl | terphenyl | $CH_3$ | $CH_3$ | H | H |
| IVB-78 | phenyl | stilbene | stilbene | phenyl | $CH_3$ | $CH_3$ | H | H |
| IVB-79 | phenyl | tolyl-stilbene | tolyl-stilbene | phenyl | $CH_3$ | $CH_3$ | H | H |

TABLE 43
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IVB-80 |  | 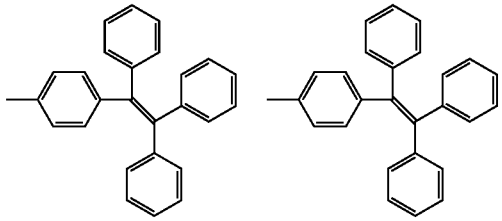 |  | 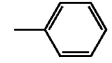 | CH₃ | CH₃ | H | H |
| IVB-81 | 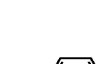 |  |  |  | CH₃ | CH₃ | H | H |
| IVB-82 | 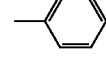 | 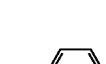 |  | 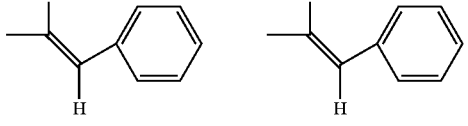 | CH₃ | CH₃ | H | H |
| IVB-83 |  | 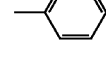 | 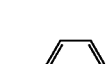 |  | CH₃ | CH₃ | H | H |
| IVB-84 | 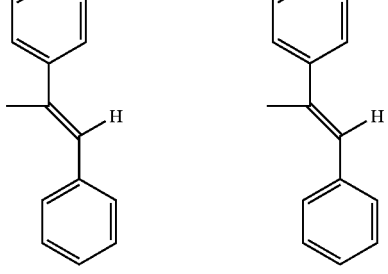 |  | 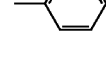 | 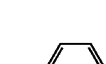 | CH₃ | CH₃ | CH₃ | CH₃ |
| IVB-85 |  | 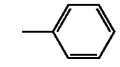 |  | 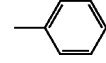 | CH₃ | CH₃ | CH₃ | CH₃ |
| IVB-86 | 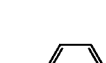 |  | 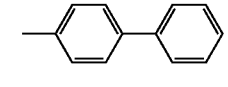 | 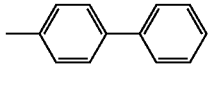 | CH₃ | CH₃ | CH₃ | CH₃ |
| IVB-87 | 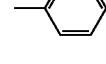 | 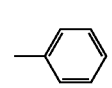 |  | 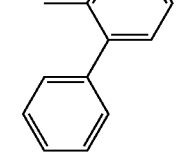 | CH₃ | CH₃ | CH₃ | CH₃ |

TABLE 44

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-88 | phenyl | 2-naphthyl | 2-naphthyl | phenyl | $CH_3$ | $CH_3$ | $CH_3$ | $CH_3$ |
| IVB-89 | phenyl | 1-naphthyl | 1-naphthyl | phenyl | $CH_3$ | $CH_3$ | $CH_3$ | $CH_3$ |
| IVB-90 | phenyl | 2-anthryl | 2-anthryl | phenyl | $CH_3$ | $CH_3$ | $CH_3$ | $CH_3$ |
| IVB-91 | biphenyl | phenyl | phenyl | biphenyl | $CH_3$ | $CH_3$ | $CH_3$ | $CH_3$ |
| IVB-92 | biphenyl | biphenyl | biphenyl | biphenyl | $CH_3$ | $CH_3$ | $CH_3$ | $CH_3$ |
| IVB-93 | biphenyl | 4-phenoxyphenyl | 4-phenoxyphenyl | biphenyl | $CH_3$ | $CH_3$ | $CH_3$ | $CH_3$ |

TABLE 44-continued

SUBSTITUENT

| Compound No. | Q$^{10}$ | Q$^{20}$ | Q$^{30}$ | Q$^{40}$ | Q$^{50}$ | Q$^{60}$ | Q$^{70}$ | Q$^{80}$ |
|---|---|---|---|---|---|---|---|---|
| IVB-94 | biphenyl | anthracenyl | anthracenyl | biphenyl | CH$_3$ | CH$_3$ | CH$_3$ | CH$_3$ |
| IVB-95 | biphenyl | 2-naphthyl | 2-naphthyl | biphenyl | CH$_3$ | CH$_3$ | CH$_3$ | CH$_3$ |
| IVB-96 | biphenyl | 1-naphthyl | 1-naphthyl | biphenyl | CH$_3$ | CH$_3$ | CH$_3$ | CH$_3$ |
| IVB-97 | phenyl | 4-(N,N-dimethylamino)phenyl | 4-(N,N-dimethylamino)phenyl | phenyl | CH$_3$ | CH$_3$ | CH$_3$ | CH$_3$ |
| IVB-98 | phenyl | 4-(N,N-diphenylamino)phenyl | 4-(N,N-diphenylamino)phenyl | phenyl | CH$_3$ | CH$_3$ | CH$_3$ | CH$_3$ |

TABLE 45

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-99 | phenyl | biphenyl | biphenyl | phenyl | CH₃ | CH₃ | CH₃ | CH₃ |
| IVB-100 | phenyl | biphenyl (o-methyl) | biphenyl (o-methyl) | phenyl | CH₃ | CH₃ | CH₃ | CH₃ |
| IVB-101 | biphenyl | terphenyl | terphenyl | biphenyl | CH₃ | CH₃ | CH₃ | CH₃ |
| IVB-102 | biphenyl | terphenyl (o-methyl) | terphenyl (o-methyl) | biphenyl | CH₃ | CH₃ | CH₃ | CH₃ |
| IVB-103 | terphenyl | tetraphenyl | tetraphenyl | terphenyl | CH₃ | CH₃ | CH₃ | CH₃ |
| IVB-104 | terphenyl | tetraphenyl (o-methyl) | tetraphenyl (o-methyl) | terphenyl | CH₃ | CH₃ | CH₃ | CH₃ |

TABLE 45-continued
| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-105 |  |  |  |  | $CH_3$ | $CH_3$ | $CH_3$ | $CH_3$ |
| IVB-106 |  |  | 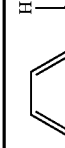 |  | $CH_3$ | $CH_3$ | $CH_3$ | $CH_3$ |
| IVB-107 | 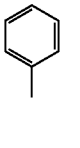 |  | 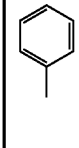 | 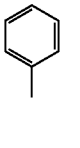 | $CH_3$ | $CH_3$ | $CH_3$ | $CH_3$ |
| IVB-108 | 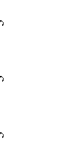 |  | 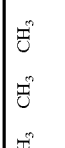 | 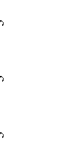 | $CH_3$ | $CH_3$ | $CH_3$ | $CH_3$ |

TABLE 46
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IVB-109 | 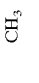 |  |  |  | $CH_3$ | $CH_3$ | $CH_3$ | $CH_3$ |
| IVB-110 |  |  |  |  | $CH_3$ | $CH_3$ | $CH_3$ | $CH_3$ |
| IVB-111 |  |  |  | | $CH_3$ | $CH_3$ | $CH_3$ | $CH_3$ |
| IVB-112 |  |  |  |  | $CH_3$ | $CH_3$ | $CH_3$ | $CH_3$ |

TABLE 46-continued
| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-113 | 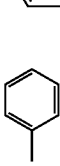 |  | 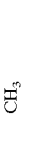 | 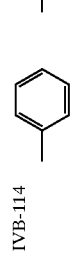 | CH$_3$ | CH$_3$ | CH$_3$ | CH$_3$ |
| IVB-114 |  | 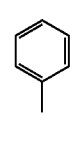 | 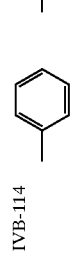 | 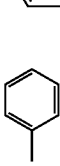 |  | 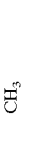 | 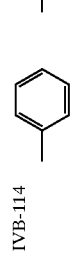 |  |
| IVB-115 | 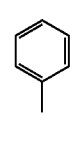 | 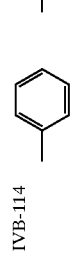 | 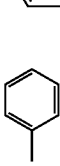 |  | 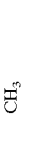 | 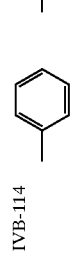 |  | 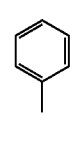 |
| IVB-116 | 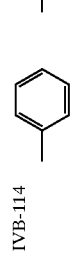 | 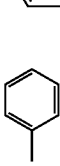 |  | 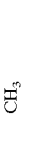 | 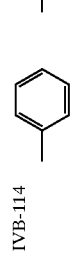 |  | 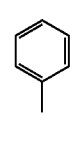 | 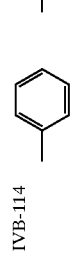 |

TABLE 47
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IVB-117 | 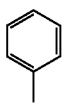 |  |  | 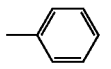 | 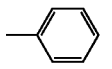 |  |  |  |
| IVB-118 |  |  |  |  |  |  |  |  |
| IVB-119 |  |  |  |  | | | | |
| IVB-120 | | | | | | | | |

TABLE 47-continued

SUBSTITUENT

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-121 | biphenyl | phenoxyphenyl | phenoxyphenyl | biphenyl | biphenyl | phenyl | phenyl | phenyl |
| IVB-122 | biphenyl | anthracenyl | anthracenyl | biphenyl | biphenyl | phenyl | phenyl | phenyl |
| IVB-123 | biphenyl | naphthyl | naphthyl | biphenyl | biphenyl | phenyl | phenyl | phenyl |
| IVB-124 | biphenyl | naphthyl | naphthyl | biphenyl | biphenyl | phenyl | phenyl | phenyl |
| IVB-125 | phenyl | 4-(N,N-dimethylamino)phenyl | 4-(N,N-dimethylamino)phenyl | phenyl | phenyl | phenyl | phenyl | phenyl |

TABLE 48

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-126 | phenyl | N(phenyl)(p-tolyl)(phenyl) | N(phenyl)(p-tolyl)(phenyl) | phenyl | | | | phenyl |
| IVB-127 | phenyl | quinquephenyl (o-tolyl-terminated) | quinquephenyl | phenyl | phenyl | phenyl | phenyl | phenyl |
| IVB-128 | phenyl | quaterphenyl (o-tolyl-terminated) | terphenyl (o-tolyl-terminated) | phenyl | phenyl | phenyl | phenyl | phenyl |
| IVB-129 | biphenyl | quinquephenyl | quinquephenyl | biphenyl | phenyl | phenyl | phenyl | phenyl |
| IVB-130 | biphenyl | m-terphenyl-biphenyl | m-terphenyl-biphenyl | biphenyl | phenyl | phenyl | phenyl | phenyl |

TABLE 48-continued
| Compound No. | Substituent $Q^{10}, Q^{20}, Q^{30}, Q^{40}, Q^{50}, Q^{60}, Q^{70}, Q^{80}$ |
|---|---|
| IVB-131 | 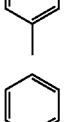 |
| IVB-132 |  |
| IVB-133 |  |
| IVB-134 |  |

TABLE 49
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-135 | | | | | | | | |
| IVB-136 | | | | | | | | |
| IVB-137 | | | | | | | | |
| IVB-138 | | | | | | | | |

TABLE 49-continued
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-139 |  |  |  |  |  |  |  |  |
| IVB-140 |  |  |  |  |  |  |  |  |
| IVB-141 |  |  |  |  |  |  |  |  |

TABLE 50
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-142 | 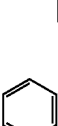 | 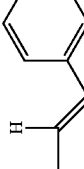 | 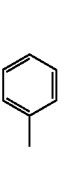 | 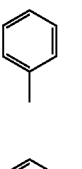 |  | 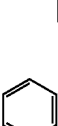 | 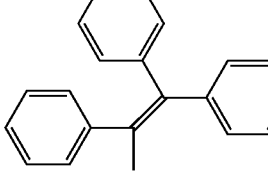 | 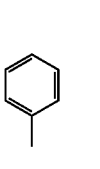 |
| IVB-143 | 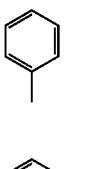 |  |  | 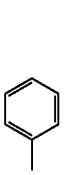 | 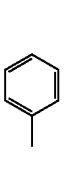 |  |  | 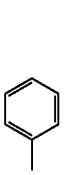 |
| IVB-144 | 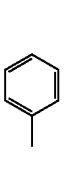 |  |  | 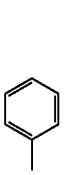 | 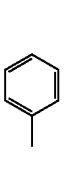 |  | H | H |
| IVB-145 | | | | | | | H | H |
| IVB-146 | | | | | | | H | H |

TABLE 50-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| IVB-147 | 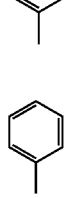 | 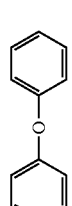 | 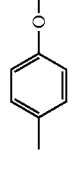 |  | 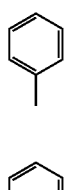 | 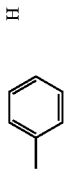 | H | H |
| IVB-148 | 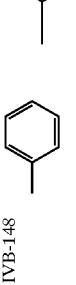 | 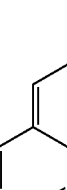 | 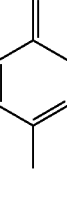 |  | 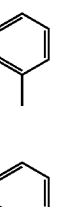 | 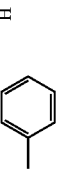 | H | H |
| IVB-149 | 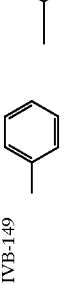 |  | 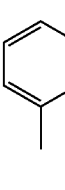 |  | 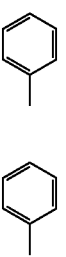 | 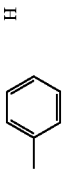 | H | H |
| IVB-150 | 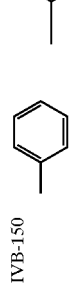 |  | 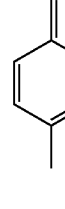 |  | 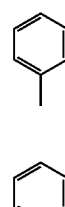 | 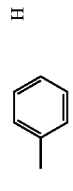 | H | H |

TABLE 51
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-151 |  |  |  |  |  |  | H | H |
| IVB-152 |  |  |  |  |  |  | H | H |
| IVB-153 |  |  |  |  |  |  | H | H |
| IVB-154 |  |  |  | | | | H | H |
| IVB-155 | | | | | | | H | H |
| IVB-156 | | | | | | | H | H |

TABLE 51-continued
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-157 |  |  |  |  |  |  | H | H |
| IVB-158 |  |  |  |  |  |  | H | H |
| IVB-159 |  |  |  |  |  |  | H | H |
| IVB-160 |  |  |  |  |  |  | H | H |
| IVB-161 |  |  |  |  |  |  | H | H |

TABLE 52

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-162 | biphenyl | biphenyl | biphenyl | biphenyl | phenyl | phenyl | H | H |
| IVB-163 | biphenyl | biphenyl | biphenyl | biphenyl | phenyl | phenyl | H | H |
| IVB-164 | biphenyl | biphenyl | biphenyl | biphenyl | phenyl | phenyl | H | H |
| IVB-165 | phenyl | styryl | styryl | phenyl | phenyl | phenyl | H | H |
| IVB-166 | phenyl | stilbenyl | stilbenyl | phenyl | phenyl | phenyl | H | H |

TABLE 52-continued
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-167 | 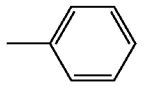 |  | |  |  |  | H | H |
| IVB-168 |  |  | |  |  |  | H | H |
| IVB-169 |  |  | | 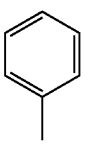 |  |  | H | H |

TABLE 53

| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-170 | Ph | CH₃C(Ph)=CH | CH₃C(Ph)=CH | Ph | Ph | Ph | H | H |
| IVB-171 | Ph | PhC(CH₃)=CHPh | PhC(CH₃)=CHPh | Ph | Ph | Ph | H | H |
| IVB-172 | Ph | CH₃C(=CPh₂)H | CH₃C(=CPh₂)H | Ph | Ph | Ph | H | H |

TABLE 53-continued

SUBSTITUENT

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-173 | phenyl | 1,2,2-triphenylpropenyl | 1,2,2-triphenylpropenyl | phenyl | phenyl | phenyl | H | H |
| IVB-174 | phenyl | phenyl | phenyl | phenyl | 1-propenyl | 1-propenyl | H | H |
| IVB-175 | phenyl | biphenyl | biphenyl | phenyl | 1-propenyl | 1-propenyl | H | H |

TABLE 54
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-176 | 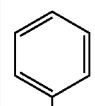 | 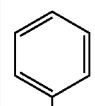 | 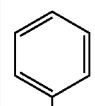 | 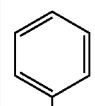 |  |  | H | H |
| IVB-177 | 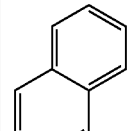 | 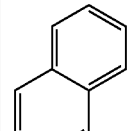 | 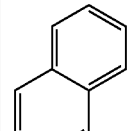 | 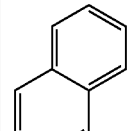 |  |  | H | H |
| IVB-178 | 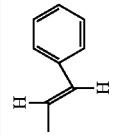 | 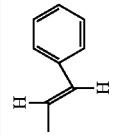 | 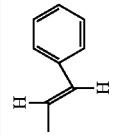 | 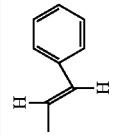 | 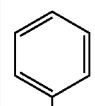 |  | H | H |
| IVB-179 |  |  |  |  | 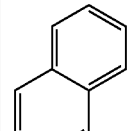 |  | H | H |
| IVB-180 |  |  |  |  | 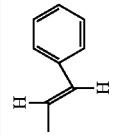 | 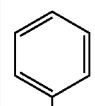 | H | H |
| IVB-181 |  |  |  |  |  | 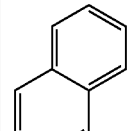 | H | H |

TABLE 54-continued
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-182 | 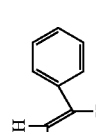 | 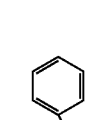 | | 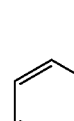 |  |  | H | H |
| IVB-183 |  |  | |  |  |  | H | H |
| IVB-184 | 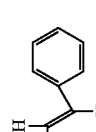 | 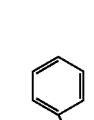 | | 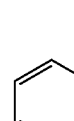 | 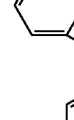 | 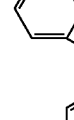 | H | H |
| IVB-185 | 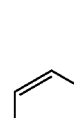 |  | | 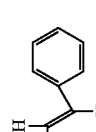 | 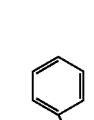 | 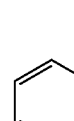 | H | H |

TABLE 55

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| IVB-186 | Ph | Ph-CH=CH- | Ph-CH=CH- | Ph | Ph-CH=CH(Me)- | Ph-CH=CH(Me)- | H | H |
| IVB-187 | Ph | (4-Me-Ph)-CH=CH- | (4-Me-Ph)-CH=CH- | Ph | Ph-CH=CH(Me)- | Ph-CH=CH(Me)- | H | H |
| IVB-188 | Ph | Me-CH=CH- | Me-CH=CH- | Ph | Ph-CH=CH(Me)- | Ph-CH=CH(Me)- | H | H |
| IVB-189 | Ph | Ph-CH=CH(Me)- | Ph-CH=CH(Me)- | Ph | Ph-CH=CH(Me)- | Ph-CH=CH(Me)- | H | H |
| IVB-190 | Ph | Ph | Ph | Ph | Ph-CH=CH(Me)- | Ph-CH=CH(Me)- | Ph-CH=CH(Me)- | Ph-CH=CH(Me)- |

TABLE 55-continued
| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-191 | 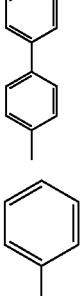 | 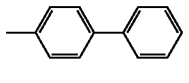 |  | 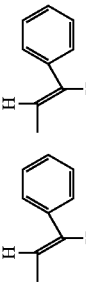 | 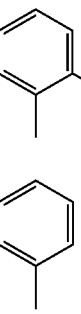 | 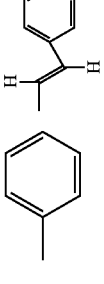 |  |  |
| IVB-192 | 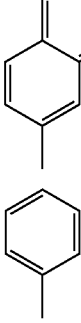 | 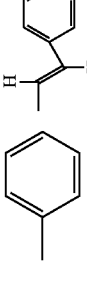 | 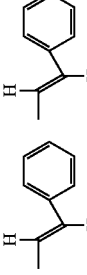 | 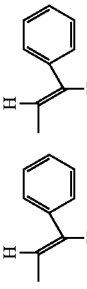 | | | | |
| IVB-193 | 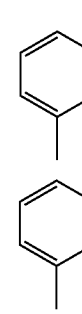 | 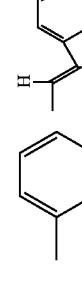 | 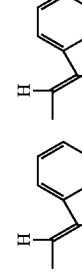 | 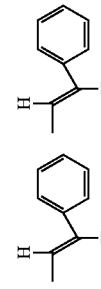 | | | | |
| IVB-194 | | | | | | | | |

TABLE 56
| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-195 | 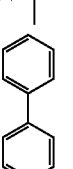 |  | 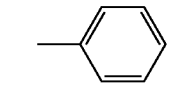 | 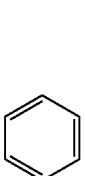 | 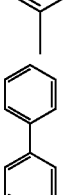 |  |  |  |
| IVB-196 |  |  |  |  |  |  |  |  |
| IVB-197 | 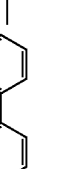 |  | 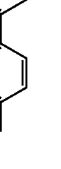 | 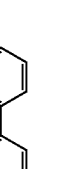 | 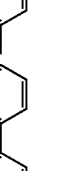 |  |  |  |
| IVB-198 | 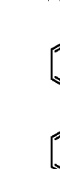 |  | 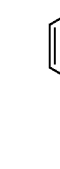 |  | 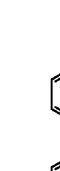 |  |  |  |
| IVB-199 | 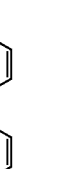 |  | 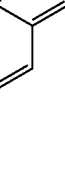 | 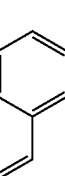 | 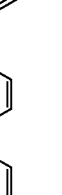 |  |  |  |

TABLE 56-continued
| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| IVB-200 |  |  |  |  |  |  |  |  |
| IVB-201 |  |  |  |  |  |  |  |  |
| IVB-202 |  |  |  | | | | | |
| IVB-203 | | | | | | | | |

TABLE 57

| Compound No. | Q10 | Q20 | Q30 | Q40 | Q50 | Q70 | Q70 | Q80 |
|---|---|---|---|---|---|---|---|---|
| IVB-204 | | | | | | | | |
| IVB-205 | | | | | | | | |
| IVB-206 | | | | | | | | |

TABLE 58
| Compound No. | SUBSTITUENT | | | | | | | |
|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| VB-1 | H | 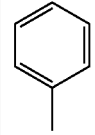 | 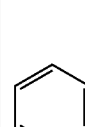 | H | H | H | H | H |
| VB-2 | H | 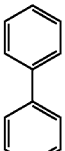 | 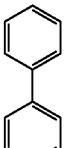 | H | H | H | H | H |
| VB-3 | H | 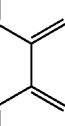 | 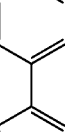 | H | H | H | H | H |
| VB-4 | H | 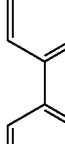 | 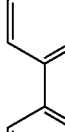 | H | H | H | H | H |
| VB-5 | H | 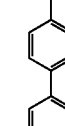 | 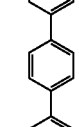 | H | H | H | H | H |
| VB-6 | H | 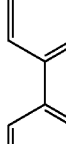 | 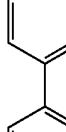 | H | H | H | H | H |

TABLE 58-continued

| Compound No. | SUBSTITUENT | | | | | | | | |
|---|---|---|---|---|---|---|---|---|---|
| | $Q^{10}$ | $Q^{20}$ | $Q^{30}$ | $Q^{40}$ | $Q^{50}$ | $Q^{60}$ | $Q^{70}$ | $Q^{80}$ |
| VB-7 | H | (2-methyl-[1,1':4',1''-terphenyl]) | (2-methyl-[1,1':4',1''-terphenyl]) | H | H | H | H | H |
| VB-8 | H | (2-methyl-5-phenyl-biphenyl) | (2-methyl-5-phenyl-biphenyl) | H | H | H | H | H |
| VB-9 | H | (4-methyl-2,2'-diphenyl-biphenyl) | (4-methyl-2,2'-diphenyl-biphenyl) | H | H | H | H | H |
| VB-10 | H | (2-methyl-4-phenyl-biphenyl with extra phenyl) | (2-methyl-4-phenyl-biphenyl with extra phenyl) | H | H | H | H | H |
| VB-11 | H | (2-methyl-1,1':3',1''-terphenyl) | (2-methyl-1,1':3',1''-terphenyl) | H | H | H | H | H |

TABLE 58-continued

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| VB-12 | H | [structure] | [structure] | H | H | H | H | H |
| VB-13 | H | [structure] | [structure] | H | H | H | H | H |
| VB-14 | H | [structure] | [structure] | H | H | H | H | H |

TABLE 59

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-15 | H | (2,3,6-triphenylphenyl-methyl) | (2,3,6-triphenylphenyl-methyl) | H | H | H | H | H |
| VB-16 | H | (2,3,5-triphenylphenyl-methyl) | (2,3,5-triphenylphenyl-methyl) | H | H | H | H | H |
| VB-17 | H | 4-(naphthalen-2-yl)phenyl-methyl | 4-(naphthalen-2-yl)phenyl-methyl | H | H | H | H | H |
| VB-18 | H | 3-(naphthalen-2-yl)phenyl-methyl | 3-(naphthalen-2-yl)phenyl-methyl | H | H | H | H | H |
| VB-19 | H | 2-(naphthalen-2-yl)phenyl-methyl | 2-(naphthalen-2-yl)phenyl-methyl | H | H | H | H | H |
| VB-20 | H | 4-(naphthalen-1-yl)phenyl-methyl | 4-(naphthalen-1-yl)phenyl-methyl | H | H | H | H | H |
| VB-21 | H | 3-(naphthalen-1-yl)phenyl-methyl | 3-(naphthalen-1-yl)phenyl-methyl | H | H | H | H | H |
| VB-22 | H | 2-(naphthalen-1-yl)phenyl-methyl | 2-(naphthalen-1-yl)phenyl-methyl | H | H | H | H | H |

TABLE 59-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-23 | H | 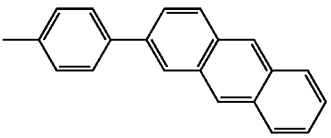 | 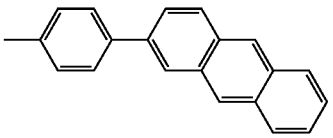 | H | H | H | H | H |
| VB-24 | H | 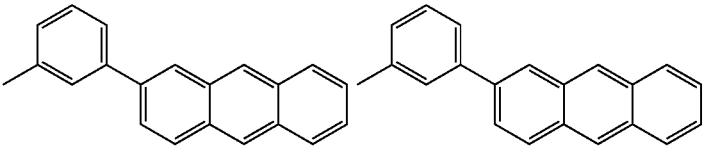 | 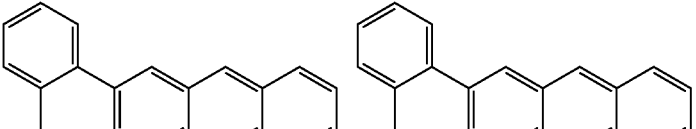 | H | H | H | H | H |
| VB-25 | H |  | 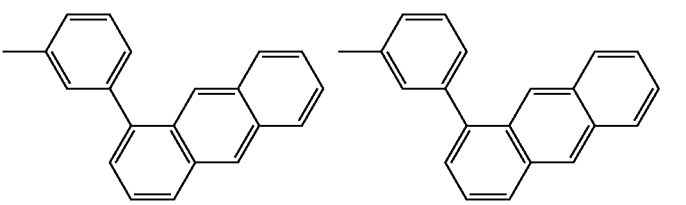 | H | H | H | H | H |
| VB-26 | H | 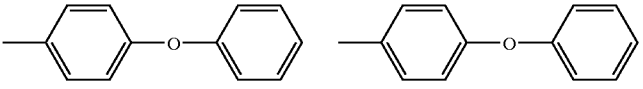 |  | H | H | H | H | H |
TABLE 60
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-27 | H | | | H | H | H | H | H |
| VB-28 | H | | | H | H | H | H | H |
| VB-29 | H | | | H | H | H | H | H |

TABLE 60-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-30 | H | 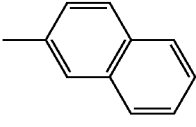 | 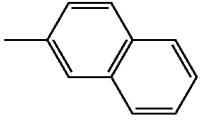 | H | H | H | H | H |
| VB-31 | H | 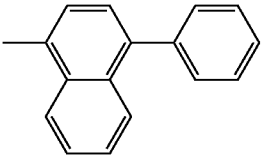 | 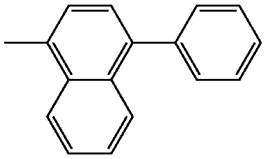 | H | H | H | H | H |
| VB-32 | H | 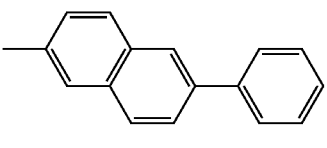 | 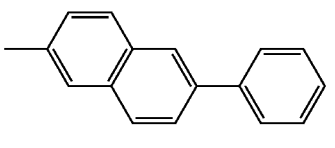 | H | H | H | H | H |
| VB-33 | H | 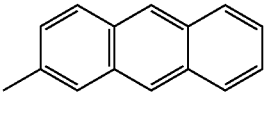 | 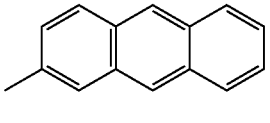 | H | H | H | H | H |
| VB-34 | H | 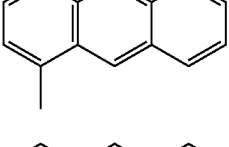 | 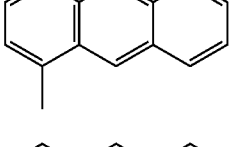 | H | H | H | H | H |
| VB-35 | H | 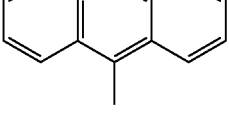 | 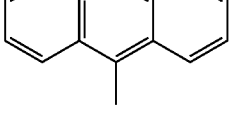 | H | H | H | H | H |
| VB-36 | H | 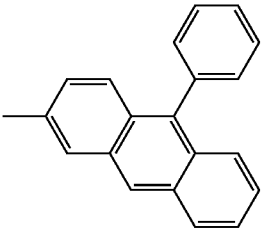 | 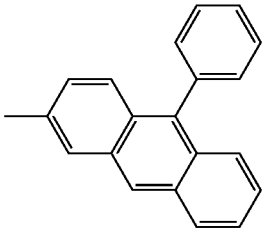 | H | H | H | H | H |
| VB-37 | H | 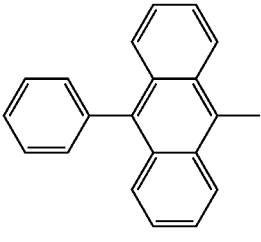 | 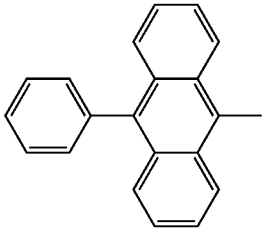 | H | H | H | H | H |
| VB-38 | H | 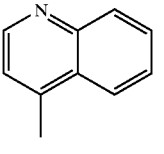 | 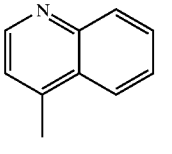 | H | H | H | H | H |

TABLE 60-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-39 | H | 5-methylquinolinyl | 5-methylquinolinyl | H | H | H | H | H |

TABLE 61

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-40 | H | methylquinoxalinyl | methylquinoxalinyl | H | H | H | H | H |
| VB-41 | H | methylquinazolinyl | methylquinazolinyl | H | H | H | H | H |
| VB-42 | H | methylphenazinyl | methylphenazinyl | H | H | H | H | H |
| VB-43 | H | methylacridinyl | methylacridinyl | H | H | H | H | H |
| VB-44 | H | methylacridinyl | methylacridinyl | H | H | H | H | H |
| VB-45 | H | methylphenazinyl | methylphenazinyl | H | H | H | H | H |
| VB-46 | H | methylphenazinyl | methylphenazinyl | H | H | H | H | H |
| VB-47 | H | methylcoumarinyl | methylcoumarinyl | H | H | H | H | H |

TABLE 61-continued

| Compound No. | Q$^{10}$ | Q$^{20}$ | Q$^{30}$ | Q$^{40}$ | Q$^{50}$ | Q$^{60}$ | Q$^{70}$ | Q$^{80}$ |
|---|---|---|---|---|---|---|---|---|
| VB-48 | H | 5-methylcoumarin-yl | 5-methylcoumarin-yl | H | H | H | H | H |
| VB-49 | H | bis(4-methylphenyl)(4-methylphenyl)amino | bis(4-methylphenyl)(4-methylphenyl)amino | H | H | H | H | H |
| VB-50 | H | 4-(dimethylamino)phenyl | 4-(dimethylamino)phenyl | H | H | H | H | H |
| VB-51 | H | 4-(diphenylamino)phenyl | 4-(diphenylamino)phenyl | H | H | H | H | H |

TABLE 62

| Compound No. | Q$^{10}$ | Q$^{20}$ | Q$^{30}$ | Q$^{40}$ | Q$^{50}$ | Q$^{60}$ | Q$^{70}$ | Q$^{80}$ |
|---|---|---|---|---|---|---|---|---|
| VB-52 | H | N-phenyl-N-(4-methylphenyl)amino-phenyl | N-phenyl-N-(4-methylphenyl)amino-phenyl | H | H | H | H | H |

TABLE 62-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-53 | H |  | 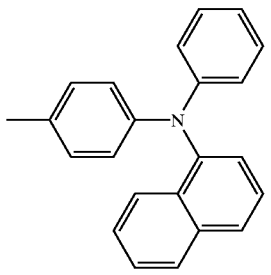 | H | H | H | H | H |
| VB-54 | H |  |  | H | H | H | H | H |
| VB-55 | H |  | 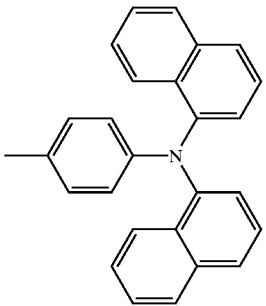 | H | H | H | H | H |
| VB-56 | H | 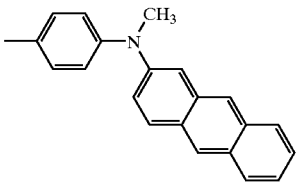 | 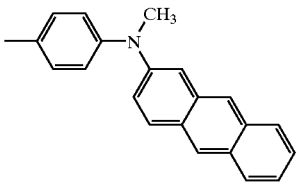 | H | H | H | H | H |
| VB-57 | H | 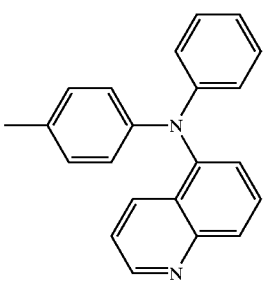 | 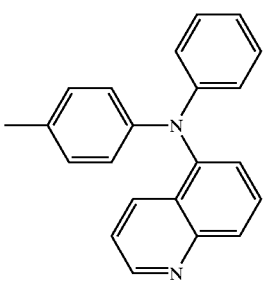 | H | H | H | H | H |

TABLE 62-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-58 | H | [N-(quinolin-5-yl)-N-(p-tolyl)-naphthalen-1-amine group] | [N-(quinolin-5-yl)-N-(p-tolyl)-naphthalen-1-amine group] | H | H | H | H | H |
| VB-59 | H | [(E)-4-styryl-phenyl group] | [(E)-4-styryl-phenyl group] | H | H | H | H | H |
| VB-60 | H | [(E)-4-(2,2-diphenylvinyl)phenyl group] | [(E)-4-(2,2-diphenylvinyl)phenyl group] | H | H | H | H | H |

TABLE 63

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-61 | H | [4-(1,2,2-triphenylvinyl)phenyl group] | [4-(1,2,2-triphenylvinyl)phenyl group] | H | H | H | H | H |
| VB-62 | H | [(E)-4-vinylphenyl group] | [(E)-4-vinylphenyl group] | H | H | H | H | H |
| VB-63 | H | [(1E,3E)-4-phenylbuta-1,3-dien-1-yl-phenyl group] | [(1E,3E)-4-phenylbuta-1,3-dien-1-yl-phenyl group] | H | H | H | H | H |

TABLE 63-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-64 | H | (structure) | (structure) | H | H | H | H | H |
| VB-65 | H | (structure) | (structure) | H | H | H | H | H |
| VB-66 | H | (structure) | (structure) | H | H | H | H | H |
| VB-67 | H | (structure) | (structure) | H | H | H | H | H |
| VB-68 | H | (structure) | (structure) | H | H | H | H | H |
| VB-69 | H | (structure) | (structure) | H | H | H | H | H |
| VB-70 | H | (structure) | (structure) | H | H | H | H | H |

TABLE 64

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-71 | H | (structure) | (structure) | H | Ph | Ph | Ph | Ph |

TABLE 64-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-72 | H | biphenyl | biphenyl | H | Ph | Ph | Ph | Ph |
| VB-73 | H | terphenyl | terphenyl | H | Ph | Ph | Ph | Ph |
| VB-74 | H | triphenylbenzene | triphenylbenzene | H | Ph | Ph | Ph | Ph |
| VB-75 | H | diphenyl(methyl)phenyl | diphenyl(methyl)phenyl | H | Ph | Ph | Ph | Ph |
| VB-76 | H | 2-methyl-1,3-diphenylphenyl | 2-methyl-1,3-diphenylphenyl | H | Ph | Ph | Ph | Ph |
| VB-77 | H | 4-(naphthalen-2-yl)phenyl | 4-(naphthalen-2-yl)phenyl | H | Ph | Ph | Ph | Ph |
| VB-78 | H | 4-(naphthalen-1-yl)phenyl | 4-(naphthalen-1-yl)phenyl | H | Ph | Ph | Ph | Ph |
| VB-79 | H | 4-(anthracen-2-yl)phenyl | 4-(anthracen-2-yl)phenyl | H | Ph | Ph | Ph | Ph |
| VB-80 | H | 4-(anthracen-9-yl)phenyl | 4-(anthracen-9-yl)phenyl | H | Ph | Ph | Ph | Ph |
| VB-81 | H | 4-phenoxyphenyl | 4-phenoxyphenyl | H | Ph | Ph | Ph | Ph |

TABLE 64-continued

SUBSTITUENT

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-82 | H | methylnaphthyl | methylnaphthyl | H | Ph | Ph | Ph | Ph |
| VB-83 | H | methyl(phenyl)naphthyl | methyl(phenyl)naphthyl | H | Ph | Ph | Ph | Ph |
| VB-84 | H | methylanthracenyl | methylanthracenyl | H | Ph | Ph | Ph | Ph |

TABLE 65

SUBSTITUENT

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-85 | H | methyl(phenyl)anthracenyl | methyl(phenyl)anthracenyl | H | Ph | Ph | Ph | Ph |
| VB-86 | H | methylquinolinyl | methylquinolinyl | H | Ph | Ph | Ph | Ph |
| VB-87 | H | methylquinoxalinyl | methylquinoxalinyl | H | Ph | Ph | Ph | Ph |
| VB-88 | H | methylphenazinyl | methylphenazinyl | H | Ph | Ph | Ph | Ph |
| VB-89 | H | methylacridinyl | methylacridinyl | H | Ph | Ph | Ph | Ph |

US 6,613,454 B2
TABLE 65-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-90 | H | 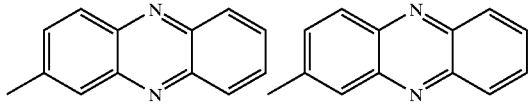 | 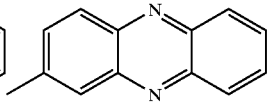 | H | Ph | Ph | Ph | Ph |
| VB-91 | H | 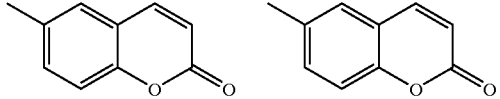 | 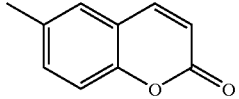 | H | Ph | Ph | Ph | Ph |
| VB-92 | | 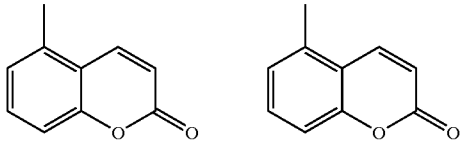 | 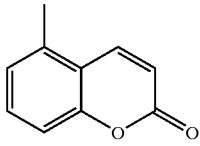 | H | Ph | Ph | Ph | Ph |
| VB-93 | H | 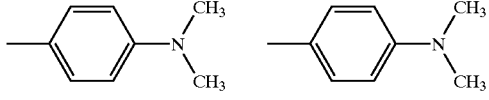 | 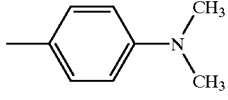 | H | Ph | Ph | Ph | Ph |
| VB-94 | H | 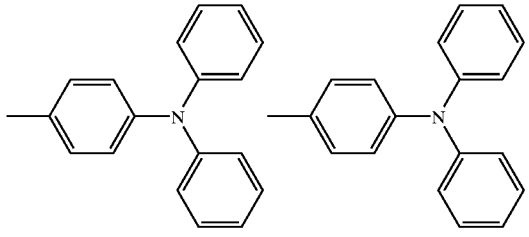 | 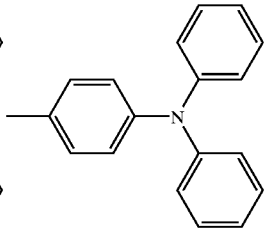 | H | Ph | Ph | Ph | Ph |
| VB-95 | H | 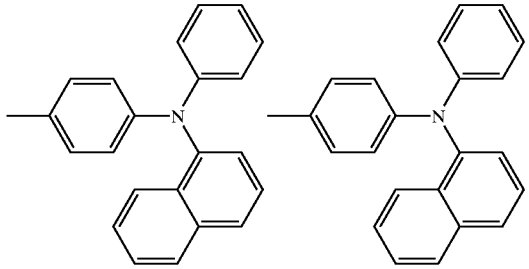 | 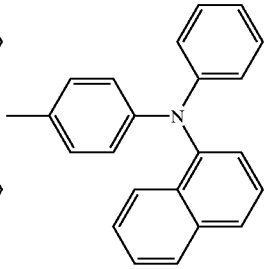 | H | Ph | Ph | Ph | Ph |
| VB-96 | H | 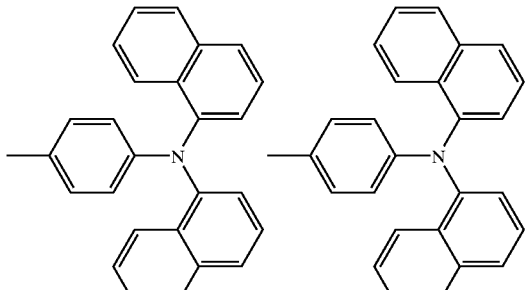 | 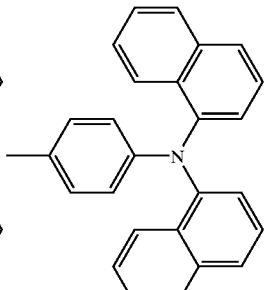 | H | Ph | Ph | Ph | Ph |

TABLE 66

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-97 | H | *p-tolyl-N(CH₃)-(2-anthracenyl)* | *p-tolyl-N(CH₃)-(2-anthracenyl)* | H | Ph | Ph | Ph | Ph |
| VB-98 | H | *p-tolyl-N(Ph)-(5-quinolinyl)* | *p-tolyl-N(Ph)-(5-quinolinyl)* | H | Ph | Ph | Ph | Ph |
| VB-99 | H | *p-tolyl-CH=CH-Ph* | *p-tolyl-CH=CH-Ph* | H | Ph | Ph | Ph | Ph |
| VB-100 | H | *p-tolyl-CH=CH₂* | *p-tolyl-CH=CH₂* | H | Ph | Ph | Ph | Ph |
| VB-101 | H | *p-tolyl-CH=CH-CH=CH-Ph* | *p-tolyl-CH=CH-CH=CH-Ph* | H | Ph | Ph | Ph | Ph |
| VB-102 | H | *p-tolyl-CH=CH-C₆H₄-CH=CH₂* | *p-tolyl-CH=CH-C₆H₄-CH=CH₂* | H | Ph | Ph | Ph | Ph |
| VB-103 | H | *CH₃-CH=CH₂* | *CH₃-CH=CH₂* | H | Ph | Ph | Ph | Ph |
| VB-104 | H | *CH₃-C(=CH-Ph)* | *CH₃-C(=CH-Ph)* | H | Ph | Ph | Ph | Ph |
| VB-105 | H | *CH₃-CH=CH-CH=CH-Ph* | *CH₃-CH=CH-CH=CH-Ph* | H | Ph | Ph | Ph | Ph |

TABLE 66-continued
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-106 | H | 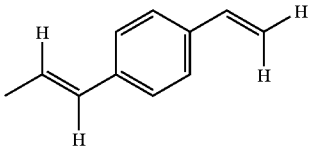 | 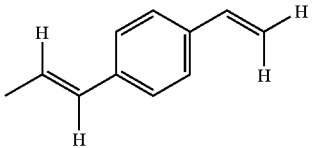 | H | Ph | Ph | Ph | Ph |
TABLE 67
| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-107 | H | 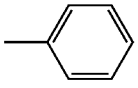 | 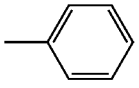 | H | Ph | Ph | H | H |
| VB-108 | H | 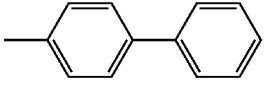 | 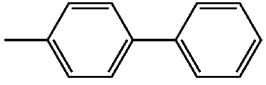 | H | Ph | Ph | H | H |
| VB-109 | H | 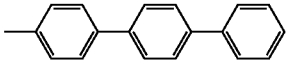 | 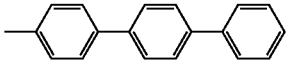 | H | Ph | Ph | H | H |
| VB-110 | H | 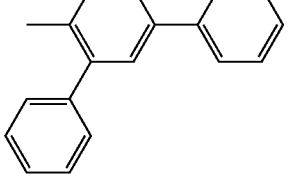 | 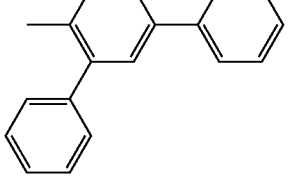 | H | Ph | Ph | H | H |
| VB-111 | H | 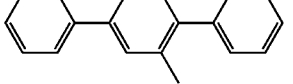 | 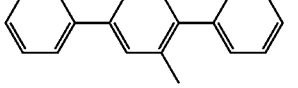 | H | Ph | Ph | H | H |
| VB-112 | H | 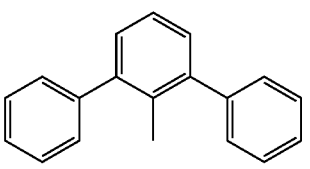 | 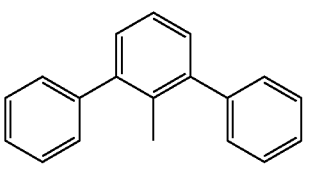 | H | Ph | Ph | H | H |
| VB-113 | H | 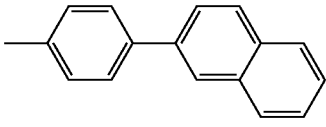 | 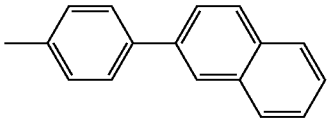 | H | Ph | Ph | H | H |
| VB-114 | H | 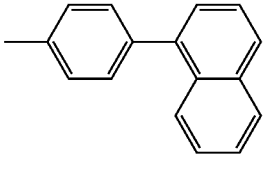 | 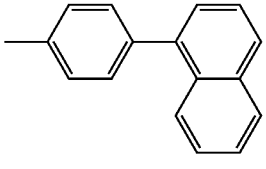 | H | Ph | Ph | H | H |

TABLE 67-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-115 | H | *4-(anthracen-2-yl)phenyl* | *4-(anthracen-2-yl)phenyl* | H | Ph | Ph | H | H |
| VB-116 | H | *4-(anthracen-9-yl)phenyl* | *4-(anthracen-9-yl)phenyl* | H | Ph | Ph | H | H |
| VB-117 | H | *4-phenoxyphenyl* | *4-phenoxyphenyl* | H | Ph | Ph | H | H |
| VB-118 | H | *naphthalen-1-yl* | *naphthalen-1-yl* | H | Ph | Ph | H | H |
| VB-119 | H | *4-phenylnaphthalen-1-yl* | *4-phenylnaphthalen-1-yl* | H | Ph | Ph | H | H |
| VB-120 | H | *anthracen-2-yl* | *anthracen-2-yl* | H | Ph | Ph | H | H |

TABLE 68

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-121 | H | *10-phenylanthracen-2-yl* | *10-phenylanthracen-2-yl* | H | Ph | Ph | H | H |
| VB-122 | H | *quinolin-5-yl* | *quinolin-5-yl* | H | Ph | Ph | H | H |

TABLE 68-continued
SUBSTITUENT
| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| VB-123 | H | 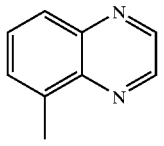 |  | H | Ph | Ph | H | H |
| VB-124 | H | 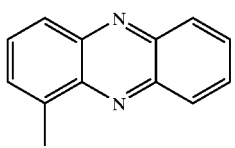 | 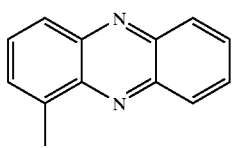 | H | Ph | Ph | H | H |
| VB-125 | H | 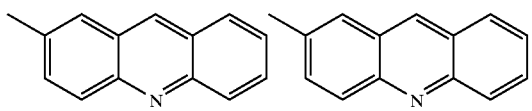 | 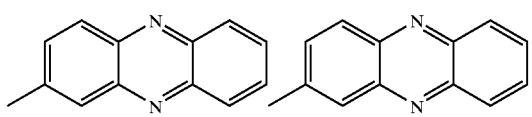 | H | Ph | Ph | H | H |
| VB-126 | H | 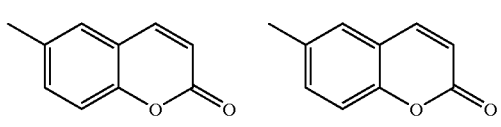 | 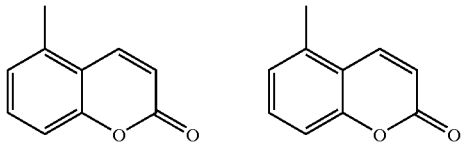 | H | Ph | Ph | H | H |
| VB-127 | H | 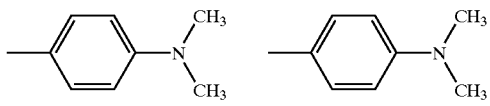 | 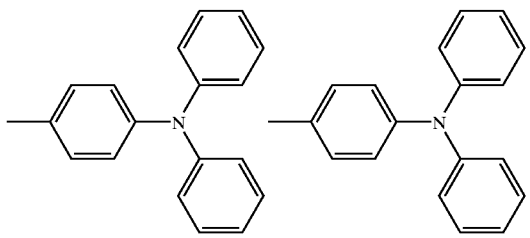 | H | Ph | Ph | H | H |
| VB-128 | H | 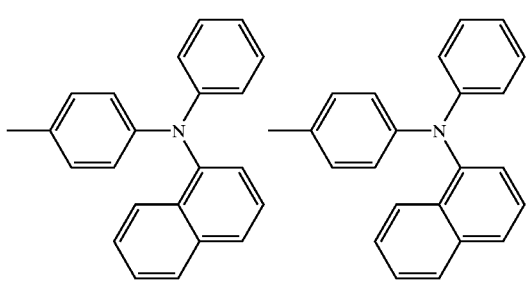 | | H | Ph | Ph | H | H |
| VB-129 | H | | | H | Ph | Ph | H | H |
| VB-130 | H | | | H | Ph | Ph | H | H |
| VB-131 | H | | | H | Ph | Ph | H | H |

TABLE 68-continued

SUBSTITUENT

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| VB-132 | H | *ditolyl-dinaphthylamino group* | *ditolyl-dinaphthylamino group* | H | Ph | Ph | H | H |

TABLE 69

SUBSTITUENT

| Compound No. | $Q^{10}$ | $Q^{20}$ | $Q^{30}$ | $Q^{40}$ | $Q^{50}$ | $Q^{60}$ | $Q^{70}$ | $Q^{80}$ |
|---|---|---|---|---|---|---|---|---|
| VB-133 | H | | *N-methyl-N-tolyl-aminoanthracenyl* | H | Ph | Ph | H | H |
| VB-134 | H | | *N-phenyl-N-tolyl-aminoquinolinyl* | H | Ph | Ph | H | H |
| VB-135 | H | | *trans-stilbenyl (tolyl)* | H | Ph | Ph | H | H |
| VB-136 | H | | *cis-stilbenyl (tolyl)* | H | Ph | Ph | H | H |
| VB-137 | H | | *tolyl-butadienyl-phenyl* | H | Ph | Ph | H | H |

TABLE 69-continued

| Compound No. | Q¹⁰ | Q²⁰ | Q³⁰ | Q⁴⁰ | Q⁵⁰ | Q⁶⁰ | Q⁷⁰ | Q⁸⁰ |
|---|---|---|---|---|---|---|---|---|
| VB-138 | H | (4-methylstyryl-styryl) | (4-methylstyryl-styryl) | H | Ph | Ph | H | H |
| VB-139 | H | (1-propenyl) | (1-propenyl) | H | Ph | Ph | H | H |
| VB-140 | H | (2-phenyl-1-propenyl) | (2-phenyl-1-propenyl) | H | Ph | Ph | H | H |
| VB-141 | H | (4-phenyl-1,3-butadienyl) | (4-phenyl-1,3-butadienyl) | H | Ph | Ph | H | H |
| VB-142 | H | (4-styryl-1-propenyl) | (4-styryl-1-propenyl) | H | Ph | Ph | H | H |

The naphthacene derivatives used herein can be synthesized, for example, using diphenyltetracene quinone and analogues. A typical synthesis scheme is shown below.

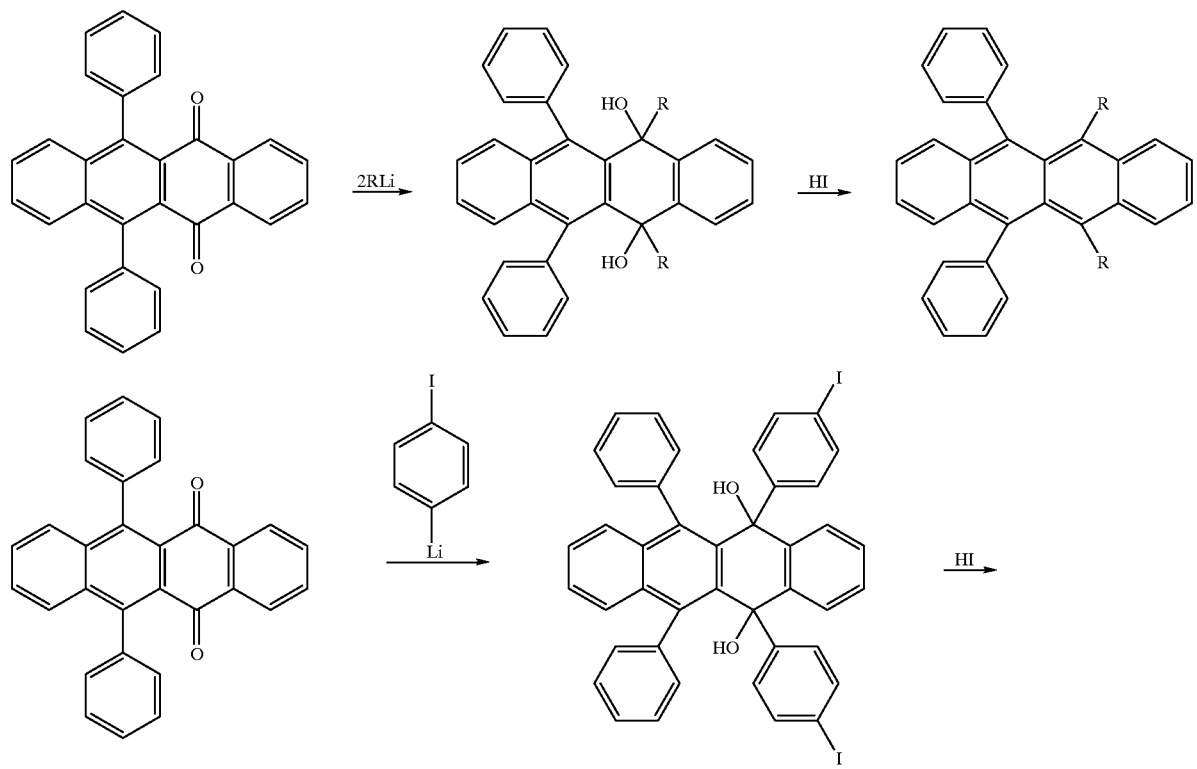

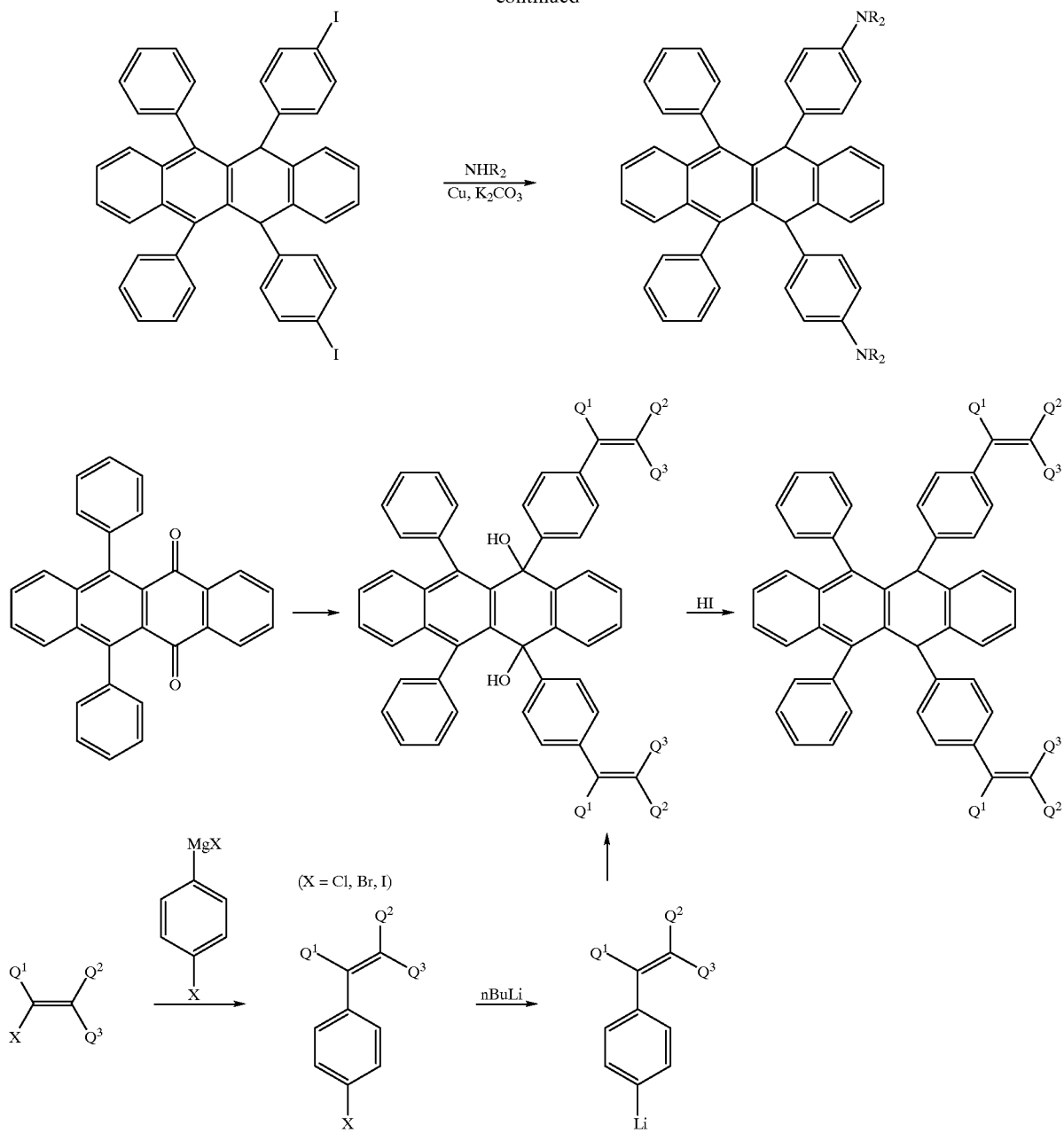

The naphthacene derivatives are used as the host material in combination with dopants.

Tetraaryldiamine Compounds

Another class of organic compounds useful as the host material according to the invention are tetraaryldiamine derivatives of the following formula (II).

In the device of the invention, the use of the tetraaryldiamine derivative, preferably as the host material, helps induce strong light emission from the dopant while controlling the interaction with the dopant.

In an exemplary organic EL device which was fabricated using a tetraaryldiamine derivative doped with a dibenzo[f,f']diindeno[1,2,3-cd:1',2',3'-lm]perylene derivative, a luminance of at least 300 cd/m² at maximum was obtained at a current density of 10 mA/cm² and a drive voltage as low as about 6.5 V. When operated at a current density of about 500 mA/cm², the device consistently produced a luminance of greater than about 15,000 cd/m². When operated at a current density of about 50 mA/cm², the device marked a very long lifetime as demonstrated by a half-life time of more than 300 hours at an initial luminance of at least 2400 cd/cm². Since the tetraaryldiamine derivative has hole transporting ability, a mixture thereof with another of the above-mentioned host materials enables to control carrier balance, resulting in a device with a high efficiency and long lifetime.

In organic EL devices as mentioned above, the dopant concentration ensuring a chromatic purity and maximum efficiency is about 1% by weight although dopant concentrations of about 2 or 3% by weight lead to devices which are practically acceptable albeit a drop of less than about 10%.

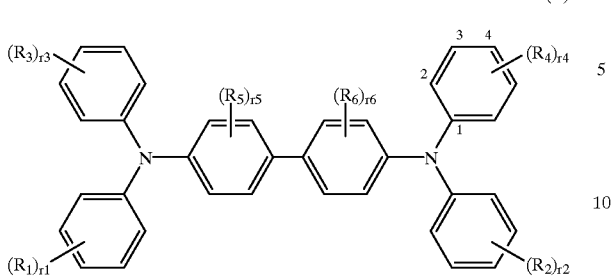

(II)

In formula (II), $R_1$ to $R_4$ are independently aryl, fluorene, carbazolyl, alkyl, alkoxy, aryloxy, amino or halogen radicals, at least one of $R_1$ to $R_4$ is aryl, and r1 to r4 each are 0 or an integer of 1 to 5, with the proviso that r1 to r4 are not 0 at the same time, that is, r1+r2+r3+r4 is an integer of at least 1. $R_5$ and $R_6$ are independently alkyl, alkoxy, amino or halogen radicals and may be the same or different, and r5 and r6 each are 0 or an integer of 1 to 4.

The aryl radicals represented by $R_1$ to $R_4$ may be monocyclic or polycyclic, inclusive of fused rings and a collection of rings. Those aryl radicals having 6 to 20 carbon atoms in total are preferred. They may have substituents, examples of which are alkyl, alkoxy, aryl, aryloxy, amino and halogen groups. Preferred examples of the aryl radical represented by $R_1$ to $R_4$ include phenyl, o-, m- and p-tolyl, pyrenyl, naphthyl, anthryl, biphenylyl, phenylanthryl and tolylanthryl. Of these, phenyl is most preferred. Preferably the aryl radical, especially phenyl is bonded at the 3- or 4-position.

The alkyl radicals represented by $R_1$ to $R_4$ may be straight or branched alkyl radicals, preferably of 1 to 10 carbon atoms. They may have substituents, examples of which are as illustrated for the aryl radicals. Preferred examples of the alkyl radical represented by $R_1$ to $R_4$ include methyl, ethyl, n- and i-propyl, n-, i-, sec- and tert-butyl.

The alkoxy radicals represented by $R_1$ to $R_4$ are preferably those having an alkyl moiety of 1 to 6 carbon atoms, for example, methoxy, ethoxy, and t-butoxy. The alkoxy radicals may have substituents.

Examples of the aryloxy radicals represented by $R_1$ to $R_4$ include phenoxy, 4-methylphenoxy, and 4-(t-butyl)phenoxy.

The amino radicals represented by $R_1$ to $R_4$ may be substituted or unsubstituted, with the substituted amino radicals being preferred. Illustrative examples include dimethylamino, diethylamino, diphenylamino, phenyltolylamino and bis(biphenyl)amino radicals.

Examples of the halogen atom represented by $R_1$ to $R_4$ are chlorine and bromine.

At least one of $R_1$ to $R_4$ is an aryl radical, and preferably at least two, more preferably at least three of $R_1$ to $R_4$ are aryl radicals. It is then preferred that at least two, more preferably at least three of r1 to r4 are integers of at least 1. Especially at least two, even more preferably at least three of r1 to r4 are equal to 1.

In formula (II), the alkyl, alkoxy, amino and halogen radicals represented by $R_5$ and $R_6$ are the same as illustrated for $R_1$ to $R_4$.

It is preferred that both r5 and r6 be 0, that is, the biphenylene radical connecting two arylamino radicals be an unsubstituted one.

When r1 to r4 are integers of at least 2, the $R_1$ groups, $R_2$ groups, $R_3$ groups and $R_4$ groups may be identical or different, respectively. When r5 and r6 are integers of at least 2, the $R_5$ groups and $R_6$ groups may be identical or different, respectively.

Of the compounds of formula (II), those compounds of the following formulas (II-1) and (II-2) are preferred.

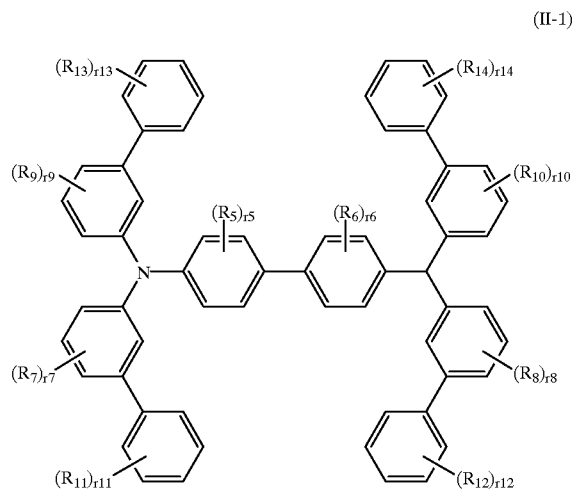

(II-1)

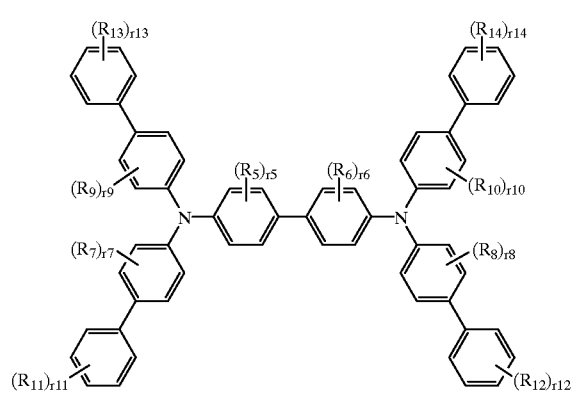

(II-2)

In formulas (II-1) and (II-2), $R_7$ to $R_{10}$ are independently alkyl, alkoxy, aryl, aryloxy, amino radicals or halogen atoms, and may be the same or different. Illustrative examples are the same as described for $R_1$ to $R_4$ in formula (II). Letters r7 to r10 are each 0 or an integer of 1 to 4. It is preferred that r7 to r10 be 0 in both formulas (II-1) and (II-2).

$R_{11}$ to $R_{14}$ are independently alkyl, alkoxy, aryl, aryloxy, amino radicals or halogen atoms, and may be the same or different. Illustrative examples are the same as described for $R_1$ to $R_4$ in formula (II). Letters r11 to r14 are each 0 or an integer of 1 to 5.

$R_5$, $R_6$, r5 and r6 in formulas (II-1) and (II-2) are as defined in formula (II). It is preferred that r5 and r6 be 0.

In formulas (II-1) and (II-2), when each of r7 to r10 is an integer of at least 2, the $R_7$ groups, $R_8$ groups, $R_9$ groups and $R_{10}$ groups may be the same or different, respectively; and when each of r11 to r14 is an integer of at least 2, the $R_{11}$ groups, $R_{12}$ groups, $R_{13}$ groups and $R_{14}$ groups may be the same or different, respectively.

Of the compounds of formula (II), those compounds of the following formula (II-3) are also preferred.

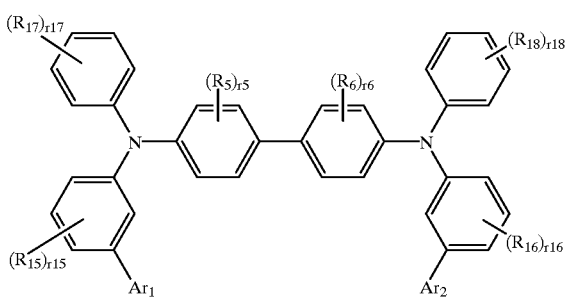

(II-3)

$R_5$, $R_6$, r5 and r6 in formula (II-3) are as defined in formula (II). It is preferred that r5 and r6 be 0.

$Ar_1$ and $Ar_2$ each are an aryl radical and may be the same or different. Illustrative examples of the aryl radical are as described for $R_1$ to $R_4$ in formula (II). Phenyl and biphenyl radicals are preferred among others.

$R_{15}$ and $R_{16}$ are independently alkyl, alkoxy, aryl, aryloxy, amino radicals or halogen atoms, and may be the same or different. Illustrative examples are the same as described for $R_1$ to $R_4$ in formula (II). Letters r15 and r16 are each 0 or an integer of 1 to 4. It is preferred that r15 and r16 be 0.

$R_{17}$ and $R_{18}$ are independently alkyl, alkoxy, aryloxy, amino radicals or halogen atoms, and may be the same or different. Illustrative examples are the same as described for $R_1$ to $R_4$ in formula (II). Letters r17 and r18 are each 0 or an integer of 1 to 5. It is preferred that r17 and r18 be 0.

In formula (II-3), when each of r15 and r16 is an integer of at least 2, the $R_{15}$ groups and $R_{16}$ groups may be the same or different, respectively; and when each of r17 and r18 is an integer of at least 2, the $R_{17}$ groups and $R_{18}$ groups may be the same or different, respectively.

Illustrative, non-limiting, examples of the compound of formula (II) are given below. It is noted that general formulas are followed by lists of R's to show illustrative examples by combinations of R's and optionally Ar's. As to a set of R's, when all R's in that set are hydrogen, H is assigned to that set. When a substituent is present as any of R's in a set, only the substituent is designated in the set, indicating that the remainders are hydrogen. $Ar_1$ and $Ar_2$ are individually shown.

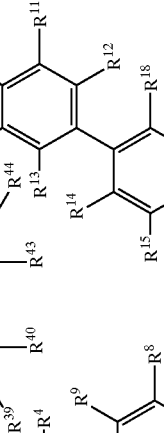

| Compound No. | $R^1 \sim R^4$ | $R^5 \sim R^9$ | $R^{10} \sim R^{13}$ | $R^{14} \sim R^{18}$ | $R^{19} \sim R^{22}$ | $R^{23} \sim R^{27}$ | $R^{28} \sim R^{31}$ | $R^{32} \sim R^{36}$ | $R^{37} \sim R^{44}$ |
|---|---|---|---|---|---|---|---|---|---|
| I-1 | H | H | H | H | H | H | H | H | H |
| I-2 | H | $R^6 = CH_3$ | H | $R^{17} = CH_3$ | H | $R^{26} = CH_3$ | H | $R^{35} = CH_3$ | H |
| I-3 | H | $R^7 = CH_3$ | H | $R^{16} = CH_3$ | H | $R^{25} = CH_3$ | H | $R^{34} = CH_3$ | H |
| I-4 | H | $R^7 = t\text{-}C_4H_9$ | H | $R^{16} = t\text{-}C_4H_9$ | H | $R^{25} = t\text{-}C_4H_9$ | H | $R^{34} = t\text{-}C_4H_9$ | H |
| I-5 | H | $R^7 = OCH_3$ | H | $R^{16} = OCH_3$ | H | $R^{25} = OCH_3$ | H | $R^{34} = OCH_3$ | H |
| I-6 | H | $R^7 = Ph$ | H | $R^{16} = Ph$ | H | $R^{25} = Ph$ | H | $R^{34} = Ph$ | H |
| I-7 | H | $R^7 =$ 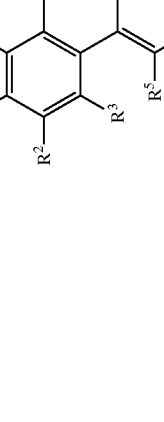 | H | $R^{16} =$  | H | $R^{25} =$ (p-tolyl) | H | $R^{34} =$ (p-tolyl) | H |
| I-8 | H | $R^7 = OPh$ | H | $R^{16} = OPh$ | H | $R^{25} = OPh$ | H | $R^{34} = OPh$ | H |
| I-9 | H | $R^7 = N(C_2H_5)_2$ | H | $R^{16} = N(C_2H_5)_2$ | H | $R^{25} = N(C_2H_5)_2$ | H | $R^{34} = N(C_2H_5)_2$ | H |
| I-10 | H | $R^7 = N(Ph)_2$ | H | $R^{16} = N(Ph)_2$ | $R^{20} = CH_3$ | $R^{25} = N(Ph)_2$ | $R^{29} = CH_3$ | $R^{34} = N(Ph)_2$ | H |
| I-11 | $R^{11} = CH_3$ | $R^7 = Cl$ | $R^{11} = CH_3$ | $R^{16} = Cl$ | H | $R^{25} = Cl$ | H | $R^{34} = Cl$ | H |
| I-12 | $R^2 = CH_3$ | H | H | H | H | H | H | H | H |
| I-13 | H | $R^6 = Ph$ | H | $R^{17} = Ph$ | H | $R^{26} = Ph$ | H | $R^{35} = Ph$ | H |
| I-14 | H | $R^7 = Ph$ | H | $R^{16} = Ph$ | H | H | H | H | H |
| I-15 | H | $R^6 = Ph$ | H | $R^{17} = Ph$ | H | H | H | H | H |

-continued

| Compound No. | $R^1$~$R^4$ | $R^5$~$R^9$ | $R^{10}$~$R^{13}$ | $R^{14}$~$R^{18}$ | $R^{19}$~$R^{22}$ | $R^{23}$~$R^{27}$ | $R^{28}$~$R^{31}$ | $R^{32}$~$R^{36}$ | $R^{37}$~$R^{44}$ |
|---|---|---|---|---|---|---|---|---|---|
| I-16 | $R^2 = OCH_3$ | H | $R^{11} = OCH_3$ | H | $R^{20} = OCH_3$ | H | $R^{29} = OCH_3$ | H | H |
| I-17 | $R^2 = Ph$ | H | $R^{11} = Ph$ | H | $R^{20} = Ph$ | H | $R^{29} = Ph$ | H | H |
| I-18 | $R^2 = OPh$ | H | $R^{11} = OPh$ | H | $R^{20} = OPh$ | H | $R^{29} = OPh$ | H | H |
| I-19 | $R^2 = N(C_2H_5)_2$ | H | $R^{11} = N(C_2H_5)_2$ | H | $R^{20} = N(C_2H_5)_2$ | H | $R^{29} = N(C_2H_5)_2$ | H | H |
| I-20 | $R^2 = Cl$ | H | $R^{11} = Cl$ | H | $R^{20} = Cl$ | H | $R^{29} = Cl$ | H | H |
| I-21 | H | H | H | H | H | H | H | H | H |
| I-22 | H | H | H | H | H | H | H | H | $R^{37} = R^{42} = CH_3$ |
| I-23 | H | H | H | H | H | H | H | H | $R^{37} = R^{42} = OCH_3$ |
| I-24 | H | H | H | H | H | H | H | H | $R^{37} = R^{42} = N(C_2H_5)_2$ |
| I-25 | H | H | H | H | H | H | H | H | $R^{37} = R^{42} = Cl$ |
| I-26 | $R^2 = Ph$ | $R^7 = Ph$ | $R^{11} = Ph$ | $R^{16} = Ph$ | $R^{20} = Ph$ | $R^{25} = Ph$ | $R^{29} = Ph$ | $R^{34} = Ph$ | H |
| I-27 | $R^2 = N(Ph)_2$ | H | $R^{11} = Ph$ | $R^{16} = Ph$ | $R^{20} = Ph$ | $R^{26} = CH_3$ | $R^{29} = Ph$ | H | H |
| I-28 | H | $R^6 = CH_3$ | H | $R^{16} = CH_3$ | H | $R^{26} = CH_3$ | H | $R^{34} = CH_3$ | $R^{40} = R^{43} = CH_3$ |
| I-29 | H | $R^6 = R^8 = CH_3$ | H | H | H | $R^{24} = R^{26} = CH_3$ | H | H | H |

| Compound No. | $R^{51}$~$R^{54}$ | $R^{55}$~$R^{59}$ | $R^{60}$~$R^{63}$ | $R^{64}$~$R^{68}$ | $R^{69}$~$R^{72}$ | $R^{73}$~$R^{77}$ | $R^{78}$~$R^{81}$ | $R^{82}$~$R^{86}$ | $R^{87}$~$R^{94}$ |
|---|---|---|---|---|---|---|---|---|---|
| II-1 | H | H | H | H | H | H | H | H | H |
| II-2 | H | $R^{56}$ = $CH_3$ | H | $R^{67}$ = $CH_3$ | H | $R^{74}$ = $CH_3$ | H | $R^{85}$ = $CH_3$ | H |
| II-3 | H | $R^{57}$ = $CH_3$ | H | $R^{66}$ = $CH_3$ | H | $R^{75}$ = $CH_3$ | H | $R^{84}$ = $CH_3$ | H |
| II-4 | H | $R^{57}$ = t-$C_4H_9$ | H | $R^{66}$ = t-$C_4H_9$ | H | $R^{75}$ = t-$C_4H_9$ | H | $R^{84}$ = t-$C_4H_9$ | H |
| II-5 | H | $R^{57}$ = $OCH_3$ | H | $R^{66}$ = $OCH_3$ | H | $R^{75}$ = $OCH_3$ | H | $R^{84}$ = $OCH_3$ | H |
| II-6 | H | $R^{57}$ = Ph | H | $R^{66}$ = Ph | H | $R^{75}$ = Ph | H | $R^{84}$ = Ph | H |
| II-7 | H | $R^{57}$ =  | H | $R^{66}$ =  | H | $R^{75}$ =  | H | $R^{84}$ = | H |
| II-8 | H | $R^{57}$ = OPh | H | $R^{66}$ = OPh | H | $R^{75}$ = OPh | H | $R^{84}$ = OPh | H |
| II-9 | H | $R^{57}$ = $N(C_2H_5)_2$ | H | $R^{66}$ = $N(C_2H_5)_2$ | H | $R^{75}$ = $N(C_2H_5)_2$ | H | $R^{84}$ = $N(C_2H_5)_2$ | H |
| II-10 | H | $R^{57}$ = $N(Ph)_2$ | H | $R^{66}$ = $N(Ph)_2$ | H | $R^{75}$ = $N(Ph)_2$ | H | $R^{84}$ = $N(Ph)_2$ | H |
| II-11 | H | $R^{57}$ = Cl | H | $R^{66}$ = Cl | H | $R^{75}$ = Cl | H | $R^{84}$ = Cl | H |
| II-12 | $R^{52}$ = $CH_3$ | H | $R^{62}$ = $CH_3$ | H | $R^{72}$ = $CH_3$ | H | H | H | H |
| II-13 | $R^{52}$ = $OCH_3$ | H | $R^{62}$ = $OCH_3$ | H | $R^{72}$ = $OCH_3$ | $R^{79}$ = $CH_3$ | H | H | H |
| II-14 | $R^{52}$ = Ph | H | $R^{62}$ = Ph | H | $R^{72}$ = Ph | $R^{79}$ = $OCH_3$ | H | H | H |
| II-15 | $R^{52}$ = OPh | H | $R^{62}$ = OPh | H | $R^{72}$ = OPh | $R^{79}$ = Ph | H | H | H |
|  |  |  |  |  |  | $R^{79}$ = OPh |  |  |  |

-continued

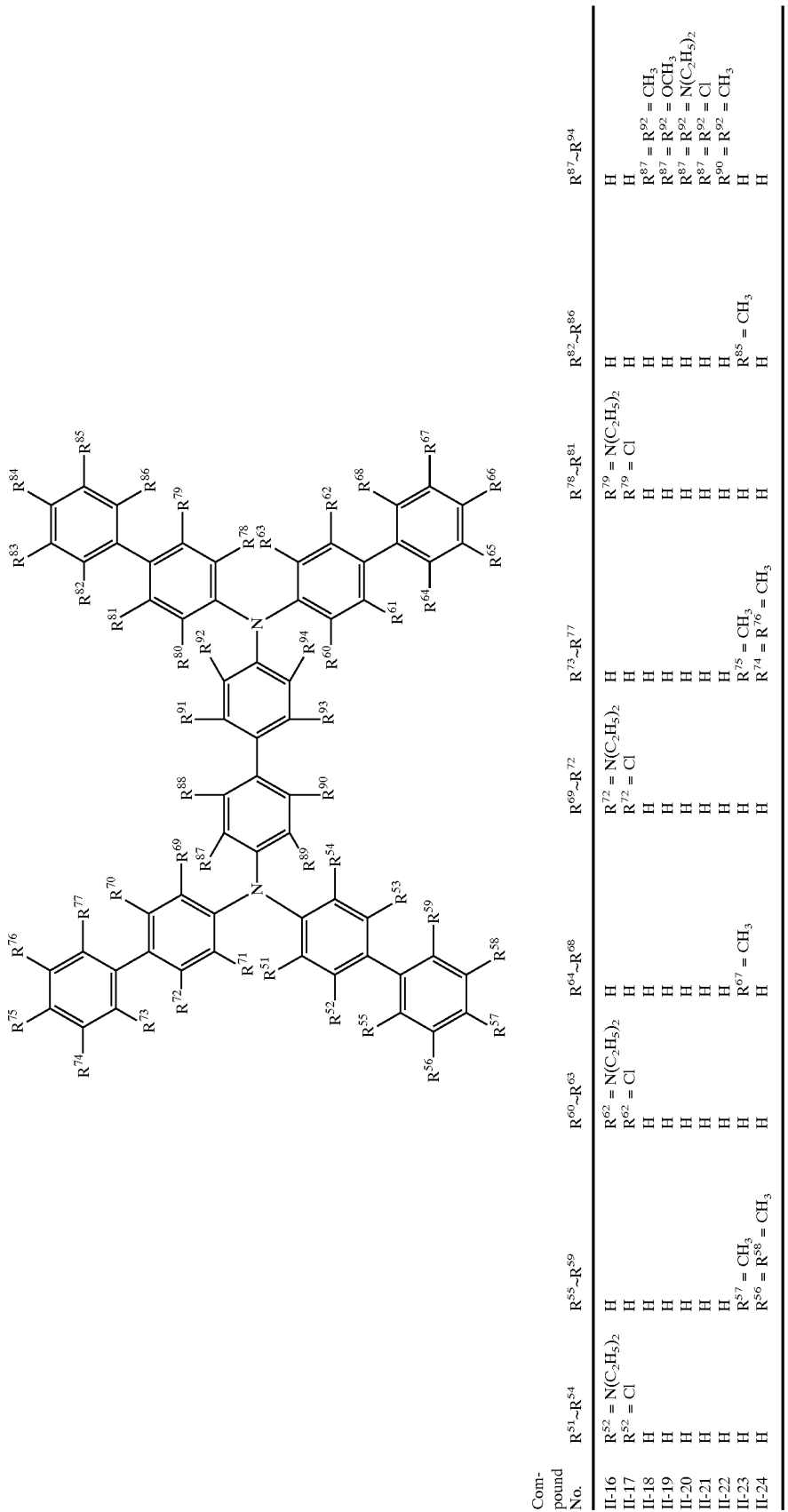

| Compound No. | $R^{51}$–$R^{54}$ | $R^{55}$–$R^{59}$ | $R^{60}$–$R^{63}$ | $R^{64}$–$R^{68}$ | $R^{69}$–$R^{72}$ | $R^{73}$–$R^{77}$ | $R^{78}$–$R^{81}$ | $R^{82}$–$R^{86}$ | $R^{87}$–$R^{94}$ |
|---|---|---|---|---|---|---|---|---|---|
| II-16 | $R^{52}$ = N($C_2H_5$)$_2$ | H | $R^{62}$ = N($C_2H_5$)$_2$ | H | $R^{72}$ = N($C_2H_5$)$_2$ | H | $R^{79}$ = N($C_2H_5$)$_2$ | H | H |
| II-17 | $R^{52}$ = Cl | H | $R^{62}$ = Cl | H | $R^{72}$ = Cl | H | $R^{79}$ = Cl | H | H |
| II-18 | H | H | H | H | H | H | H | H | $R^{87}$ = $R^{92}$ = $CH_3$ |
| II-19 | H | H | H | H | H | H | H | H | $R^{87}$ = $R^{92}$ = $OCH_3$ |
| II-20 | H | H | H | H | H | H | H | H | $R^{87}$ = $R^{92}$ = N($C_2H_5$)$_2$ |
| II-21 | H | H | H | H | H | H | H | H | $R^{87}$ = $R^{92}$ = Cl |
| II-22 | H | H | H | H | H | H | H | H | $R^{90}$ = $R^{92}$ = $CH_3$ |
| II-23 | H | $R^{57}$ = $CH_3$ | H | $R^{67}$ = $CH_3$ | H | $R^{75}$ = $CH_3$ | H | $R^{85}$ = $CH_3$ | H |
| II-24 | H | $R^{56}$ = $R^{58}$ = $CH_3$ | H | H | H | $R^{74}$ = $R^{76}$ = $CH_3$ | H | H | H |

| Compound No. | Ar$_1$ | Ar$_2$ | R$^{101}$~R$^{104}$ | R$^{105}$~R$^{108}$ | R$^{109}$~R$^{113}$ | R$^{114}$~R$^{118}$ | R$^{119}$~R$^{126}$ |
|---|---|---|---|---|---|---|---|
| III-1 | Ph | Ph | H | H | H | H | H |
| III-2 | Ph | Ph | H | H | R$^{110}$ = CH$_3$ | R$^{115}$ = CH$_3$ | H |
| III-3 | Ph | Ph | H | H | R$^{111}$ = CH$_3$ | R$^{116}$ = CH$_3$ | H |
| III-4 | Ph | Ph | H | H | R$^{111}$ = t-C$_4$H$_9$ | R$^{116}$ = t-C$_4$H$_9$ | H |
| III-5 | Ph | Ph | H | H | R$^{111}$ = OCH$_3$ | R$^{116}$ = OCH$_3$ | H |
| III-6 | Ph | Ph | H | H | R$^{111}$ = Ph | R$^{116}$ = Ph | H |
| III-7 | Ph | Ph | H | H | R$^{111}$ =  | R$^{116}$ = (p-tolyl) | H |
| III-8 | Ph | Ph | H | H | R$^{111}$ = OPh | R$^{116}$ = OPh | H |
| III-9 | Ph | Ph | H | H | R$^{111}$ = N(C$_2$H$_5$)$_2$ | R$^{116}$ = N(C$_2$H$_5$)$_2$ | H |
| III-10 | Ph | Ph | H | H | R$^{111}$ = N(Ph)$_2$ | R$^{116}$ = N(Ph)$_2$ | H |
| III-11 | Ph | Ph | H | H | R$^{111}$ = Cl | R$^{116}$ = Cl | H |
| III-12 | Ph | Ph | H | H | R$^{111}$ = CH$_3$ | R$^{115}$ = CH$_3$ | H |
| III-13 | Ph | Ph | H | H | R$^{111}$ = OCH$_3$ | R$^{115}$ = OCH$_3$ | H |
| III-14 | Ph | Ph | R$^{102}$ = CH$_3$ | R$^{106}$ = CH$_3$ | H | H | H |
| III-15 | Ph | Ph | R$^{102}$ = OCH$_3$ | R$^{106}$ = OCH$_3$ | H | H | H |
| III-16 | Ph | Ph | R$^{102}$ = Ph | R$^{106}$ = Ph | H | H | H |
| III-17 | Ph | Ph | R$^{102}$ = OPh | R$^{106}$ = OPh | H | H | H |
| III-18 | Ph | Ph | R$^{102}$ = N(C$_2$H$_5$)$_2$ | R$^{106}$ = N(C$_2$H$_5$)$_2$ | H | H | H |
| III-19 | Ph | Ph | R$^{102}$ = Cl | R$^{106}$ = Cl | H | H | H |
| III-20 | Ph | Ph | H | H | H | H | R$^{119}$ = R$^{124}$ = CH$_3$ |
| III-21 | Ph | Ph | H | H | H | H | R$^{119}$ = R$^{124}$ = OCH$_3$ |
| III-22 | Ph | Ph | H | H | H | H | R$^{119}$ = R$^{124}$ = N(C$_2$H$_5$)$_2$ |
| III-23 | Ph | Ph | H | H | H | H | R$^{119}$ = R$^{124}$ = Cl |

-continued

| Compound No. | Ar₁ | Ar₂ | R¹⁰¹~R¹⁰⁴ | R¹⁰⁵~R¹⁰⁸ | R¹⁰⁹~R¹¹³ | R¹¹⁴~R¹¹⁸ | R¹¹⁹~R¹²⁶ |
|---|---|---|---|---|---|---|---|
| III-24 | 4-methylphenyl | 4-methylphenyl | H | H | H | H | H |
| III-25 | 4'-methylbiphenyl | 4'-methylbiphenyl | H | H | H | H | H |
| III-26 | 4-methylnaphthyl | 4-methylnaphthyl | H | H | H | H | H |
| III-27 | Ph | 4-methylphenyl | H | H | H | H | H |
| III-28 | 3-phenylphenyl | 3-phenylphenyl | H | H | H | H | H |

IV-1 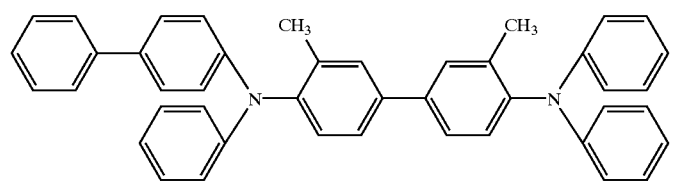
IV-2 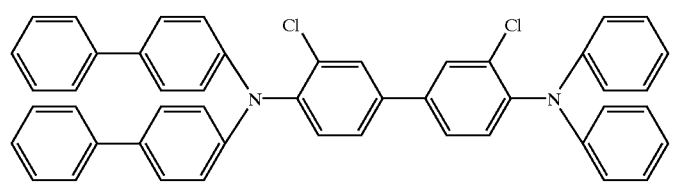
IV-3 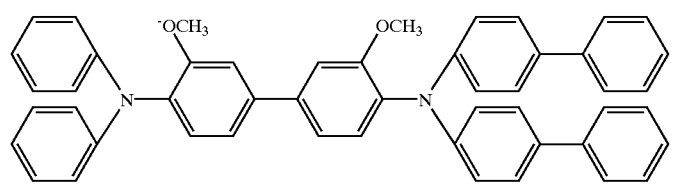
IV-4 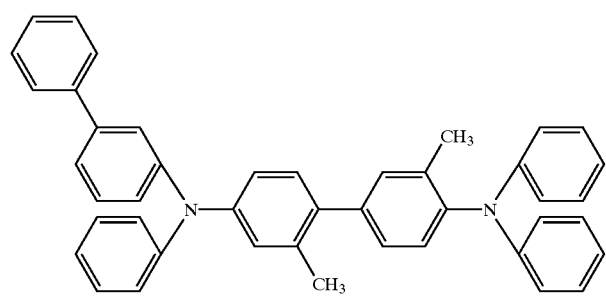
IV-5 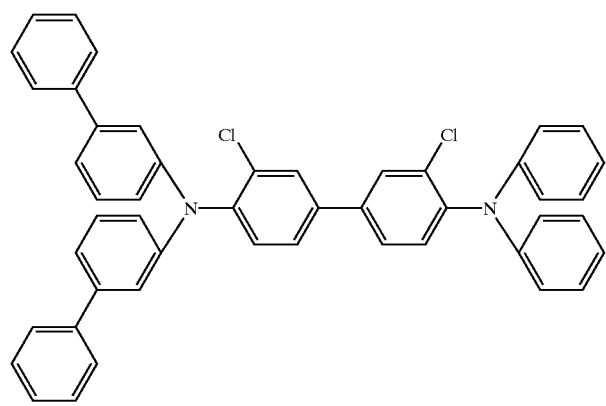
V-1 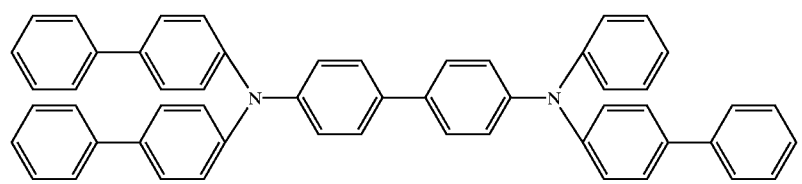

-continued
V-2
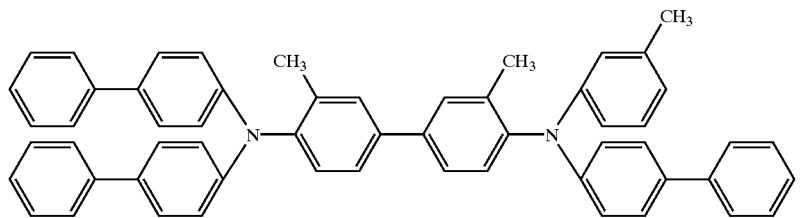
V-3
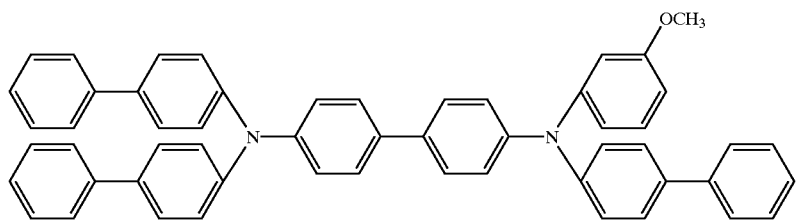
V-4
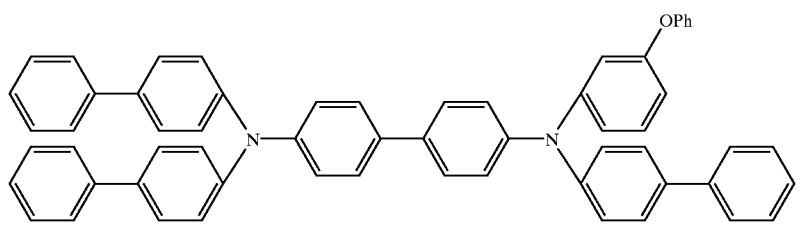
V-5
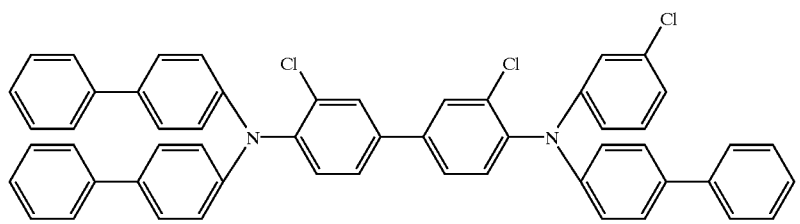
VI-1
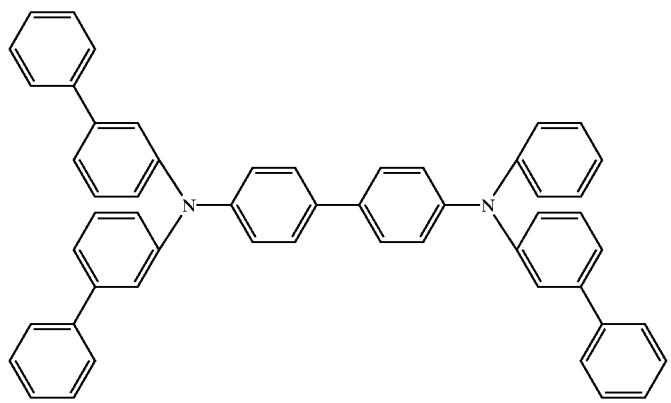

VI-2
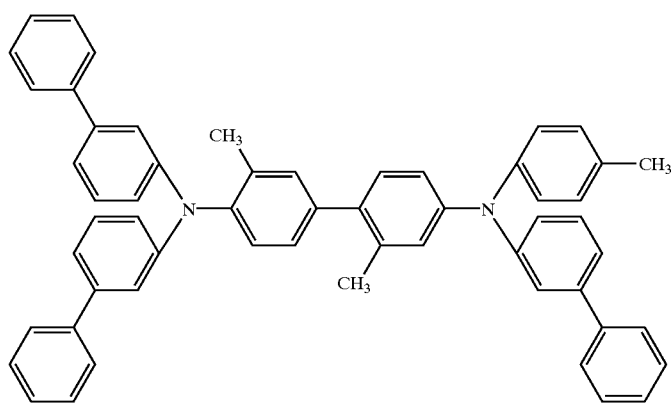
VI-3
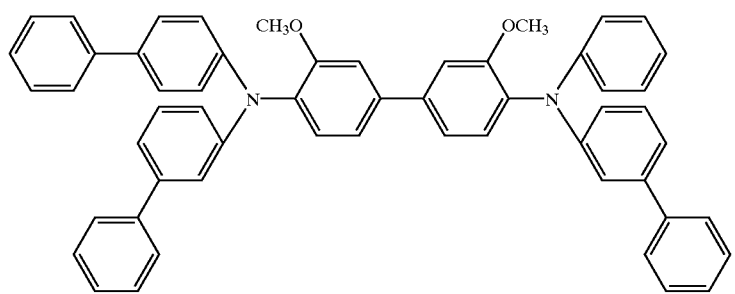
VI-4
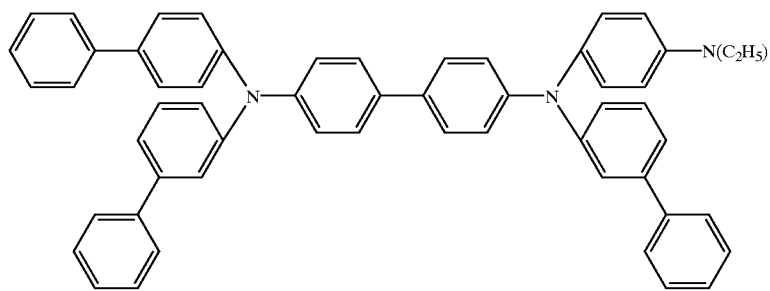
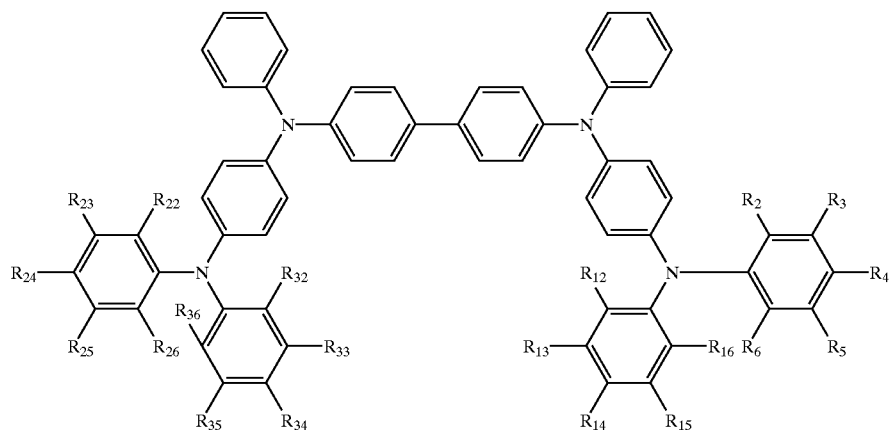

-continued

| $R_3 = R_{23}$ | $R_4 = R_{24}$ | $R_{13} = R_{33}$ | $R_{14} = R_{44}$ |
|---|---|---|---|
| Ph | H | H | H |
| H | Ph | H | H |
| Ph | H | Ph | H |
| H | Ph | H | Ph |
| $CH_3$ | H | H | H |
| H | $CH_3$ | H | H |
| $CH_3$ | H | $CH_3$ | H |
| H | $CH_3$ | H | $CH_3$ |

The above-described host compounds can be synthesized by the method described in Jean Piccard, Herr. Chim. Acta., 7, 789 (1924), Jean Piccard, J. Am. Chem. Soc., 48, 2878 (1926), etc. or similar methods. More particularly, Ullmann reaction is effected by heating in the presence of copper a combination of a di(biphenyl)amine compound with a diiodobiphenyl compound or a combination of a N,N'-diphenylbenzidine compound with a iodobiphenyl compound, selected in accordance with the end compound.

The host compounds can be identified by mass analysis, infrared (IR) absorption spectroscopy or nuclear magnetic resonance spectroscopy ($^1$H-NMR).

These compounds have a molecular weight of about 640 to about 800, a high melting point of about 190 to about 300° C., and a high glass transition temperature of about 80 to about 150° C. On conventional vacuum evaporation, they form satisfactory smooth films which are transparent and remain amorphous even above room temperature. The films maintain the stable amorphous state over a long period of time. Accordingly, thin films can be formed from the compounds alone without a need for binder resins.

Anthracene Compounds

A further class of organic compounds useful as the host material according to the invention are phenylanthracene derivatives of the following formula (III).

In the device of the invention, the use of the anthracene derivative of formula (III), preferably as the host material, helps induce strong light emission from the dopant while controlling the interaction with the dopant. Since the anthracene derivatives are fully heat resistant and durable, organic EL devices with a longer lifetime are obtainable.

In an exemplary organic EL device which was fabricated using an anthracene derivative doped with a dibenzo[f,f'] diindeno[1,2,3-cd:1',2',3'-lm]perylene derivative, a luminance of at least 250 cd/m$^2$ was obtained at a current density of 10 mA/cm$^2$ and a drive voltage as low as about 6.5 V. When operated at a current density of about 600 mA/cm$^2$, the device consistently produced a luminance of greater than about 13,000 cd/m$^2$. When operated at a current density of about 50 mA/cm$^2$, the device marked a very long lifetime as demonstrated by a half-life time of more than 300 hours at an initial luminance of at least 2400 cd/cm$^2$.

In organic EL devices as mentioned above, the dopant concentration ensuring a chromatic purity and maximum efficiency is about 1% by weight although dopant concentrations of about 2 or 3% by weight lead to devices which are practically acceptable albeit a drop of less than about 10%.

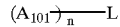

(III)

Herein $A_{101}$ is a monophenylanthryl or diphenylanthryl radical and may be the same or different, L is hydrogen, a single bond or a divalent linkage, and n is an integer of 1 or 2.

Of the compounds of formula (III), those compounds of the following formulas (III-1) and (III-2) are preferred.

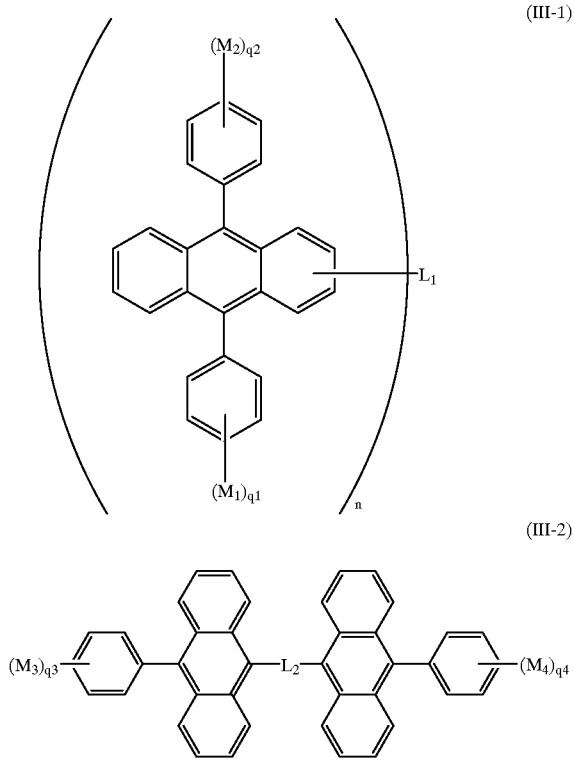

Evaporated films of these compounds remain in a stable amorphous state, that is, have sufficient physical properties to produce consistent uniform light emission. The films remain stable over one year in the ambient atmosphere without crystallization.

Referring to formula (III), $A_{101}$ is a monophenylanthryl or diphenylanthryl radical and may be the same or different, and n is an integer of 1 or 2. The monophenylanthryl or diphenylanthryl radical represented by $A_{101}$ may be substituted or unsubstituted. Exemplary substituents are alkyl, aryl, alkoxy, aryloxy and amino groups. These substituents may further have substituents thereon and will be described later. The position of a substituent on the monophenylanthryl or diphenylanthryl radical is not critical although the preferred substitution position is on the phenyl group bonded to the anthracene ring rather than the anthracene ring.

Preferably the phenyl group is bonded to the anthracene ring at the 9- and 10-positions.

In formula (III), L is hydrogen, a single bond or a divalent linkage. The divalent linkage represented by L is preferably an arylene radical which may be separated by an alkylene or analogous group. The arylene radical will be described later.

Of the phenylanthracene derivatives of formula (III), those of formulas (III-1) and (III-2) are preferred. Formula (III-1) is described in detail.

In formula (III-1), $M_1$ and $M_2$ each are alkyl, cycloalkyl, aryl, alkoxy, aryloxy, amino or heterocyclic radicals.

The alkyl radicals represented by $M_1$ and $M_2$ may be substituted or unsubstituted, straight or branched alkyl radicals, preferably of 1 to 10 carbon atoms, more preferably 1 to 4 carbon atoms. Unsubstituted alkyl radicals of 1 to 4 carbon atoms are preferred, such as, for example, methyl, ethyl, n- and i-propyl, and n-, i-, sec- and tert-butyl.

Exemplary of the cycloalkyl radicals represented by $M_1$ and $M_2$ are cyclohexyl and cyclopentyl.

The aryl radicals represented by $M_1$ and $M_2$ are preferably those aryl radicals having 6 to 20 carbon atoms which may have substituents such as phenyl and tolyl. Preferred examples of the aryl radical include phenyl, o-, m- and p-tolyl, pyrenyl, naphthyl, anthryl, biphenyl, phenylanthryl and tolylanthryl.

The alkenyl radicals represented by $M_1$ and $M_2$ are preferably those having 6 to 50 carbon atoms in total, which may be substituted or unsubstituted, with the substituted ones being preferred. Such substituents are aryl groups such as phenyl. Exemplary alkenyl radicals are triphenylvinyl, tritolylvinyl and tribiphenylvinyl.

The alkoxy radicals represented by $M_1$ and $M_2$ are preferably those having an alkyl moiety of 1 to 6 carbon atoms, for example, methoxy and ethoxy. The alkoxy radicals may have substituents.

Exemplary of the aryloxy radicals represented by $M_1$ and $M_2$ is phenoxy.

The amino radicals represented by $M_1$ and $M_2$ may be substituted or unsubstituted, with the substituted amino radicals being preferred. Such substituents are alkyl groups such as methyl and ethyl and aryl groups such as phenyl. Illustrative examples of the amino radical include diethylamino, diphenylamino and di(m-tolyl)amino radicals.

The heterocyclic radicals represented by $M_1$ and $M_2$ include bipyridyl, pyrimidyl, quinolyl, pyridyl, thienyl, furyl and oxadiazoyl radicals and may have substituents such as methyl and phenyl.

In formula (III-1), q1 and q2 each are 0 or an integer of 1 to 5, especially 0 or 1. When q1 and q2 each are an integer of 1 to 5, especially 1 or 2, $M_1$ and $M_2$ each are preferably alkyl, aryl, alkenyl, alkoxy, aryloxy or amino radicals.

In formula (III-1), $M_1$ and $M_2$ may be the same or different. Where a plurality of $M_1$ or $M_2$ are included, the $M_1$ groups or $M_2$ groups may be the same or different. Alternatively, the $M_1$ groups or $M_2$ groups bond together to form a ring such as a benzene ring. The ring formation is also a preferred embodiment.

In formula (III-1), $L_1$ is hydrogen, a single bond or an arylene radical. The arylene radicals represented by $L_1$ are preferably unsubstituted ones, for example, ordinary arylene radicals such as phenylene, biphenylene and anthrylene as well as two or more arylene radicals which are directly bonded. $L_1$ is preferably a single bond, p-phenylene or 4,4'-biphenylene.

The arylene radical represented by $L_1$ may consist of two or more arylene radicals which are connected by an alkylene radical, —O—, —S— or —NR— wherein R is an alkyl or aryl radical. Exemplary alkyl radicals are methyl and ethyl, and an exemplary aryl radical is phenyl. R is preferably an aryl radical, such as phenyl. Alternatively, R is $A_{101}$ or a phenyl radical having $A_{101}$ substituted thereon. The alkylene radicals are preferably methylene and ethylene.

Illustrative examples of the arylene radical are given below.

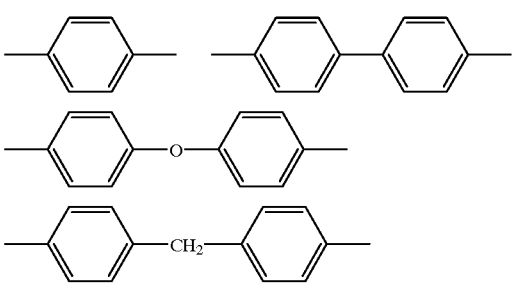

-continued

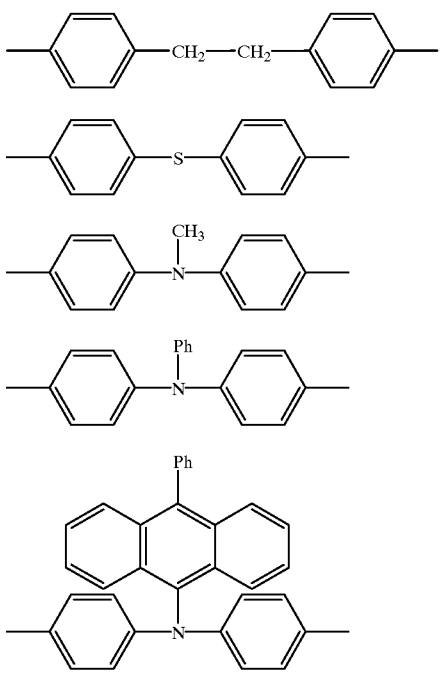

-continued

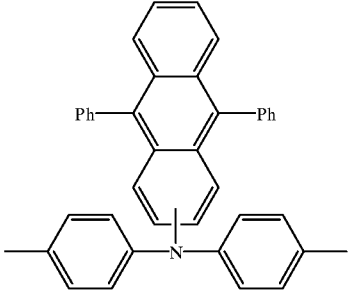

Next referring to formula (III-2), $M_3$ and $M_4$ are the same as $M_1$ and $M_2$ in formula (III-1), q3 and q4 are the same as q1 and q2 in formula (III-1), and $L_2$ is the same as $L_1$ in formula (III-1). Preferred examples of these radicals are also the same.

In formula (III-2), $M_3$ and $M_4$ may be the same or different. Where a plurality of $M_3$ or $M_4$ are included, the $M_3$ groups or $M_4$ groups may be the same or different. Alternatively, the $M_3$ groups or $M_4$ groups bond together to form a ring such as a benzene ring. The ring formation is also a preferred embodiment.

Illustrative, non-limiting, examples of the compounds of formulas (III-1) and (III-2) are given below. It is noted that general formulas are followed by lists of M's to show illustrative examples by combinations of $M_{11}$ to $M_{15}$ and $M_{21}$ to $M_{25}$ or combinations of $M_{31}$ to $M_{35}$ and $M_{41}$ to $M_{45}$.

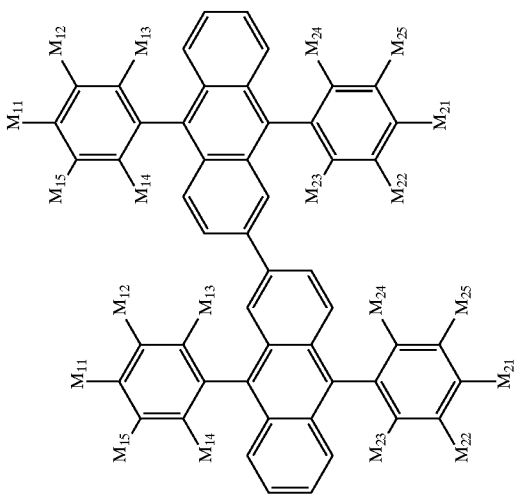
| Compound No. | M11 | M12 | M13 | M14 | M15 | M21 | M22 | M23 | M24 | M25 |
|---|---|---|---|---|---|---|---|---|---|---|
| I-1 | H | H | H | H | H | H | H | H | H | H |
| I-2 | CH$_3$ | H | H | H | H | CH$_3$ | H | H | H | H |
| I-3 | t-C$_4$H$_9$ | H | H | H | H | t-C$_4$H$_9$ | H | H | H | H |
| I-4 | OCH$_3$ | H | H | H | H | OCH$_3$ | H | H | H | H |
| I-5 | OPh | H | H | H | H | OPh | H | H | H | H |
| I-6 | N(C$_2$H$_5$)$_2$ | H | H | H | H | N(C$_2$H$_5$)$_2$ | H | H | H | H |
| I-7 | N(Ph)$_2$ | H | H | H | H | N(Ph)$_2$ | H | H | H | H |
| I-8 | Ph | H | H | H | H | Ph | H | H | H | H |
| I-9 | 4-tolyl | | | | | 4-tolyl | | | | |
| I-10 | H | CH$_3$ | H | CH$_3$ | H | H | CH$_3$ | H | H | H |
| I-11 | H | CH$_3$ | H | H | H | H | CH$_3$ | H | CH$_3$ | H |
| I-12 | H | H | CH$_3$ | H | CH$_3$ | H | H | CH$_3$ | H | H |
| I-13 | H | CH$_3$ | H | H | CH$_3$ | H | CH$_3$ | H | H | CH$_3$ |
| I-14 | t-C$_4$H$_9$ | H | H | H | H | H | H | H | H | H |

-continued
| Compound No. | M11 | M12 | M13 | M14 | M15 | M21 | M22 | M23 | M24 | M25 |
|---|---|---|---|---|---|---|---|---|---|---|
| I-15 | 4-MeC6H4- | H | H | H | H | 4-MeC6H4- | H | H | H | H |
| I-16 | H | Ph | H | H | H | H | Ph | H | H | H |
| I-17 | H | H | Ph | H | H | H | H | Ph | H | H |
| I-18 | CPh2(CH3) | H | H | H | H | CPh2(CH3) | H | H | H | H |
| I-19 | n-C4H9 | H | H | H | H | n-C4H9 | H | H | H | H |
| I-20 | 4-MeC6H4- | H | H | H | H | 4-MeC6H4- | H | H | H | H |
| I-21 | H | H | 4-PhC6H4- | H | H | H | H | 4-PhC6H4- | H | H |

-continued

| Compound No. | M11 | M12 | M13 | M14 | M15 | M21 | M22 | M23 | M24 | M25 |
|---|---|---|---|---|---|---|---|---|---|---|
| I-22 | 2-biphenyl | H | H | H | H | 2-biphenyl | H | H | H | H |
| I-23 | H | H | 2-biphenyl | H | H | H | H | 2-biphenyl | H | H |
| I-24 | H | H | Ph | Ph | H | H | H | Ph | H | Ph |
| I-25 | H | H | Ph | H | H | H | H | Ph | Ph | H |

| Compound No. | M11 | M12 | M13 | M14 | M15 | M21 | M22 | M23 | M24 | M25 |
|---|---|---|---|---|---|---|---|---|---|---|
| II-1 | H | H | H | H | H | H | H | H | H | H |
| II-2 | $CH_3$ | H | H | H | H | $CH_3$ | H | H | H | H |
| II-3 | $t\text{-}C_4H_9$ | H | H | H | H | $t\text{-}C_4H_9$ | H | H | H | H |
| II-4 | $OCH_3$ | H | H | H | H | $OCH_3$ | H | H | H | H |
| II-5 | OPh | H | H | H | H | OPh | H | H | H | H |
| II-6 | $N(C_2H_5)_2$ | H | H | H | H | $N(C_2H_5)_2$ | H | H | H | H |
| II-7 | $N(Ph)_2$ | H | H | H | H | $N(Ph)_2$ | H | H | H | H |
| II-8 | Ph | H | H | H | H | Ph | H | H | H | H |
| II-9 | p-tolyl | H | H | H | H | p-tolyl | H | H | H | H |
| II-10 | H | $CH_3$ | H | H | H | H | $CH_3$ | H | H | H |
| II-11 | H | H | $CH_3$ | $CH_3$ | H | H | $CH_3$ | $CH_3$ | $CH_3$ | H |
| II-12 | H | H | $CH_3$ | $CH_3$ | $CH_3$ | H | H | $CH_3$ | H | $CH_3$ |
| II-13 | $CH_3$ | $CH_3$ | $CH_3$ | $CH_3$ | $CH_3$ | $CH_3$ | $CH_3$ | $CH_3$ | $CH_3$ | $CH_3$ |
| II-14 | $t\text{-}C_4H_9$ | H | H | H | H | H | H | H | H | H |
| II-15 | | | | | | | | | | |

-continued
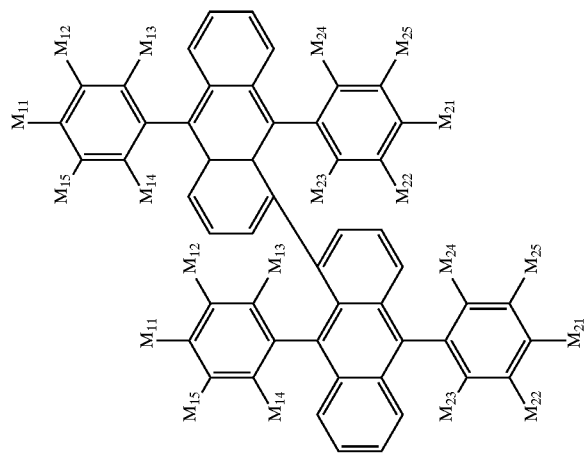
| Compound No. | M11 | M12 | M13 | M14 | M15 | M21 | M22 | M23 | M24 | M25 |
|---|---|---|---|---|---|---|---|---|---|---|
| II-16 | 4-biphenyl | H | H | H | H | H | 4-biphenyl | H | H | H |
| II-17 | H | Ph | H | H | H | H | Ph | H | H | H |
| II-18 | H | H | Ph | H | H | H | H | Ph | H | H |
| II-19 | H | H | 4-biphenyl | H | H | H | H | 4-biphenyl | H | H |
| II-20 | 4-biphenyl | H | H | H | H | H | 4-biphenyl | H | H | H |

-continued
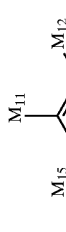
| Compound No. | M11 | M12 | M13 | M14 | M15 | M21 | M22 | M23 | M24 | M25 |
|---|---|---|---|---|---|---|---|---|---|---|
| II-21 | 2-biphenyl | H | H | H | H | 2-biphenyl | H | H | 4-biphenyl | H |
| II-22 | H | H | H | H | H | H | H | H | H | H |
| II-23 | H | H | Ph | Ph | H | H | H | Ph | H | Ph |
| II-24 | H | H | Ph | H | H | H | H | Ph | Ph | H |

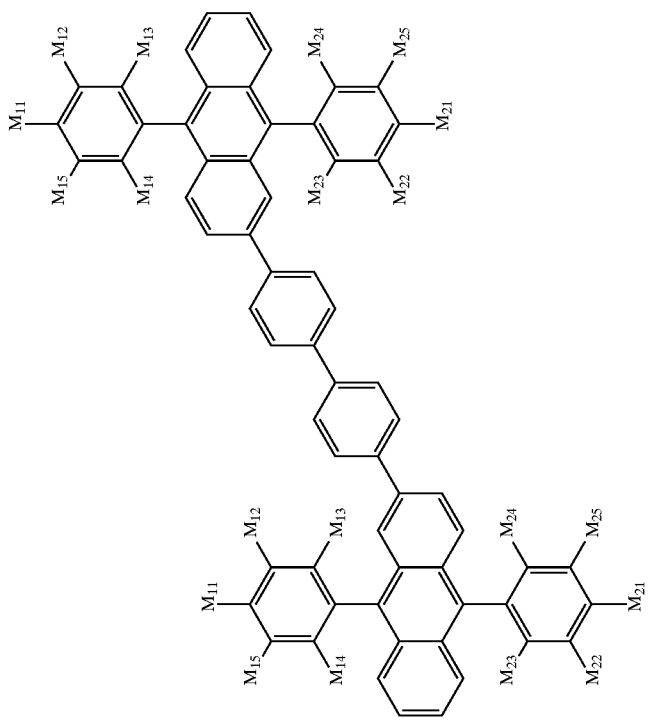
| Compound No. | M11 | M12 | M13 | M14 | M15 | M21 | M22 | M23 | M24 | M25 |
|---|---|---|---|---|---|---|---|---|---|---|
| III-1 | H | H | H | H | H | H | H | H | H | H |
| III-2 | $CH_3$ | H | H | H | H | $CH_3$ | H | H | H | H |
| III-3 | $t\text{-}C_4H_9$ | H | H | H | H | $t\text{-}C_4H_9$ | H | H | H | H |
| III-4 | $OCH_3$ | H | H | H | H | $OCH_3$ | H | H | H | H |
| III-5 | OPh | H | H | H | H | OPh | H | H | H | H |
| III-6 | $N(C_2H_5)_2$ | H | H | H | H | $N(C_2H_5)_2$ | H | H | H | H |
| III-7 | $N(Ph)_2$ | H | H | H | H | $N(Ph)_2$ | H | H | H | H |
| III-8 | Ph | H | H | H | H | Ph | H | H | H | H |
| III-9 | p-tolyl | H | H | H | H | p-tolyl | H | H | H | H |
| III-10 | H | $CH_3$ | H | H | H | H | $CH_3$ | H | H | H |
| III-11 | H | H | $CH_3$ | H | H | H | H | $CH_3$ | H | H |
| III-12 | H | H | $CH_3$ | $CH_3$ | H | H | H | $CH_3$ | $CH_3$ | H |

-continued
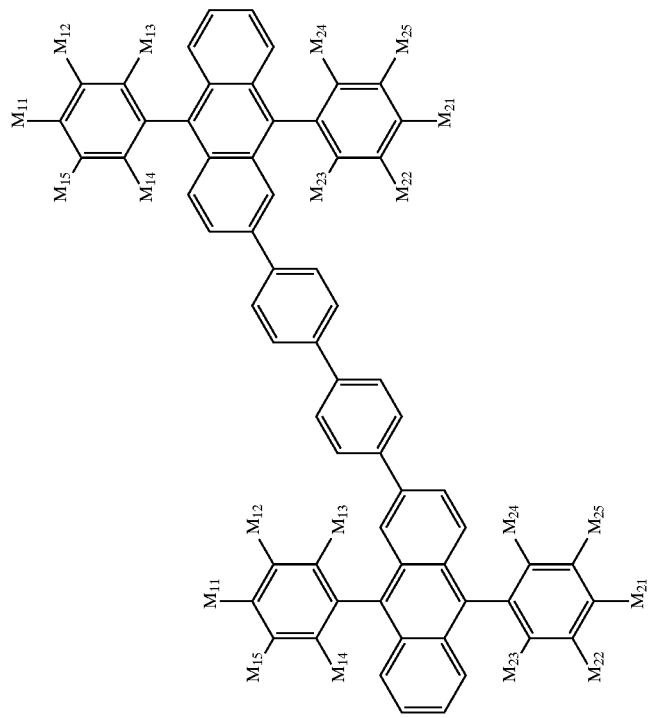
| Compound No. | M11 | M12 | M13 | M14 | M15 | M21 | M22 | M23 | M24 | M25 |
|---|---|---|---|---|---|---|---|---|---|---|
| III-13 | H | H | CH₃ | H | CH₃ | H | H | CH₃ | H | CH₃ |
| III-14 | CH₃ | CH₃ | CH₃ | CH₃ | CH₃ | CH₃ | CH₃ | CH₃ | CH₃ | CH₃ |
| III-15 | H | Ph | H | H | H | H | Ph | H | H | H |
| III-16 | H | H | Ph | H | H | H | H | Ph | H | H |
| III-17 | H | H | H | H | H | H | H | H | H | H |
| III-18 | t-C₄H₉ | H | H | H | H | H | H | H | H | H |
| III-19 | H | H | H | H | H | H | H | H | H | H |

-continued

| Compound No. | $M_{11}$ | $M_{12}$ | $M_{13}$ | $M_{14}$ | $M_{15}$ | $M_{21}$ | $M_{22}$ | $M_{23}$ | $M_{24}$ | $M_{25}$ |
|---|---|---|---|---|---|---|---|---|---|---|
| III-20 | 2-phenyl-1,3,4-oxadiazol-5-yl | H | H | H | H | 2-phenyl-1,3,4-oxadiazol-5-yl | H | H | H | H |
| III-21 | 5-methylthiophen-2-yl | H | H | H | H | 5-methylthiophen-2-yl | H | H | H | H |
| III-22 | 10-methylanthracen-9-yl | H | H | H | H | 10-methylanthracen-9-yl | H | H | H | H |

-continued

| Compound No. | $M_{11}$ | $M_{12}$ | $M_{13}$ | $M_{14}$ | $M_{15}$ | $M_{21}$ | $M_{22}$ | $M_{23}$ | $M_{24}$ | $M_{25}$ |
|---|---|---|---|---|---|---|---|---|---|---|
| III-23 | 4-methylbiphenyl | H | H | H | H | H | H | 4-methylbiphenyl | H | H |
| III-24 | H | H | 4-methylbiphenyl | H | H | H | H | 4-methylbiphenyl | H | H |
| III-25 | 2-methylbiphenyl | H | H | H | H | H | H | 2-methylbiphenyl | H | H |

-continued
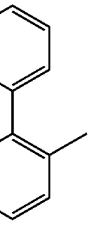
| Compound No. | M11 | M12 | M13 | M14 | M15 | M21 | M22 | M23 | M24 | M25 |
|---|---|---|---|---|---|---|---|---|---|---|
| III-26 | H | H | H | H | H | H | H | 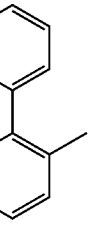 | H | H |
| III-27 | H | H | Ph | Ph | H | H | H | Ph | H | Ph |
| III-28 | H | H | Ph | H | H | H | H | Ph | Ph | H |

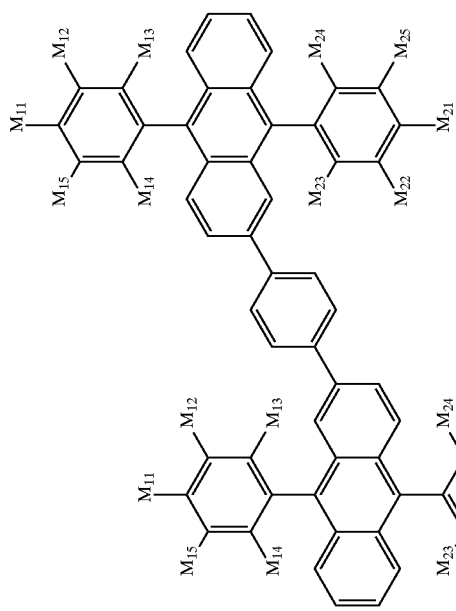
| Compound No. | M₁₁ | M₁₂ | M₁₃ | M₁₄ | M₁₅ | M₂₁ | M₂₂ | M₂₃ | M₂₄ | M₂₅ |
|---|---|---|---|---|---|---|---|---|---|---|
| IV-1 | H | H | H | H | H | H | H | H | H | H |
| IV-2 | CH₃ | H | H | H | H | CH₃ | H | H | H | H |
| IV-3 | t-C₄H₉ | H | H | H | H | t-C₄H₉ | H | H | H | H |
| IV-4 | OCH₃ | H | H | H | H | OCH₃ | H | H | H | H |
| IV-5 | OPh | H | H | H | H | OPh | H | H | H | H |
| IV-6 | N(C₂H₅)₂ | H | H | H | H | N(C₂H₅)₂ | H | H | H | H |
| IV-7 | N(Ph)₂ | H | H | H | H | N(Ph)₂ | H | H | H | H |
| IV-8 | Ph | H | H | H | H | Ph | H | H | H | H |
| IV-9 | 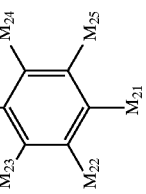 | H | H | H | H | 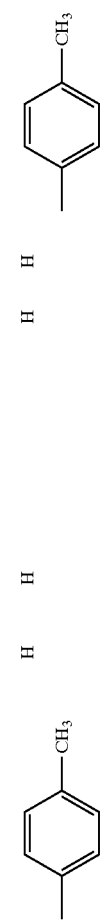 | H | H | H | H |
| IV-10 | H | CH₃ | H | H | H | H | CH₃ | H | H | H |
| IV-11 | H | H | CH₃ | CH₃ | H | H | H | CH₃ | H | H |
| IV-12 | H | H | CH₃ | H | CH₃ | H | CH₃ | CH₃ | H | H |
| IV-13 | CH₃ | CH₃ | CH₃ | CH₃ | CH₃ | CH₃ | CH₃ | CH₃ | CH₃ | CH₃ |
| IV-14 | H | H | H | H | H | H | H | H | H | H |
| IV-15 | H | H | H | H | H | H | H | H | H | H |

-continued
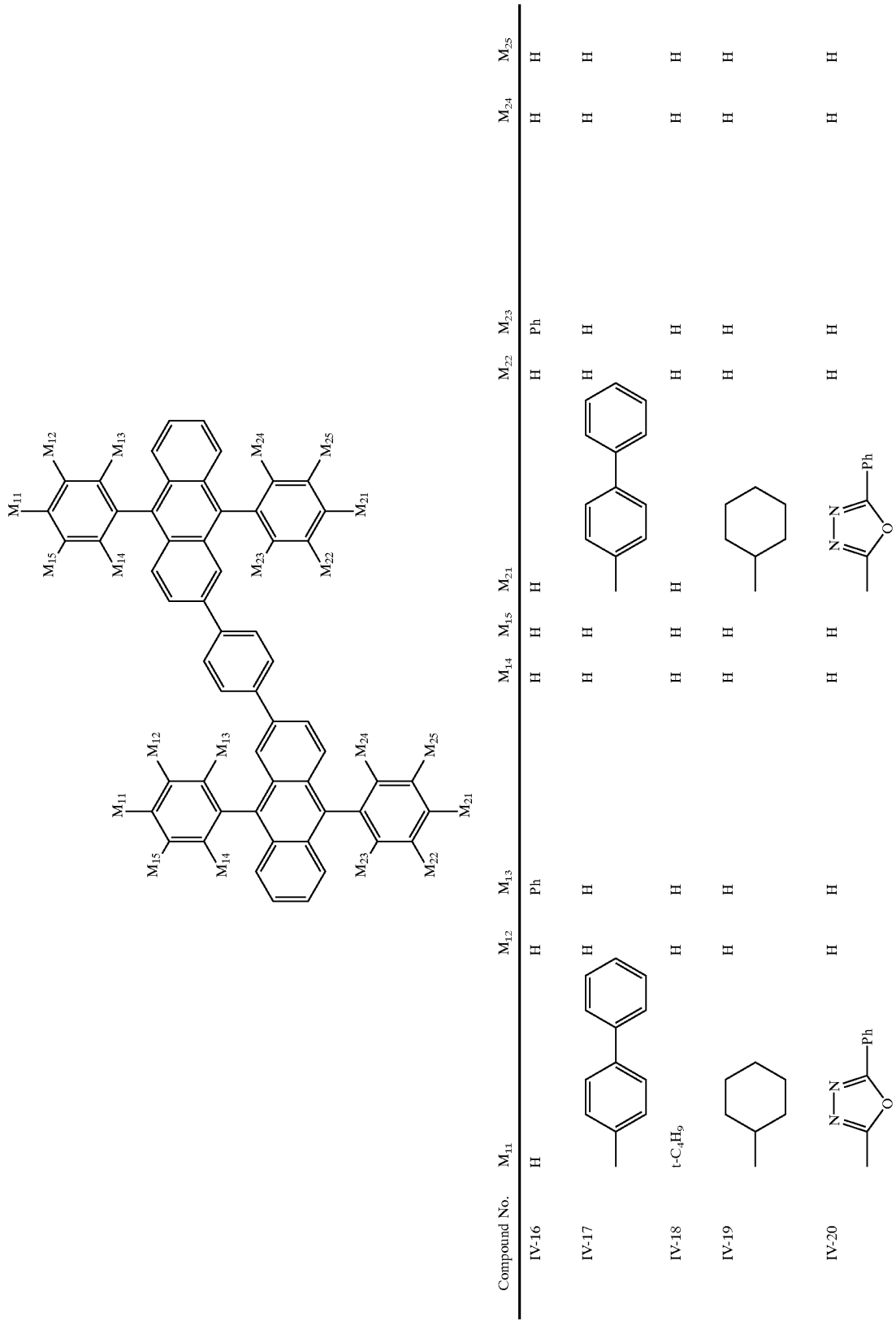
| Compound No. | $M_{11}$ | $M_{12}$ | $M_{13}$ | $M_{14}$ | $M_{15}$ | $M_{21}$ | $M_{22}$ | $M_{23}$ | $M_{24}$ | $M_{25}$ |
|---|---|---|---|---|---|---|---|---|---|---|
| IV-16 | H | H | Ph | H | H | H | H | Ph | H | H |
| IV-17 | | H | H | H | H | | H | H | H | H |
| IV-18 | t-$C_4H_9$ | H | H | H | H | H | H | H | H | H |
| IV-19 | | H | H | H | H | | H | H | H | H |
| IV-20 | | H | H | H | H | | H | H | H | H |

-continued

| Compound No. | $M_{11}$ | $M_{12}$ | $M_{13}$ | $M_{14}$ | $M_{15}$ | $M_{21}$ | $M_{22}$ | $M_{23}$ | $M_{24}$ | $M_{25}$ |
|---|---|---|---|---|---|---|---|---|---|---|
| IV-21 | 4-methylbiphenyl | 4-methylbiphenyl | H | H | H | H | 4-methylbiphenyl | H | H | H |
| IV-22 | H | H | H | 4-methylbiphenyl | H | H | H | 4-methylbiphenyl | H | H |
| IV-23 | 2-methylbiphenyl | H | H | H | H | H | H | 2-methylbiphenyl | H | H |

-continued
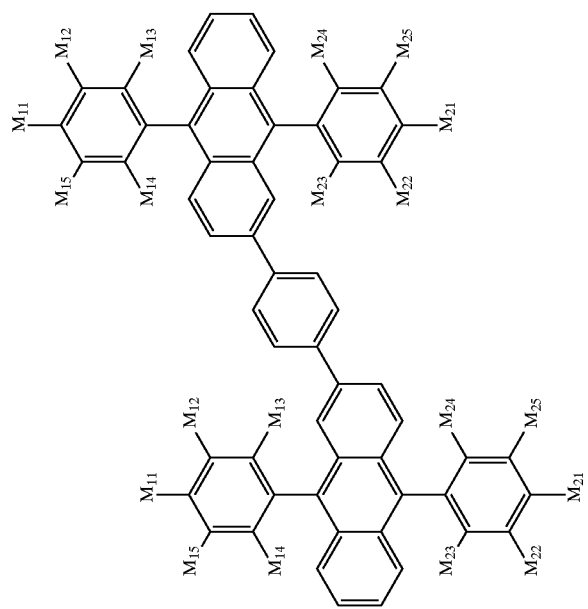
| Compound No. | M₁₁ | M₁₂ | M₁₃ | M₁₄ | M₁₅ | M₂₁ | M₂₂ | M₂₃ | M₂₄ | M₂₅ |
|---|---|---|---|---|---|---|---|---|---|---|
| IV-24 | H | H | 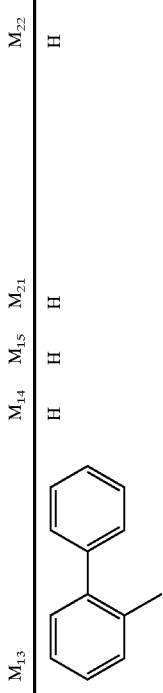 | H | H | H | H | 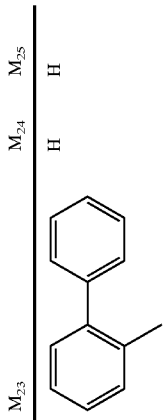 | H | H |
| IV-25 | H | H | Ph | H | Ph | H | H | Ph | H | Ph |
| IV-26 | H | H | Ph | Ph | H | H | H | Ph | Ph | H |

| Compound No. | M₃₁ | M₃₂ | M₃₃ | M₃₄ | M₃₅ | M₄₁ | M₄₂ | M₄₃ | M₄₄ | M₄₅ |
|---|---|---|---|---|---|---|---|---|---|---|
| V-1 | H | H | H | H | H | H | H | H | H | H |
| V-2 | CH₃ | H | H | H | H | CH₃ | H | H | H | H |
| V-3 | t-C₄H₉ | H | H | H | H | t-C₄H₉ | H | H | H | H |
| V-4 | OCH₃ | H | H | H | H | OCH₃ | H | H | H | H |
| V-5 | OPh | H | H | H | H | OPh | H | H | H | H |
| V-6 | N(C₂H₅)₂ | H | H | H | H | N(C₂H₅)₂ | H | H | H | H |
| V-7 | N(Ph)₂ | H | H | H | H | N(Ph)₂ | H | H | H | H |
| V-8 | Ph | H | H | H | H | Ph | H | H | H | H |
| V-9 |  (p-tolyl) | | | | |  (p-tolyl) | | | | |
| V-10 | H | CH₃ | H | H | H | H | CH₃ | H | H | H |
| V-11 | H | H | CH₃ | H | H | H | H | CH₃ | H | H |
| V-12 | H | CH₃ | CH₃ | CH₃ | CH₃ | H | CH₃ | CH₃ | CH₃ | CH₃ |
| V-13 | CH₃ | CH₃ | CH₃ | CH₃ | CH₃ | CH₃ | CH₃ | CH₃ | CH₃ | CH₃ |
| V-14 | H | Ph | Ph | Ph | H | H | Ph | Ph | Ph | H |
| V-17 |  (4-biphenylyl) | | | | |  (4-biphenylyl) | | | | |
| V-18 | t-C₄H₉ | H | H | H | H | t-C₄H₉ | H | H | H | H |
| V-19 |  (10-methylanthracen-9-yl) | | | | | (10-methylanthracen-9-yl) | | | | |

-continued

| Compound No. | M31 | M32 | M33 | M34 | M35 | M41 | M42 | M43 | M44 | M45 |
|---|---|---|---|---|---|---|---|---|---|---|
| V-20 | 1-naphthyl | H | H | H | H | 1-naphthyl | H | H | H | H |
| V-21 | cyclohexyl | H | H | H | H | cyclohexyl | H | H | H | H |
| V-22 | 2-phenyl-oxadiazolyl | H | H | H | H | 2-phenyl-oxadiazolyl | H | H | H | H |
| V-23 | 5-methyl-thienyl | H | H | H | H | 5-methyl-thienyl | H | H | H | H |
| V-24 | biphenyl | H | H | H | H | biphenyl | H | H | H | H |

-continued

| Compound No. | M31 | M32 | M33 | M34 | M35 | M41 | M42 | M43 | M44 | M45 |
|---|---|---|---|---|---|---|---|---|---|---|
| V-25 | H | H | 2-biphenyl | H | H | H | H | 4-methylbiphenyl | H | H |
| V-26 | H | H | H | H | H | 2-biphenyl | H | H | H | H |
| V-27 | H | H | 4-methylbiphenyl | H | H | H | H | 2-biphenyl | H | H |
| V-28 | H | H | Ph | Ph | H | H | H | Ph | H | Ph |
| V-29 | H | H | Ph | Ph | Ph | H | H | Ph | Ph | H |

| Compound No. | M31 | M32 | M33 | M34 | M35 | M41 | M42 | M43 | M44 | M45 |
|---|---|---|---|---|---|---|---|---|---|---|
| VI-1 | H | H | H | H | H | H | H | H | H | H |
| VI-2 | CH$_3$ | H | H | H | H | CH$_3$ | H | H | H | H |
| VI-3 | t-C$_4$H$_9$ | H | H | H | H | t-C$_4$H$_9$ | H | H | H | H |
| VI-4 | OCH$_3$ | H | H | H | H | OCH$_3$ | H | H | H | H |
| VI-5 | OPh | H | H | H | H | OPh | H | H | H | H |
| VI-6 | N(C$_2$H$_5$)$_2$ | H | H | H | H | N(C$_2$H$_5$)$_2$ | H | H | H | H |
| VI-7 | N(Ph)$_2$ | H | H | H | H | N(Ph)$_2$ | H | H | H | H |
| VI-8 | Ph | H | H | H | H | Ph | H | H | H | H |
| VI-9 | p-tolyl | H | H | H | H | p-tolyl | H | H | H | H |
| VI-10 | H | CH$_3$ | H | H | H | H | CH$_3$ | H | H | H |
| VI-11 | H | H | CH$_3$ | H | H | H | H | CH$_3$ | H | H |
| VI-12 | H | H | H | CH$_3$ | H | H | H | H | CH$_3$ | H |
| VI-13 | CH$_3$ | H | H | H | CH$_3$ | CH$_3$ | H | H | H | CH$_3$ |
| VI-14 | H | Ph | H | H | H | H | Ph | H | H | H |
| VI-15 | H | H | Ph | H | H | H | H | Ph | H | H |
| VI-16 | H | H | H | Ph | H | H | H | H | Ph | H |
| VI-17 | 4-biphenylyl | H | H | H | H | 4-biphenylyl | H | H | H | H |
| VI-18 | t-C$_4$H$_9$ | H | H | H | H | 10-methylanthracen-9-yl | H | H | H | H |
| VI-19 | 10-methylanthracen-9-yl | H | H | H | H | 10-methylanthracen-9-yl | H | H | H | H |

-continued

| Compound No. | M31 | M32 M33 | M34 M35 | M41 | M42 M43 | M44 M45 |
|---|---|---|---|---|---|---|
| VI-20 | 1-naphthyl | H H | H H | 1-naphthyl | H H | H H |
| VI-21 | 9-Ph-10-anthryl | H H | H H | H | H H | H H |
| VI-22 | 10-(4-methylphenyl)-9-anthryl | H H | H H | CH₃ | H H | H H |
| VI-23 | 4-cyclohexyl | H H | H H | 4-cyclohexyl | H H | H H |

-continued
| Compound No. | M31 | M32 | M33 | M34 | M35 | M41 | M42 | M43 | M44 | M45 |
|---|---|---|---|---|---|---|---|---|---|---|
| VI-24 | ![oxadiazole] | H | H | H | H | ![oxadiazole] | H | H | H | H |
| VI-25 | H | H | Ph | Ph | H | H | H | Ph | H | H |
| VI-26 | H | H | Ph | Ph | H | H | Ph | Ph | H | H |
| VI-27 | H | ![4-methylbiphenyl] | H | ![4-methylbiphenyl] | H | H | H | ![4-methylbiphenyl] | H | H |
| VI-28 | H | H | ![2-methylbiphenyl] | H | H | H | H | ![2-methylbiphenyl] | H | H |

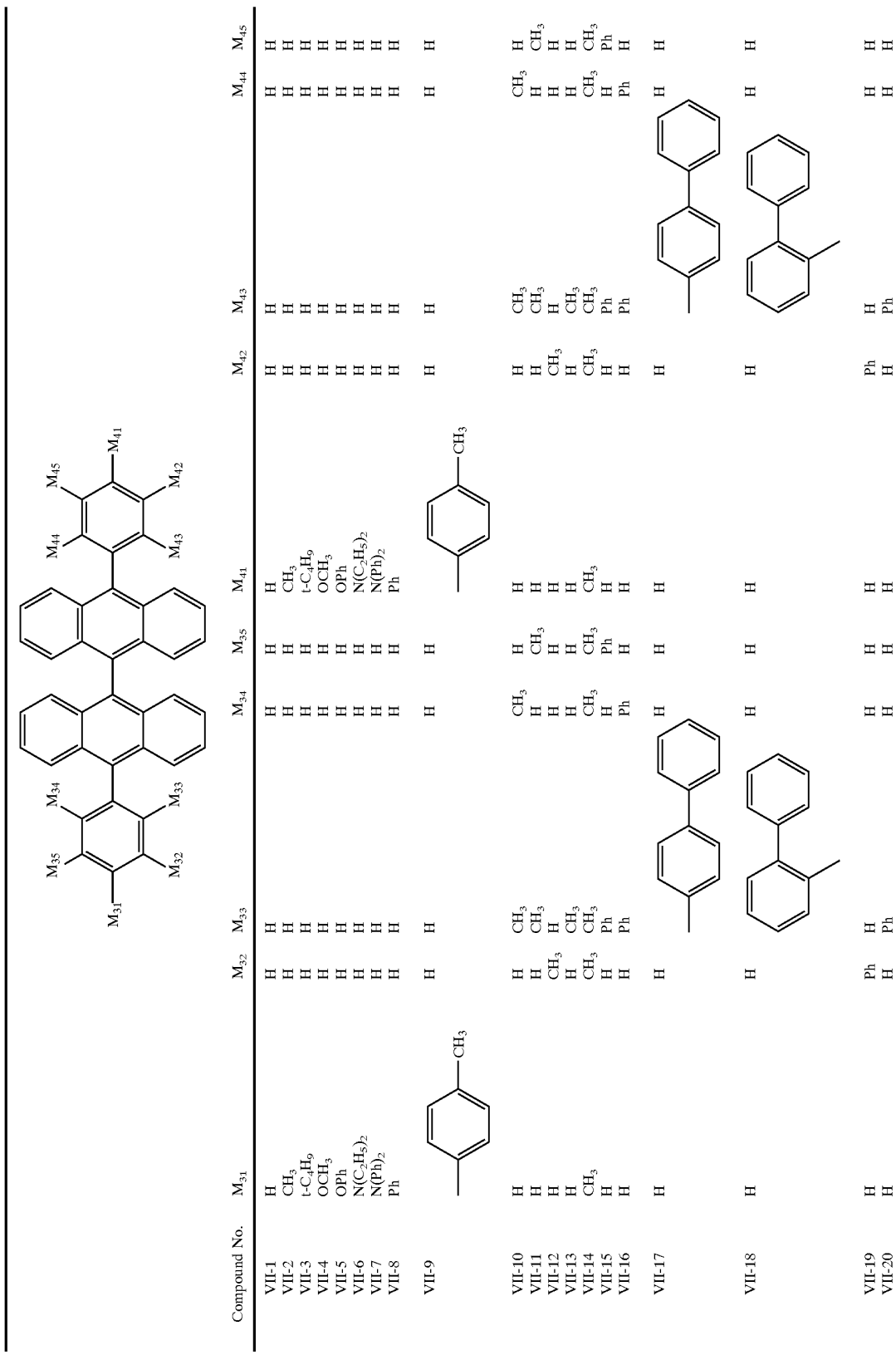

| Compound No. | M₃₁ | M₃₂ | M₃₃ | M₃₄ | M₃₅ | M₄₁ | M₄₂ | M₄₃ | M₄₄ | M₄₅ |
|---|---|---|---|---|---|---|---|---|---|---|
| VII-1 | H | H | H | H | H | H | H | H | H | H |
| VII-2 | CH₃ | H | H | H | H | CH₃ | H | H | H | H |
| VII-3 | t-C₄H₉ | H | H | H | H | t-C₄H₉ | H | H | H | H |
| VII-4 | OCH₃ | H | H | H | H | OCH₃ | H | H | H | H |
| VII-5 | OPh | H | H | H | H | OPh | H | H | H | H |
| VII-6 | N(C₂H₅)₂ | H | H | H | H | N(C₂H₅)₂ | H | H | H | H |
| VII-7 | N(Ph)₂ | H | H | H | H | N(Ph)₂ | H | H | H | H |
| VII-8 | Ph | H | H | H | H | Ph | H | H | H | H |
| VII-9 | p-tolyl | H | H | H | H | p-tolyl | H | H | H | H |
| VII-10 | H | H | CH₃ | CH₃ | H | H | H | CH₃ | CH₃ | H |
| VII-11 | H | CH₃ | H | H | CH₃ | H | CH₃ | H | H | CH₃ |
| VII-12 | H | H | CH₃ | CH₃ | H | H | H | CH₃ | CH₃ | H |
| VII-13 | CH₃ | CH₃ | CH₃ | H | CH₃ | CH₃ | CH₃ | CH₃ | H | CH₃ |
| VII-14 | H | H | Ph | Ph | H | H | H | Ph | Ph | H |
| VII-15 | 4-methylbiphenyl-4'-yl | H | H | H | H | 4-methylbiphenyl-4'-yl | H | H | H | H |
| VII-16 | 2-methylbiphenyl-2'-yl | H | H | H | H | 2-methylbiphenyl-2'-yl | H | H | H | H |
| VII-17 | H | H | H | H | H | H | H | H | H | H |
| VII-18 | H | H | H | H | H | H | H | H | H | H |
| VII-19 | H | Ph | H | H | H | H | Ph | H | H | H |
| VII-20 | H | H | Ph | H | H | H | H | Ph | H | H |

-continued

| Compound No. | $M_{31}$ | $M_{32}$ | $M_{33}$ | $M_{34}$ | $M_{35}$ | $M_{41}$ | $M_{42}$ | $M_{43}$ | $M_{44}$ | $M_{45}$ |
|---|---|---|---|---|---|---|---|---|---|---|
| VII-21 | 4-methylphenyl | H | H | H | H | 4-methylphenyl | H | H | H | H |
| VII-22 | t-C$_4$H$_9$ | H | H | H | H | H | H | H | H | H |
| VII-23 | 4-methylbiphenyl | H | H | H | H | 4-methylbiphenyl | H | H | H | H |
| VII-24 | cyclohexyl | H | H | H | H | cyclohexyl | H | H | H | H |
| VII-25 | 2-phenyl-5-methyl-oxadiazolyl | H | H | H | H | 2-phenyl-5-methyl-oxadiazolyl | H | H | H | H |
| VII-26 | 2,5-dimethylthienyl | H | H | H | H | 2,5-dimethylthienyl | H | H | H | H |
| VII-27 | C(CH$_3$)=C(Ph)$_2$ with Ph | H | H | H | H | C(CH$_3$)=C(Ph)$_2$ with Ph | H | H | H | H |
| VII-28 | n-C$_4$H$_9$ | H | H | H | H | n-C$_4$H$_9$ | H | H | H | H |
| VII-29 | H | H | OCH$_3$ | H | H | H | H | OCH$_3$ | H | H |
| VII-30 | H | R$_{32}$ and R$_{33}$ form a fused benzene ring. | | H | H | H | R$_{32}$ and R$_{33}$ form a fused benzene ring. | | H | H |

-continued
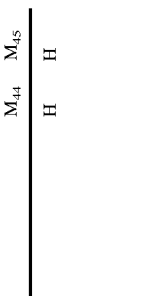
| Compound No. | M31 | M32 | M33 | M34 | M35 | M41 | M42 | M43 | M44 | M45 |
|---|---|---|---|---|---|---|---|---|---|---|
| VII-31 |  | H | H | H | H |  | H | H | H | H |
| VII-32 | H | H | 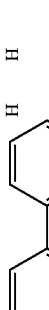 | H | H | H | H | 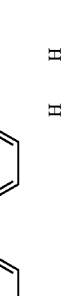 | H | H |
| VII-33 | H | H | H | H | H | H | H | H | H | H |
| VII-34 | H | H |  | H | H | H | H |  | H | H |
| VII-35 | H | H | 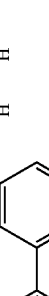 | H | H | H | H |  | H | H |
| VII-36 | H | Ph | Ph | Ph | Ph | H | H | Ph | H | Ph |
| VII-37 | H | Ph | Ph | Ph | H | H | Ph | Ph | Ph | H |

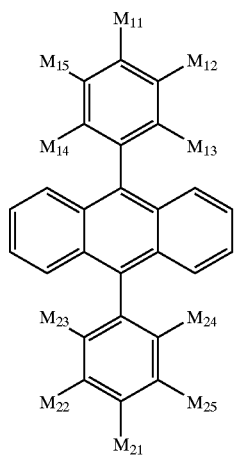

| Compound No. | $M^{11}=M^{21}$ | $M^{12}=M^{22}$ | $M^{13}=M^{23}$ | $M^{14}=M^{24}$ | $M^{15}=M^{25}$ |
|---|---|---|---|---|---|
| VIII'-1 | H | H | H | H | H |
| VIII'-2 | CH₃ | H | H | H | H |
| VIII'-3 | H | CH₃ | H | H | H |
| VIII'-4 | H | H | CH₃ | H | H |
| VIII'-5 | Ph | H | CH₃ | CH₃ | H |
| VIII'-6 | H | Ph | H | H | H |
| VIII'-7 | H | H | Ph | H | H |
| VIII'-8 | H | H | Ph | Ph | H |
| VIII'-9 | H | H | Ph | H | Ph |
| VIII'-10 | H | H | –C₆H₄–C₆H₄– (4,4'-biphenyl) | H | H |
| VIII'-11 | –C₆H₄–C₆H₄– (4,4'-biphenyl) | H | H | H | H |
| VIII'-12 | H | H | 2-methylbiphenyl | H | H |
| VIII'-13 | 2-methylbiphenyl | H | H | H | H |
| VIII'-14 | N(Ph)₂ | H | H | H | H |
| VIII'-15 | N(C₂H₅)₂ | H | H | H | H |
| VIII'-16 | OCH₃ | H | H | H | H |
| VIII'-17 | Oph | H | H | H | H |
| VIII'-18 | 4-methylphenyl | H | H | H | H |
| VIII'-19 | styryl (–CH=CH–C₆H₅) | H | H | H | H |

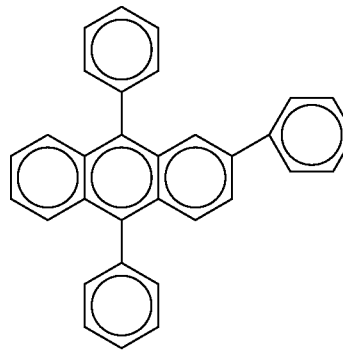
VIII-1
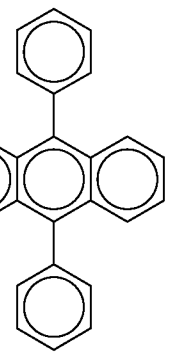
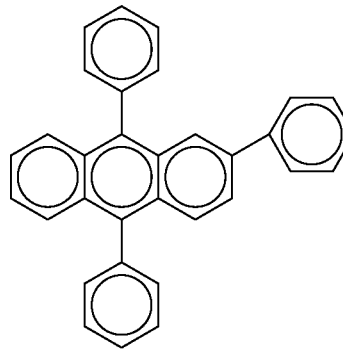
VIII-2
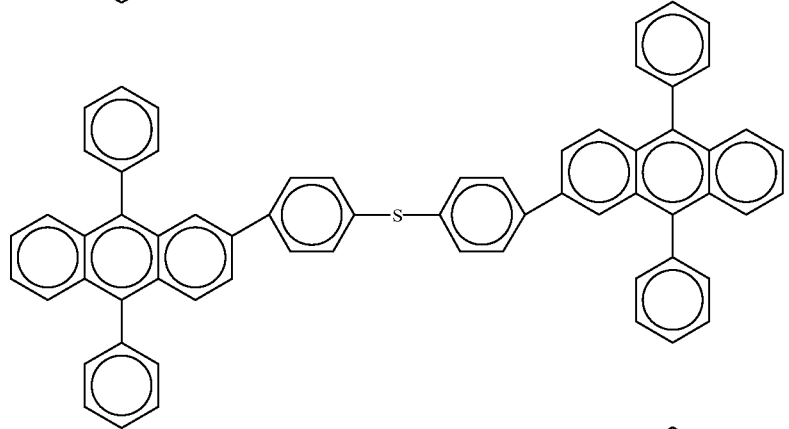
VIII-3
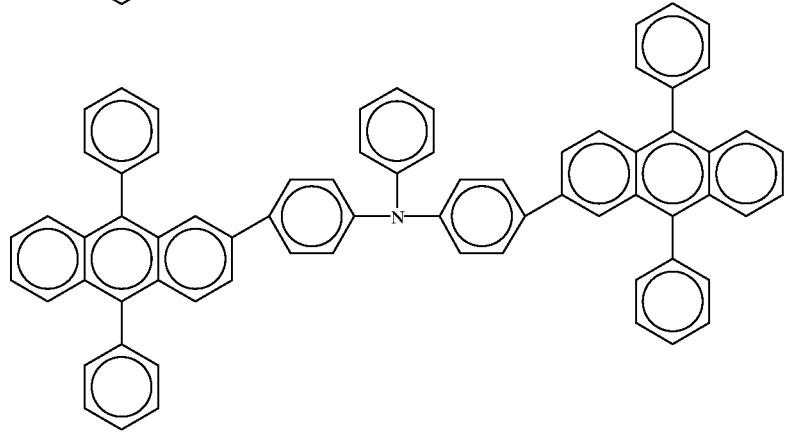
VIII-4

VIII-5
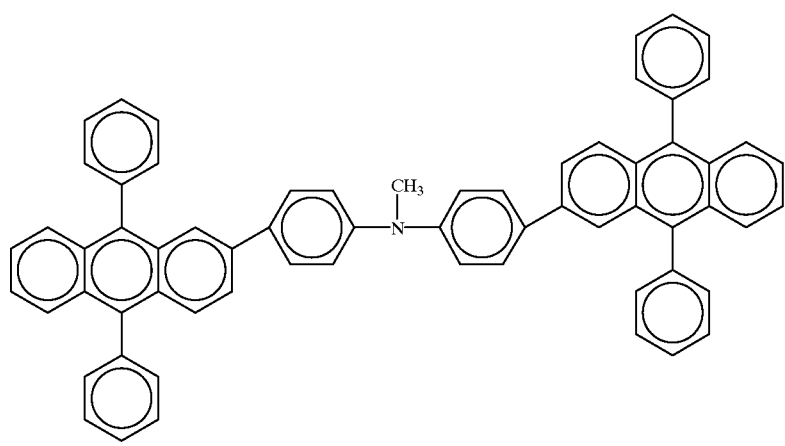
VIII-6
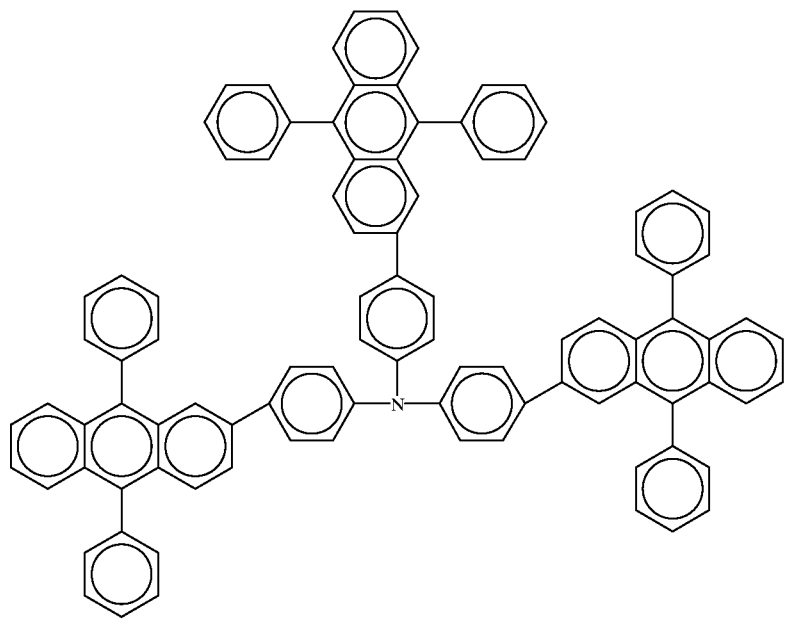
VIII-7
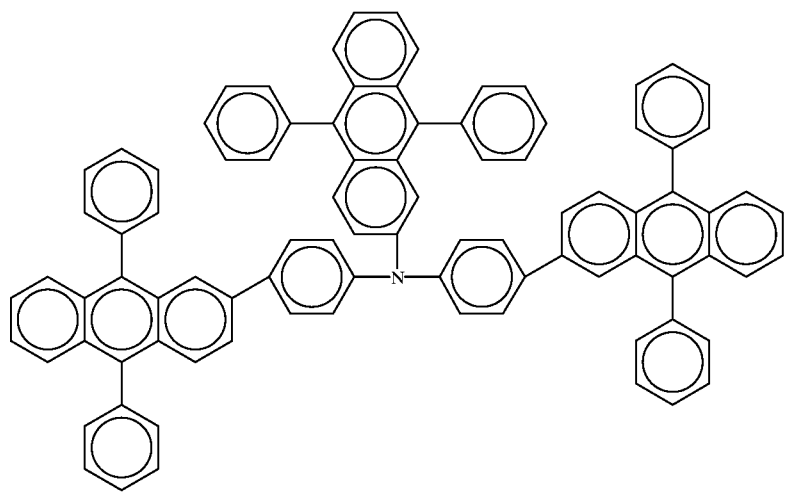

-continued
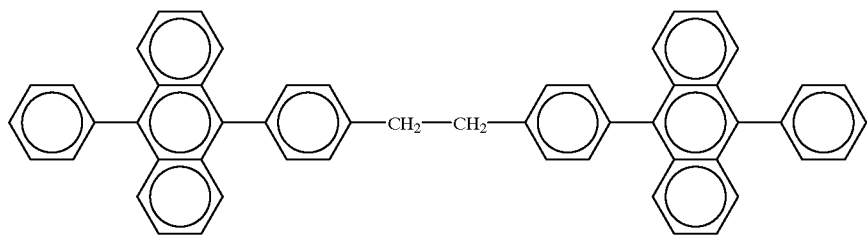
IX-1
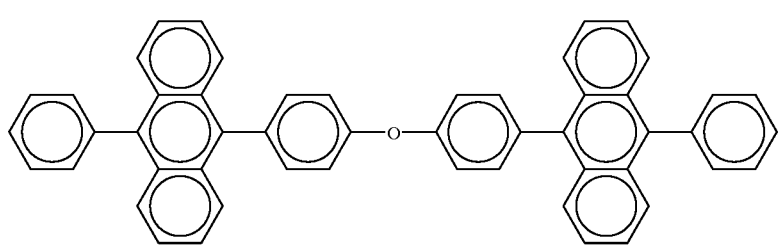
IX-2
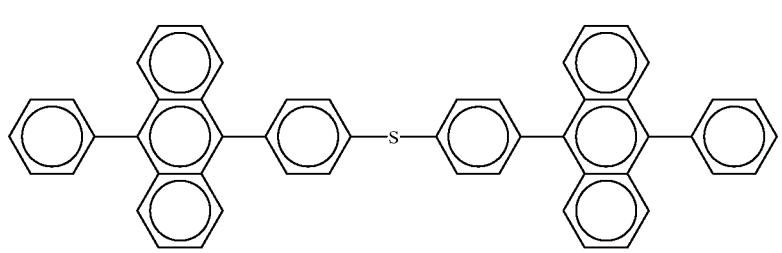
IX-3
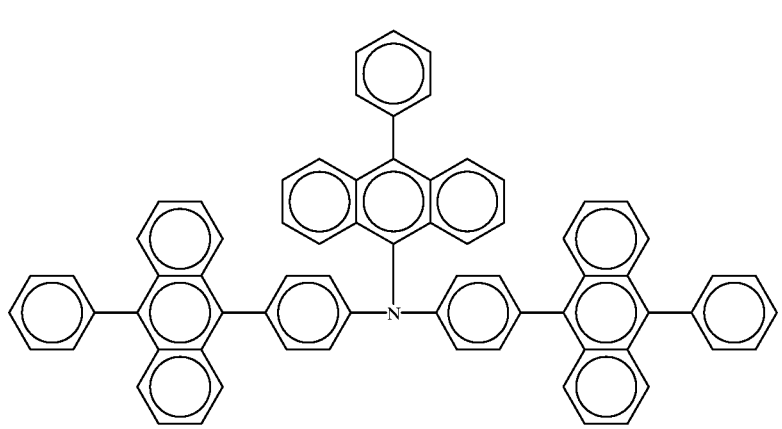
IX-4
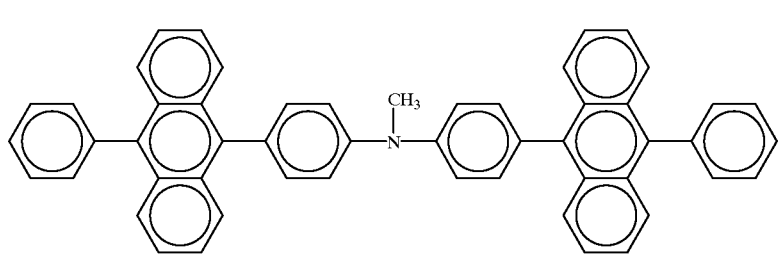
IX-5

-continued

IX-6

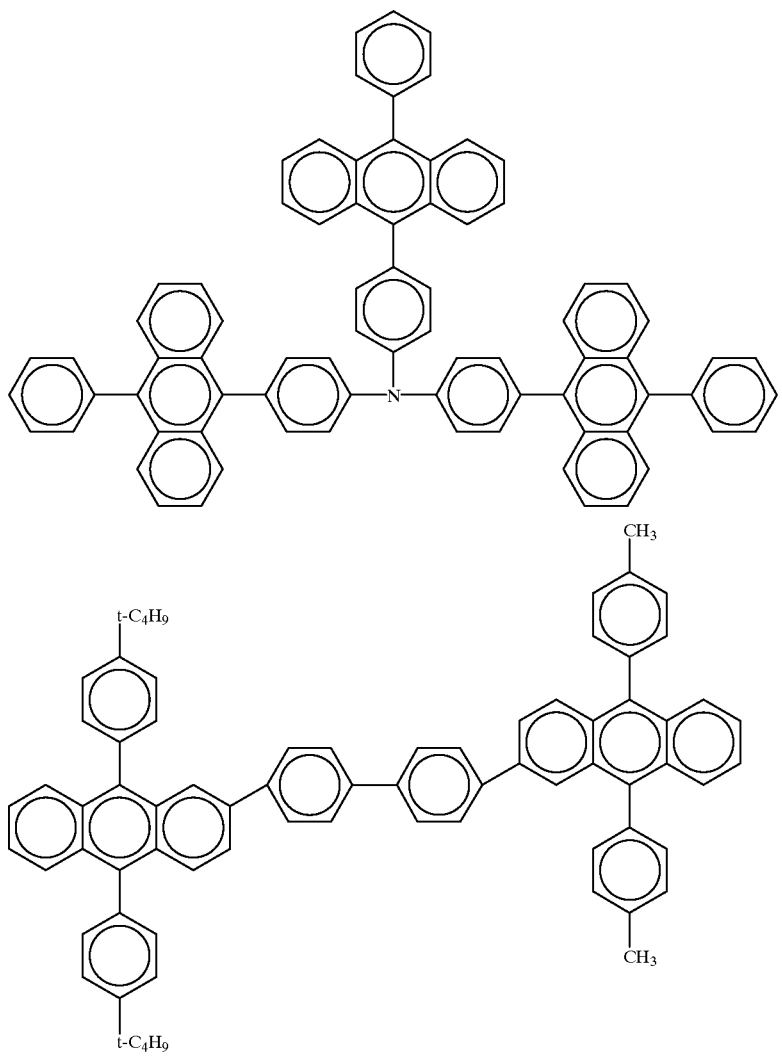

The phenylanthracene derivatives used herein can be prepared by coupling a halogenated diphenylanthracene compound with Ni(cod)$_2$ wherein cod represents 1,5-cyclooctadiene, or cross-coupling a Grignard reagent of a dihalogenated aryl with a nickel complex such as NiCl$_2$(dppe) or NiCl$_2$(dppp) wherein dppe represents diphenylphosphinoethane and dppp represents diphenylphosphinopropane. Alternatively, the phenylanthracene derivatives are prepared by a cross-coupling process involving reacting anthraquinone, benzoquinone, phenylanthrone or bianthrone with a Grignard reagent of aryl or a lithiated aryl followed by reduction.

These compounds can be identified by elemental analysis, mass analysis, IR spectroscopy, $^1$H and $^{13}$C NMR, etc.

In general, the phenylanthracene derivatives have a molecular weight of about 400 to about 2,000, preferably about 400 to about 1,000, a high melting point of about 200 to about 500° C., and a high glass transition temperature (Tg) of about 80 to about 250° C., preferably about 100 to 250° C., more preferably about 130 to 250° C., especially about 150 to 250° C. By conventional vacuum deposition or the like, they form a transparent, smooth film of quality which maintains a stable amorphous state even above room temperature and over a long period of time.

Since the phenylanthracene derivatives are relatively neutral compounds, better results are obtained on use of them in a light emitting layer. A freedom of design of the recombination/light emitting region is available by controlling the film thickness in consideration of the carrier mobility and carrier density (which is dependent on ionization potential and electron affinity) of the light emitting layer, hole injecting and transporting layer, and electron injecting and transporting layer to be combined. This enables free design of luminous color, control of the luminance and spectrum of light emission by the interference of the electrodes, and control of the space distribution of light emission.

Quinoxaline Compounds

A still further class of organic compounds useful as the host material according to the invention are quinoxaline compounds of the following formula (IV).

$$Q_n\text{-}L_{101} \tag{IV}$$

Herein Q is a pyrazinyl radical having fused thereto a six-membered aromatic ring containing 0 to 2 nitrogen atoms and may be the same or different, and n is 2 or 3. Two or three Q radicals may be the same or different. The six-membered aromatic rings forming part of Q are preferably benzene, pyridine, pyrimidine and pyridazine rings. Such a six-membered aromatic ring may be fused to the pyrazine ring at any positions although it is preferred that carbon atoms be present and nitrogen atoms be absent at the fusion positions. It is therefore preferred that fusion be on the side between the 2 and 3-positions or 5 and 6-positions on the pyrazine ring, and on the side between the 2 and 3-positions (or 5 and 6-positions) or the side between the 3 and 4-positions (or 4 and 5-positions) on the pyridine ring, on the side between the 4 and 5-positions (or 5 and 6-positions) on the pyrimidine ring, and on the side between the 3 and 4-positions (or 5 and 6-positions) or the side between the 5 and 4-positions on the pyridazine ring.

$L_{101}$ is a single bond or n-valent radical, i.e., di- or trivalent radical. Preferred divalent radicals are arenediyl radicals, such as phenylene, biphenyldiyl, naphthalenediyl, anthracenediyl and pyrenediyl. Preferred trivalent radicals are arenetriyl radicals (e.g., benzenetriyl), nitrogen atoms, and triarylaminetriyl radicals (e.g., triphenylaminetriyl).

The radicals represented by Q and $L_{101}$ may further have substituents. Such substituents may be ones containing Q therein. The total number of Q radicals per molecule should preferably be 2 to 10, more preferably 2 to 4. Two or more Q radicals included in one molecule may be the same or different although they are often the same for the sake of easy synthesis.

Of the quinoxaline compounds of formula (IV), those of formula (VIII) are preferred.

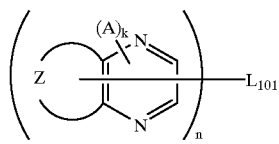

(VIII)

In formula (VIII), Z is a group of atoms necessary to form a benzene, pyridine, pyrimidine or pyridazine ring with the two carbon atoms of the pyrazine ring.

The ring completed by Z may further have a substituent(s) or a fused ring. The preferred positions of fusion of the ring completed by Z to the pyrazine ring are the same as described above in conjunction with formula (IV).

A is a monovalent substituent attached to the pyrazine ring, and k is 0, 1 or 2. Preferred examples of the substituents on the ring completed by Z and the substituents represented by A are the same as $A_{13}$ etc. in formulas (VIII-a) to (VIII-m) to be described later and will be described later.

The letter n is 2 or 3. When n is 2, $L_{101}$ is a single bond, phenylene, biphenyldiyl or naphthalenediyl radical. When n is 3, $L_{101}$ is a benzenetriyl radical, nitrogen atom or triphenylaminetriyl radical. These radicals will be described later in conjunction with formulas (VIII-a) to (VIII-m).

The rings completed by Z may be the same or different although they are preferably the same as described in conjunction with formula (IV).

The fused pyrazine ring having the ring completed by Z may be bonded, at any position, to $L_{101}$.

Of the quinoxaline compounds of formula (VIII), those of formulas (VIII-a) to (VIII-m) are preferred.

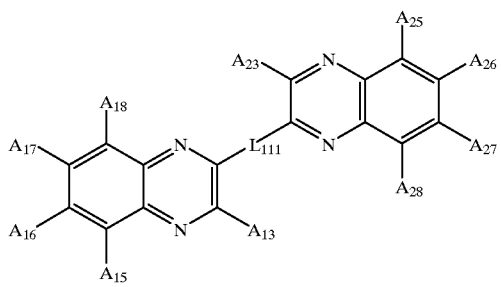

(VIII-a)

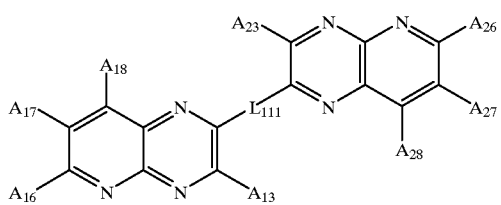

(VIII-b)

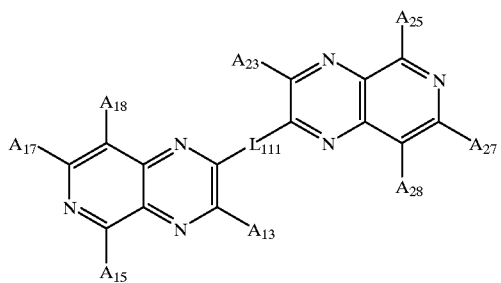

(VIII-c)

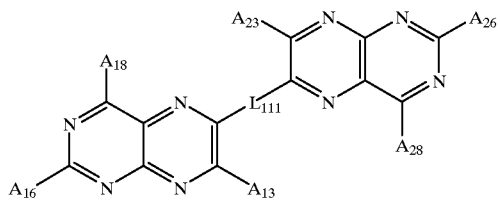

(VIII-d)

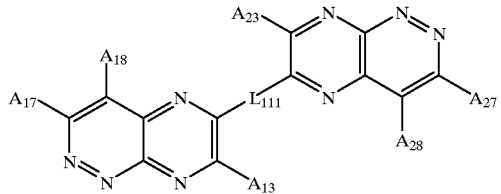

(VIII-e)

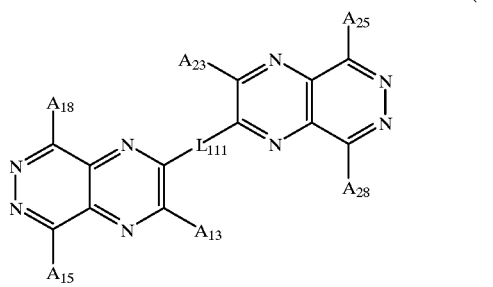

(VIII-f)

-continued
(VIII-g)
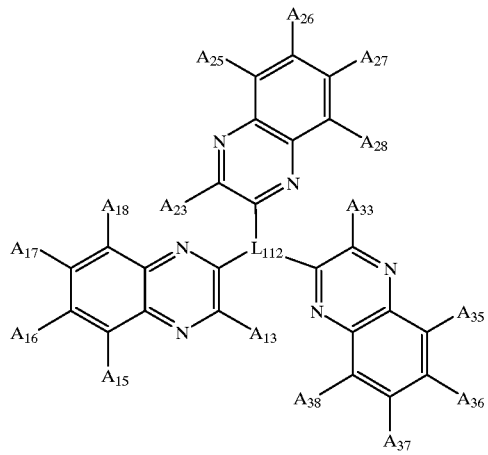
(VIII-h)
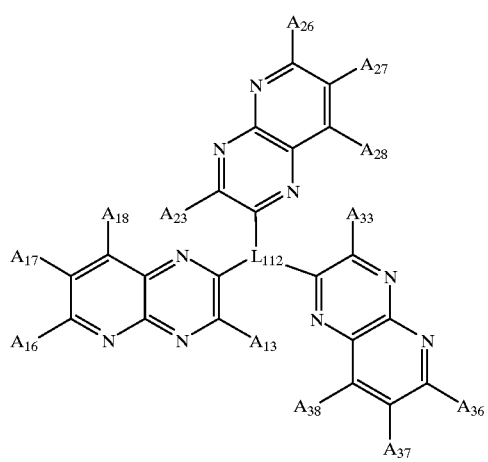
(VIII-i)
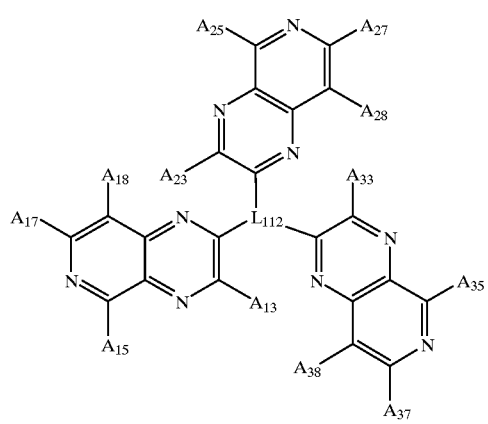
-continued
(VIII-j)
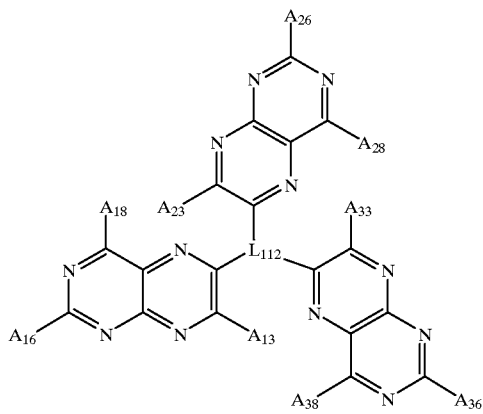
(VIII-k)
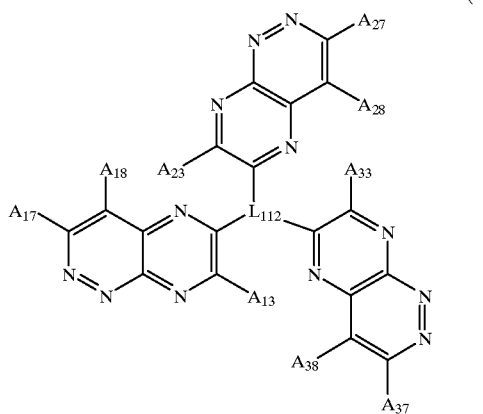
(VIII-l)
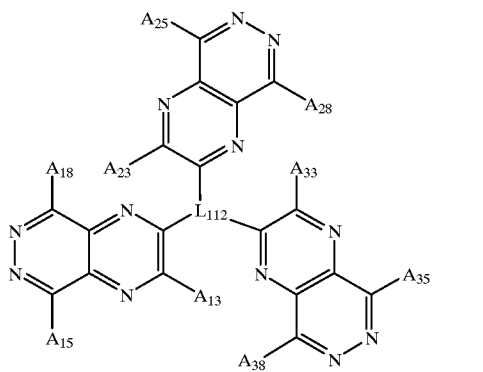
(VIII-m)
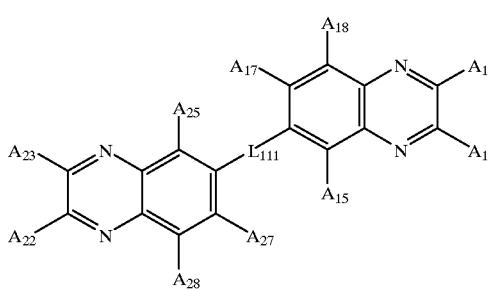

-continued (VIII-m)

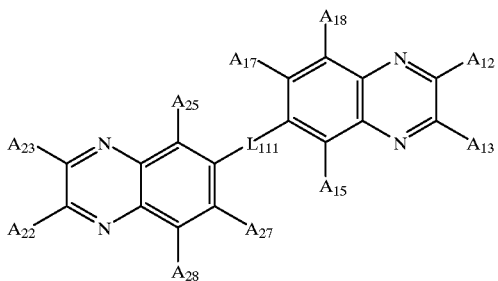

First described are those compounds wherein $L_{101}$ in formula (VIII) is a divalent radical $L_{111}$ or single bond, as represented by formulas (VIII-a) to (VIII-f) and (VIII-m).

In formulas (VIII-a) to (VIII-f) and (VIII-m), $L_{111}$ is a phenylene, biphenyldiyl or naphthalenediyl radical. The phenylene radical represented by $L_{111}$ may be an o-, m- or p-phenylene radical, with the p-phenylene being especially preferred. The preferred biphenyldiyl radical represented by $L_{111}$ is 4,4'-biphenyl-1,1'-diyl. The preferred naphthalenediyl radical represented by $L_{111}$ is 1,5-naphthalenediyl. These divalent radicals are preferably unsubstituted although they may have substituents such as alkyl and aryl groups.

$A_{13}$, $A_{15}$ to $A_{18}$, $A_{23}$, $A_{25}$ to $A_{28}$ in formula (VIII-a), $A_{13}$, $A_{16}$ to $A_{18}$, $A_{23}$, $A_{26}$ to $A_{28}$ in formula (VIII-b), $A_{13}$, $A_{15}$, $A_{17}$, $A_{18}$, $A_{23}$, $A_{25}$, $A_{27}$ and $A_{28}$ in formula (VIII-c), $A_{13}$, $A_{16}$, $A_{18}$, $A_{23}$, $A_{26}$ and $A_{28}$ in formula (VIII-d), $A_{13}$, $A_{17}$, $A_{18}$, $A_{23}$, $A_{27}$ and $A_{28}$ in formula (VIII-e), $A_{13}$, $A_{15}$, $A_{18}$, $A_{23}$, $A_{25}$ and $A_{28}$ in formula (VIII-f), $A_{12}$, $A_{13}$, $A_{15}$, $A_{17}$, $A_{18}$, $A_{22}$, $A_{23}$, $A_{25}$, $A_{27}$ and $A_{28}$ in formula (VIII-m) each independently stand for hydrogen, halogen atoms, hydroxyl, carboxy, nitro, cyano, alkyl, aryl, alkoxy, aryloxy, amino, alkylthio, arylthio and heterocyclic radicals. In each formula, these radicals may be the same or different.

Examples of the halogen atoms represented by $A_{13}$ etc. include fluorine and chlorine atoms.

The alkyl radicals represented by $A_{13}$ etc. are preferably those of 1 to 6 carbon atoms in total, which may be straight or branched. The alkyl radicals are preferably unsubstituted ones although they may have substituents such as halogen atoms (e.g., F and Cl). Illustrative examples of the alkyl radicals include methyl, ethyl, n-propyl, isopropyl, n-butyl, isobutyl, sec-butyl, t-butyl, pentyl and hexyl.

The aryl radicals represented by $A_{13}$ etc. are preferably those of 6 to 30 carbon atoms in total, which may be monocyclic or polycyclic (fused ring or ring collection) or have substituents. Such substituents are halogen atoms (e.g., F and Cl), alkyl groups (e.g., methyl) and heterocyclic groups. The heterocyclic groups as the substituent are preferably the same as the fused pyrazinyl radical bonded to $L_{111}$ in formula (VIII-a), such as quinoxalinyl. Illustrative examples of the aryl radicals represented by $A_{13}$, etc. include phenyl, 1-naphthyl, 2-naphthyl, 2-biphenylyl, 3-biphenylyl, and 4-biphenylyl radicals, which may have substituted thereon a fused pyradinyl group such as quinoxalinyl.

The alkoxy radicals represented by $A_{13}$, etc. are preferably those of alkyls of 1 to 6 carbon atoms in total. The alkoxy radicals are preferably unsubstituted ones although they may have substituents. Illustrative examples of the alkoxy radicals include methoxy, ethoxy, propoxy, isopropoxy, butoxy, isobutoxy, sec-butoxy and t-butoxy.

Exemplary of the aryloxy radicals represented by $A_{13}$, etc. is phenoxy.

The amino radicals represented by $A_{13}$, etc. may have substituents such as alkyl and aryl groups. Exemplary amino radicals are amino, methylamino, dimethylamino, phenylamino and diphenylamino.

Examples of the alkylthio radical represented by $A_{13}$, etc. include methylthio and ethylthio.

Exemplary of the arylthio radical represented by $A_{13}$, etc. is phenylthio.

Examples of the heterocyclic radicals represented by $A_{13}$, etc. include furyl, thienyl, pyrrole, pyridyl, and quinolyl as well as the same as the fused pyradinyl radical bonded to $L_{111}$ in formula (VIII-a) such as quinoxalinyl.

Two adjoining ones among $A_{15}$ to $A_{18}$ and $A_{25}$ to $A_{28}$ in formula (VIII-a), two adjoining ones among $A_{16}$ to $A_{18}$ and $A_{26}$ to $A_{28}$ in formula (VIII-b), a pair of $A_{17}$ and $A_{18}$ or a pair of $A_{27}$ and $A_{28}$ in formula (VIII-c), a pair of $A_{17}$ and $A_{18}$ or a pair of $A_{27}$ and $A_{28}$ in formula (VIII-e), and a pair of $A_{12}$ and $A_{13}$, a pair of $A_{17}$ and $A_{18}$, a pair of $A_{22}$ and $A_{23}$ or a pair of $A_{27}$ and $A_{28}$ in formula (VIII-m) may bond together to form a ring. The ring formed herein is preferably a benzene ring. Two or more benzene rings thus formed may be fused together, or the benzene ring thus formed may further have a ring fused thereto.

In preferred embodiments, $A_{13}$ and $A_{23}$ in formulas (VIII-a) to (VIII-f) and $A_{12}$, $A_{13}$, $A_{22}$ and $A_{23}$ in formula (VIII-m) are aryl radicals; $A_{15}$ to $A_{18}$ and $A_{25}$ to $A_{28}$ in formula (VIII-a) are hydrogen, alkyl or alkoxy radicals or two adjoining ones thereof bond together to form a benzene ring; and $A_{16}$ to $A_{18}$ and $A_{26}$ to $A_{28}$ in formula (VIII-b), $A_{15}$, $A_{17}$, $A_{18}$, $A_{25}$, $A_{27}$ and $A_{28}$ in formula (VIII-c), $A_{16}$, $A_{18}$, $A_{26}$ and $A_{28}$ in formula (VIII-d), $A_{17}$, $A_{18}$, $A_{27}$ and $A_{28}$ in formula (VIII-e), $A_{15}$, $A_{18}$, $A_{25}$ and $A_{28}$ in formula (VIII-f), and $A_{15}$, $A_{17}$, $A_{18}$, $A_{25}$, $A_{27}$ and $A_{28}$ in formula (VIII-m) are hydrogen.

Described next are those compounds wherein $L_{101}$ in formula (VIII) is a trivalent radical $L_{112}$, as represented by formulas (VIII-g) to (VIII-l).

In formulas (VIII-g) to (VIII-l), $L_{112}$ is a benzenetriyl radical, nitrogen atom or triphenylaminetriyl radical. The preferred benzenetriyl radical represented by $L_{112}$ is 1,3,5-benzenetriyl. The preferred triphenylaminetriyl radical represented by $L_{112}$ is 4,4',4''-triphenyl-1,1',1''-triyl. These trivalent radicals are preferably unsubstituted although they may have substituents such as alkyl and aryl groups.

$A_{13}$, $A_{15}$ to $A_{18}$, $A_{23}$, $A_{25}$ to $A_{28}$, $A_{33}$, $A_{35}$ to $A_{38}$ in formula (VIII-g), $A_{13}$, $A_{16}$ to $A_{18}$, $A_{23}$, $A_{26}$ to $A_{28}$, $A_{33}$, $A_{36}$ to $A_{38}$ in formula (VIII-h), $A_{13}$, $A_{15}$, $A_{17}$, $A_{18}$, $A_{23}$, $A_{25}$, $A_{27}$, $A_{28}$, $A_{33}$, $A_{35}$, $A_{37}$ and $A_{38}$ in formula (VIII-i), $A_{13}$, $A_{16}$, $A_{18}$, $A_{23}$, $A_{26}$, $A_{28}$, $A_{33}$, $A_{36}$ and $A_{38}$ in formula (VIII-j), $A_{13}$, $A_{17}$, $A_{18}$, $A_{23}$, $A_{27}$, $A_{28}$, $A_{33}$, $A_{37}$ and $A_{38}$ in formula (VIII-k), $A_{13}$, $A_{15}$, $A_{18}$, $A_{23}$, $A_{25}$ $A_{28}$, $A_{33}$, $A_{35}$ and $A_{38}$ in formula (VIII-l) each independently stand for hydrogen, halogen atoms, hydroxyl, carboxy, nitro, cyano, alkyl, aryl, alkoxy, aryloxy, amino, alkylthio, arylthio and heterocyclic radicals. In each formula, these radicals may be the same or different. Illustrative examples of these radicals are the same as described above in conjunction with formulas (VIII-a) to (VIII-f).

Two adjoining ones among $A_{15}$ to $A_{18}$, $A_{25}$ to $A_{28}$ and $A_{35}$ to $A_{38}$ in formula (VIII-g), two adjoining ones among $A_{16}$ to $A_{18}$, $A_{26}$ to $A_{28}$ and $A_{36}$ to $A_{38}$ in formula (VIII-h), a pair of $A_{17}$ and $A_{18}$ or a pair of $A_{27}$ and $A_{28}$, or a pair of $A_{37}$ and $A_{38}$ in formula (VIII-i), and a pair of $A_{17}$ and $A_{18}$, a pair of $A_{27}$ and $A_{28}$ or a pair of $A_{37}$ and $A_{38}$ in formula (VIII-k) may bond together to form a ring. Illustrative examples of the ring are the same as described above in conjunction with formulas (VIII-a) to (VIII-f). $A_{13}$, $A_{23}$ and $A_{33}$ in formulas (VIII-a) to (VIII-l) are preferably hydrogen and aryl radicals such as phenyl.

In preferred embodiments, $A_{15}$ to $A_{18}$, $A_{25}$ to $A_{28}$ and $A_{35}$ to $A_{38}$ in formula (VIII-g) are hydrogen, or two adjoining ones among them bond together to form a ring; $A_{16}$ to $A_{18}$, $A_{26}$ to $A_{28}$, and $A_{36}$ to $A_{38}$ in formula (VIII-h), $A_{15}$, $A_{17}$, $A_{18}$, $A_{25}$, $A_{27}$, $A_{28}$, $A_{35}$, $A_{37}$ and $A_{38}$ in formula (VIII-i), $A_{16}$, $A_{18}$, $A_{26}$, $A_{28}$, $A_{36}$ and $A_{38}$ in formula (VIII-j), $A_{17}$, $A_{18}$, $A_{27}$, $A_{28}$, $A_{37}$ and $A_{38}$ in formula (VIII-k), $A_{15}$, $A_{18}$, $A_{25}$ $A_{28}$, $A_{35}$ and $A_{38}$ in formula (VIII-l) are hydrogen.

Illustrative, non-limiting, examples of the quinoxaline compounds of formula (IV) are given below. They are shown by combinations of $L_{111}$, $L_{112}$, and A's in formulas (VIII-a) to (VIII-m). When $A_{13}$ and $A_{23}$ are different, they are individually shown. The expressions of formulas (VIII-a) to (VIII-m) are typical examples and to be construed to encompass corresponding structural isomers because an actual product as synthesized is a mixture of structural isomers due to the synthesis route.

Formula (VIII)

| Compound No. | $L_{111}$ | $A_{13}=A_{23}$ | $A_{15}=A_{15}$ | $A_{16}=A_{26}$ | $A_{17}=A_{27}$ | $A_{18}=A_{28}$ |
|---|---|---|---|---|---|---|
| VIII-a-1 | biphenyl | —Ph | H | H | H | H |
| VIII-a-2 | biphenyl | —Ph | H | H | $CH_3$ | H |
| VIII-a-3 | biphenyl | —Ph | H | $CH_3$ | $CH_3$ | H |
| VIII-a-4 | biphenyl | —Ph | H | H | $C_2H_5$ | H |
| VIII-a-5 | biphenyl | —Ph | H | H | $n\text{-}C_3H_7$ | H |
| VIII-a-6 | biphenyl | —Ph | H | H | $n\text{-}C_4H_9$ | H |
| VIII-a-7 | biphenyl | —Ph | H | H | $t\text{-}C_4H_9$ | H |
| VIII-a-8 | biphenyl | —Ph | H | H | —$OCH_3$ | H |
| VIII-a-9 | biphenyl | —Ph | | | $A_{17}$ and $A_{18}$ form a benzene ring, $A_{27}$, $A_{28}$ form a benzene ring | |

-continued

| | Structure | | | |
|---|---|---|---|---|
| VIII-a-10 | biphenyl | —Ph | H | H |
| VIII-a-11 | biphenyl | —Ph | H | $A_{16}$ and $A_{17}$ form a benzene ring. $A_{26}$ and $A_{27}$ form a benzene ring. |
| VIII-a-12 | biphenyl | —Ph | H | $A_{17}$ and $A_{18}$ form a benzene ring. $A_{27}$ and $A_{28}$ form a benzene ring. |
| VIII-a-13 | biphenyl | —Ph | $A_{15}$ and $A_{16}$ form a benzene ring. $A_{25}$ and $A_{26}$ form a benzene ring | $A_{16}$ and $A_{18}$, and $A_{17}$ and $A_{18}$ form benzene rings, respectively, which are fused to form a phenalene ring as a whole. (The same applies to $A_{26}$ to $A_{28}$.) |
| VIII-a-14 | biphenyl | —Ph | H | $A_{15}$ and $A_{16}$, $A_{16}$ and $A_{17}$, and $A_{17}$ and $A_{18}$ form benzene rings, respectively, which form a phenanthrene ring as a whole. (The same applies to $A_{25}$ to $A_{28}$.) |
| VIII-a-15 | biphenyl | —Ph | H | —Ph |
| VIII-a-16 | biphenyl | —Ph | —Ph | —Ph |
| VIII-a-17 | biphenyl | —Ph | H | H |
| VIII-a-18 | biphenyl | —Ph | H | H |
| VIII-a-19 | biphenyl | —Ph | H | H |

Additional column (rightmost substituent) for rows VIII-a-17 to VIII-a-19: 1-naphthyl, 2-naphthyl, 4-biphenylyl respectively (with H in the final column).

-continued

| | | | | | |
|---|---|---|---|---|---|
| VIII-a-20 | biphenyl-Ph | —Ph | H | H | 3-biphenylyl | H |
| VIII-a-21 | biphenyl-Ph | —Ph | H | H | 2-biphenylyl | H |
| VIII-a-22 | biphenyl-Ph | —Ph | H | 4-biphenylyl | 4-biphenylyl | H |
| VIII-a-23 | biphenyl-Ph | —Ph | H | H | Cl | H |
| VIII-a-24 | biphenyl-Ph | —Ph | H | H | —OH | H |
| VIII-a-25 | biphenyl-Ph | —Ph | H | H | —NO$_2$ | H |
| VIII-a-26 | biphenyl-Ph | —Ph | H | H | —CN | H |
| VIII-a-27 | biphenyl-Ph | —Ph | H | H | —OPh | H |
| VIII-a-28 | biphenyl-Ph | —Ph | H | H | —SCH$_3$ | H |
| VIII-a-29 | biphenyl-Ph | —Ph | H | H | —SPh | H |

-continued
| | | | | | | |
|---|---|---|---|---|---|---|
| VIII-a-30 | 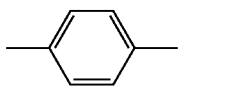 | —Ph | H | H | H | H |
| VIII-a-31 | 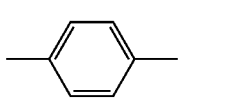 | —Ph | H | H | CH$_3$ | H |
| VIII-a-32 |  | —Ph | H | CH$_3$ | CH$_3$ | H |
| VIII-a-33 | 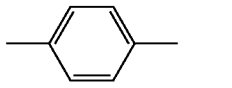 | —Ph | CH$_3$ | CH$_3$ | H | H |
| VIII-a-34 |  | —Ph | H | H | C$_2$H$_5$ | CH$_3$ |
| VIII-a-35 |  | —Ph | H | H | n-C$_3$H$_7$ | H |
| VIII-a-36 | 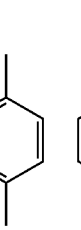 | —Ph | H | H | n-C$_4$H$_9$ | H |
| VIII-a-37 | 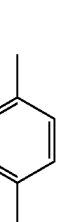 | —Ph | H | H | t-C$_4$H$_9$ | H |
| VIII-a-38 | 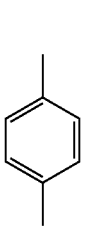 | —Ph | H | H | —OCH$_3$ | H |
| VIII-a-39 | 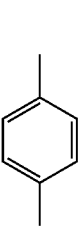 | —Ph | H | H | H | A$_{17}$ and A$_{18}$ form a benzene ring. A$_{27}$ and A$_{28}$ form a benzene ring. |

| | | | |
|---|---|---|---|
| VIII-a-40 | ⬡ | —Ph | H | H | A₁₆ and A₁₇ form a benzene ring, A₂₆ and A₂₇ form a benzene ring |
| VIII-a-41 | ⬡ | —Ph | A₁₅ and A₁₆ form a benzene ring, A₂₅ and A₂₆ form a benzene ring. | A₁₇ and A₁₈ form a benzene ring. A₂₇ and A₂₈ form a benzene ring. |
| VIII-a-42 | ⬡ | —Ph | H | A₁₆ and A₁₈ and A₁₇ and A₁₈ form benzene rings, respectively, which are fused to form a phenalene ring as a whole. (The same applies to A₂₆ to A₂₈.) |
| VIII-a-43 | ⬡ | —Ph | A₁₅ and A₁₆A₁₆ and A₁₇, and A₁₇ and A₁₈ form benzene rings, respectively, which form a phenanthrene ring as a whole. (The same applies to A₂₅ to A₂₈.) |
| VIII-a-44 | ⬡ | —Ph | H | H |
| VIII-a-45 | ⬡ | —Ph | H | —Ph |
| VIII-a-46 | ⬡ | —Ph | —Ph | H |
| VIII-a-47 | ⬡ | —Ph | H | 1-naphthyl |
| VIII-a-48 | ⬡ | —Ph | H | 2-naphthyl |
| VIII-a-49 | ⬡ | —Ph | H | 4-biphenylyl |

-continued

| ID | Ar | | | | | |
|---|---|---|---|---|---|---|
| VIII-a-50 | (1,4-phenylene) | —Ph | H | H | 3-biphenylyl | H |
| VIII-a-51 | (1,4-phenylene) | —Ph | H | H | 2-biphenylyl | H |
| VIII-a-52 | (1,4-phenylene) | —Ph | H | H | Cl | H |
| VIII-a-53 | (1,4-phenylene) | —Ph | H | H | —OH | H |
| VIII-a-54 | (1,4-phenylene) | —Ph | H | H | —NO₂ | H |
| VIII-a-55 | (1,4-phenylene) | —Ph | H | H | —CN | H |
| VIII-a-56 | (1,4-phenylene) | —Ph | H | H | —OPh | H |
| VIII-a-57 | (1,4-phenylene) | —Ph | H | H | —SCH₃ | H |
| VIII-a-58 | (1,4-phenylene) | —Ph | H | H | —SPh | H |
| VIII-a-59 | (2,6-naphthylene) | —Ph | H | H | H | H |

-continued

| | | | | | |
|---|---|---|---|---|---|
| VIII-a-60 | naphthyl | —Ph | H | H | CH₃ | H |
| VIII-a-61 | naphthyl | —Ph | H | CH₃ | CH₃ | H |
| VIII-a-62 | naphthyl | —Ph | CH₃ | CH₃ | H | CH₃ |
| VIII-a-63 | naphthyl | —Ph | CH₃ | H | CH₃ | H |
| VIII-a-64 | naphthyl | —Ph | CH₃ | CH₃ | CH₃ | CH₃ |
| VIII-a-65 | naphthyl | —Ph | H | H | C₂H₅ | H |
| VIII-a-66 | naphthyl | —Ph | H | H | n-C₃H₇ | H |
| VIII-a-67 | naphthyl | —Ph | H | H | n-C₄H₉ | H |
| VIII-a-68 | naphthyl | —Ph | H | H | t-C₄H₉ | H |

-continued

| | | | | | |
|---|---|---|---|---|---|
| VIII-a-69 | [naphthyl] | —Ph | H | H | —OCH₃ | H |
| VIII-a-70 | [naphthyl] | —Ph | H | H | $A_{17}$ and $A_{18}$ form a benzene ring. $A_{27}$ and $A_{28}$ form a benzene ring. | |
| VIII-a-71 | [naphthyl] | —Ph | H | $A_{16}$ and $A_{17}$ form a benzene ring. $A_{26}$ and $A_{27}$ form a benzene ring. | H | |
| VIII-a-72 | [naphthyl] | —Ph | H | $A_{15}$ and $A_{16}$ form a benzene ring. $A_{25}$ and $A_{26}$ form a benzene ring. | $A_{17}$ and $A_{18}$ form a benzene ring. $A_{27}$ and $A_{28}$ form a benzene ring | |
| VIII-a-73 | [naphthyl] | —Ph | H | H | $A_{16}$ and $A_{18}$ and $A_{17}$ and $A_{16}$ form benzene rings, respectively, which are fused to form a phenalene ring as a whole. (The same applies to $A_{26}$ to $A_{26}$.) | |
| VIII-a-74 | [naphthyl] | —Ph | $A_{15}$ and $A_{16}$ $A_{16}$ and $A_{17}$ and $A_{17}$ and $A_{18}$ form benzene rings, respectively, which form a phenanthrene ring as a whole. (The same applies to $A_{25}$ to $A_{28}$.) | | | |
| VIII-a-75 | [naphthyl] | —Ph | H | H | —Ph | H |
| VIII-a-76 | [naphthyl] | —Ph | H | —Ph | H | H |
| VIII-a-77 | [naphthyl] | —Ph | —Ph | H | H | —Ph |

-continued

| | | | | | |
|---|---|---|---|---|---|
| VIII-a-78 | naphthyl-2,6-diyl | —Ph | H | H | 1-naphthyl | H |
| VIII-a-79 | naphthyl-2,6-diyl | —Ph | H | H | 2-naphthyl | H |
| VIII-a-80 | naphthyl-2,6-diyl | —Ph | H | H | 4-biphenylyl | H |
| VIII-a-81 | naphthyl-2,6-diyl | —Ph | H | H | 3-biphenylyl | H |
| VIII-a-82 | naphthyl-2,6-diyl | —Ph | H | H | 2-biphenylyl | H |
| VIII-a-83 | naphthyl-2,6-diyl | —Ph | H | H | Cl | H |
| VIII-a-84 | naphthyl-2,6-diyl | —Ph | H | H | —OH | H |
| VIII-a-85 | naphthyl-2,6-diyl | —Ph | H | H | —NO$_2$ | H |
| VIII-a-86 | naphthyl-2,6-diyl | —Ph | H | H | —CN | H |

-continued
| | | | | | |
|---|---|---|---|---|---|
| VIII-a-87 | 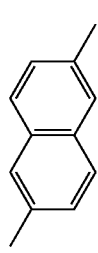 | —Ph | H | H | H |
| VIII-a-88 |  | —Ph | H | —OPh | H |
| VIII-a-89 | 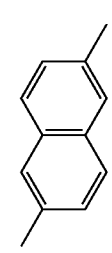 | —Ph | H | —SCH₃ | H |
| VIII-a-90 | 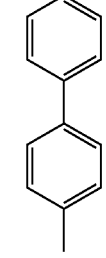 | $A_{13}=$ 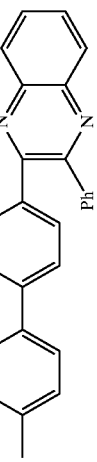 | H | —SPh | H |
| VIII-a-91 | 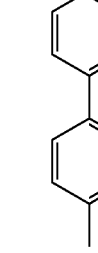 | $A_{23}=$ —Ph<br>$A_{13}=$  | H | H | H |
| VIII-a-92 |  | $A_{23}=$ —Ph<br>$A_{13}=$ 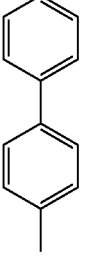 | $A_{15}$ and $A_{16}$ form a benzene ring.<br>$A_{25}$ and $A_{26}$ form a benzen ring. | H | H |
|  |  |  | $A_{15}$ and $A_{16}$ form a benzene ring.<br>$A_{25}$ and $A_{26}$ form a benzene ring. | $A_{17}$ and $A_{18}$ form a benzene ring.<br>$A_{27}$ and $A_{28}$ form a benzene ring. | H |

-continued

| | | | |
|---|---|---|---|
| VIII-a-93 | [p-tolyl] | [phenyl-quinoxaline with Ph]<br>A₂₃ = —Ph<br>A₁₃ = | H | H | H |
| VIII-a-94 | [p-tolyl] | [benzo-quinoxaline with Ph]<br>A₂₃ = —Ph<br>A₁₃ = | H | A₁₅ and A₁₆ form a benzene ring.<br>A₂₅ and A₂₆ form a benzene ring. | H |
| VIII-a-95 | [p-tolyl] | [dibenzo-quinoxaline with Ph]<br>A₂₃ = —Ph<br>A₁₃ = | H | A₁₅ and A₁₆ form a benzene ring.<br>A₂₅ and A₂₆ form a benzene ring. | A₁₇ and A₁₈ form a benzene ring.<br>A₂₇ and A₂₈ form a benzene ring. |
| VIII-a-96 | [biphenyl-methyl] | —Ph | H | —NPh₂ | H |
| VIII-a-97 | [biphenyl-methyl] | —Ph | H | —COOH | H |

| Compound No. | | | | | |
|---|---|---|---|---|---|
| VIII-a-98 | 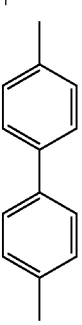 | —Ph | H | H | 2-pyridyl | H |
| VIII-a-99 | 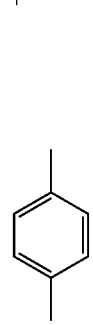 | —Ph | H | H | —NPh$_2$ | H |
| VIII-a-100 | 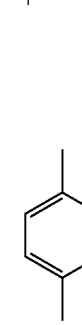 | —Ph | H | H | —COOH | H |
| VIII-a-101 | 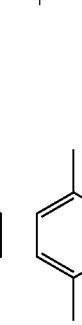 | —Ph | H | H | 2-pyridyl | H |
| VIII-a-102 | 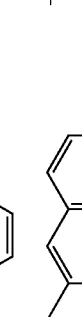 | —Ph | H | H | —NPh$_2$ | H |
| VIII-a-103 | 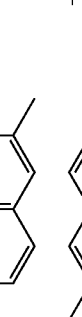 | —Ph | H | H | —COOH | H |
| VIII-a-104 | 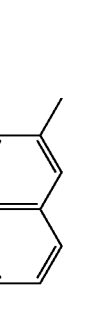 | —Ph | H | H | 2-pyridyl | H |
| Formula (VIII) Compound No. | L$_{111}$ | A$_{13}$=A$_{23}$ | A$_{16}$=A$_{26}$ | A$_{17}$=A$_{27}$ | A$_{18}$=A$_{28}$ |
|---|---|---|---|---|---|
| VIII-b-1 | 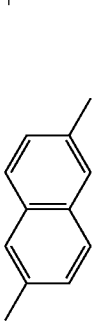 | —Ph | H | H | H |
| VIII-b-2 | 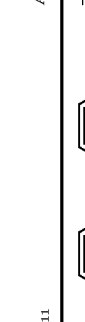 | —Ph | H | H | H |

-continued
| | | | | | |
|---|---|---|---|---|---|
| VIII-b-3 | 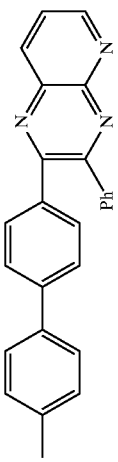 | —Ph | H | H | H |
| VIII-b-4 | 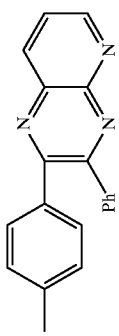 | $A_{13}=$ 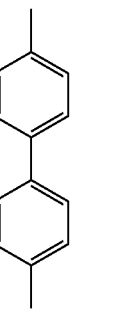 | H | H | H |
| VIII-b-5 | 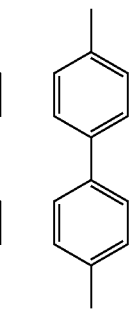 | $A_{23}=$ —Ph<br>$A_{13}=$ 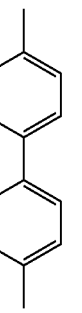 | H | H | H |
| VIII-b-6 | 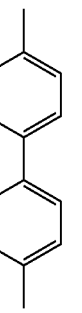 | $A_{23}=$ —Ph | H | H | CH$_3$ |
| VIII-b-7 | | —Ph | H | CH$_3$ | H |
| VIII-b-8 | | —Ph | CH$_3$ | H | H |
| VIII-b-9 | | —Ph | H | C$_2$H$_5$ | H |

| | | | | |
|---|---|---|---|---|
| VIII-b-10 | biphenyl | —Ph | H | n-C$_3$H$_7$ | H |
| VIII-b-11 | biphenyl | —Ph | H | n-C$_4$H$_9$ | H |
| VIII-b-12 | biphenyl | —Ph | H | t-C$_4$H$_9$ | H |
| VIII-b-13 | biphenyl | —Ph | H | —OCH$_3$ | H |
| VIII-b-14 | biphenyl | —Ph | | A$_{16}$ and A$_{17}$ form a benzene ring. A$_{26}$ and A$_{27}$ form a benzene ring. | H |
| VIII-b-15 | biphenyl | —Ph | H | | A$_{17}$ and A$_{18}$ form a benzene ring. A$_{27}$ and A$_{28}$ form a benzene ring. |
| VIII-b-16 | biphenyl | —Ph | H | Ph | H |
| VIII-b-17 | biphenyl | —Ph | Ph | Ph | H |
| VIII-b-18 | biphenyl | —Ph | H | 1-naphthyl | H |
| VIII-b-19 | biphenyl | —Ph | 1-naphthyl | 1-naphthyl | H |

-continued

| | | | | |
|---|---|---|---|---|
| VIII-b-20 | biphenyl | —Ph | H | 2-naphthyl | H |
| VIII-b-21 | biphenyl | —Ph | 2-naphthyl | 2-naphthyl | H |
| VIII-b-22 | biphenyl | —Ph | H | 4-biphenylyl | H |
| VIII-b-23 | biphenyl | —Ph | 4-biphenylyl | 4-biphenylyl | H |
| VIII-b-24 | biphenyl | —Ph | H | 3-biphenylyl | H |
| VIII-b-25 | biphenyl | —Ph | 3-biphenylyl | 3-biphenylyl | H |
| VIII-b-26 | biphenyl | —Ph | H | 2-biphenylyl | H |
| VIII-b-27 | biphenyl | —Ph | 2-biphenylyl | 2-biphenylyl | H |
| VIII-b-28 | biphenyl | —Ph | H | Cl | H |
| VIII-b-29 | biphenyl | —Ph | H | —OH | H |

-continued

| | | | | |
|---|---|---|---|---|
| VIII-b-30 | biphenyl | —Ph | H | —NO₂ | H |
| VIII-b-31 | biphenyl | —Ph | H | —CN | H |
| VIII-b-32 | biphenyl | —Ph | H | —OPh | H |
| VIII-b-33 | biphenyl | —Ph | H | —SCH₃ | H |
| VIII-b-34 | biphenyl | —Ph | H | —SPh | H |
| VIII-b-35 | biphenyl | —Ph | H | —NPh₂ | H |
| VIII-b-36 | biphenyl | —Ph | H | —COOH | H |
| VIII-b-37 | biphenyl | —Ph | H | 2-pyridyl | H |
| VIII-b-38 | phenyl | —Ph | H | H | CH₃ |
| VIII-b-39 | phenyl | —Ph | H | CH₃ | H |

-continued

| | | | | |
|---|---|---|---|---|
| VIII-b-40 | —Ph | —⟨benzene⟩— | CH₃ | H | H |
| VIII-b-41 | —Ph | —⟨benzene⟩— | H | H | H |
| VIII-b-42 | —Ph | —⟨benzene⟩— | H | $C_2H_5$ | H |
| VIII-b-43 | —Ph | —⟨benzene⟩— | H | $n\text{-}C_3H_7$ | H |
| VIII-b-44 | —Ph | —⟨benzene⟩— | H | $n\text{-}C_4H_9$ | H |
| VIII-b-45 | —Ph | —⟨benzene⟩— | H | $t\text{-}C_4H_9$ | H |
| VIII-b-46 | —Ph | —⟨benzene⟩— | H | —OCH₃ | H |
| VIII-b-47 | —Ph | —⟨benzene⟩— | H | $A_{16}$ and $A_{17}$ form a benzene ring. $A_{26}$ and $A_{27}$ form a benzene ring. | H |
| VIII-b-48 | —Ph | —⟨benzene⟩— | H | Ph | $A_{17}$ and $A_{18}$ form a benzene ring. $A_{27}$ and $A_{28}$ form a benzene ring. |
| VIII-b-49 | —Ph | —⟨benzene⟩— | Ph | Ph | H |

-continued

| | | | | |
|---|---|---|---|---|
| VIII-b-50 | ⌬ (para-disubstituted phenyl) | —Ph | H | 1-naphthyl | H |
| VIII-b-51 | ⌬ | —Ph | 1-naphthyl | 1-naphthyl | H |
| VIII-b-52 | ⌬ | —Ph | H | 2-naphthyl | H |
| VIII-b-53 | ⌬ | —Ph | 2-naphthyl | 2-naphthyl | H |
| VIII-b-54 | ⌬ | —Ph | H | 4-biphenylyl | H |
| VIII-b-55 | ⌬ | —Ph | 4-biphenylyl | 4-biphenylyl | H |
| VIII-b-56 | ⌬ | —Ph | H | 3-biphenylyl | H |
| VIII-b-57 | ⌬ | —Ph | 3-biphenylyl | 3-biphenylyl | H |
| VIII-b-58 | ⌬ | —Ph | H | 2-biphenylyl | H |
| VIII-b-59 | ⌬ | —Ph | 2-biphenylyl | 2-biphenylyl | H |

-continued

| | | | | |
|---|---|---|---|---|
| VIII-b-60 | phenylene | —Ph | H | Cl | H |
| VIII-b-61 | phenylene | —Ph | H | —OH | H |
| VIII-b-62 | phenylene | —Ph | H | —NO$_2$ | H |
| VIII-b-63 | phenylene | —Ph | H | —CN | H |
| VIII-b-64 | phenylene | —Ph | H | —OPh | H |
| VIII-b-65 | phenylene | —Ph | H | —SCH$_3$ | H |
| VIII-b-66 | phenylene | —Ph | H | —SPh | H |
| VIII-b-67 | phenylene | —Ph | H | —NPh$_2$ | H |
| VIII-b-68 | phenylene | —Ph | H | —COOH | H |
| VIII-b-69 | phenylene | —Ph | H | 2-pyridyl | H |

-continued

| | | | | | |
|---|---|---|---|---|---|
| VIII-b-70 | naphthalene | —Ph | H | H | CH₃ |
| VIII-b-71 | naphthalene | —Ph | H | CH₃ | H |
| VIII-b-72 | naphthalene | —Ph | CH₃ | H | H |
| VIII-b-73 | naphthalene | —Ph | H | C₂H₅ | H |
| VIII-b-74 | naphthalene | —Ph | H | n-C₃H₇ | H |
| VIII-b-75 | naphthalene | —Ph | H | n-C₄H₉ | H |
| VIII-b-76 | naphthalene | —Ph | H | H | t-C₄H₉ |
| VIII-b-77 | naphthalene | —Ph | H | t-C₄H₉ | H |
| VIII-b-78 | naphthalene | —Ph | H | —OCH₃ | H |

| | | | |
|---|---|---|---|
| VIII-b-79 | naphthalene-2,6-diyl | —Ph | H | H |
| VIII-b-80 | naphthalene-2,6-diyl | —Ph | H | A$_{16}$ and A$_{17}$ form a benzene ring. A$_{26}$ and A$_{27}$ form a benzene ring. |
| VIII-b-81 | naphthalene-2,6-diyl | —Ph | H | A$_{17}$ and A$_{18}$ form a benzene ring. A$_{27}$ and A$_{28}$ form a benzene ring. |
| VIII-b-82 | naphthalene-2,6-diyl | —Ph | —Ph | H |
| VIII-b-83 | naphthalene-2,6-diyl | —Ph | Ph | Ph |
| VIII-b-84 | naphthalene-2,6-diyl | —Ph | H | 1-naphthyl |
| VIII-b-85 | naphthalene-2,6-diyl | —Ph | 1-naphthyl | H |
| VIII-b-86 | naphthalene-2,6-diyl | —Ph | H | 1-naphthyl |
| VIII-b-87 | naphthalene-2,6-diyl | —Ph | H | 2-naphthyl |
| VIII-b-88 | naphthalene-2,6-diyl | —Ph | 2-naphthyl | H |
| VIII-b-89 | naphthalene-2,6-diyl | —Ph | H | 2-naphthyl |
| VIII-b-90 | naphthalene-2,6-diyl | —Ph | H | 4-biphenylyl |

Note: row labels VIII-b-79 through VIII-b-87 as shown.

-continued

| | | | | | |
|---|---|---|---|---|---|
| VIII-b-88 | naphthalene | —Ph | 4-biphenylyl | 4-biphenylyl | H |
| VIII-b-89 | naphthalene | —Ph | H | 3-biphenylyl | H |
| VIII-b-90 | naphthalene | —Ph | 3-biphenylyl | 3-biphenylyl | H |
| VIII-b-91 | naphthalene | —Ph | H | 2-biphenylyl | H |
| VIII-b-92 | naphthalene | —Ph | 2-biphenylyl | 2-biphenylyl | H |
| VIII-b-93 | naphthalene | —Ph | H | Cl | H |
| VIII-b-94 | naphthalene | —Ph | H | —OH | H |
| VIII-b-95 | naphthalene | —Ph | H | —NO$_2$ | H |
| VIII-b-96 | naphthalene | —Ph | H | —CN | H |

-continued
| | | | | |
|---|---|---|---|---|
| VIII-b-97 | 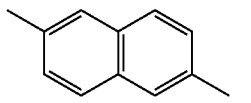 | —Ph | H | —OPh | H |
| VIII-b-98 | 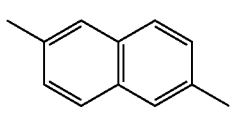 | —Ph | H | —SCH$_3$ | H |
| VIII-b-99 | 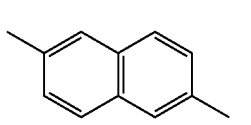 | —Ph | H | —SPh | H |
| VIII-b-100 | 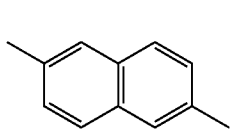 | —Ph | H | —NPh$_2$ | H |
| VIII-b-101 | 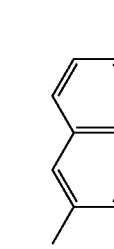 | —Ph | H | —COOH | H |
| VIII-b-102 | 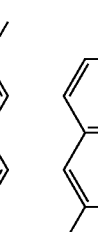 | —Ph | H | 2-pyridyl | H |
| Formula (VIII) Compound No. | L$_{111}$ | A$_{13}$=A$_{23}$ | A$_{15}$=A$_{25}$ | A$_{17}$=A$_{27}$ | A$_{18}$=A$_{28}$ |
|---|---|---|---|---|---|
| VIII-c-1 | 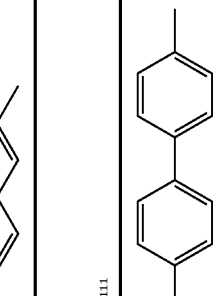 | —Ph | H | H | H |
| VIII-c-2 | 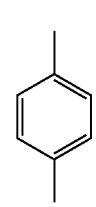 | —Ph | H | H | H |

| | | | | | |
|---|---|---|---|---|---|
| VIII-c-3 | 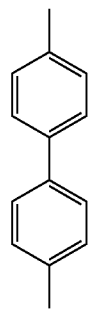 | —Ph | H | H | H |
| VIII-c-4 | 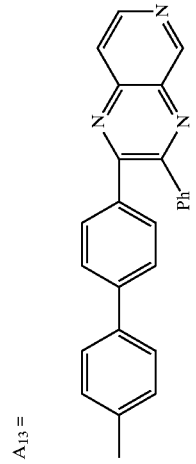 | $A_{13}=$ 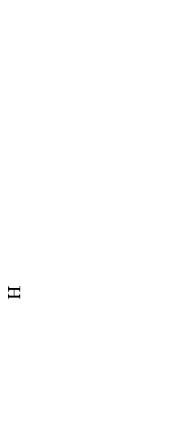 | H | H | H |
| VIII-c-5 | 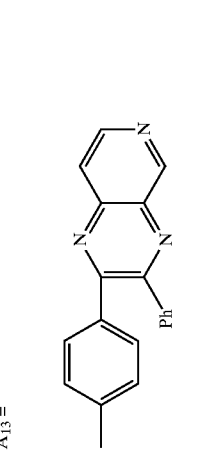 | $A_{23}=$ —Ph<br>$A_{13}=$ 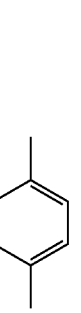 | H | H | H |
| VIII-c-6 | 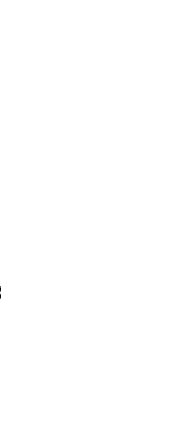 | $A_{23}=$ —Ph<br>—Ph | H | H | CH$_3$ |
| VIII-c-7 |  | —Ph | H | CH$_3$ | H |
| VIII-c-8 |  | —Ph | CH$_3$ | H | H |
| VIII-c-9 |  | —Ph | H | C$_2$H$_5$ | H |

-continued

| | | | | | |
|---|---|---|---|---|---|
| VIII-c-10 | biphenyl | —Ph | H | n-C$_3$H$_7$ | H |
| VIII-c-11 | biphenyl | —Ph | H | n-C$_4$H$_9$ | H |
| VIII-c-12 | biphenyl | —Ph | H | t-C$_4$H$_9$ | H |
| VIII-c-13 | biphenyl | —Ph | H | —OCH$_3$ | H |
| VIII-c-14 | biphenyl | —Ph | H | A$_{17}$ and A$_{18}$ form a benzene ring. A$_{27}$ and A$_{28}$ form a beozene ring. | |
| VIII-c-15 | biphenyl | —Ph | H | H | —Ph |
| VIII-c-16 | biphenyl | —Ph | H | —Ph | H |
| VIII-c-17 | biphenyl | —Ph | —Ph | H | H |
| VIII-c-18 | biphenyl | —Ph | H | 1-naphthyl | H |
| VIII-c-19 | biphenyl | —Ph | H | 2-naphthyl | H |

-continued

| | | | | |
|---|---|---|---|---|
| VIII-c-20 | biphenyl-Ph | —Ph | H | 4-biphenylyl | H |
| VIII-c-21 | biphenyl-Ph | —Ph | H | 3-biphenylyl | H |
| VIII-c-22 | biphenyl-Ph | —Ph | H | 2-biphenylyl | H |
| VIII-c-23 | biphenyl-Ph | —Ph | H | Cl | H |
| VIII-c-24 | biphenyl-Ph | —Ph | H | —OH | H |
| VIII-c-25 | biphenyl-Ph | —Ph | H | —NO$_2$ | H |
| VIII-c-26 | biphenyl-Ph | —Ph | H | —CN | H |
| VIII-c-27 | biphenyl-Ph | —Ph | H | —OPh | H |
| VIII-c-28 | biphenyl-Ph | —Ph | H | —SCH$_3$ | H |
| VIII-c-29 | biphenyl-Ph | —Ph | H | —SPh | H |

-continued
| | | | | |
|---|---|---|---|---|
| VIII-c-30 | 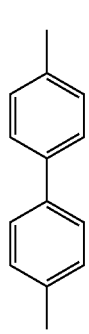 | —Ph | H | —NPh₂ | H |
| VIII-c-31 | 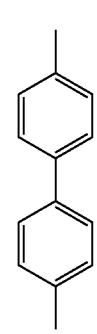 | —Ph | H | —COOH | H |
| VIII-c-32 | 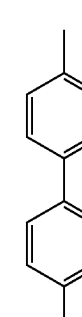 | —Ph | H | 2-pyridyl | H |
| VIII-c-33 |  | —Ph | H | H | CH₃ |
| VIII-c-34 |  | —Ph | H | CH₃ | H |
| VIII-c-35 |  | —Ph | CH₃ | H | H |
| VIII-c-36 |  | —Ph | H | C₂H₅ | H |
| VIII-c-37 |  | —Ph | H | n-C₃H₇ | H |
| VIII-c-38 |  | —Ph | H | n-C₄H₉ | H |
| VIII-c-39 |  | —Ph | H | t-C₄H₉ | H |

-continued

| | | | | |
|---|---|---|---|---|
| VIII-c-40 | ⌬ | —Ph | —OCH₃ | H | H |
| VIII-c-41 | ⌬ | —Ph | H | H | $A_{17}$ and $A_{18}$ form a benzene ring. $A_{27}$ and $A_{28}$ form a benzene ring. |
| VIII-c-42 | ⌬ | —Ph | H | H | —Ph |
| VIII-c-43 | ⌬ | —Ph | H | —Ph | H |
| VIII-c-44 | ⌬ | —Ph | —Ph | H | H |
| VIII-c-45 | ⌬ | —Ph | H | 1-naphthyl | H |
| VIII-c-46 | ⌬ | —Ph | H | 2-naphthyl | H |
| VIII-c-47 | ⌬ | —Ph | H | 4-biphenylyl | H |
| VIII-c-48 | ⌬ | —Ph | H | 3-biphenylyl | H |
| VIII-c-49 | ⌬ | —Ph | H | 2-biphenylyl | H |

-continued
| | | | | |
|---|---|---|---|---|
| VIII-c-50 | 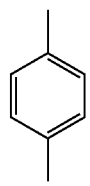 | —Ph | H | Cl | H |
| VIII-c-51 | 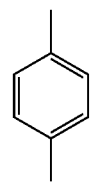 | —Ph | H | —OH | H |
| VIII-c-52 | 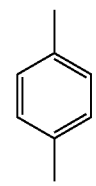 | —Ph | H | —NO$_2$ | H |
| VIII-c-53 | 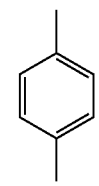 | —Ph | H | —CN | H |
| VIII-c-54 | 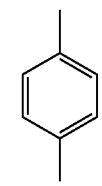 | —Ph | H | —OPh | H |
| VIII-c-55 | 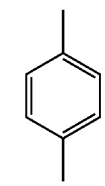 | —Ph | H | —SCH$_3$ | H |
| VIII-c-56 | 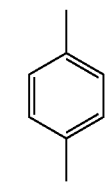 | —Ph | H | —SPh | H |
| VIII-c-57 | 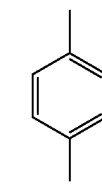 | —Ph | H | —NPh$_2$ | H |
| VIII-c-58 | 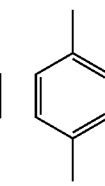 | —Ph | H | —COOH | H |
| VIII-c-59 | 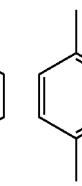 | —Ph | H | 2-pyridyl | H |

-continued

| | | | | | |
|---|---|---|---|---|---|
| VIII-c-60 | naphthyl | —Ph | H | H | CH$_3$ |
| VIII-c-61 | naphthyl | —Ph | H | CH$_3$ | H |
| VIII-c-62 | naphthyl | —Ph | CH$_3$ | H | H |
| VIII-c-63 | naphthyl | —Ph | H | C$_2$H$_5$ | H |
| VIII-c-64 | naphthyl | —Ph | H | n-C$_3$H$_7$ | H |
| VIII-c-65 | naphthyl | —Ph | H | n-C$_4$H$_9$ | H |
| VIII-c-66 | naphthyl | —Ph | H | t-C$_4$H$_9$ | H |
| VIII-c-67 | naphthyl | —Ph | H | —OCH$_3$ | H |
| VIII-c-68 | naphthyl | —Ph | H | | A$_{17}$ and A$_{18}$ form a benzene ring. A$_{27}$ and A$_{28}$ form a benzene ring. |

-continued

| | | | | |
|---|---|---|---|---|
| VIII-c-69 | naphthyl | —Ph | H | H | —Ph |
| VIII-c-70 | naphthyl | —Ph | H | —Ph | H |
| VIII-c-71 | naphthyl | —Ph | —Ph | H | H |
| VIII-c-72 | naphthyl | —Ph | H | 1-naphthyl | H |
| VIII-c-73 | naphthyl | —Ph | H | 2-naphthyl | H |
| VIII-c-74 | naphthyl | —Ph | H | 4-biphenylyl | H |
| VIII-c-75 | naphthyl | —Ph | H | 2-biphenylyl | H |
| VIII-c-76 | naphthyl | —Ph | H | Cl | H |
| VIII-c-77 | naphthyl | —Ph | H | —OH | H |

-continued

| | | | | |
|---|---|---|---|---|
| VIII-c-78 | naphthyl | —Ph | H | —NO₂ | H |
| VIII-c-79 | naphthyl | —Ph | H | —CN | H |
| VIII-c-80 | naphthyl | —Ph | H | —OPh | H |
| VIII-c-81 | naphthyl | —Ph | H | —SCH₃ | H |
| VIII-c-82 | naphthyl | —Ph | H | —SPh | H |
| VIII-c-83 | naphthyl | —Ph | H | —NPh₂ | H |
| VIII-c-84 | naphthyl | —Ph | H | —COOH | H |
| VIII-c-85 | naphthyl | —Ph | H | 2-pyridyl | H |

| Formula (VIII) Compound No. | $L_{111}$ | $A_{13}=A_{23}$ | $A_{16}=A_{26}$ | $A_{18}=A_{28}$ |
|---|---|---|---|---|
| VIII-d-1 | (4,4'-dimethylbiphenyl) | —Ph | H | H |
| VIII-d-2 | (p-tolyl) | —Ph | H | H |
| VIII-d-3 | (2,6-dimethylnaphthyl) | —Ph | H | H |
| VIII-d-4 | (4,4'-dimethylbiphenyl) | $A_{13}$ = (tolyl-phenyl-pteridinyl-Ph); $A_{23}$ = —Ph | H | H |
| VIII-d-5 | (p-tolyl) | $A_{13}$ = (tolyl-pteridinyl-Ph); $A_{23}$ = —Ph | H | H |
| VIII-d-6 | (4,4'-dimethylbiphenyl) | —Ph | H | $CH_3$ |
| VIII-d-7 | (4,4'-dimethylbiphenyl) | —Ph | $CH_3$ | H |

-continued

| | | | |
|---|---|---|---|
| VIII-d-8 | biphenyl | —Ph | CH₃ | CH₃ |
| VIII-d-9 | biphenyl | —Ph | C₂H₅ | H |
| VIII-d-10 | biphenyl | —Ph | n-C₃H₇ | H |
| VIII-d-11 | biphenyl | —Ph | n-C₄H₉ | H |
| VIII-d-12 | biphenyl | —Ph | t-C₄H₉ | H |
| VIII-d-13 | biphenyl | —Ph | —OCH₃ | H |
| VIII-d-14 | biphenyl | —Ph | H | —Ph |
| VIII-d-15 | biphenyl | —Ph | —Ph | H |
| VIII-d-16 | biphenyl | —Ph | 1-naphthyl | H |
| VIII-d-17 | biphenyl | —Ph | 2-naphthyl | H |

-continued

| | | | |
|---|---|---|---|
| VIII-d-18 | ⌬—⌬— | —Ph | 4-biphenylyl | H |
| VIII-d-19 | ⌬—⌬— | —Ph | 3-biphenylyl | H |
| VIII-d-20 | ⌬—⌬— | —Ph | 2-biphenylyl | H |
| VIII-d-21 | ⌬—⌬— | —Ph | Cl | H |
| VIII-d-22 | ⌬—⌬— | —Ph | —OH | H |
| VIII-d-23 | ⌬—⌬— | —Ph | —NO$_2$ | H |
| VIII-d-24 | ⌬—⌬— | —Ph | —CN | H |
| VIII-d-25 | ⌬—⌬— | —Ph | —OPh | H |
| VIII-d-26 | ⌬—⌬— | —Ph | —SCH$_3$ | H |
| VIII-d-27 | ⌬—⌬— | —Ph | —SPh | H |

-continued

| | | | |
|---|---|---|---|
| VIII-d-28 | biphenyl | —Ph | —NH$_2$ | H |
| VIII-d-29 | biphenyl | —Ph | —NH—Ph | H |
| VIII-d-30 | biphenyl | —Ph | —NPh$_2$ | H |
| VIII-d-31 | biphenyl | —Ph | —COOH | H |
| VIII-d-32 | biphenyl | —Ph | 2-pyridyl | H |
| VIII-d-33 | phenyl | —Ph | H | CH$_3$ |
| VIII-d-34 | phenyl | —Ph | CH$_3$ | H |
| VIII-d-35 | phenyl | —Ph | CH$_3$ | CH$_3$ |
| VIII-d-36 | phenyl | —Ph | C$_2$H$_5$ | H |
| VIII-d-37 | phenyl | —Ph | n-C$_3$H$_7$ | H |

-continued

| | | | |
|---|---|---|---|
| VIII-d-38 | ⬡ | —Ph | n-C₄H₉ | H |
| VIII-d-39 | ⬡ | —Ph | t-C₄H₉ | H |
| VIII-d-40 | ⬡ | —Ph | —OCH₃ | H |
| VIII-d-41 | ⬡ | —Ph | H | —Ph |
| VIII-d-42 | ⬡ | —Ph | —Ph | H |
| VIII-d-43 | ⬡ | —Ph | 1-naphthyl | H |
| VIII-d-44 | ⬡ | —Ph | 4-biphenylyl | H |
| VIII-d-45 | ⬡ | —Ph | 3-biphenylyl | H |
| VIII-d-46 | ⬡ | —Ph | 2-biphenylyl | H |
| VIII-d-47 | ⬡ | —Ph | Cl | H |

-continued

| | | | |
|---|---|---|---|
| VIII-d-48 | para-phenylene | —Ph | —OH | H |
| VIII-d-49 | para-phenylene | —Ph | —NO₂ | H |
| VIII-d-50 | para-phenylene | —Ph | —CN | H |
| VIII-d-51 | para-phenylene | —Ph | —OPh | H |
| VIII-d-52 | para-phenylene | —Ph | —SCH₃ | H |
| VIII-d-53 | para-phenylene | —Ph | —SPh | H |
| VIII-d-54 | para-phenylene | —Ph | —NPh₂ | H |
| VIII-d-55 | para-phenylene | —Ph | —COOH | H |
| VIII-d-56 | para-phenylene | —Ph | 2-pyridyl | H |
| VIII-d-57 | 2,6-naphthylene | —Ph | H | CH₃ |

-continued
| | | | |
|---|---|---|---|
| VIII-d-58 | 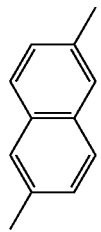 | —Ph | CH₃ | H |
| VIII-d-59 |  | —Ph | CH₃ | CH₃ |
| VIII-d-60 | 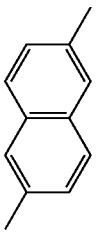 | —Ph | H | C₂H₅ |
| VIII-d-61 | 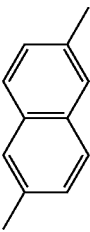 | —Ph | C₂H₅ | H |
| VIII-d-62 | 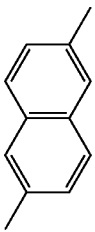 | —Ph | n-C₃H₇ | H |
| VIII-d-63 | 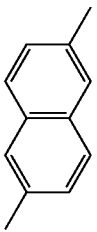 | —Ph | n-C₄H₉ | H |
| VIII-d-64 | 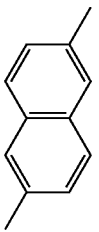 | —Ph | t-C₄H₉ | H |
| VIII-d-65 | 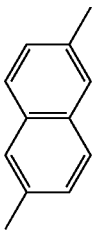 | —Ph | H | —OCH₃ |
| VIII-d-66 | 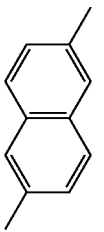 | —Ph | —OCH₃ | H |

-continued

| | | | | |
|---|---|---|---|---|
| VIII-d-67 | naphthyl | —Ph | —OCH₃ | —OCH₃ |
| VIII-d-68 | naphthyl | —Ph | H | —Ph |
| VIII-d-69 | naphthyl | —Ph | —Ph | H |
| VIII-d-70 | naphthyl | —Ph | H | 1-naphthyl |
| VIII-d-71 | naphthyl | —Ph | 1-naphthyl | H |
| VIII-d-72 | naphthyl | —Ph | 2-naphthyl | H |
| VIII-d-73 | naphthyl | —Ph | H | 4-biphenylyl |
| VIII-d-74 | naphthyl | —Ph | 4-biphenylyl | H |
| VIII-d-75 | naphthyl | —Ph | 3-biphenylyl | H |

-continued

| | | | |
|---|---|---|---|
| VIII-d-76 | naphthalene-2,6-diyl | —Ph | 2-biphenylyl | H |
| VIII-d-77 | naphthalene-2,6-diyl | —Ph | Cl | H |
| VIII-d-78 | naphthalene-2,6-diyl | —Ph | —OH | H |
| VIII-d-79 | naphthalene-2,6-diyl | —Ph | —NO$_2$ | H |
| VIII-d-80 | naphthalene-2,6-diyl | —Ph | —CN | H |
| VIII-d-81 | naphthalene-2,6-diyl | —Ph | —OPh | H |
| VIII-d-82 | naphthalene-2,6-diyl | —Ph | —SCH$_3$ | H |
| VIII-d-83 | naphthalene-2,6-diyl | —Ph | —SPh | H |
| VIII-d-84 | naphthalene-2,6-diyl | —Ph | —NPh$_2$ | H |

-continued
| | | | |
|---|---|---|---|
| VIII-d-85 | 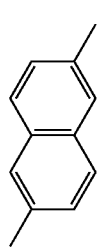 | —COOH | H |
| VIII-d-86 | 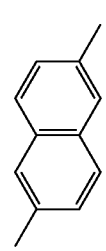 | 2-pyridyl | H |
| Formula (VIII) Compound No. | $L_{111}$ | $A_{13}=A_{23}$ | $A_{17}=A_{27}$ | $A_{18}=A_{28}$ |
|---|---|---|---|---|
| VIII-e-1 | 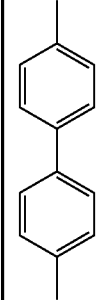 | —Ph | H | H |
| VIII-e-2 | 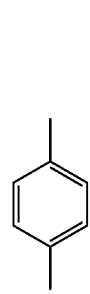 | —Ph | H | H |
| VIII-e-3 |  | —Ph | H | H |
| VIII-e-4 | 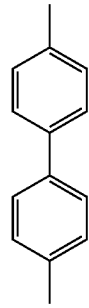 | —Ph | H | $CH_3$ |
| VIII-e-5 | 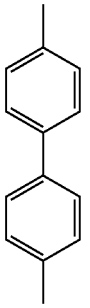 | —Ph | $CH_3$ | H |
| VIII-e-6 | 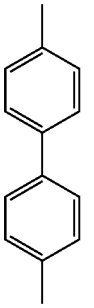 | —Ph | $CH_3$ | $CH_3$ |
| VIII-e-7 | 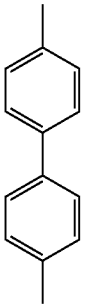 | —Ph | $C_2H_5$ | H |

-continued

| | | | |
|---|---|---|---|
| VIII-e-8 | biphenyl | —Ph | n-C₃H₇ | H |
| VIII-e-9 | biphenyl | —Ph | n-C₃H₇ | n-C₃H₇ |
| VIII-e-10 | biphenyl | —Ph | n-C₄H₉ | H |
| VIII-e-11 | biphenyl | —Ph | t-C₄H₉ | H |
| VIII-e-12 | biphenyl | —Ph | —OCH₃ | H |
| VIII-e-13 | biphenyl | —Ph | | A₁₇ and A₁₈ form a benzene ring. A₂₇ and A₂₈ form a benzene ring. |
| VIII-e-14 | biphenyl | —Ph | H | —Ph |
| VIII-e-15 | biphenyl | —Ph | —Ph | H |
| VIII-e-16 | biphenyl | —Ph | —Ph | —Ph |
| VIII-e-17 | biphenyl | —Ph | 1-naphthyl | H |

-continued

| | | | |
|---|---|---|---|
| VIII-e-18 | biphenyl | —Ph | 2-naphthyl | H |
| VIII-e-19 | biphenyl | —Ph | 4-biphenylyl | H |
| VIII-e-20 | biphenyl | —Ph | 3-biphenylyl | H |
| VIII-e-21 | biphenyl | —Ph | 2-biphenylyl | H |
| VIII-e-22 | biphenyl | —Ph | Cl | H |
| VIII-e-23 | biphenyl | —Ph | —OH | H |
| VIII-e-24 | biphenyl | —Ph | —NO$_2$ | H |
| VIII-e-25 | biphenyl | —Ph | —CN | H |
| VIII-e-26 | biphenyl | —Ph | —OPh | H |
| VIII-e-27 | biphenyl | —Ph | —SCH$_3$ | H |

| | | | |
|---|---|---|---|
| VIII-e-28 | biphenyl | —Ph | —SPh | H |
| VIII-e-29 | biphenyl | —Ph | —NPh$_2$ | H |
| VIII-e-30 | biphenyl | —Ph | —COOH | H |
| VIII-e-31 | biphenyl | —Ph | 2-pyridyl | H |
| VIII-e-32 | phenyl | —Ph | H | CH$_3$ |
| VIII-e-33 | phenyl | —Ph | CH$_3$ | H |
| VIII-e-34 | phenyl | —Ph | CH$_3$ | CH$_3$ |
| VIII-e-35 | phenyl | —Ph | C$_2$H$_5$ | H |
| VIII-e-36 | phenyl | —Ph | n-C$_3$H$_7$ | H |
| VIII-e-37 | phenyl | —Ph | n-C$_3$H$_7$ | n-C$_3$H$_7$ |

| | | | |
|---|---|---|---|
| VIII-e-38 | [p-phenylene] | —Ph | n-C₄H₉ | H |
| VIII-e-39 | [p-phenylene] | —Ph | t-C₄H₉ | H |
| VIII-e-40 | [p-phenylene] | —Ph | H | —OCH₃ |
| VIII-e-41 | [p-phenylene] | —Ph | —OCH₃ | H |
| VIII-e-42 | [p-phenylene] | —Ph | $A_{17}$ and $A_{18}$ form a benzene ring. $A_{27}$ and $A_{28}$ form a benzene ring. | |
| VIII-e-43 | [p-phenylene] | —Ph | H | —Ph |
| VIII-e-44 | [p-phenylene] | —Ph | —Ph | H |
| VIII-e-45 | [p-phenylene] | —Ph | —Ph | —Ph |
| VIII-e-46 | [p-phenylene] | —Ph | 1-naphthyl | H |
| VIII-e-47 | [p-phenylene] | —Ph | 2-naphthyl | H |

-continued

| | | | | |
|---|---|---|---|---|
| VIII-e-48 | para-phenylene | —Ph | H | 4-biphenylyl |
| VIII-e-49 | para-phenylene | —Ph | 4-biphenylyl | 4-biphenylyl |
| VIII-e-50 | para-phenylene | —Ph | 3-biphenylyl | H |
| VIII-e-51 | para-phenylene | —Ph | 2-biphenylyl | H |
| VIII-e-52 | para-phenylene | —Ph | Cl | H |
| VIII-e-53 | para-phenylene | —Ph | —OH | H |
| VIII-e-54 | para-phenylene | —Ph | —NO$_2$ | H |
| VIII-e-55 | para-phenylene | —Ph | —CN | H |
| VIII-e-56 | para-phenylene | —Ph | —OPh | H |
| VIII-e-57 | para-phenylene | —Ph | —SCH$_3$ | H |

| | | | |
|---|---|---|---|
| VIII-e-58 | p-phenylene | —SPh | H |
| VIII-e-59 | p-phenylene | —NPh₂ | H |
| VIII-e-60 | p-phenylene | —COOH | H |
| VIII-e-61 | p-phenylene | 2-pyridyl | H |
| VIII-e-62 | 2,6-naphthylene | —Ph | CH₃ |
| VIII-e-63 | 2,6-naphthylene | —Ph | H |
| VIII-e-64 | 2,6-naphthylene | —Ph | CH₃ |
| VIII-e-65 | 2,6-naphthylene | —Ph | H |
| VIII-e-66 | 2,6-naphthylene | —Ph | H |

| | | | |
|---|---|---|---|
| VIII-e-62 | | H | |
| VIII-e-63 | | CH₃ | |
| VIII-e-64 | | CH₃ | |
| VIII-e-65 | | C₂H₅ | |
| VIII-e-66 | | n-C₃H₇ | |

| | | | |
|---|---|---|---|
| VIII-e-67 | 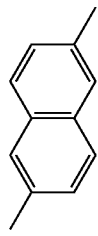 | —Ph | n-C$_3$H$_7$ | n-C$_3$H$_7$ |
| VIII-e-68 |  | —Ph | n-C$_4$H$_9$ | H |
| VIII-e-69 | 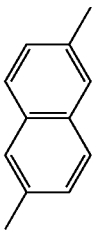 | —Ph | t-C$_4$H$_9$ | H |
| VIII-e-70 | 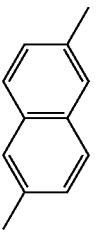 | —Ph | t-C$_4$H$_9$ | t-C$_4$H$_9$ |
| VIII-e-71 | 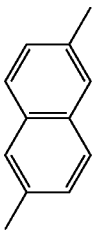 | —Ph | —OCH$_3$ | H |
| VIII-e-72 | 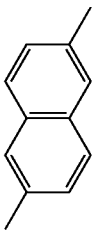 | —Ph | A$_{17}$ and A$_{18}$ form a benzene ring. A$_{27}$ and A$_{28}$ form a benzene ring. | |
| VIII-e-73 | 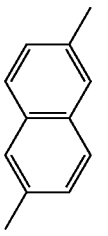 | —Ph | H | —Ph |
| VIII-e-74 | 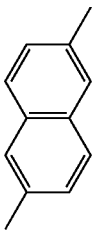 | —Ph | —Ph | H |
| VIII-e-75 | 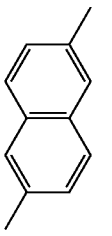 | —Ph | —Ph | —Ph |

-continued
| | | | |
|---|---|---|---|
| VIII-e-76 | 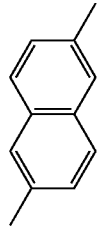 | —Ph | 1-naphthyl | H |
| VIII-e-77 |  | —Ph | 2-naphthyl | H |
| VIII-e-78 | 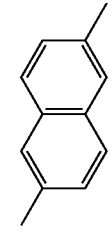 | —Ph | 3-biphenylyl | H |
| VIII-e-79 | 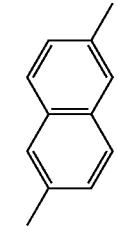 | —Ph | 2-biphenylyl | H |
| VIII-e-80 | 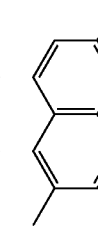 | —Ph | Cl | H |
| VIII-e-81 | 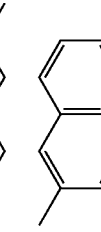 | —Ph | —OH | H |
| VIII-e-82 | 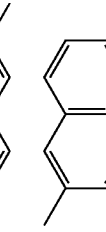 | —Ph | —NO$_2$ | H |
| VIII-e-83 | 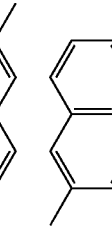 | —Ph | —CN | H |
| VIII-e-84 | 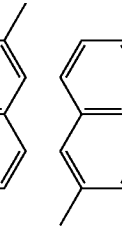 | —Ph | —OPh | H |

| | | | |
|---|---|---|---|
| VIII-e-85 | ![2,6-naphthyl] | —Ph | —SCH$_3$ | H |
| VIII-e-86 | ![2,6-naphthyl] | —Ph | —SPh | H |
| VIII-e-87 | ![2,6-naphthyl] | —Ph | —NPh$_2$ | H |
| VIII-e-88 | ![2,6-naphthyl] | —Ph | —COOH | H |
| VIII-e-89 | ![2,6-naphthyl] | —Ph | 2-pyridyl | H |

| Formula (VIII) Compound No. | L$_{111}$ | A$_{13}$=A$_{23}$ | A$_{15}$=A$_{25}$ | A$_{18}$=A$_{28}$ |
|---|---|---|---|---|
| VIII-f-1 | ![biphenyl] | —Ph | H | H |
| VIII-f-2 | ![phenyl] | —Ph | H | H |
| VIII-f-3 | ![2,6-naphthyl] | —Ph | H | H |
| VIII-f-4 | ![biphenyl] | —Ph | H | CH$_3$ |

-continued
| | | | | |
|---|---|---|---|---|
| VIII-f-5 |  | —Ph | CH₃ | H |
| VIII-f-6 |  | —Ph | CH₃ | CH₃ |
| VIII-f-7 |  | —Ph | C₂H₅ | H |
| VIII-f-8 |  | —Ph | n-C₃H₇ | H |
| VIII-f-9 |  | —Ph | n-C₄H₉ | H |
| VIII-f-10 |  | —Ph | t-C₄H₉ | H |
| VIII-f-11 |  | —Ph | —OCH₃ | H |
| VIII-f-12 |  | —Ph | H | —Ph |
| VIII-f-13 |  | —Ph | —Ph | H |
| VIII-f-14 |  | —Ph | —Ph | —Ph |

-continued

| | | | |
|---|---|---|---|
| VIII-f-15 | biphenyl | —Ph | H | 1-naphthyl |
| VIII-f-16 | biphenyl | —Ph | 1-naphthyl | H |
| VIII-f-17 | biphenyl | —Ph | 2-naphthyl | H |
| VIII-f-18 | biphenyl | —Ph | 4-biphenylyl | H |
| VIII-f-19 | biphenyl | —Ph | 3-biphenylyl | H |
| VIII-f-20 | biphenyl | —Ph | 2-biphenylyl | H |
| VIII-f-21 | biphenyl | —Ph | Cl | H |
| VIII-f-22 | biphenyl | —Ph | —OH | H |
| VIII-f-23 | biphenyl | —Ph | —NO$_2$ | H |
| VIII-f-24 | biphenyl | —Ph | —CN | H |

-continued

| | | | |
|---|---|---|---|
| VIII-f-25 | biphenyl | —Ph | —OPh | H |
| VIII-f-26 | biphenyl | —Ph | —SCH$_3$ | H |
| VIII-f-27 | biphenyl | —Ph | —SPh | H |
| VIII-f-28 | biphenyl | —Ph | —NPh$_2$ | H |
| VIII-f-29 | biphenyl | —Ph | —COOH | H |
| VIII-f-30 | biphenyl | —Ph | 2-pyridyl | H |
| VIII-f-31 | phenyl | —Ph | H | CH$_3$ |
| VIII-f-32 | phenyl | —Ph | CH$_3$ | H |
| VIII-f-33 | phenyl | —Ph | CH$_3$ | CH$_3$ |
| VIII-f-34 | phenyl | —Ph | C$_2$H$_5$ | H |

-continued

| | | | |
|---|---|---|---|
| VIII-f-35 | phenyl | —Ph | n-C₃H₇ | H |
| VIII-f-36 | phenyl | —Ph | n-C₄H₉ | H |
| VIII-f-37 | phenyl | —Ph | t-C₄H₉ | H |
| VIII-f-38 | phenyl | —Ph | —OCH₃ | H |
| VIII-f-39 | phenyl | —Ph | H | —Ph |
| VIII-f-40 | phenyl | —Ph | —Ph | H |
| VIII-f-41 | phenyl | —Ph | —Ph | —Ph |
| VIII-f-42 | phenyl | —Ph | 1-naphthyl | H |
| VIII-f-43 | phenyl | —Ph | 2-naphthyl | H |
| VIII-f-44 | phenyl | —Ph | 4-biphenylyl | H |

-continued

| | | | |
|---|---|---|---|
| VIII-f-45 | phenyl | —Ph | 3-biphenylyl | H |
| VIII-f-46 | phenyl | —Ph | 2-biphenylyl | H |
| VIII-f-47 | phenyl | —Ph | Cl | H |
| VIII-f-48 | phenyl | —Ph | OH | H |
| VIII-f-49 | phenyl | —Ph | —NO$_2$ | H |
| VIII-f-50 | phenyl | —Ph | —CN | H |
| VIII-f-51 | phenyl | —Ph | —OPh | H |
| VIII-f-52 | phenyl | —Ph | —SCH$_3$ | H |
| VIII-f-53 | phenyl | —Ph | —SPh | H |
| VIII-f-54 | phenyl | —Ph | —NPh$_2$ | H |

-continued

| | | | | |
|---|---|---|---|---|
| VIII-f-55 | p-C6H4 | —Ph | —COOH | H |
| VIII-f-56 | p-C6H4 | —Ph | 2-pyridyl | H |
| VIII-f-57 | 2,6-naphthyl | —Ph | H | CH3 |
| VIII-f-58 | 2,6-naphthyl | —Ph | CH3 | H |
| VIII-f-59 | 2,6-naphthyl | —Ph | CH3 | CH3 |
| VIII-f-60 | 2,6-naphthyl | —Ph | C2H5 | H |
| VIII-f-61 | 2,6-naphthyl | —Ph | n-C3H7 | H |
| VIII-f-62 | 2,6-naphthyl | —Ph | n-C4H9 | H |
| VIII-f-63 | 2,6-naphthyl | —Ph | t-C4H9 | H |

-continued

| | | | |
|---|---|---|---|
| VIII-f-64 | naphthyl | —Ph | —OCH₃ | H |
| VIII-f-65 | naphthyl | —Ph | H | —Ph |
| VIII-f-66 | naphthyl | —Ph | —Ph | H |
| VIII-f-67 | naphthyl | —Ph | —Ph | —Ph |
| VIII-f-68 | naphthyl | —Ph | 1-naphthyl | H |
| VIII-f-69 | naphthyl | —Ph | 2-naphthyl | H |
| VIII-f-70 | naphthyl | —Ph | 4-biphenylyl | H |
| VIII-f-71 | naphthyl | —Ph | 3-biphenylyl | H |
| VIII-f-72 | naphthyl | —Ph | 2-biphenylyl | H |

-continued

| | | | |
|---|---|---|---|
| VIII-f-73 | naphthalene | —Ph | Cl | H |
| VIII-f-74 | naphthalene | —Ph | —OH | H |
| VIII-f-75 | naphthalene | —Ph | —NO$_2$ | H |
| VIII-f-76 | naphthalene | —Ph | —CN | H |
| VIII-f-77 | naphthalene | —Ph | —OPh | H |
| VIII-f-78 | naphthalene | —Ph | —SCH$_3$ | H |
| VIII-f-79 | naphthalene | —Ph | —SPh | H |
| VIII-f-80 | naphthalene | —Ph | —NPh$_2$ | H |
| VIII-f-81 | naphthalene | —Ph | —COOH | H |

-continued

| Formula (VIII) Compound No. | L112 | | $A_{13}=A_{23}=A_{33}$ | $A_{15}=A_{25}=A_{35}$ | $A_{16}=A_{26}=A_{36}$ | 2-pyridyl | $A_{17}=A_{27}=A_{37}$ | $A_{18}=A_{28}=A_{38}$ |
|---|---|---|---|---|---|---|---|---|
| VIII-f-82 |  | —Ph | | | | | | |
| VIII-g-1 | 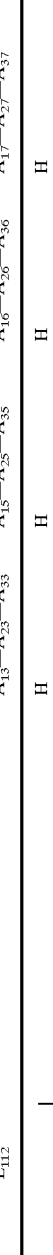 | | H | H | H | | H | H |
| VIII-g-2 |  | | H | $A_{15}$ and $A_{16}$ form a benzene ring. $A_{25}$ and $A_{26}$ form a benzene ring. $A_{35}$ and $A_{36}$ form a benzene ring. | | | $A_{17}$ and $A_{18}$ form a benzene ring. $A_{27}$ and $A_{28}$ form a benzene ring. $A_{37}$ and $A_{38}$ form a benzene ring. | |
| VIII-g-3 |  | | H | $A_{15}$ and $A_{16}$ form a benzene ring. $A_{25}$ and $A_{26}$ form a benzene ring. $A_{35}$ and $A_{36}$ form a benzene ring. | | | H | H |
| VIII-g-4 |  | | —Ph | H | H | | H | H |
| VIII-g-5 |  | | —Ph | $A_{15}$ and $A_{16}$ form a benzene ring. $A_{25}$ and $A_{26}$ form a benzene ring. $A_{35}$ and $A_{36}$ form a benzene ring. | | | $A_{17}$ and $A_{18}$ form a benzene ring. $A_{27}$ and $A_{28}$ form a benzene ring. $A_{37}$ and $A_{38}$ form a benzene ring. | |

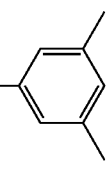

| | | | | | |
|---|---|---|---|---|---|
| VIII-g-6 | | –Ph | $A_{15}$ and $A_{16}$ form a benzene ring. $A_{25}$ and $A_{26}$ form a benzene ring. $A_{35}$ and $A_{36}$ form a benzene ring. | H | H |
| VIII-g-7 | | H | H | H | H |
| VIII-g-8 | | H | $A_{15}$ and $A_{16}$ form a benzene ring. $A_{25}$ and $A_{26}$ form a benzene ring. $A_{35}$ and $A_{36}$ form a benzene ring. | H | $A_{17}$ and $A_{18}$ form a benzene ring. $A_{27}$ and $A_{28}$ form a benzene ring. $A_{37}$ and $A_{38}$ form a benzene ring. |
| VIII-g-9 | | H | $A_{15}$ and $A_{16}$ form a benzene ring. $A_{25}$ and $A_{26}$ form a benzene ring. $A_{35}$ and $A_{36}$ form a benzene ring. | H | H |
| VIII-g-10 | | –Ph | H | H | H |
| VIII-g-11 | | –Ph | $A_{15}$ and $A_{16}$ form a benzene ring. $A_{25}$ and $A_{26}$ form a benzene ring. $A_{35}$ and $A_{36}$ form a benzene ring. | H | $A_{17}$ and $A_{18}$ form a benzene ring. $A_{27}$ and $A_{28}$ form a benzene ring. $A_{37}$ and $A_{38}$ form a benzene ring. |
| VIII-g-12 | | –Ph | $A_{15}$ and $A_{16}$ form a benzene ring. $A_{25}$ and $A_{26}$ form a benzene ring. $A_{35}$ and $A_{36}$ form a benzene ring. | H | H |
| VIII-g-13 | | H | H | H | H |
| VIII-g-14 | | H | $A_{15}$ and $A_{16}$ form a benzene ring. $A_{25}$ and $A_{26}$ form a benzene ring. $A_{35}$ and $A_{36}$ form a benzene ring. | H | H |

-continued

| | | | | | |
|---|---|---|---|---|---|
| VIII-g-15 | 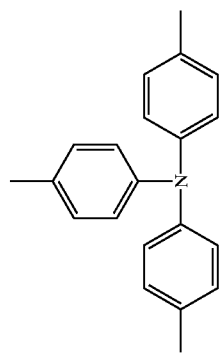 | H | $A_{15}$ and $A_{16}$ form a benzene ring. $A_{25}$ and $A_{26}$ form a benzene ring. $A_{35}$ and $A_{36}$ form a benzene ring. | H | $A_{17}$ and $A_{18}$ form a benzene ring. $A_{27}$ and $A_{28}$ form a benzene ring. $A_{37}$ and $A_{38}$ form a benzene ring. |
| VIII-g-16 | 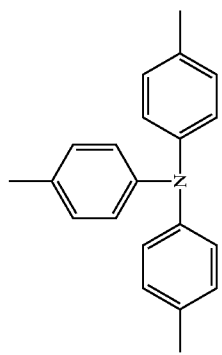 | —Ph | H | H | H |
| VIII-g-17 | 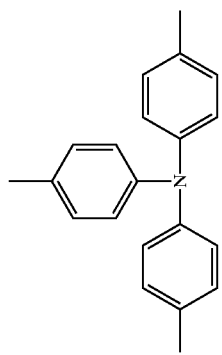 | —Ph | $A_{15}$ and $A_{16}$ form a benzene ring. $A_{25}$ and $A_{26}$ form a benzene ring. $A_{35}$ and $A_{36}$ form a benzene ring. | H | $A_{17}$ and $A_{18}$ form a benzene ring. $A_{27}$ and $A_{28}$ form a benzene ring. $A_{37}$ and $A_{38}$ form a benzene ring. |
| VIII-g-18 | 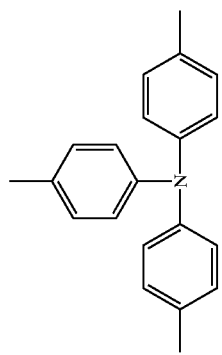 | —Ph | $A_{15}$ and $A_{16}$ form a benzene ring. $A_{25}$ and $A_{26}$ form a benzene ring. $A_{35}$ and $A_{36}$ form a benzene ring. | H | H |

-continued

| | | | | | | |
|---|---|---|---|---|---|---|
| VIII-g-19 | 3,5-dimethylphenyl | —Ph | —Ph | H | —Ph | H |
| VIII-g-20 | 3,5-dimethylphenyl | —Ph | —Ph | H | H | H |
| VIII-g-21 | 3,5-dimethylphenyl | —Ph | H | —Ph | H | H |
| VIII-g-22 | 3,5-dimethylphenyl | —Ph | H | H | H | —Ph |
| VIII-g-23 | 3,5-dimethylphenyl | —Ph | H | H | Cl | H |
| VIII-g-24 | 3,5-dimethylphenyl | —Ph | H | H | —OH | H |
| VIII-g-25 | 3,5-dimethylphenyl | —Ph | H | H | —NO$_2$ | H |

-continued
| | | | | | |
|---|---|---|---|---|---|
| VIII-g-26 | 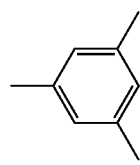 | —Ph | H | H | —CN | H |
| VIII-g-27 | 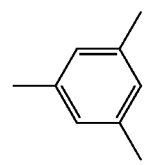 | —Ph | H | H | —OPh | H |
| VIII-g-28 | 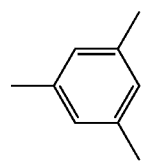 | —Ph | H | H | —SCH$_3$ | H |
| VIII-g-29 | 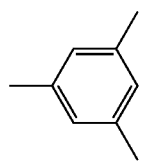 | —Ph | H | H | —SPh | H |
| VIII-g-30 | 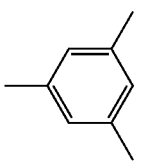 | —Ph | H | H | —NPh | H |
| VIII-g-31 | 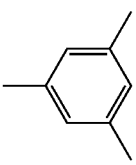 | —Ph | H | H | CH$_3$ | H |

| | | | | | | |
|---|---|---|---|---|---|---|
| VIII-g-32 | 3,5-dimethylphenyl | —Ph | H | H | —OCH₃ | H |
| VIII-g-33 | 3,5-dimethylphenyl | —Ph | H | H | —COOH | H |
| VIII-g-34 | 3,5-dimethylphenyl | —Ph | H | H | 2-pyridyl | H |
| VIII-g-35 | N | —Ph | H | H | —Ph | H |
| VIII-g-36 | N | —Ph | —Ph | H | H | H |
| VIII-g-37 | N | —Ph | H | —Ph | H | H |
| VIII-g-38 | N | —Ph | H | H | H | —Ph |
| VIII-g-39 | N | —Ph | H | H | Cl | H |
| VIII-g-40 | N | —Ph | H | H | —OH | H |
| VIII-g-41 | N | —Ph | H | H | —NO₂ | H |
| VIII-g-42 | N | —Ph | H | H | —CN | H |

-continued

| | | | | | |
|---|---|---|---|---|---|
| VIII-g-43 | —N< | —Ph | H | —OPh | H |
| VIII-g-44 | —N< | —Ph | H | —SCH₃ | H |
| VIII-g-45 | —N< | —Ph | H | —SPh | H |
| VIII-g-46 | —N< | —Ph | H | —NPh | H |
| VIII-g-47 | —N< | —Ph | H | CH₃ | H |
| VIII-g-48 | —N< | —Ph | H | —OCH₃ | H |
| VIII-g-49 | —N< | —Ph | H | —COOH | H |
| VIII-g-50 | —N< | —Ph | H | 2-pyridyl | H |
| VIII-g-51 | (tri-tolylamine group) | —Ph | —Ph | —Ph | H |
| VIII-g-52 | (tri-tolylamine group) | —Ph | —Ph | H | H |

-continued

| | | | | | | |
|---|---|---|---|---|---|---|
| VIII-g-53 | N(p-tolyl)₃ | —Ph | H | —Ph | H | H |
| VIII-g-54 | N(p-tolyl)₃ | —Ph | H | H | H | —Ph |
| VIII-g-55 | N(p-tolyl)₃ | —Ph | H | H | Cl | H |
| VIII-g-56 | N(p-tolyl)₃ | —Ph | H | H | —OH | H |

-continued

| | | | | | |
|---|---|---|---|---|---|
| VIII-g-57 | [N(C6H4CH3)3] | —Ph | H | H | —NO2 | H |
| VIII-g-58 | [N(C6H4CH3)3] | —Ph | H | H | —CN | H |
| VIII-g-59 | [N(C6H4CH3)3] | —Ph | H | H | —OPh | H |
| VIII-g-60 | [N(C6H4CH3)3] | —Ph | H | H | —SCH3 | H |

-continued

| | | | | | |
|---|---|---|---|---|---|
| VIII-g-61 | (tri-p-tolyl)Z— | —Ph | H | H | —SPh | H |
| VIII-g-62 | (tri-p-tolyl)Z— | —Ph | H | H | —NPh | H |
| VIII-g-63 | (tri-p-tolyl)Z— | —Ph | H | H | CH$_3$ | H |
| VIII-g-64 | (tri-p-tolyl)Z— | —Ph | H | H | —OCH$_3$ | H |

-continued

| Compound No. | | | | | |
|---|---|---|---|---|---|
| VIII-g-65 | [N(p-tolyl)₃ structure] | —Ph | H | —COOH | H |
| VIII-g-66 | [N(p-tolyl)₃ structure] | —Ph | H | 2-pyridyl | H |

| Formula (VIII) Compound No. | L₁₁₂ | A₁₃=A₂₃=A₃₃ | A₁₆=A₂₆=A₃₆ | A₁₇=A₂₇=A₃₇ | A₁₈=A₂₈=A₃₈ |
|---|---|---|---|---|---|
| VIII-h-1 | 3,5-dimethylphenyl | H | H | H | H |
| VIII-h-2 | 3,5-dimethylphenyl | —Ph | H | H | H |
| VIII-h-3 | N(CH₃)₂ | H | H | H | H |
| VIII-h-4 | N(CH₃)₂ | —Ph | H | H | H |

-continued

| | | | | | |
|---|---|---|---|---|---|
| VIII-h-5 | [structure: N(4-tolyl)₃] | H | H | H | H |
| VIII-h-6 | [structure: N(4-tolyl)₃] | —Ph | H | H | H |
| VIII-h-7 | [3,5-dimethylphenyl] | H | H | A₁₆ and A₁₇ form a benzene ring. A₂₆ and A₂₇ form a benzene ring. A₃₆ and A₃₇ form a benzene ring. | H |
| VIII-h-8 | [3,5-dimethylphenyl] | —Ph | H | A₁₆ and A₁₇ form a benzene ring. A₂₆ and A₂₇ form a benzene ring. A₃₆ and A₃₇ form a benzene ring. | H |
| VIII-h-9 | [3,5-dimethylphenyl] | H | H | H | A₁₇ and A₁₈ form a benzene ring. A₂₇ and A₂₈ form a benzene ring. A₃₇ and A₃₈ form a benzene ring. |
| VIII-h-10 | [3,5-dimethylphenyl] | —Ph | H | H | A₁₇ and A₁₈ form a benzene ring. A₂₇ and A₂₈ form a benzene ring. A₃₇ and A₃₈ form a benzene ring. |

-continued
| | | | | | | |
|---|---|---|---|---|---|---|
| VIII-h-11 | 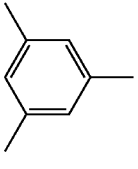 | —Ph | —Ph | H | H | H |
| VIII-h-12 | 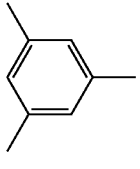 | —Ph | H | —Ph | H | H |
| VIII-h-13 | 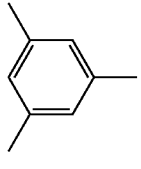 | —Ph | H | H | —Ph | H |
| VIII-h-14 | 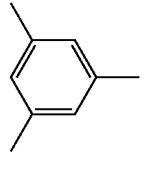 | —Ph | H | Cl | H | H |
| VIII-h-15 | 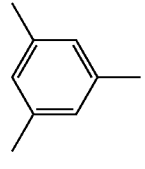 | —Ph | H | —OH | H | H |
| VIII-h-16 | 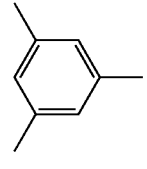 | —Ph | H | —NO$_2$ | H | H |

-continued

| | | | | |
|---|---|---|---|---|
| VIII-h-17 | 3,5-dimethylphenyl | —Ph | H | —CN | H |
| VIII-h-18 | 3,5-dimethylphenyl | —Ph | H | —OPh | H |
| VIII-h-19 | 3,5-dimethylphenyl | —Ph | H | —SCH$_3$ | H |
| VIII-h-20 | 3,5-dimethylphenyl | —Ph | H | —SPh | H |
| VIII-h-21 | 3,5-dimethylphenyl | —Ph | H | —NPh$_2$ | H |
| VIII-h-22 | 3,5-dimethylphenyl | —Ph | H | CH$_3$ | H |
| VIII-h-23 | 3,5-dimethylphenyl | —Ph | H | —OCH$_3$ | H |

-continued

| ID | Structure | | | | |
|---|---|---|---|---|---|
| VIII-h-24 | 3,5-dimethylphenyl | —Ph | H | —COOH | H |
| VIII-h-25 | 3,5-dimethylphenyl | —Ph | H | 2-pyridyl | H |
| VIII-h-26 | —N< | H | H | $A_{16}$ and $A_{17}$ form a benzene ring. $A_{26}$ and $A_{27}$ form a benzene ring. $A_{36}$ and $A_{37}$ form a benzene ring. | H |
| VIII-h-27 | —N< | —Ph | H | $A_{16}$ and $A_{17}$ form a benzene ring. $A_{26}$ and $A_{27}$ form a benzene ring. $A_{36}$ and $A_{37}$ form a benzene ring. | H |
| VIII-h-28 | —N< | H | H | $A_{17}$ and $A_{16}$ form a benzene ring. $A_{27}$ and $A_{28}$ form a benzene ring. $A_{37}$ and $A_{38}$ form a benzene ring. | H |
| VIII-h-29 | —N< | —Ph | H | $A_{17}$ and $A_{16}$ form a benzene ring. $A_{27}$ and $A_{28}$ form a benzene ring. $A_{37}$ and $A_{36}$ form a benzene ring. | H |
| VIII-h-30 | —N< | —Ph | —Ph | H | H |
| VIII-h-31 | —N< | —Ph | H | —Ph | H |
| VIII-h-32 | —N< | —Ph | H | H | —Ph |
| VIII-h-33 | —N< | —Ph | H | Cl | H |
| VIII-h-34 | —N< | —Ph | H | —OH | H |

-continued
| | | | | |
|---|---|---|---|---|
| VIII-h-35 | —N | —Ph | H | —NO$_2$ | H |
| VIII-h-36 | —N | —Ph | H | —CN | H |
| VIII-h-37 | —N | —Ph | H | —OPh | H |
| VIII-h-38 | —N | —Ph | H | —SCH$_3$ | H |
| VIII-h-39 | —N | —Ph | H | —SPh | H |
| VIII-h-40 | —N | —Ph | H | —NPh$_2$ | H |
| VIII-h-41 | —N | —Ph | H | CH$_3$ | H |
| VIII-h-42 | —N | —Ph | H | —OCH$_3$ | H |
| VIII-h-43 | —N | —Ph | H | —COOH | H |
| VIII-h-44 | —N | —Ph | H | 2-pyridyl | H |
| VIII-h-45 | | H | | A$_{16}$ and A$_{17}$ form a benzene ring. A$_{26}$ and A$_{27}$ form a benzene ring. A$_{36}$ and A$_{37}$ form a benzene ring. | H |
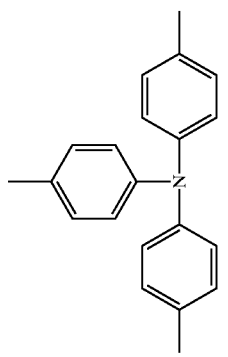

-continued
| | | | | |
|---|---|---|---|---|
| VIII-h-46 | 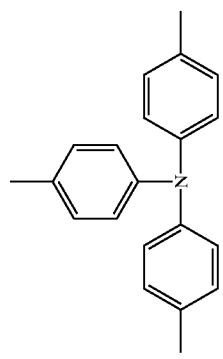 | —Ph | A₁₆ and A₁₇ form a benzene ring.<br>A₂₆ and A₂₇ form a benzene ring.<br>A₃₆ and A₃₇ form a benzene ring. | H |
| VIII-h-47 | 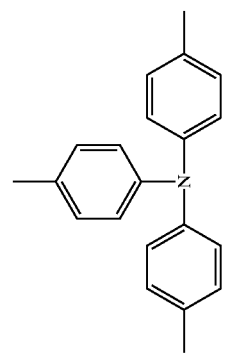 | H | H | A₁₇ and A₁₈ form a benzene ring.<br>A₂₇ and A₂₈ form a benzene ring.<br>A₃₇ and A₃₈ form a benzene ring. |
| VIII-h-48 | 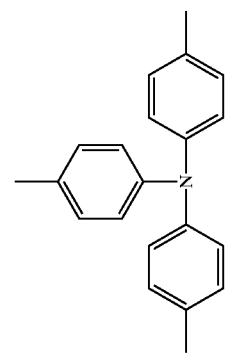 | —Ph | H | A₁₇ and A₁₈ form a benzene ring.<br>A₂₇ and A₂₈ form a benzene ring.<br>A₃₇ and A₃₈ form a benzene ring. |
| VIII-h-49 | 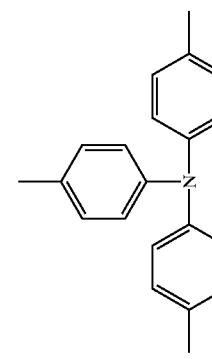 | —Ph | —Ph | H |

-continued
| | | | | |
|---|---|---|---|---|
| VIII-h-50 | 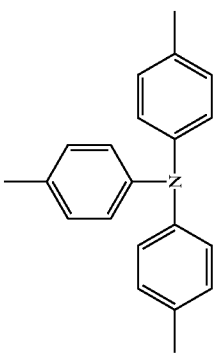 | —Ph | H | —Ph | H |
| VIII-h-51 | 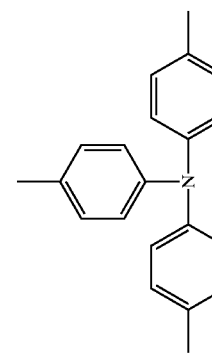 | —Ph | H | H | —Ph |
| VIII-h-52 | 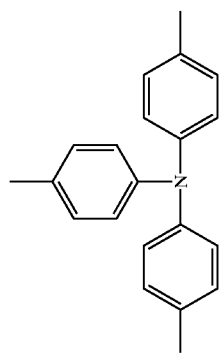 | —Ph | H | Cl | H |
| VIII-h-53 | 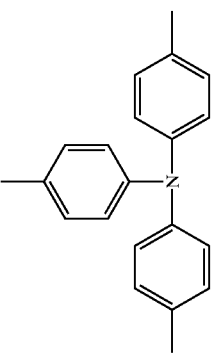 | —Ph | H | —OH | H |

| | | | | |
|---|---|---|---|---|
| VIII-h-54 | ![N(tolyl)3] | —Ph | H | —NO$_2$ | H |
| VIII-h-55 | ![N(tolyl)3] | —Ph | H | —CN | H |
| VIII-h-56 | ![N(tolyl)3] | —Ph | H | —OPh | H |
| VIII-h-57 | ![N(tolyl)3] | —Ph | H | —SCH$_3$ | H |

-continued
| | | | | |
|---|---|---|---|---|
| VIII-h-58 | 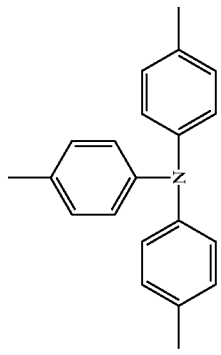 | —Ph | H | —SPh | H |
| VIII-h-59 | 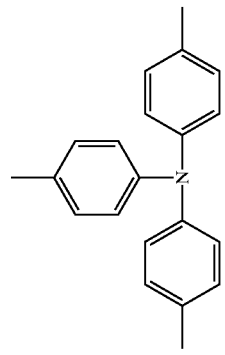 | —Ph | H | —NPh$_2$ | H |
| VIII-h-60 | 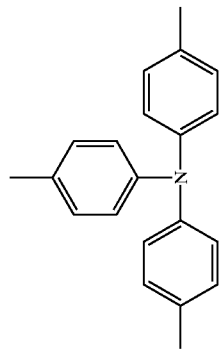 | —Ph | H | CH$_3$ | H |
| VIII-h-61 | 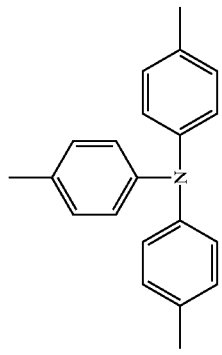 | —Ph | H | —OCH$_3$ | H |

-continued

| | | | | | |
|---|---|---|---|---|---|
| VIII-h-62 | ![triarylamine with tolyl groups] | —Ph | H | —COOH | H |
| VIII-h-63 | ![triarylamine with tolyl groups] | —Ph | H | 2-pyridyl | H |

| Formula (VIII) Compound No. | | $A_{13}=A_{23}=A_{33}$ | $A_{15}=A_{25}=A_{35}$ | $A_{17}=A_{27}=A_{37}$ | $A_{18}=A_{28}=A_{38}$ |
|---|---|---|---|---|---|
| VIII-i-1 | $L_{112}$ | H | H | H | H |
| VIII-i-2 | 3,5-dimethylphenyl | —Ph | H | H | H |
| VIII-i-3 | N(CH₃)₂ | H | H | H | H |

-continued

| | | | | | |
|---|---|---|---|---|---|
| VIII-i-4 | ![structure] | H | H | H | H |
| VIII-i-5 | ![structure] | —Ph | H | H | H |
| VIII-i-6 | ![structure] | H | H | | $A_{17}$ and $A_{18}$ form a benzene ring.<br>$A_{27}$ and $A_{28}$ form a benzene ring.<br>$A_{37}$ and $A_{38}$ form a benzene ring. |
| VIII-i-7 | ![structure] | —Ph | H | | $A_{17}$ and $A_{18}$ form a benzene ring.<br>$A_{27}$ and $A_{28}$ form a benzene ring.<br>$A_{37}$ and $A_{38}$ form a benzene ring. |
| VIII-i-8 | ![structure] | H | H | | $A_{17}$ and $A_{18}$ form a benzene ring.<br>$A_{27}$ and $A_{28}$ form a benzene ring.<br>$A_{37}$ and $A_{38}$ form a benzene ring. |
| VIII-i-9 | ![structure] | H | H | | $A_{17}$ and $A_{18}$ form a benzene ring.<br>$A_{27}$ and $A_{28}$ form a benzene ring.<br>$A_{37}$ and $A_{38}$ form a benzene ring. |

-continued
| | | | | | |
|---|---|---|---|---|---|
| VIII-i-10 | 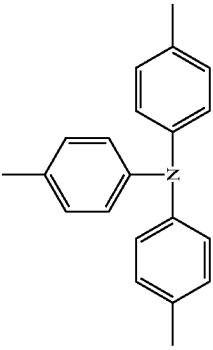 | —Ph | H | H | H | A$_{17}$ and A$_{18}$ form a benzene ring.<br>A$_{27}$ and A$_{28}$ form a benzene ring.<br>A$_{37}$ and A$_{38}$ form a benzene ring. |
| VIII-i-11 | 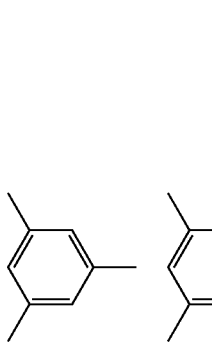 | —Ph | —Ph | H | H | |
| VIII-i-12 | 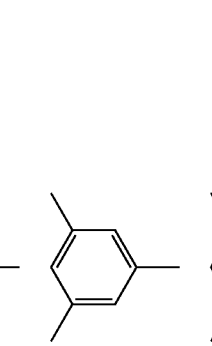 | —Ph | H | —Ph | H | |
| VIII-i-13 | 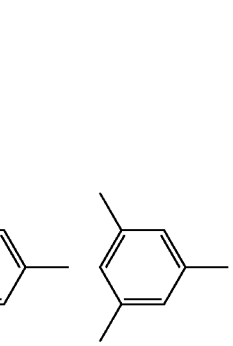 | —Ph | H | H | —Ph | |
| VIII-i-14 | 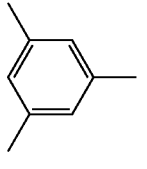 | —Ph | H | Cl | H | |
| VIII-i-15 | 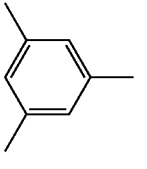 | —Ph | H | —OH | H | |

-continued

| | | | | | |
|---|---|---|---|---|---|
| VIII-i-16 | [3,5-disub phenyl] | —Ph | H | —NO$_2$ | H |
| VIII-i-17 | [3,5-disub phenyl] | —Ph | H | —CN | H |
| VIII-i-18 | [3,5-disub phenyl] | —Ph | H | —OPh | H |
| VIII-i-19 | [3,5-disub phenyl] | —Ph | H | —SCH$_3$ | H |
| VIII-i-20 | [3,5-disub phenyl] | —Ph | H | —SPh | H |
| VIII-i-21 | [3,5-disub phenyl] | —Ph | H | —N—Ph$_2$ | H |
| VIII-i-22 | [3,5-disub phenyl] | —Ph | H | CH$_3$ | H |

-continued

| ID | Group | | | | |
|---|---|---|---|---|---|
| VIII-i-23 | 3,5-dimethylphenyl | —Ph | H | —OCH₃ | H |
| VIII-i-24 | 3,5-dimethylphenyl | —Ph | H | —COOH | H |
| VIII-i-25 | 3,5-dimethylphenyl | —Ph | H | 2-pyridyl | H |
| VIII-i-26 | —N< | —Ph | —Ph | H | H |
| VIII-i-27 | —N< | —Ph | H | —Ph | H |
| VIII-i-28 | —N< | —Ph | H | H | —Ph |
| VIII-i-29 | —N< | —Ph | H | Cl | H |
| VIII-i-30 | —N< | —Ph | H | —OH | H |
| VIII-i-31 | —N< | —Ph | H | —NO₂ | H |
| VIII-i-32 | —N< | —Ph | H | —CN | H |

-continued
| | | | | |
|---|---|---|---|---|
| VIII-i-33 | —N(—)— | —Ph | H | —OPh | H |
| VIII-i-34 | —N(—)— | —Ph | H | —SCH₃ | H |
| VIII-i-35 | —N(—)— | —Ph | H | —SPh | H |
| VIII-i-36 | —N(—)— | —Ph | H | —N—Ph₂ | H |
| VIII-i-37 | —N(—)— | —Ph | H | CH₃ | H |
| VIII-i-38 | —N(—)— | —Ph | H | —OCH₃ | H |
| VIII-i-39 | —N(—)— | —Ph | H | —COOH | H |
| VIII-i-40 | —N(—)— | —Ph | H | 2-pyridyl | H |
| VIII-i-41 | | | —Ph | H | |
| VIII-i-42 | —N(—)— | —Ph | H | —Ph | H |
VIII-i-41:

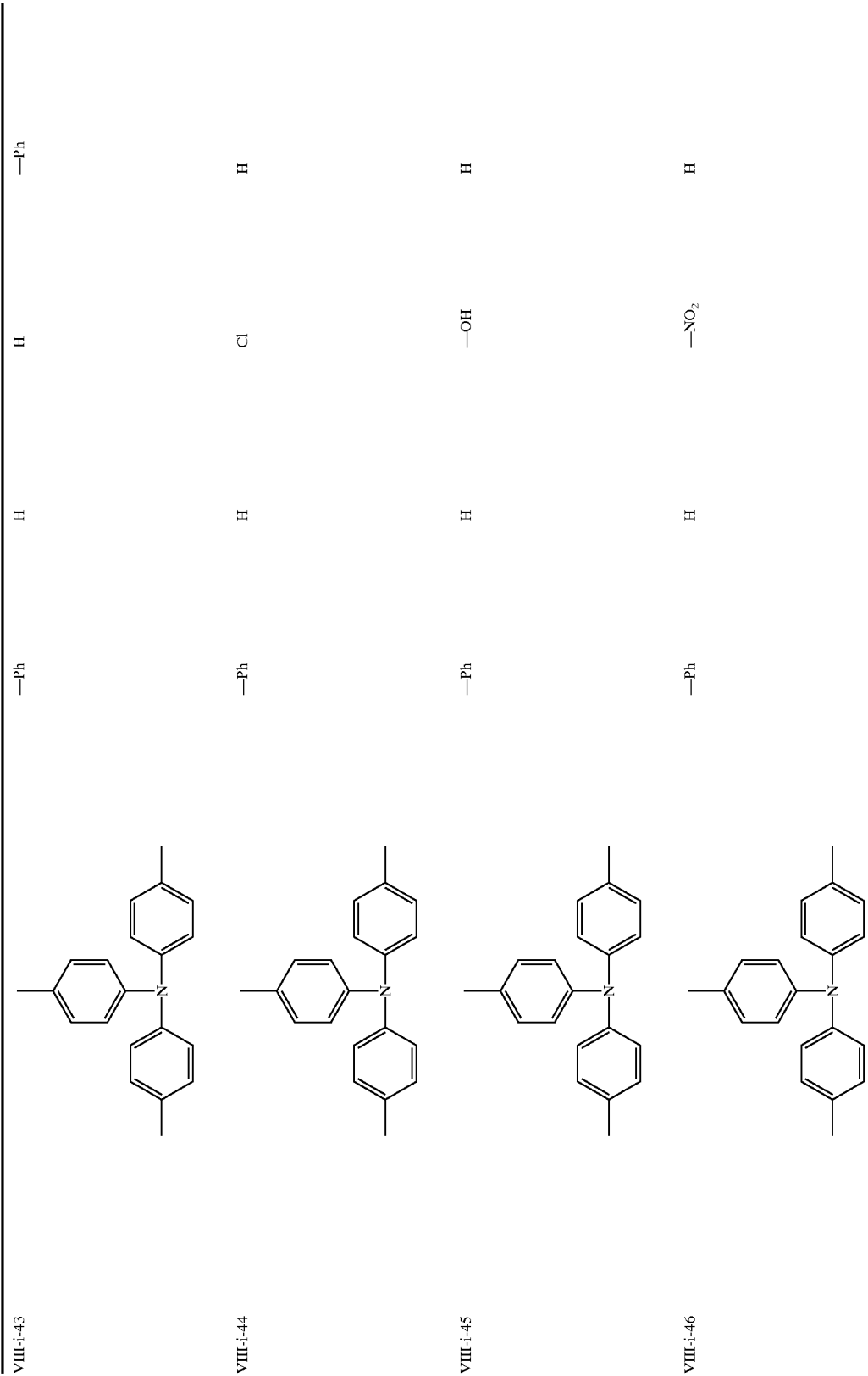

-continued

| | | | | |
|---|---|---|---|---|
| VIII-i-47 | ![structure] | —Ph | H | —CN | H |
| VIII-i-48 | ![structure] | —Ph | H | —OPh | H |
| VIII-i-49 | ![structure] | —Ph | H | —SCH₃ | H |
| VIII-i-50 | ![structure] | —Ph | H | —SPh | H |

-continued

| | | | | |
|---|---|---|---|---|
| VIII-i-51 | ![tri(p-tolyl)amine] | —Ph | H | —N—Ph₂ | H |
| VIII-i-52 | ![tri(p-tolyl)amine] | —Ph | H | CH₃ | H |
| VIII-i-53 | ![tri(p-tolyl)amine] | —Ph | H | —OCH₃ | H |
| VIII-i-54 | ![tri(p-tolyl)amine] | —Ph | H | —COOH | H |

-continued

| | | | | | | |
|---|---|---|---|---|---|---|
| VIII-i-55 | ![structure: N(p-tolyl)3] | —Ph | H | 2-pyridyl | H |

Formula (VIII)

| Compound No. | $L_{112}$ | $A_{13}=A_{23}=A_{33}$ | $A_{16}=A_{26}=A_{36}$ | $A_{18}=A_{28}=A_{38}$ |
|---|---|---|---|---|
| VIII-j-1 | 3,5-dimethylphenyl | H | H | H |
| VIII-j-2 | 3,5-dimethylphenyl | —Ph | H | H |
| VIII-j-3 | —N< | H | H | H |
| VIII-j-4 | N(p-tolyl)3 | H | H | H |

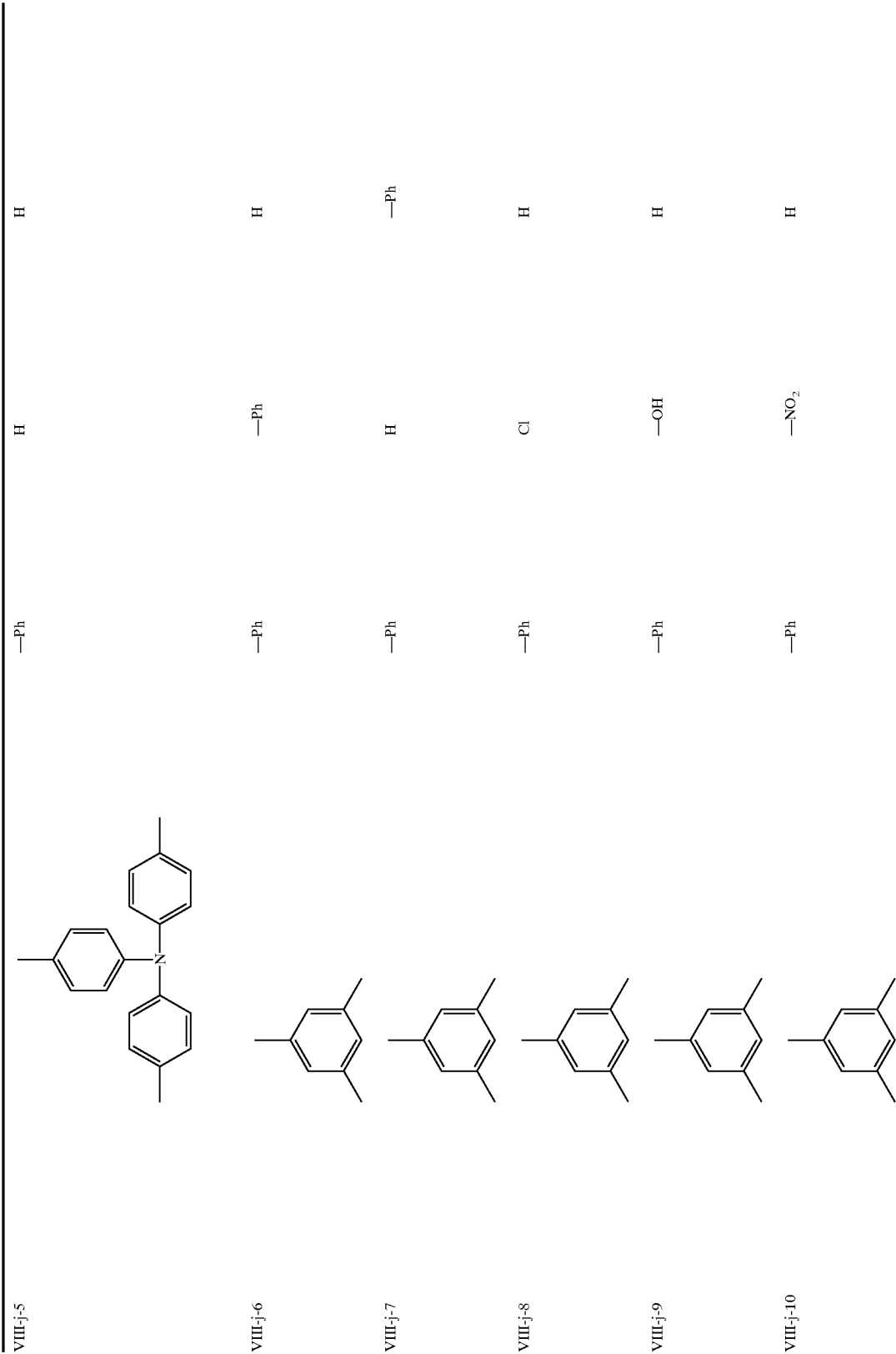

-continued

| | | | |
|---|---|---|---|
| VIII-j-11 | 3,5-dimethylphenyl | —Ph | —CN | H |
| VIII-j-12 | 3,5-dimethylphenyl | —Ph | —OPh | H |
| VIII-j-13 | 3,5-dimethylphenyl | —Ph | —SCH$_3$ | H |
| VIII-j-14 | 3,5-dimethylphenyl | —Ph | —SPh | H |
| VIII-j-15 | 3,5-dimethylphenyl | —Ph | —N—Ph$_2$ | H |
| VIII-j-16 | 3,5-dimethylphenyl | —Ph | CH$_3$ | H |
| VIII-j-17 | 3,5-dimethylphenyl | —Ph | —OCH$_3$ | H |

-continued

| | | | |
|---|---|---|---|
| VIII-j-18 | 3,5-dimethylphenyl | —Ph | —COOH | H |
| VIII-j-19 | 3,5-dimethylphenyl | —Ph | 2-pyridyl | |
| VIII-j-20 | —N< | —Ph | —Ph | H |
| VIII-j-21 | —N< | —Ph | H | —Ph |
| VIII-j-22 | —N< | —Ph | Cl | H |
| VIII-j-23 | —N< | —Ph | —OH | H |
| VIII-j-24 | —N< | —Ph | —NO$_2$ | H |
| VIII-j-25 | —N< | —Ph | —CN | H |
| VIII-j-26 | —N< | —Ph | —OPh | H |
| VIII-j-27 | —N< | —Ph | —SCH$_3$ | H |
| VIII-j-28 | —N< | —Ph | —SPh | H |

-continued

| | | | |
|---|---|---|---|
| VIII-j-29 | —N(—)— | —Ph | —N—Ph₂ | H |
| VIII-j-30 | —N(—)— | —Ph | CH₃ | H |
| VIII-j-31 | —N(—)— | —Ph | —OCH₃ | H |
| VIII-j-32 | —N(—)— | —Ph | —COOH | H |
| VIII-j-33 | —N(—)— | —Ph | 2-pyridyl | H |
| VIII-j-34 | —N(—)— | —Ph | —Ph | H |
| VIII-j-35 | N(p-tolyl)₃ structure | —Ph | H | —Ph |
| VIII-j-36 | N(p-tolyl)₃ structure | —Ph | Cl | H |

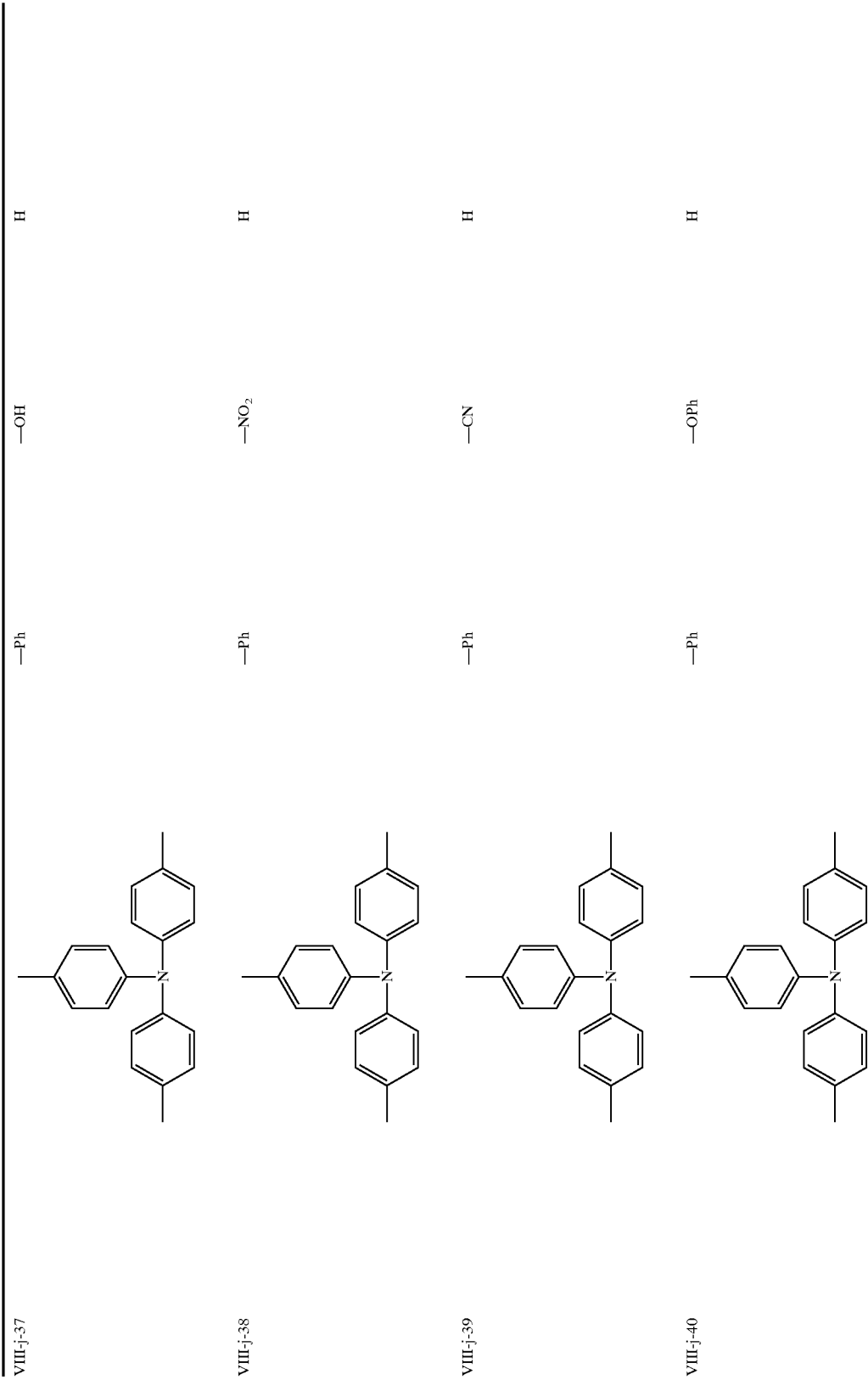

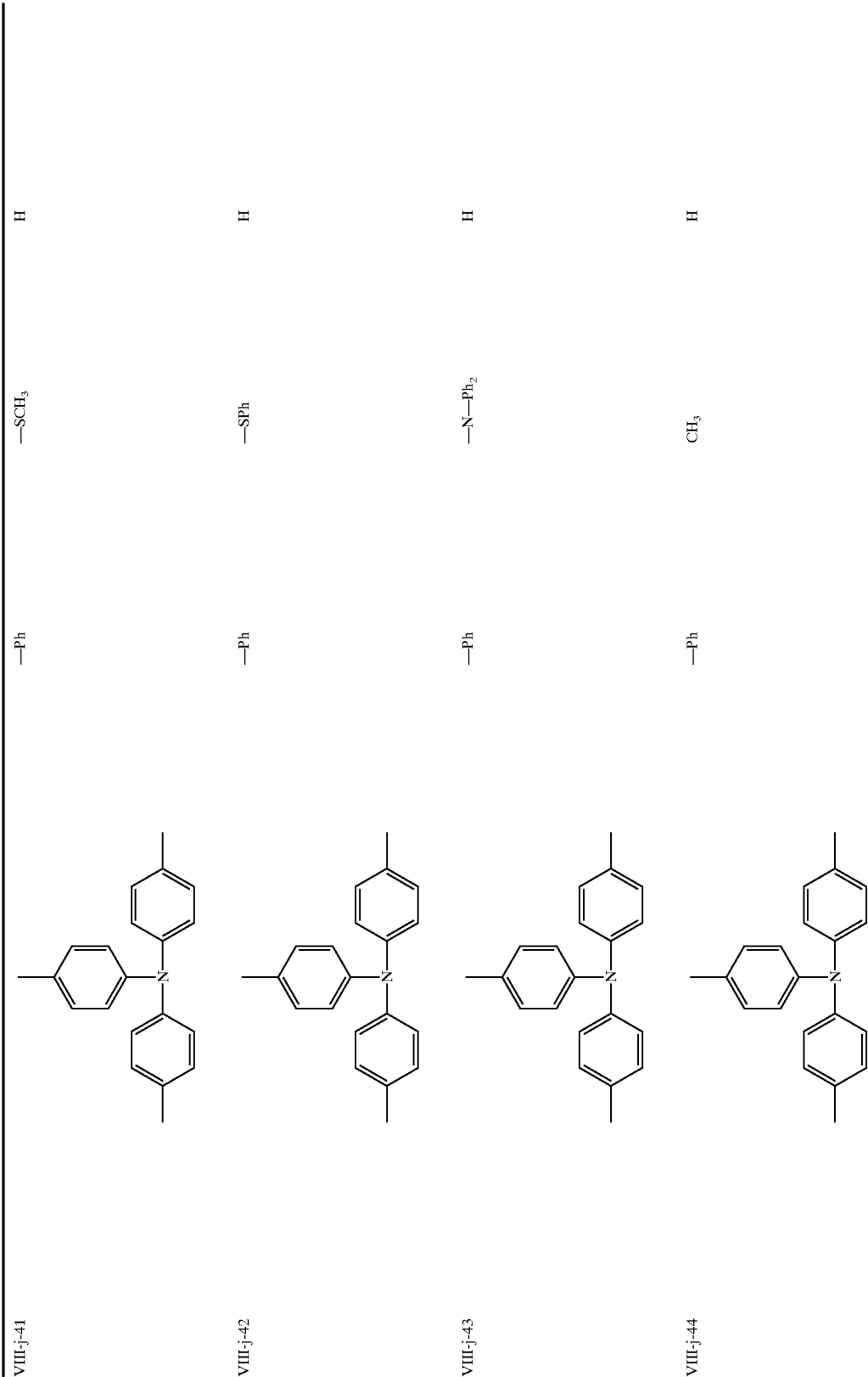

-continued

| | | | |
|---|---|---|---|
| VIII-j-45 | [tri(4-methylphenyl)amine group] | —Ph | —OCH$_3$ | H |
| VIII-j-46 | [tri(4-methylphenyl)amine group] | —Ph | —COOH | H |
| VIII-j-47 | [tri(4-methylphenyl)amine group] | —Ph | 2-pyridyl | H |

| Formula (VIII) Compound No. | L$_{112}$ | A$_{13}$=A$_{23}$=A$_{33}$ | A$_{17}$=A$_{27}$=A$_{37}$ | A$_{18}$=A$_{28}$=A$_{38}$ |
|---|---|---|---|---|
| VIII-k-1 | [3,5-dimethylphenyl group] | H | H | H |
| VIII-k-2 | [3,5-dimethylphenyl group] | —Ph | H | H |

| | | | | |
|---|---|---|---|---|
| VIII-k-3 |  | H | H | h |
| VIII-k-4 |  | —Ph | H | H |
| VIII-k-5 | | H | H | H |
| VIII-k-6 | 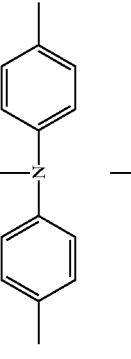 | —Ph | H | |
| VIII-k-7 | 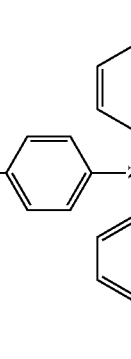 | H | H | $A_{17}$ and $A_{18}$ form a benzene ring. $A_{27}$ and $A_{28}$ form a benzene ring. $A_{37}$ and $A_{38}$ form a benzene ring. |
| VIII-k-8 | 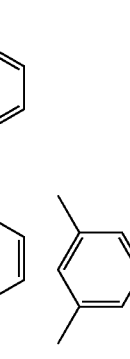 | —Ph | H | $A_{17}$ and $A_{18}$ form a benzene ring. $A_{27}$ and $A_{28}$ form a benzene ring. $A_{37}$ and $A_{38}$ form a benzene ring. |
| VIII-k-9 |  | H | H | $A_{17}$ and $A_{18}$ form a benzene ring. $A_{27}$ and $A_{28}$ form a benzene ring. $A_{37}$ and $A_{38}$ form a benzene ring. |
| VIII-k-10 |  | —Ph | H | $A_{17}$ and $A_{18}$ form a benzene ring. $A_{27}$ and $A_{28}$ form a benzene ring. $A_{37}$ and $A_{38}$ form a benzene ring. |

-continued
| | | | | |
|---|---|---|---|---|
| VIII-k-11 | 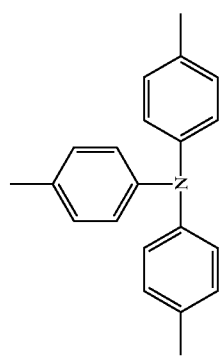 | H | | $A_{17}$ and $A_{18}$ form a benzene ring.<br>$A_{27}$ and $A_{28}$ form a benzene ring.<br>$A_{37}$ and $A_{38}$ form a benzene ring. |
| VIII-k-12 | 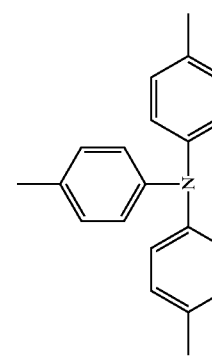 | —Ph | | $A_{17}$ and $A_{18}$ form a benzene ring.<br>$A_{27}$ and $A_{28}$ form a benzene ring.<br>$A_{37}$ and $A_{38}$ form a benzene ring. |
| VIII-k-13 | 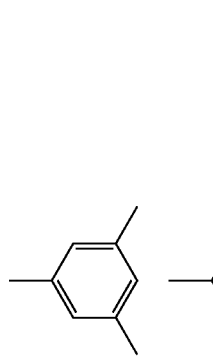 | —Ph | —Ph | H |
| VIII-k-14 | 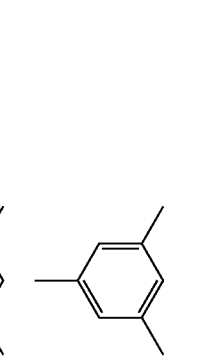 | —Ph | H | —Ph |
| VIII-k-15 | 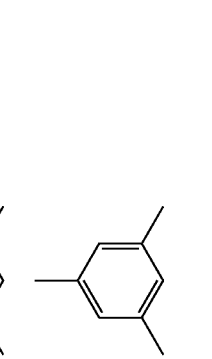 | —Ph | Cl | H |

-continued

| | | | |
|---|---|---|---|
| VIII-k-16 | 3,5-dimethylphenyl | —Ph | —OH | H |
| VIII-k-17 | 3,5-dimethylphenyl | —Ph | —NO$_2$ | H |
| VIII-k-18 | 3,5-dimethylphenyl | —Ph | —CN | H |
| VIII-k-19 | 3,5-dimethylphenyl | —Ph | —OPh | H |
| VIII-k-20 | 3,5-dimethylphenyl | —Ph | —SCH$_3$ | H |
| VIII-k-21 | 3,5-dimethylphenyl | —Ph | —SPh | H |
| VIII-k-22 | 3,5-dimethylphenyl | —Ph | —N—Ph$_2$ | H |

| | | | |
|---|---|---|---|
| VIII-k-23 | 3,5-dimethylphenyl | —Ph | CH₃ | H |
| VIII-k-24 | 3,5-dimethylphenyl | —Ph | —OCH₃ | H |
| VIII-k-25 | 3,5-dimethylphenyl | —Ph | —COOH | H |
| VIII-k-26 | 3,5-dimethylphenyl | —Ph | 2-pyridyl | H |
| VIII-k-27 | N(tBu) | —Ph | —Ph | H |
| VIII-k-28 | N(tBu) | —Ph | H | —Ph |
| VIII-k-29 | N(tBu) | —Ph | Cl | H |
| VIII-k-30 | N(tBu) | —Ph | —OH | H |
| VIII-k-31 | N(tBu) | —Ph | —NO₂ | H |

-continued

| | | | |
|---|---|---|---|
| VIII-k-32 | —N< | —Ph | —CN | H |
| VIII-k-33 | —N< | —Ph | —OPh | H |
| VIII-k-34 | —N< | —Ph | —SCH₃ | H |
| VIII-k-35 | —N< | —Ph | —SPh | H |
| VIII-k-36 | —N< | —Ph | —N—Ph₂ | H |
| VIII-k-37 | —N< | —Ph | CH₃ | H |
| VIII-k-38 | —N< | —Ph | —OCH₃ | H |
| VIII-k-39 | —N< | —Ph | —COOH | H |
| VIII-k-40 | —N< | —Ph | 2-pyridyl | H |
| VIII-k-41 | —N< | | —Ph | H |

-continued
| | | | |
|---|---|---|---|
| VIII-k-42 | 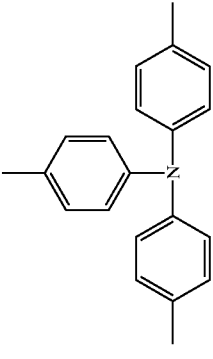 | —Ph | H | —Ph |
| VIII-k-43 | 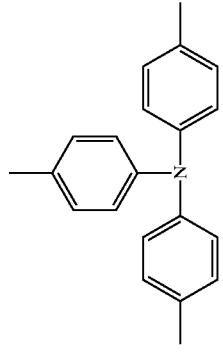 | —Ph | Cl | H |
| VIII-k-44 | 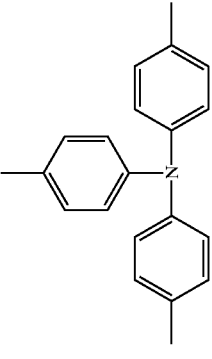 | —Ph | —OH | H |
| VIII-k-45 | 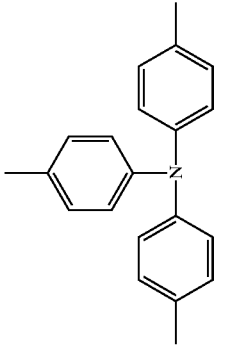 | —Ph | —NO$_2$ | H |

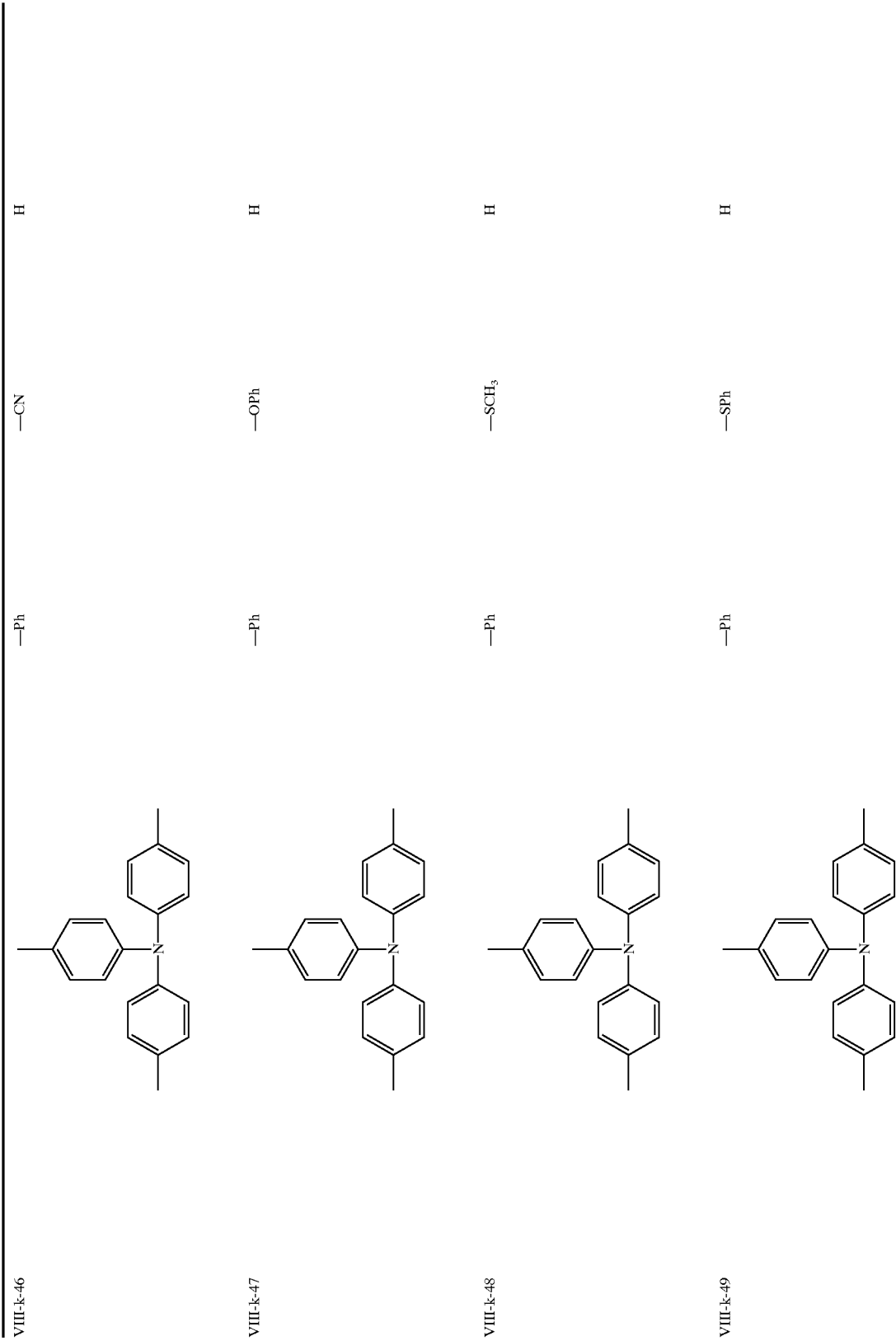

| | | | |
|---|---|---|---|
| VIII-k-50 | (tri-p-tolylamine)— | —Ph | —N—Ph$_2$ | H |
| VIII-k-51 | (tri-p-tolylamine)— | —Ph | CH$_3$ | H |
| VIII-k-52 | (tri-p-tolylamine)— | —Ph | —OCH$_3$ | H |
| VIII-k-53 | (tri-p-tolylamine)— | —Ph | —COOH | H |

| | | | |
|---|---|---|---|
| VIII-k-54 | (tri-p-tolylamine group) | —Ph | 2-pyridyl | H |

| Formula (VIII) Compound No. | $L_{112}$ | $A_{13}=A_{23}=A_{33}$ | $A_{15}=A_{25}=A_{35}$ | $A_{18}=A_{28}=A_{38}$ |
|---|---|---|---|---|
| VIII-l-1 | 3,5-dimethylphenyl | H | H | H |
| VIII-l-2 | 3,5-dimethylphenyl | —Ph | H | H |
| VIII-l-3 | —N< | H | H | H |
| VIII-l-4 | —N< | —Ph | H | H |
| VIII-l-5 | (tri-p-tolylamine group) | H | H | H |

-continued
| | | | | |
|---|---|---|---|---|
| VIII-I-6 | 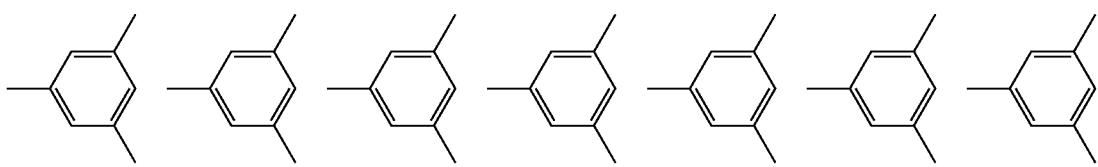 | —Ph | —Ph | H |
| VIII-I-7 | | —Ph | H | —Ph |
| VIII-I-8 | | —Ph | Cl | H |
| VIII-I-9 | | —Ph | —OH | H |
| VIII-I-10 | | —Ph | —NO$_2$ | H |
| VIII-I-11 | | —Ph | —CN | H |
| VIII-I-12 | | —Ph | —OPh | H |

-continued

| | | | |
|---|---|---|---|
| VIII-I-13 | 3,5-dimethylphenyl | —Ph | —SCH$_3$ | H |
| VIII-I-14 | 3,5-dimethylphenyl | —Ph | —SPh | H |
| VIII-I-15 | 3,5-dimethylphenyl | —Ph | —N—Ph$_2$ | H |
| VIII-I-16 | 3,5-dimethylphenyl | —Ph | CH$_3$ | H |
| VIII-I-17 | 3,5-dimethylphenyl | —Ph | —OCH$_3$ | H |
| VIII-I-18 | 3,5-dimethylphenyl | —Ph | —COOH | H |

-continued

| | | | | |
|---|---|---|---|---|
| VIII-I-19 | mesityl | —Ph | 2-pyridyl | H |
| VIII-I-20 | | —Ph | —Ph | H |
| VIII-I-21 | | —Ph | H | —Ph |
| VIII-I-22 | | —Ph | Cl | H |
| VIII-I-23 | | —Ph | —OH | H |
| VIII-I-24 | | —Ph | —NO$_2$ | H |
| VIII-I-25 | | —Ph | —CN | H |
| VIII-I-26 | | —Ph | —OPh | H |
| VIII-I-27 | | —Ph | —SCH$_3$ | H |
| VIII-I-28 | | —Ph | —SPh | H |
| VIII-I-29 | | —Ph | —N—Ph$_2$ | H |
| VIII-I-30 | | —Ph | CH$_3$ | H |
| VIII-I-31 | | —Ph | —OCH$_3$ | H |

-continued

| | | | |
|---|---|---|---|
| VIII-I-32 | —N— —N— | —Ph | —COOH | H |
| VIII-I-33 | | —Ph | 2-pyridyl | H |
| VIII-I-34 | | —Ph | —Ph | H |
| VIII-I-35 | N(p-tolyl)(p-tolyl)(Ph) | —Ph | H | —Ph |
| VIII-I-36 | N(p-tolyl)(p-tolyl)(p-tolyl) | —Ph | Cl | H |
| VIII-I-37 | N(p-tolyl)(p-tolyl)(Ph) | —Ph | —OH | H |

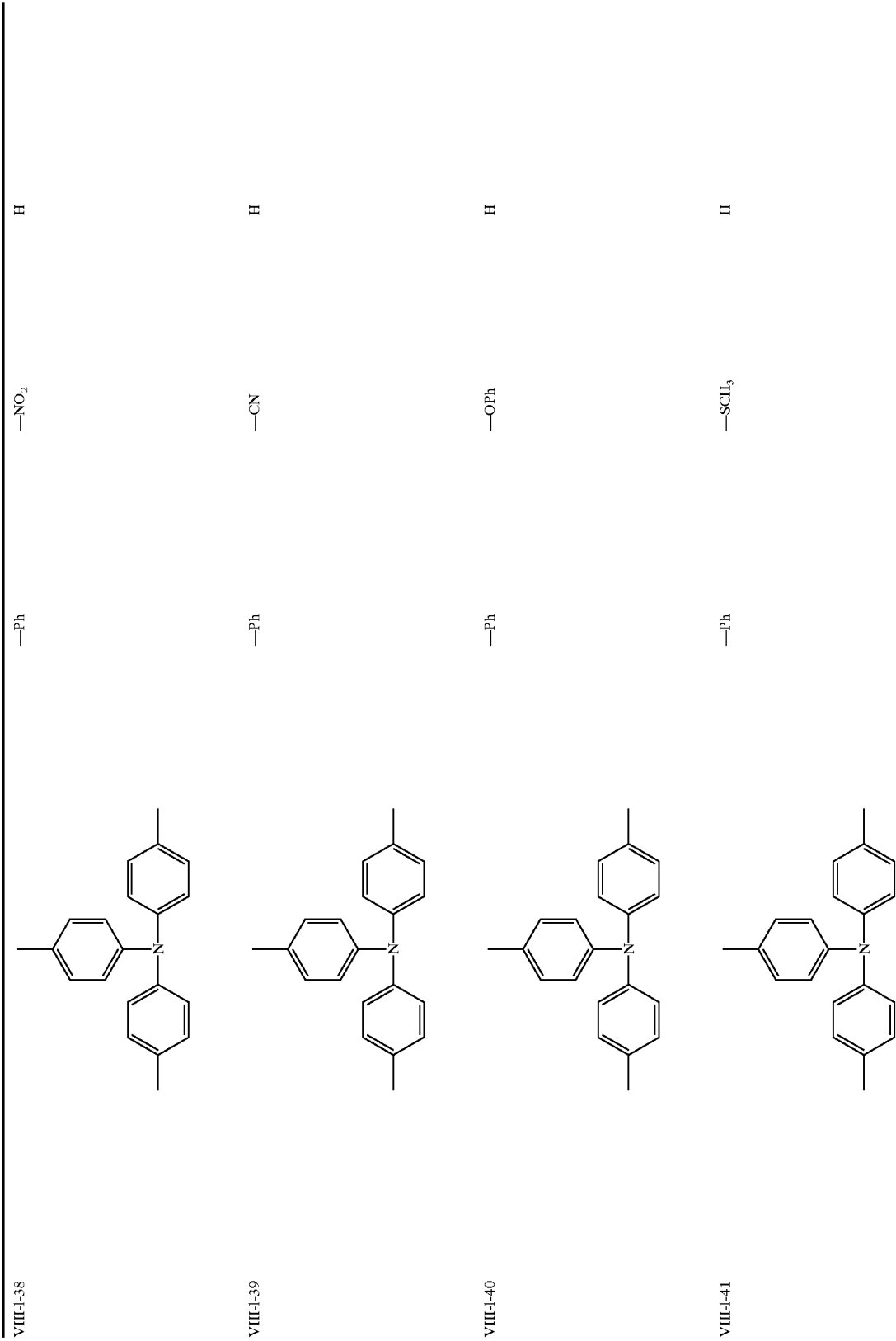

-continued
| | | | |
|---|---|---|---|
| VIII-I-42 | 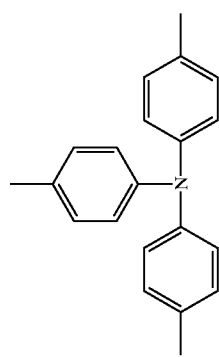 | —Ph | —SPh | H |
| VIII-I-43 | 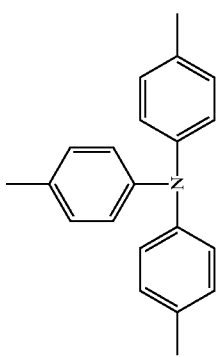 | —Ph | —N—Ph$_2$ | H |
| VIII-I-44 | 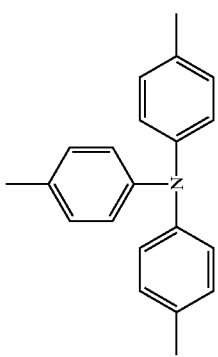 | —Ph | CH$_3$ | H |
| VIII-I-45 | 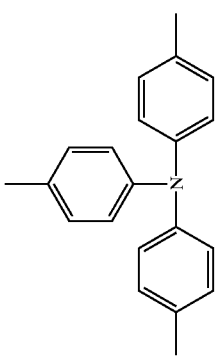 | —Ph | —OCH$_3$ | H |

-continued

| | | | | |
|---|---|---|---|---|
| VIII-l-46 | 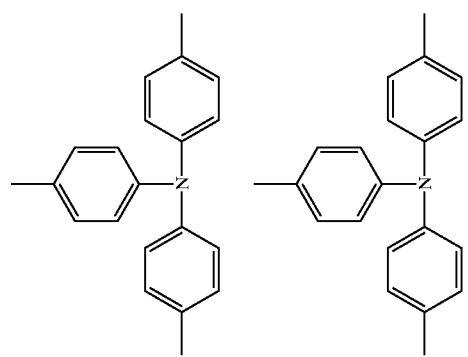 | —Ph | —COOH | H |
| VIII-l-47 | | —Ph | 2-pyridyl | H |

| Formula (VIII) Compound No. | $L_{111}$ | $A_{12}=A_{22}$ | $A_{13}=A_{23}$ | $A_{15}=A_{25}$ | $A_{17}=A_{27}$ | $A_{18}=A_{28}$ |
|---|---|---|---|---|---|---|
| VIII-m-1 | single bond | H | H | H | H | H |
| VIII-m-2 | single bond | H | H | $CH_3$ | H | H |
| VIII-m-3 | single bond | H | H | H | $CH_3$ | $CH_3$ |
| VIII-m-4 | single bond | H | H | H | H | $CH_3$ |
| VIII-m-5 | single bond | H | H | H | $n-C_2H_5$ | H |
| VIII-m-6 | single bond | H | H | H | $n-C_3H_7$ | H |
| VIII-m-7 | single bond | H | H | H | $n-C_4H_9$ | H |
| VIII-m-8 | single bond | H | H | H | $t-C_4H_9$ | H |
| VIII-m-9 | single bond | H | H | Ph | H | H |
| VIII-m-10 | single bond | H | H | H | Ph | Ph |
| VIII-m-11 | single bond | H | H | H | 1-naphthyl | H |
| VIII-m-12 | single bond | H | H | H | 2-naphthyl | H |
| VIII-m-13 | single bond | H | H | H | 4-biphenylyl | H |
| VIII-m-14 | single bond | H | H | H | 3-biphenylyl | H |
| VIII-m-15 | single bond | H | H | H | 2-biphenylyl | H |
| VIII-m-16 | single bond | H | H | H | 2-biphenylyl | H |
| VIII-m-17 | single bond | H | Ph | H | H | H |
| VIII-m-18 | single bond | Ph | Ph | H | H | H |
| VIII-m-19 | single bond | Ph | Ph | $CH_3$ | $CH_3$ | H |
| VIII-m-20 | single bond | Ph | Ph | H | H | $CH_3$ |
| VIII-m-21 | single bond | Ph | Ph | H | $CH_3$ | H |
| VIII-m-22 | single bond | Ph | Ph | H | $n-C_2H_5$ | H |
| VIII-m-23 | single bond | Ph | Ph | H | $n-C_3H_7$ | H |
| VIII-m-24 | single bond | Ph | Ph | H | $n-C_4H_9$ | H |
| VIII-m-25 | single bond | Ph | Ph | H | $t-C_4H_9$ | H |
| VIII-m-26 | single bond | Ph | Ph | Ph | H | H |

| ID | Linker | Sub1 | Structure | Sub2 | R | R' |
|---|---|---|---|---|---|---|
| VIII-m-27 | single bond | Ph | terphenyl | H | Ph | H |
| VIII-m-28 | single bond | Ph | terphenyl | H | H | Ph |
| VIII-m-29 | single bond | Ph | terphenyl | H | 1-naphthyl | H |
| VIII-m-30 | single bond | Ph | terphenyl | H | 2-naphthyl | H |
| VIII-m-31 | single bond | Ph | terphenyl | H | 4-biphenylyl | H |
| VIII-m-32 | single bond | Ph | terphenyl | H | 3-biphenylyl | H |
| VIII-m-33 | single bond | Ph | terphenyl | H | 2-biphenylyl | H |
| VIII-m-34 | single bond | Ph | terphenyl | H | H | H |
| VIII-m-35 | single bond | Ph | terphenyl | $CH_3$ | $CH_3$ | H |
| VIII-m-36 | single bond | Ph | terphenyl | H | $CH_3$ | H |
| VIII-m-37 | single bond | Ph | terphenyl | H | H | $CH_3$ |
| VIII-m-38 | single bond | Ph | terphenyl | H | $n$-$C_2H_5$ | H |
| VIII-m-39 | single bond | Ph | terphenyl | H | $n$-$C_3H_7$ | H |
| VIII-m-40 | single bond | Ph | terphenyl | H | $n$-$C_4H_9$ | H |
| VIII-m-41 | single bond | Ph | terphenyl | H | $t$-$C_4H_9$ | H |
| VIII-m-42 | single bond | Ph | terphenyl | —Ph | H | H |

-continued
| | | | | | |
|---|---|---|---|---|---|
| VIII-m-43 | single bond |  | H | —Ph | H |
| VIII-m-44 | single bond |  | H | H | Ph |
| VIII-m-45 | single bond | 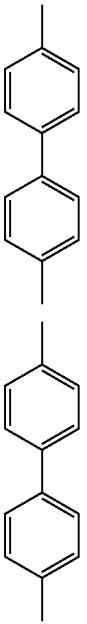 | H | 1-naphthyl | H |
| VIII-m-46 | single bond |  | H | 2-naphthyl | H |
| VIII-m-47 | single bond | 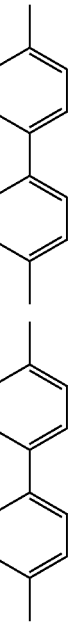 | H | 4-biphenylyl | H |
| VIII-m-48 | single bond |  | H | 3-biphenylyl | H |
| VIII-m-49 | single bond | 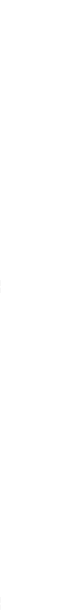 | H | 2-biphenylyl | H |
| VIII-m-50 |  | H | H | H | H |
| VIII-m-51 |  | H | CH$_3$ | H | H |
| VIII-m-52 | 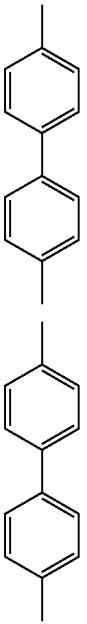 | H | H | CH$_3$ | H |

-continued

| | | | | | | |
|---|---|---|---|---|---|---|
| VIII-m-53 | phenyl | H | H | H | H | CH₃ |
| VIII-m-54 | phenyl | H | H | H | n-C₂H₅ | H |
| VIII-m-55 | phenyl | H | H | H | n-C₃H₇ | H |
| VIII-m-56 | phenyl | H | H | H | n-C₄H₉ | H |
| VIII-m-57 | phenyl | H | H | H | t-C₄H₉ | H |
| VIII-m-58 | phenyl | H | H | Ph | H | H |
| VIII-m-59 | phenyl | H | H | H | Ph | H |
| VIII-m-60 | phenyl | H | H | H | H | Ph |
| VIII-m-61 | phenyl | H | H | H | 1-naphthyl | H |
| VIII-m-62 | phenyl | H | H | H | 2-naphthyl | H |

-continued

| | | | | | | |
|---|---|---|---|---|---|---|
| VIII-m-63 | ⬡ | H | H | H | 4-biphenylyl | H |
| VIII-m-64 | ⬡ | H | H | H | 3-biphenylyl | H |
| VIII-m-65 | ⬡ | H | H | H | 2-biphenylyl | H |
| VIII-m-66 | ⬡ | H | H | H | 2-biphenylyl | H |
| VIII-m-67 | ⬡ | Ph | Ph | H | H | H |
| VIII-m-68 | ⬡ | Ph | Ph | $CH_3$ | H | H |
| VIII-m-69 | ⬡ | Ph | Ph | H | $CH_3$ | H |
| VIII-m-70 | ⬡ | Ph | Ph | H | H | H |
| VIII-m-71 | ⬡ | Ph | Ph | H | n-$C_2H_5$ | $CH_3$ |
| VIII-m-72 | ⬡ | Ph | Ph | H | n-$C_3H_7$ | H |

| | | | | |
|---|---|---|---|---|
| VIII-m-73 | Ph | Ph | H | n-C₄H₉ | H |
| VIII-m-74 | Ph | Ph | H | t-C₄H₉ | H |
| VIII-m-75 | Ph | Ph | Ph | H | H |
| VIII-m-76 | Ph | Ph | H | Ph | H |
| VIII-m-77 | Ph | Ph | H | H | Ph |
| VIII-m-78 | Ph | Ph | H | 1-naphthyl | H |
| VIII-m-79 | Ph | Ph | H | 2-naphthyl | H |
| VIII-m-80 | Ph | Ph | H | 4-biphenylyl | H |
| VIII-m-81 | Ph | Ph | H | 3-biphenylyl | H |
| VIII-m-82 | Ph | Ph | H | 2-biphenylyl | H |

| | | | | |
|---|---|---|---|---|
| VIII-m-83 | | H | H | H |
| VIII-m-84 | | CH₃ | H | H |
| VIII-m-85 | | H | CH₃ | H |
| VIII-m-86 | | H | H | CH₃ |
| VIII-m-87 | | H | n-C₂H₅ | H |
| VIII-m-88 | | H | n-C₃H₇ | H |
| VIII-m-89 | | H | n-C₄H₉ | H |
| VIII-m-90 | | H | t-C₄H₉ | H |
| VIII-m-91 | | Ph | H | H |
| VIII-m-92 | | H | Ph | H |

-continued

| | | | | | |
|---|---|---|---|---|---|
| VIII-m-93 | ph-ph | H | ph-ph | H | Ph |
| VIII-m-94 | ph-ph | H | ph-ph | 1-naphthyl | H |
| VIII-m-95 | ph-ph | H | ph-ph | 2-naphthyl | H |
| VIII-m-96 | ph-ph | H | ph-ph | 4-biphenylyl | H |
| VIII-m-97 | ph-ph | H | ph-ph | 3-biphenylyl | H |
| VIII-m-98 | ph-ph | H | ph-ph | 2-biphenylyl | H |
| VIII-m-99 | ph | H | ph-ph | H | H |
| VIII-m-100 | ph | CH₃ | ph-ph | H | H |
| VIII-m-101 | ph | H | ph-ph | CH₃ | H |
| VIII-m-102 | ph | H | ph-ph | H | CH₃ |

-continued

| | | | | | |
|---|---|---|---|---|---|
| VIII-m-103 | biphenyl | H | H | n-C₂H₅ | H |
| VIII-m-104 | biphenyl | H | H | n-C₃H₇ | H |
| VIII-m-105 | biphenyl | H | H | n-C₄H₉ | H |
| VIII-m-106 | biphenyl | H | H | t-C₄H₉ | H |
| VIII-m-107 | biphenyl | H | Ph | H | H |
| VIII-m-108 | biphenyl | H | H | Ph | H |
| VIII-m-109 | biphenyl | H | H | H | Ph |
| VIII-m-110 | biphenyl | H | H | 1-naphthyl | H |
| VIII-m-111 | biphenyl | H | H | 2-naphthyl | H |
| VIII-m-112 | biphenyl | H | H | 4-biphenylyl | H |

-continued

| ID | Structure | | | | |
|---|---|---|---|---|---|
| VIII-m-113 | biphenyl | H | H | H | 3-biphenylyl | H |
| VIII-m-114 | biphenyl | H | H | H | 2-biphenylyl | H |
| VIII-m-115 | biphenyl | H | H | H | 2-biphenylyl | H |
| VIII-m-116 | biphenyl | Ph | Ph | H | H | H |
| VIII-m-117 | biphenyl | Ph | Ph | $CH_3$ | H | H |
| VIII-m-118 | biphenyl | Ph | Ph | H | $CH_3$ | H |
| VIII-m-119 | biphenyl | Ph | Ph | H | H | $CH_3$ |
| VIII-m-120 | biphenyl | Ph | Ph | H | $n\text{-}C_2H_5$ | H |
| VIII-m-121 | biphenyl | Ph | Ph | H | $n\text{-}C_3H_7$ | H |
| VIII-m-122 | biphenyl | Ph | Ph | H | $n\text{-}C_4H_9$ | H |

-continued

| | | | | | |
|---|---|---|---|---|---|
| VIII-m-123 | [biphenyl] | Ph | Ph | H | t-C$_4$H$_9$ | H |
| VIII-m-124 | [biphenyl] | Ph | Ph | Ph | H | H |
| VIII-m-125 | [biphenyl] | Ph | Ph | H | Ph | H |
| VIII-m-126 | [biphenyl] | Ph | Ph | H | H | Ph |
| VIII-m-127 | [biphenyl] | Ph | Ph | H | 1-naphthyl | H |
| VIII-m-128 | [biphenyl] | Ph | Ph | H | 2-naphthyl | H |
| VIII-m-129 | [biphenyl] | Ph | Ph | H | 4-biphenylyl | H |
| VIII-m-130 | [biphenyl] | Ph | Ph | H | 3-biphenylyl | H |
| VIII-m-131 | [biphenyl] | Ph | Ph | H | 2-biphenylyl | H |
| VIII-m-132 | [quaterphenyl] | [biphenyl] | Ph | H | H | H |

-continued

| | | | | |
|---|---|---|---|---|
| VIII-m-133 | | CH₃ | H | H |
| VIII-m-134 | | H | CH₃ | H |
| VIII-m-135 | | H | CH₃ | CH₃ |
| VIII-m-136 | | H | n-C₂H₅ | H |
| VIII-m-137 | | H | n-C₃H₇ | H |
| VIII-m-138 | | H | n-C₄H₉ | H |
| VIII-m-139 | | H | t-C₄H₉ | H |
| VIII-m-140 | | Ph | H | H |
| VIII-m-141 | | H | Ph | H |
| VIII-m-142 | | H | H | Ph |

| | | | |
|---|---|---|---|
| VIII-m-143 | 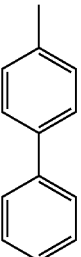 | H | 1-naphthyl | H |
| VIII-m-144 | 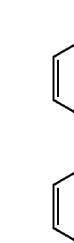 | H | 2-naphthyl | H |
| VIII-m-145 | 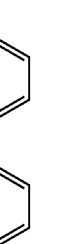 | H | 4-biphenylyl | H |
| VIII-m-146 | 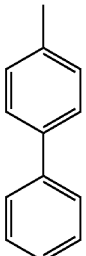 | H | 3-biphenylyl | H |
| VIII-m-147 | 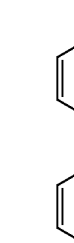 | H | 3-biphenylyl | H |

These quinoxaline compounds are obtained by (i) a process involving condensing diaminobenzene or derivatives thereof, diaminopyridine or derivatives thereof, diaminopyrimidine or derivatives thereof, diaminopyridazine or derivatives thereof with a halogenated diketone compound, followed by coupling using a nickel complex of 1,5-cyclooctadiene or the like, (ii) condensing diaminobenzene or derivatives thereof, diaminopyridine or derivatives thereof, diaminopyrimidine or derivatives thereof, diaminopyridazine or derivatives thereof with a bisdiketone compound, (iii) condensing a bisdiamine compound with a diketone compound, or (iv) converting a starting compound into an organometallic reagent of tin or the like, followed by cross-coupling.

These compounds can be identified by elemental analysis, mass analysis, IR spectroscopy, $^1$H and $^{13}$C NMR, etc.

In general, the quinoxaline compounds have a molecular weight of about 500 to about 2,000, a melting point of about 250 to about 500° C., and a glass transition temperature (Tg) of about 90 to about 200° C. By conventional vacuum deposition or the like, they form a transparent, smooth film of quality which maintains a stable amorphous state even above room temperature and over a long period of time.

The term "host material" used herein means a material which participates in light emission, but does not emit light by itself or emits light at a very low luminance. Specifically, an appropriate difference in luminance between the host and the dopant is such that the maximum luminance of the host is equal to or less than 10%, especially equal to or less than 2% of the maximum luminance of the dopant.

Dopants

A class of organic compounds useful as the dopant according to the invention are compounds of the following formula (V).

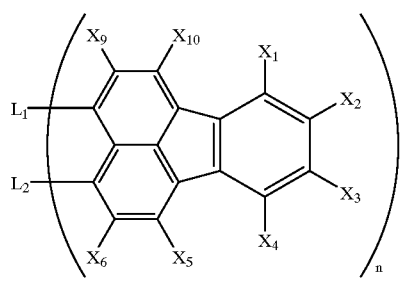

(V)

Herein $X_1$ to $X_{10}$, $L_1$ and $L_2$ are independently hydrogen, halogen atoms, straight, branched or cyclic alkyl radicals which may have substituents, straight, branched or cyclic alkoxy radicals which may have substituents, straight, branched or cyclic alkylthio radicals which may have substituents, straight, branched or cyclic alkenyl radicals which may have substituents, straight, branched or cyclic alkenyloxy radicals which may have substituents, straight, branched or cyclic alkenylthio radicals which may have substituents, substituted or unsubstituted aralkyl radicals, substituted or unsubstituted aralkyloxy radicals, substituted or unsubstituted aralkylthio radicals, substituted or unsubstituted aryl radicals, substituted or unsubstituted aryloxy radicals, substituted or unsubstituted arylthio radicals, substituted or unsubstituted amino radicals, cyano, hydroxyl, —COOR$^1$ radicals (wherein R$^1$ is hydrogen, a substituted or unsubstituted straight, branched or cyclic alkyl radical, a substituted or unsubstituted straight, branched or cyclic alkenyl radical, a substituted or unsubstituted aralkyl radical or a substituted or unsubstituted aryl radical), —COR$^2$ radicals (wherein R$^2$ is hydrogen, a substituted or unsubstituted straight, branched or cyclic alkyl radical, a substituted or unsubstituted straight, branched or cyclic alkenyl radical, a substituted or unsubstituted aralkyl radical, a substituted or unsubstituted aryl radical or an amino radical), or —OCOR$^3$ radicals (wherein R$^3$ is a substituted or unsubstituted straight, branched or cyclic alkyl radical, a substituted or unsubstituted straight, branched or cyclic alkenyl radical, a substituted or unsubstituted aralkyl radical, or a substituted or unsubstituted aryl radical), or at least two adjoining groups selected from $X_1$ to $X_{10}$, $L_1$ and $L_2$ may bond or fuse together to form a substituted or unsubstituted carbocyclic aliphatic ring, aromatic ring or fused aromatic ring with the carbon atoms to which they are attached, or $L_1$ and $L_2$ each may be a single bond.

Preferably, at least two adjoining groups selected from $X_1$ to $X_{10}$, $L_1$ and $L_2$ bond or fuse together to form a substituted or unsubstituted carbocyclic aliphatic ring, aromatic ring or fused aromatic ring with the carbon atoms to which they are attached. $L_1$ and $L_2$ each may be a single bond. n is 1 or 2.

Of the compounds of formula (V), preferred are diindeno[1,2,3-cd:1',2',3'-lm]perylene derivatives, having a skeleton of the following formula (VI).

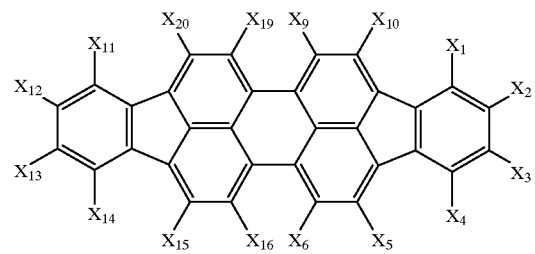

(VI)

In formula (VI), $X_1$ to $X_6$, $X_9$ to $X_{10}$, $X_{11}$ to $X_{16}$, $X_{19}$ and $X_{20}$ are independently hydrogen, halogen atoms, straight, branched or cyclic alkyl radicals which may have substituents, straight, branched or cyclic alkoxy radicals which may have substituents, straight, branched or cyclic alkylthio radicals which may have substituents, straight, branched or cyclic alkenyl radicals which may have substituents, straight, branched or cyclic alkenyloxy radicals which may have substituents, straight, branched or cyclic alkenylthio radicals which may have substituents, substituted or unsubstituted aralkyl radicals, substituted or unsubstituted aralkyloxy radicals, substituted or unsubstituted aralkylthio radicals, substituted or unsubstituted aryl radicals, substituted or unsubstituted aryloxy radicals, substituted or unsubstituted arylthio radicals, substituted or unsubstituted arylalkenyl radicals, substituted or unsubstituted alkenylaryl radicals, substituted or unsubstituted amino radicals, cyano, hydroxyl, —COOR$^1$ radicals (wherein $R^1$ is hydrogen, a substituted or unsubstituted straight, branched or cyclic alkyl radical, a substituted or unsubstituted straight, branched or cyclic alkenyl radical, a substituted or unsubstituted aralkyl radical or a substituted or unsubstituted aryl radical), —$COR^2$ radicals (wherein $R^2$ is hydrogen, a substituted or unsubstituted straight, branched or cyclic alkyl radical, a substituted or unsubstituted straight, branched or cyclic alkenyl radical, a substituted or unsubstituted aralkyl radical, a substituted or unsubstituted aryl radical or an amino radical), or —$OCOR^3$ radicals (wherein $R^3$ is a substituted or unsubstituted straight, branched or cyclic alkyl radical, a substituted or unsubstituted straight, branched or cyclic alkenyl radical, a substituted or unsubstituted aralkyl radical, or a substituted or unsubstituted aryl radical), or at least two adjoining groups selected from $X_1$ to $X_{20}$ may bond together to form a substituted or unsubstituted carbocyclic aliphatic ring, aromatic ring or fused aromatic ring with the carbon atoms to which they are attached.

The term "aryl radicals" is used herein to encompass carbocyclic aromatic radicals such as phenyl and naphthyl and heterocyclic aromatic radicals such as furyl, thienyl and pyridyl.

The straight, branched or cyclic alkyl radicals, straight, branched or cyclic alkoxy radicals, straight, branched or cyclic alkylthio radicals, straight, branched or cyclic alkenyl radicals, straight, branched or cyclic alkenyloxy radicals, and straight, branched or cyclic alkenylthio radicals, represented by $X_1$ to $X_{20}$ in formulas (V) and (VI), may have a substituent or substituents, for example, halogen atoms, aryl groups of 4 to 20 carbon atoms, alkoxy groups of 1 to 20 carbon atoms, alkoxyalkoxy groups of 2 to 20 carbon atoms, alkenyloxy groups of 2 to 20 carbon atoms, aralkyloxy groups of 4 to 20 carbon atoms, aralkyloxyalkoxy groups of 5 to 20 carbon atoms, aryloxy groups of 3 to 20 carbon atoms, aryloxyalkoxy groups of 4 to 20 carbon atoms, arylalkenyl groups of 5 to 20 carbon atoms, aralkylalkenyl groups of 6 to 20 carbon atoms, alkylthio groups of 1 to 20 carbon atoms, alkoxyalkylthio groups of 2 to 20 carbon atoms, alkylthioalkylthio groups of 2 to 20 carbon atoms, alkenylthio groups of 2 to 20 carbon atoms, aralkylthio groups of 4 to 20 carbon atoms, aralkyloxyalkylthio groups of 5 to 20 carbon atoms, aralkylthioalkylthio groups of 5 to 20 carbon atoms, arylthio groups of 3 to 20 carbon atoms, aryloxyalkylthio groups of 4 to 20 carbon atoms, arylthioalkylthio groups of 4 to 20 carbon atoms, and heteroatom-containing cyclic alkyl groups of 4 to 20 carbon atoms. The aryl groups included in these substituents may be further substituted with halogen atoms, alkyl groups of 1 to 10 carbon atoms, alkoxy groups of 1 to 10 carbon atoms, aryl groups of 3 to 10 carbon atoms, and aralkyl groups of 4 to 10 carbon atoms, among others.

The aralkyl radicals, aralkyloxy radicals, aralkylthio radicals, aryl radicals, aryloxy radicals and arylthio radicals, represented by $X_1$ to $X_{20}$ in formulas (V) and (VI), may have a substituent or substituents, for example, alkyl groups of 1 to 20 carbon atoms, alkenyl groups of 2 to 20 carbon atoms, aralkyl groups of 4 to 20 carbon atoms, aryl groups of 3 to 20 carbon atoms, alkoxy groups of 1 to 20 carbon atoms, alkoxyalkyl groups of 2 to 20 carbon atoms, alkoxyalkyloxy groups of 2 to 20 carbon atoms, alkenyloxy groups of 2 to 20 carbon atoms, alkenyloxyalkyl groups of 3 to 20 carbon atoms, alkenyloxyalkyloxy groups of 3 to 20 carbon atoms, aralkyloxy groups of 4 to 20 carbon atoms, aralkyloxyalkyl groups of 5 to 20 carbon atoms, aralkyloxyalkyloxy groups of 5 to 20 carbon atoms, aryloxy groups of 3 to 20 carbon atoms, aryloxyalkyl groups of 4 to 20 carbon atoms, aryloxyalkyloxy groups of 4 to 20 carbon atoms, alkylcarbonyl groups of 2 to 20 carbon atoms, alkenylcarbonyl groups of 3 to 20 carbon atoms, aralkylcarbonyl groups of 5 to 20 carbon atoms, arylcarbonyl groups of 4 to 20 carbon atoms, alkoxycarbonyl groups of 2 to 20 carbon atoms, alkenyloxycarbonyl groups of 3 to 20 carbon atoms, aralkyloxycarbonyl groups of 5 to 20 carbon atoms, aryloxycarbonyl groups of 4 to 20 carbon atoms, alkylcarbonyloxy groups of 2 to 20 carbon atoms, alkenylcarbonyloxy groups of 3 to 20 carbon atoms, aralkylcarbonyloxy groups of 5 to 20 carbon atoms, arylcarbonyloxy groups of 4 to 20 carbon atoms, alkylthio groups of 1 to 20 carbon atoms, aralkylthio groups of 4 to 20 carbon atoms, arylthio groups of 3 to 20 carbon atoms, nitro, cyano, formyl, halogen atoms, halogenated alkyl, hydroxyl, amino, N-mono-substituted amino groups of 1 to 20 carbon atoms, and N,N-di-substituted amino groups of 2 to 40 carbon atoms. The aryl groups included in these substituents may be further substituted with halogen atoms, alkyl groups of 1 to 10 carbon atoms, alkoxy groups of 1 to 10 carbon atoms, aryl groups of 6 to 10 carbon atoms, and aralkyl groups of 7 to 10 carbon atoms, among others.

The amino radicals represented by $X_1$ to $X_{20}$ in formulas (V) and (VI) may have a substituent or substituents, for example, be mono- or di-substituted with alkyl groups of 1 to 20 carbon atoms, aralkyl groups of 4 to 20 carbon atoms, and aryl groups of 3 to 20 carbon atoms.

The alkyl, alkenyl, aralkyl and aryl radicals represented by $R^1$, $R^2$ and $R^3$ in formulas (V) and (VI) may have a substituent or substituents, as exemplified for $X_1$ to $X_{20}$.

In a preferred embodiment, $X_5$, $X_6$, $X_9$, $X_{10}$, $X_{15}$, $X_{16}$, $X_{19}$ and $X_{20}$ are hydrogen, and $X_1$ to $X_4$ and $X_{11}$ to $X_{14}$ are independently hydrogen, halogen atoms, straight, branched or cyclic alkyl radicals of 1 to 24 carbon atoms in total which may have substituents, straight, branched or cyclic alkoxy radicals of 1 to 24 carbon atoms in total which may have substituents, straight, branched or cyclic alkenyl, alkenylaryl and arylalkenyl radicals of 2 to 24 carbon atoms in total which may have substituents, substituted or unsubstituted aralkyl groups of 7 to 24 carbon atoms in total, substituted or unsubstituted aryl radicals of 6 to 24 carbon atoms in total, cyano radicals, heterocyclic radicals, hydroxyl radicals, —$COOR^1$, —$COR^2$ or —$OCOR^3$ radicals wherein $R^1$, $R^2$ and $R^3$ are as defined above.

Two adjoining groups selected from $X_1$ to $X_{20}$ may bond or fuse together to form a substituted or unsubstituted carbocyclic aliphatic ring, aromatic ring or fused aromatic ring with the carbon atoms to which they are attached.

The organic EL device of the invention is characterized by the inclusion of at least one fluoranthene derivative or diindeno[1,2,3-cd:1',2',3'-lm]perylene derivative. The use of a diindeno[1,2,3-cd:1',2',3'-lm]perylene derivative in a light emitting layer as a luminescent component, for example, enables to produce an organic EL device having improved luminance and durability over similar EL devices of the prior art. The use of the specific derivative in combination with another luminescent component to form a light emitting layer enables to produce an organic EL device capable of emitting white light and having improved luminance and durability.

Illustrative, non-limiting, examples of the compounds of formulas (V) and (VI) according to the invention are given below. Ph designates phenyl.

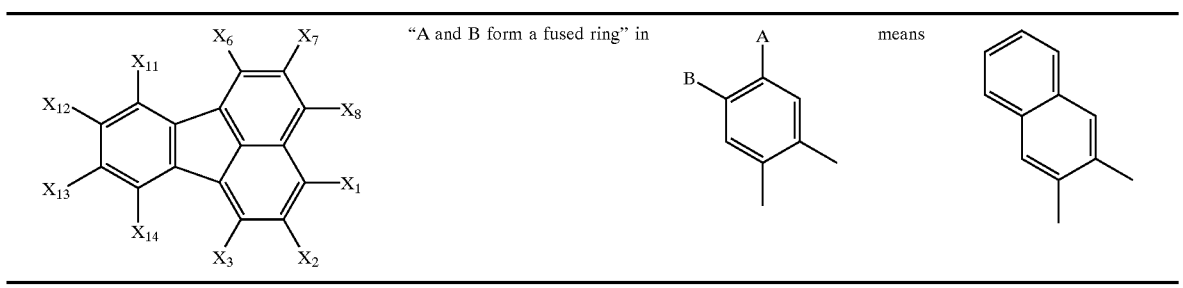

| Compound No. | X1 | X2 | X3 | X6 | X7 | X8 |
|---|---|---|---|---|---|---|
| A-1 | H | H | H | H | H | H |
| A-2 | H | H | H | H | H | H |
| A-3 | H | H | H | H | H | H |
| A-4 | H | H | H | H | H | H |
| A-5 | H | H | H | H | H | H |
| A-6 | H | H | H | H | H | H |
| A-7 | H | H | H | H | H | H |
| A-8 | H | H | H | H | H | H |
| A-9 | H | H | H | H | H | H |
| A-10 | H | H | H | H | H | H |
| A-11 | Ph | H | H | H | H | Ph |
| A-12 | 4-biphenylyl | H | H | H | H | 4-biphenylyl |
| A-13 | CH3 | H | H | H | H | CH3 |
| A-14 | H | Ph | H | H | Ph | H |
| A-15 | H | 4-biphenylyl | H | H | 4-biphenylyl | H |
| A-16 | H | CH3 | H | H | CH3 | H |
| A-17 | X1 and X2 form a fused ring. | | H | H | H | H |
| A-18 | X1 and X2 form a fused ring. | | H | H | H | H |
| A-19 | X1 and X2 form a fused ring. | | H | H | H | H |
| A-20 | X1 and X2 form a fused ring. | | H | H | H | H |
| A-21 | X1 and X2 form a fused ring. | | H | H | H | H |
| A-22 | X1 and X2 form a fused ring. | | H | H | H | H |
| A-23 | X1 and X2 form a fused ring. | | H | H | H | H |
| A-24 | X1 and X2 form a fused ring. | | H | H | H | H |
| A-25 | X1 and X2 form a fused ring. | | H | H | H | H |
| A-26 | X1 and X2 form a fused ring. | | H | H | H | H |
| A-27 | X1 and X2 form a fused ring. | | H | H | H | Ph |
| A-28 | X1 and X2 form a fused ring. | | H | H | H | 4-biphenylyl |
| A-29 | X1 and X2 form a fused ring. | | H | H | H | CH3 |
| A-30 | X1 and X2 form a fused ring. | | H | H | Ph | H |
| A-31 | X1 and X2 form a fused ring. | | H | H | 4-biphenylyl | H |
| A-32 | X1 and X2 form a fused ring. | | H | H | CH3 | H |
| A-33 | H | H | H | H | H | H |
| A-34 | H | H | H | H | H | H |
| A-35 | H | H | H | H | H | H |
| A-36 | H | H | H | H | H | H |
| A-37 | H | H | H | H | H | H |
| A-38 | H | H | H | H | H | H |
| A-39 | H | H | H | H | H | H |
| A-40 | H | H | H | H | H | H |
| A-41 | H | H | H | H | H | H |
| A-42 | H | H | H | H | H | H |
| A-43 | Ph | H | H | H | H | Ph |

-continued

| | | | | | | |
|---|---|---|---|---|---|---|
| A-44 | 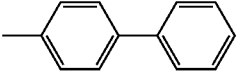 | H | H | H | H | 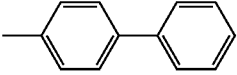 |
| A-45 | CH3 | H | H | H | H | CH3 |
| A-46 | H | Ph | H | H | Ph | H |
| A-47 | H | 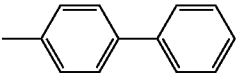 | H | H | 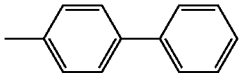 | H |
| A-48 | | CH3 | H | H | CH3 | |
| A-49 | H | H | H | H | H | H |
| A-50 | Ph | H | H | H | H | Ph |
| A-51 | 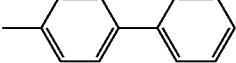 | H | H | H | H | 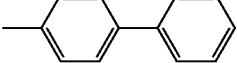 |
| A-52 | CH3 | H | H | H | H | CH3 |
| A-53 | H | Ph | H | H | Ph | H |
| A-54 | H | 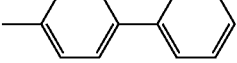 | H | H | 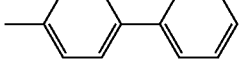 | H |
| A-55 | H | CH3 | H | H | CH3 | H |
| A-56 | X1 and X2 form a fused ring. | | H | H | X1 and X2 form a fused ring. | |
| A-57 | X1 and X2 form a fused ring. | | H | H | X1 and X2 form a fused ring. | |
| A-58 | X1 and X2 form a fused ring. | | H | H | X1 and X2 form a fused ring. | |
| A-59 | X1 and X2 form a fused ring. | | H | H | X1 and X2 form a fused ring. | |
| A-60 | X1 and X2 form a fused ring. | | H | H | X1 and X2 form a fused ring. | |
| A-61 | X1 and X2 form a fused ring. | | H | H | X1 and X2 form a fused ring. | |
| A-62 | X1 and X2 form a fused ring. | | H | H | X1 and X2 form a fused ring. | |
| A-63 | X1 and X2 form a fused ring. | | H | H | X1 and X2 form a fused ring. | |
| A-64 | X1 and X2 form a fused ring. | | H | H | X1 and X2 form a fused ring. | |
| A-65 | X1 and X2 form a fused ring. | | H | H | X1 and X2 form a fused ring. | |
| A-66 | X1 and X2 form a fused ring. | | H | H | X1 and X2 form a fused ring. | |

| Compound No. | X11 | X12 | X13 | X14 |
|---|---|---|---|---|
| A-1 | H | H | H | H |
| A-2 | Ph | H | H | Ph |
| A-3 | 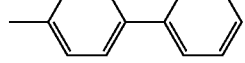 | H | H | 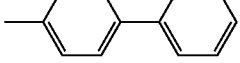 |
| A-4 | 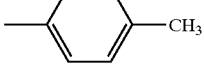 | H | H | 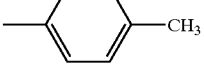 |
| A-5 | 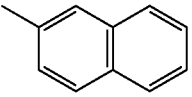 | H | H | 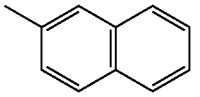 |
| A-6 | CH3 | H | H | CH3 |
| A-7 | 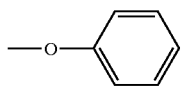 | H | H | 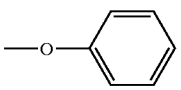 |
| A-8 | Ph | Ph | Ph | Ph |
| A-9 | Ph | 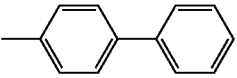 | 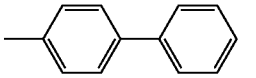 | Ph |

-continued

| | | | | |
|---|---|---|---|---|
| A-10 | Ph | CH3 | CH3 | Ph |
| A-11 | Ph | H | H | Ph |
| A-12 | Ph | H | H | Ph |
| A-13 | Ph | H | H | Ph |
| A-14 | Ph | H | H | Ph |
| A-15 | Ph | H | H | Ph |
| A-16 | Ph | H | H | Ph |
| A-17 | H | H | H | H |
| A-18 | Ph | H | H | Ph |
| A-19 | biphenyl | H | H | biphenyl |
| A-20 | p-tolyl | H | H | p-tolyl |
| A-21 | 2-naphthyl | H | H | 2-naphthyl |
| A-22 | CH3 | H | H | CH3 |
| A-23 | p-methoxyphenyl | H | H | p-methoxyphenyl |
| A-24 | Ph | Ph | Ph | Ph |
| A-25 | Ph | biphenyl | biphenyl | Ph |
| A-26 | Ph | CH3 | CH3 | Ph |
| A-27 | Ph | H | H | Ph |
| A-28 | Ph | H | H | Ph |
| A-29 | Ph | H | H | Ph |
| A-30 | Ph | H | H | Ph |
| A-31 | Ph | H | H | Ph |
| A-32 | Ph | H | H | Ph |
| A-33 | H | H | H | X13 and X14 form a fused ring. |
| A-34 | Ph | H | H | X13 and X14 form a fused ring. |
| A-35 | biphenyl | H | H | X13 and X14 form a fused ring. |
| A-36 | p-tolyl | H | H | X13 and X14 form a fused ring. |
| A-37 | 2-naphthyl | H | H | X13 and X14 form a fused ring. |
| A-38 | CH3 | H | H | X13 and X14 form a fused ring. |
| A-39 | p-methoxyphenyl | H | H | X13 and X14 form a fused ring. |
| A-40 | Ph | Ph | Ph | X13 and X14 form a fused ring. |
| A-41 | Ph | biphenyl | biphenyl | X13 and X14 form a fused ring. |

-continued

| ID | | | | |
|---|---|---|---|---|
| A-42 | Ph | CH3 | X13 and X14 form a fused ring. | |
| A-43 | Ph | H | X13 and X14 form a fused ring. | |
| A-44 | Ph | H | X13 and X14 form a fused ring. | |
| A-45 | Ph | H | X13 and X14 form a fused ring. | |
| A-46 | Ph | H | X13 and X14 form a fused ring. | |
| A-47 | Ph | H | X13 and X14 form a fused ring. | |
| A-48 | Ph | H | X13 and X14 form a fused ring. | |
| A-49 | X13 and X14 form a fused ring. | | X13 and X14 form a fused ring. | |
| A-50 | X13 and X14 form a fused ring. | | X13 and X14 form a fused ring. | |
| A-51 | X13 and X14 form a fused ring. | | X13 and X14 form a fused ring. | |
| A-52 | X13 and X14 form a fused ring. | | X13 and X14 form a fused ring. | |
| A-53 | X13 and X14 form a fused ring. | | X13 and X14 form a fused ring. | |
| A-54 | X13 and X14 form a fused ring. | | X13 and X14 form a fused ring. | |
| A-55 | X13 and X14 form a fused ring. | | X13 and X14 form a fused ring. | |
| A-56 | H | H | H | H |
| A-57 | Ph | H | H | Ph |
| A-58 | –C6H4–C6H5 (biphenyl) | H | H | –C6H4–C6H5 (biphenyl) |
| A-59 | –C6H4–CH3 | H | H | –C6H4–CH3 |
| A-60 | 2-naphthyl | H | H | 2-naphthyl |
| A-61 | CH3 | H | H | CH3 |
| A-62 | –O–C6H5 | H | H | –O–C6H5 |
| A-63 | Ph | Ph | Ph | Ph |
| A-64 | Ph | –C6H4–C6H5 (biphenyl) | –C6H4–C6H5 (biphenyl) | Ph |
| A-65 | Ph | CH3 | CH3 | Ph |
| A-66 | Ph | H | H | Ph |

| Compound No. | X1 | X2 | X3 | X6 | X7 | X8 | X11 |
|---|---|---|---|---|---|---|---|
| B-1 | H | H | H | H | H | H | H |
| B-2 | H | H | H | H | H | H | Ph |
| B-3 | H | H | H | H | H | H | 4-biphenylyl |
| B-4 | H | H | H | H | H | H | 4-methylphenyl |
| B-5 | H | H | H | H | H | H | 2-methylnaphthyl |
| B-6 | H | H | H | H | H | H | CH3 |
| B-7 | H | H | H | H | H | H | methoxyphenyl |
| B-8 | 4-biphenylyl | H | H | H | H | 4-biphenylyl | Ph |
| B-9 | CH3 | H | H | H | H | CH3 | Ph |
| B-10 | H | Ph | H | H | Ph | H | Ph |

"A and B form a fused ring in

[structure: A-B benzene with two methyl groups]

means

[structure: dimethylnaphthalene]"

-continued

| No. | | | | | |
|---|---|---|---|---|---|
| B-11 | H | [biphenyl] | H | H | Ph |
| B-12 | | CH₃ | H | H | Ph |
| B-13 | | H | H | X7 and X8 form a fused ring. | H |
| B-14 | | H | H | X7 and X8 form a fused ring. | Ph |
| B-15 | H | [4-methylbiphenyl] | H | X7 and X8 form a fused ring. | [biphenyl] |
| B-16 | H | | H | X7 and X8 form a fused ring. | [p-tolyl / CH₃-phenyl] |
| B-17 | H | | H | X7 and X8 form a fused ring. | [methylnaphthyl] |
| B-18 | H | | H | X7 and X8 form a fused ring. | CH₃ |
| B-19 | H | | H | X7 and X8 form a fused ring. | [methoxyphenyl] |
| B-20 | H | | H | X7 and X8 form a fused ring. | Ph |
| B-21 | H | | H | X7 and X8 form a fused ring. | Ph |
| B-22 | H | | H | X7 and X8 form a fused ring. | Ph |
| B-23 | H | | H | X7 and X8 form a fused ring. | Ph |
| B-24 | H | | H | X7 and X8 form a fused ring. | Ph |
| B-25 | H | | H | X7 and X8 form a fused ring. | Ph |
| B-26 | H | | H | X7 and X8 form a fused ring. | Ph |
| B-27 | Ph | | H | X7 and X8 form a fused ring. | Ph |
| B-28 | H | | H | X7 and X8 form a fused ring. | Ph |
| B-29 | H | | H | X7 and X8 form a fused ring. | Ph |
| B-30 | H | [4-methylbiphenyl] | H | X7 and X8 form a fused ring. | Ph |
| B-31 | CH₃ | H | H | H | Ph |
| B-32 | H | H | H | H | H |
| B-33 | H | H | H | H | Ph |

-continued

| | | | | | |
|---|---|---|---|---|---|
| B-34 | H | H | H | H | 4-biphenyl |
| B-35 | H | H | H | H | 4-methylphenyl (CH3) |
| B-36 | H | H | H | H | 2-methylnaphthyl |
| B-37 | H | H | H | H | 4-methoxyphenyl (OCH3) |
| B-38 | H | H | H | H | |
| B-39 | H | H | H | H | Ph |
| B-40 | H | H | H | H | Ph |
| B-41 | H | H | H | H | Ph |
| B-42 | H | H | H | H | Ph |
| B-43 | H | H | H | H | Ph |
| B-44 | H | H | H | H | Ph |
| B-45 | H | H | H | H | Ph |
| B-46 | H | H | H | H | Ph |
| B-47 | H | H | H | H | Ph |
| B-48 | Ph | Ph | Ph | Ph | |
| B-49 | H | H | H | 4-biphenyl | Ph |
| B-50 | H | H | H | | Ph |
| B-51 | CH3 | H | H | 4-methylbiphenyl | Ph |
| B-52 | H | H | H | CH3 | Ph |
| B-53 | H | H | H | H | Ph |
| B-54 | H | H | H | H | H |
| B-55 | H | H | H | H | Ph |

| No. | X1 | X2 | X3 | X4 | X7 | X8 | Ar |
|---|---|---|---|---|---|---|---|
| B-56 | 4-biphenyl | H | H | H | H | H |  |
| B-57 | p-tolyl | H | H | H | H | H |  |
| B-58 | 2-methylnaphthyl | H | H | H | H | H |  |
| B-59 | CH3 | H | H | H | H | H |  |
| B-60 | 4-methoxyphenyl | H | H | H | H | H |  |
| B-61 | H | H | H | H | H | H | Ph |
| B-62 | H | H | H | H | H | H | Ph |
| B-63 | H | H | H | H | H | H | Ph |
| B-64 | H | H | H | H | H | H | Ph |
| B-65 | H | H | H | H | H | H | Ph |
| B-66 | H | H | H | H | H | H | Ph |
| B-67 | H | H | H | H | H | H | Ph |
| B-68 | Ph | H | H | H | H | H | Ph |
| B-69 |  |  |  |  |  |  | Ph |
| B-70 | Ph | H | H | H | H | Ph | Ph |
| B-71 | 4-biphenyl | H | H | H | H | 4-biphenyl | Ph |
| B-72 | CH3 | H | H | H | H | CH3 | Ph |
| B-73 | H | Ph | H | H | Ph | H | Ph |
| B-74 | H | H | H | H | H | H | Ph |
| B-75 | X1 and X2 form a fused ring. | | H | H | X7 and X8 form a fused ring. | | Ph |
| B-76 | X1 and X2 form a fused ring. | | H | H | X7 and X8 form a fused ring. | | H |
| B-77 | H | H | H | H | H | H | Ph |

-continued

| Compound No. | X14 | X15 | X16 | X17 | X18 |
|---|---|---|---|---|---|
| B-78 | X1 and X2 form a fused ring. | H | X7 and X8 form a fused ring. | | |
| B-79 | X1 and X2 form a fused ring. | H | X7 and X8 form a fused ring. | | |
| B-80 | X1 and X2 form a fused ring. | H | X7 and X8 form a fused ring. | | |
| B-81 | X1 and X2 form a fused ring. | H | X7 and X8 form a fused ring. | | |
| B-82 | X1 and X2 form a fused ring. | H | X7 and X8 form a fused ring. | | |
| B-83 | X1 and X2 form a fused ring. | H | X7 and X8 form a fused ring. | | Ph |
| B-84 | X1 and X2 form a fused ring. | H | X7 and X8 form a fused ring. | | Ph |
| B-85 | X1 and X2 form a fused ring. | H | X7 and X8 form a fused ring. | | Ph |
| B-86 | X1 and X2 form a fused ring. | H | X7 and X8 form a fused ring. | | Ph |
| B-87 | X1 and X2 form a fused ring. | H | X7 and X8 form a fused ring. | | Ph |
| B-88 | X1 and X2 form a fused ring. | H | X7 and X8 form a fused ring. | | Ph |
| B-89 | X1 and X2 form a fused ring. | H | X7 and X8 form a fused ring. | | Ph |
| B-90 | X1 and X2 form a fused ring. | H | X7 and X8 form a fused ring. | | Ph |
| B-91 | X1 and X2 form a fused ring. | H | X7 and X8 form a fused ring. | | Ph |

| Compound No. | X14 | X15 | X16 | X17 | X18 |
|---|---|---|---|---|---|
| B-1 | H | X15 and X16 form a fused ring. | | X17 and X18 form a fused ring. | |
| B-2 | Ph | X15 and X16 form a fused ring. | | X17 and X18 form a fused ring. | |
| B-3 | 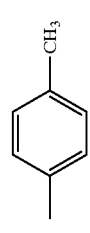 | X15 and X16 form a fused ring. | | X17 and X18 form a fused ring. | |
| B-4 |  | | | X17 and X18 form a fused ring. | |
| B-5 | 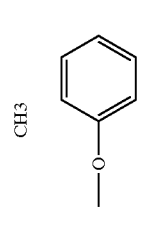 | X15 and X16 form a fused ring. | | X17 and X18 form a fused ring. | |

-continued

| ID | Col1 | Col2 | Col3 | Col4 | Col5 | Col6 | Col7 |
|---|---|---|---|---|---|---|---|
| | B-6 | CH3 | X15 and X16 form a fused ring. | | | X17 and X18 form a fused ring. | |
| B-7 | –O–Ph (methoxyphenyl) | | X15 and X16 form a fused ring. | | | X17 and X18 form a fused ring. | |
| B-8 | Ph | | X15 and X16 form a fused ring. | | | X17 and X18 form a fused ring. | |
| B-9 | Ph | | X15 and X16 form a fused ring. | | | X17 and X18 form a fused ring. | |
| B-10 | Ph | | X15 and X16 form a fused ring. | | | X17 and X18 form a fused ring. | |
| B-11 | Ph | | X15 and X16 form a fused ring. | | | X17 and X18 form a fused ring. | |
| B-12 | H | | X15 and X16 form a fused ring. | | | X17 and X18 form a fused ring. | |
| B-13 | Ph | | H | H | | H | H |
| B-14 | | | H | H | | H | H |
| B-15 | biphenyl | | H | | | H | |
| B-16 | p-tolyl (CH3) | | H | | | H | |
| B-17 | 2-methylnaphthyl | | H | | | H | |
| B-18 | CH3 | | H | | | H | |
| B-19 | methoxyphenyl (–O–) | | H | | | H | |
| B-20 | Ph | | H | | | H | |
| B-21 | Ph | | biphenyl | | | biphenyl | |
| B-22 | Ph | | p-tolyl (CH3) | | | p-tolyl (CH3) | |

-continued

| ID | | | | | | |
|---|---|---|---|---|---|---|
| B-23 | Ph | 2-methylnaphthyl | H | H | 2-methylnaphthyl | H |
| B-24 | Ph | CH₃ | H | H | CH₃ | H |
| B-25 | Ph | methoxyphenyl | H | H | methoxyphenyl | H |
| B-26 | Ph | H | Ph | Ph | H | H |
| B-27 | Ph | H | Ph | Ph | H | H |
| B-28 | Ph | H | CH₃ | CH₃ | H | H |
| B-29 | Ph | H | H | H | H | H |
| B-30 | Ph | H | H | H | H | H |
| B-31 | H | H | H | H | H | H |
| B-32 | Ph | H | H | H | H | H |
| B-33 | Ph | H | H | H | H | H |
| B-34 | X15 and X16 form a fused ring. | | | | | H |
| B-35 | biphenyl | X15 and X16 form a fused ring. | | | | H |
| B-36 | p-tolyl | X15 and X16 form a fused ring. | | | | H |
| B-37 | 2-methylnaphthyl | X15 and X16 form a fused ring. | | | | H |
| B-38 | CH₃ | X15 and X16 form a fused ring. | | | | H |
| B-39 | methoxyphenyl | X15 and X16 form a fused ring. | | | | Ph |

| | | | |
|---|---|---|---|
| B-40 | Ph | X15 and X16 form a fused ring. | H |
| B-41 | Ph | X15 and X16 form a fused ring. | 4-methylphenyl (p-tolyl, CH₃) |
| B-42 | Ph | X15 and X16 form a fused ring. | H |
| B-43 | Ph | X15 and X16 form a fused ring. | 2-methylnaphthyl |
| B-44 | Ph | X15 and X16 form a fused ring. | H |
| B-45 | Ph | X15 and X16 form a fused ring. | 2-methoxyphenyl |
| B-46 | Ph | X15 and X16 form a fused ring. | H |
| B-47 | Ph | X15 and X16 form a fused ring. | Ph |
| B-48 | Ph | X15 and X16 form a fused ring. | 4-biphenylyl-CH₃ |
| B-49 | Ph | X15 and X16 form a fused ring. | H |
| B-50 | Ph | X15 and X16 form a fused ring. | H |
| B-51 | Ph | X15 and X16 form a fused ring. | H |
| B-52 | Ph | X15 and X16 form a fused ring. | H |
| B-53 | Ph | X15 and X16 form a fused ring. | H |
| B-54 | H | H | H |
| B-55 | Ph | H | H |
| B-56 | 4-biphenylyl | H | H |
| B-57 | 4-methylphenyl | H | H |

-continued

| ID | R1 | R2 | R3 | R4 | R5 |
|---|---|---|---|---|---|
| B-58 | 2-methylnaphthyl | H | H | | H |
| B-59 | CH3 | H | H | | H |
| B-60 | 4-methoxyphenyl | H | H | | H |
| B-61 | Ph | 4-biphenylyl | H | | Ph |
| B-62 | Ph | 4-methylphenyl | H | | CH3 |
| B-63 | Ph | 2-methylnaphthyl | H | | |
| B-64 | Ph | CH3 | H | | |
| B-65 | Ph | 4-methoxyphenyl | H | | H |
| B-66 | Ph | H | H | | H |
| B-67 | Ph | H | 4-biphenylyl | | H |
| B-68 | Ph | H | 4-biphenylyl | CH3 | H |
| B-69 | Ph | H | H | H | 4-biphenylyl |
| B-70 | Ph | H | H | H | CH3 |
| B-71 | Ph | H | H | H | H |
| B-72 | Ph | H | H | H | H |
| B-73 | Ph | H | H | H | H |
| B-74 | Ph | H | H | H | H |
| B-75 | Ph | H | H | H | H |
| B-76 | H | H | H | H | H |

-continued

| | | | | |
|---|---|---|---|---|
| B-77 | Ph (biphenyl) | H | H | H |
| B-78 | Ph | H | H | H |
| B-79 | p-tolyl (CH3) | H | H | H |
| B-80 | 2-naphthyl | H | H | H |
| B-81 | p-methoxyphenyl (CH3O) | H | H | H |
| B-82 | Ph | H | H | H |
| B-83 | Ph | Ph (biphenyl) | H | Ph (biphenyl) |
| B-84 | Ph | p-tolyl (CH3) | H | p-tolyl (CH3) |
| B-85 | Ph | 2-naphthyl | H | 2-naphthyl |
| B-86 | Ph | p-methoxyphenyl (CH3O) | H | p-methoxyphenyl (CH3O) |
| B-87 | Ph | H | H | H |
| B-88 | Ph | H | H | H |
| B-89 | Ph | Ph | Ph | Ph |

-continued
| | | | | |
|---|---|---|---|---|
| B-90 | Ph | H | CH3 |  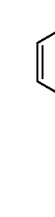 H |
| B-91 | Ph | H | CH3 |  CH3 H |
"C, A and B form a fused ring" in  means 
| Compound No. | X1 | X2 | X8 | X3 | X6 | X7 | X11 | X14 |
|---|---|---|---|---|---|---|---|---|
| B-92 | X1, X2 and X8 form a fused ring. | | | H | H | H | H | H |
| B-93 | X1, X2 and X8 form a fused ring. | | | H | H | H | Ph | Ph |
| B-94 | X1, X2 and X8 form a fused ring. | | | H | H | H | biphenyl | biphenyl |
| B-95 | X1, X2 and X8 form a fused ring. | | | H | H | H | tolyl | tolyl |
| B-96 | X1, X2 and X8 form a fused ring. | | | H | H | H | methylnaphthyl | methylnaphthyl |

-continued

| Compound No. | | | | | | | |
|---|---|---|---|---|---|---|---|
| B-97 | X1, X2 and X8 form a fused ring. | H | H | (4-methoxyphenyl) | (4-methoxyphenyl) | CH3 | CH3 |
| B-98 | X1, X2 and X8 form a fused ring. | H | H | | | | |
| B-99 | X1, X2 and X8 form a fused ring. | H | H | Ph | Ph | | |
| B-100 | X1, X2 and X8 form a fused ring. | H | H | Ph | Ph | | |
| B-101 | X1, X2 and X8 form a fused ring. | H | H | Ph | Ph | | |
| B-102 | X1, X2 and X8 form a fused ring. | H | H | Ph | Ph | | |
| B-103 | X1, X2 and X8 form a fused ring. | H | H | Ph | Ph | | |
| B-104 | X1, X2 and X8 form a fused ring. | H | H | Ph | Ph | | |
| B-105 | X1, X2 and X8 form a fused ring. | H | H | Ph | Ph | | |
| B-106 | X1, X2 and X8 form a fused ring. | H | H | Ph | Ph | | |
| B-107 | X1, X2 and X8 form a fused ring. | H | H | Ph | Ph | | |
| B-108 | X1, X2 and X8 form a fused ring. | H | H | Ph | Ph | Ph | |
| B-109 | X1, X2 and X8 form a fused ring. | H | (4-biphenylyl) | Ph | Ph | | |
| B-110 | X1, X2 and X8 form a fused ring. | H | CH3 | Ph | Ph | | |

| Compound No. | X15 | X16 | X17 | X18 |
|---|---|---|---|---|
| B-92 | H | H | H | H |
| B-93 | H | H | H | H |
| B-94 | H | H | H | H |
| B-95 | H | H | H | H |
| B-96 | H | H | H | H |
| B-97 | H | H | H | H |
| B-98 | Ph | H | H | H |
| B-99 | H | H | H | Ph |
| B-100 | (4-biphenylyl) | CH3 | (4-biphenylyl) | CH3 |
| B-101 | (4-methylphenyl) | H | (4-methylphenyl) | H |

-continued

| | | | | | |
|---|---|---|---|---|---|
| B-102 | ![2-naphthyl] | CH3 | ![methoxyphenyl] | H | H H H |
| B-103 | H | H | H | H | |
| B-104 | H | H | H | H | |
| B-105 | Ph | Ph | | | |
| B-106 | ![4-biphenyl] | ![4-biphenyl] | | | |
| B-107 | CH3 | CH3 | | | |
| B-108 | H | H | | | |
| B-109 | H | H | | | |
| B-110 | H | H | | | |

| | | | | |
|---|---|---|---|---|
| B-102 | ![2-naphthyl] | CH3 | ![methoxyphenyl] | H | H | H H H |

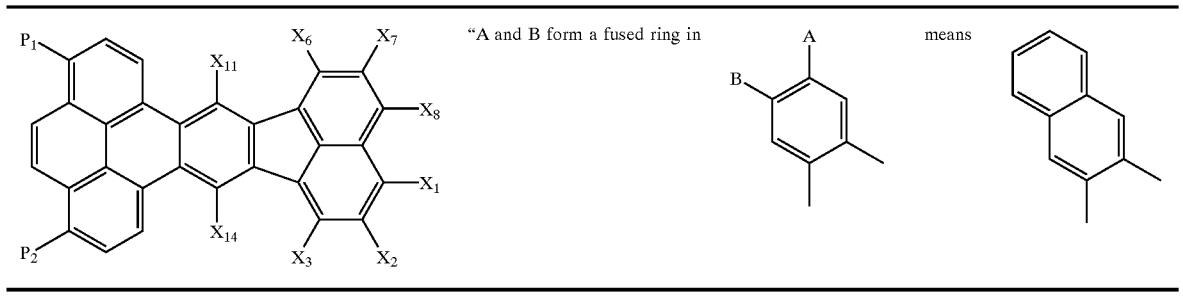

"A and B form a fused ring in [A/B structure] means [naphthalene structure]"

| Compound No. | X1 | X2 | X3 | X6 | X7 | X8 |
|---|---|---|---|---|---|---|
| C-1 | H | H | H | H | H | H |
| C-2 | H | H | H | H | H | H |
| C-3 | H | H | H | H | H | H |
| C-4 | H | H | H | H | H | H |
| C-5 | H | H | H | H | H | H |
| C-6 | H | H | H | H | H | H |
| C-7 | H | H | H | H | H | H |
| C-8 | H | H | H | H | H | H |
| C-9 | H | H | H | H | H | H |
| C-10 | H | H | H | H | H | H |
| C-11 | Ph | H | H | H | H | Ph |
| C-12 | biphenyl | H | H | H | H | biphenyl |
| C-13 | CH3 | H | H | H | H | CH3 |
| C-14 | H | Ph | H | H | Ph | H |
| C-15 | H | biphenyl | H | H | biphenyl | H |
| C-16 | H | CH3 | H | H | CH3 | H |

| Compound No. | X11 | X14 | P1 | P2 |
|---|---|---|---|---|
| C-1 | H | H | H | H |
| C-2 | Ph | Ph | H | H |
| C-3 | biphenyl | biphenyl | H | H |
| C-4 | p-tolyl | p-tolyl | H | H |
| C-5 | 2-naphthyl | 2-naphthyl | H | H |

-continued
| | | | | |
|---|---|---|---|---|
| C-6 | CH3 | CH3 | H | H |
| C-7 | 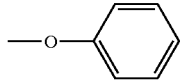 | 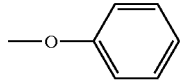 | H | H |
| C-8 | Ph | Ph | Ph | Ph |
| C-9 | Ph | Ph | 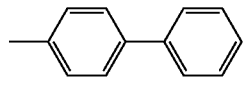 | 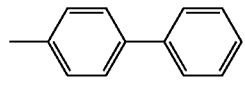 |
| C-10 | Ph | Ph | CH3 | CH3 |
| C-11 | Ph | Ph | H | H |
| C-12 | Ph | Ph | H | H |
| C-13 | Ph | Ph | H | H |
| C-14 | Ph | Ph | H | H |
| C-15 | Ph | Ph | H | H |
| C-16 | Ph | Ph | H | H |

"A and B form a fused ring" in

A—[benzene ring]—B  means  [2,3-dimethylnaphthalene structure]

| Compound No. | X1 | X2 | X3 | X4 | X5 | X6 | X7 | X8 | X11 | X14 |
|---|---|---|---|---|---|---|---|---|---|---|
| D-1 | H | H | H | H | H | H | H | H | H | H |
| D-2 | H | H | H | H | H | H | H | H | Ph | Ph |
| D-3 | H | H | H | H | H | H | H | H | 4-biphenyl | 4-biphenyl |
| D-4 | H | H | H | H | H | H | H | H | p-tolyl | p-tolyl |
| D-5 | H | H | H | H | H | H | H | H | CH3 | CH3 |
| D-6 | H | H | H | H | H | H | H | H | 2-naphthyl | 2-naphthyl |
| D-7 | H | H | H | H | H | H | H | H | OPh | OPh |
| D-8 | H | H | H | H | H | H | H | H | Ph | Ph |
| D-9 | H | H | H | H | H | H | H | H | Ph | Ph |
| D-10 | H | H | H | H | H | H | H | H | Ph | Ph |
| D-11 | H | H | H | H | H | H | H | H | Ph | Ph |
| D-12 | H | H | H | H | H | H | H | H | Ph | Ph |
| D-13 | Ph | H | H | H | H | H | H | H | Ph | Ph |
| D-14 | Ph | H | H | H | H | H | H | Ph | Ph | Ph |

-continued

| | | | | | | | | | | |
|---|---|---|---|---|---|---|---|---|---|---|
| D-15 | 4-biphenyl | H | H | H | H | H | 4-biphenyl | | | Ph |
| D-16 | CH3 | H | H | H | H | CH3 | | | | Ph |
| D-17 | H | H | H | H | H | H | | | | H |
| D-18 | H | H | H | H | X5 and X6 form a fused ring. | H | | | | Ph |
| D-19 | H | H | H | H | X5 and X6 form a fused ring. | H | 4-biphenyl | 4-biphenyl | | |
| D-20 | H | H | H | H | X5 and X6 form a fused ring. | H | 4-tolyl | 4-tolyl | | |
| D-21 | H | H | H | H | X5 and X6 form a fused ring. | H | CH3 | CH3 | | |
| D-22 | H | H | H | H | X5 and X6 form a fused ring. | H | 2-methylnaphthyl | 2-methylnaphthyl | | |
| D-23 | H | H | H | H | X5 and X6 form a fused ring. | H | phenoxyphenyl | phenoxyphenyl | | |
| D-24 | H | H | H | H | X5 and X6 form a fused ring. | H | | | | Ph |
| D-25 | H | H | H | H | X5 and X6 form a fused ring. | H | | | | Ph |
| D-26 | H | H | H | H | X5 and X6 form a fused ring. | H | | | | Ph |
| D-27 | H | H | H | H | X5 and X6 form a fused ring. | H | | | | Ph |
| D-28 | H | H | H | H | X5 and X6 form a fused ring. | H | | | | Ph |
| D-29 | H | H | H | H | X5 and X6 form a fused ring. | H | | | | Ph |
| D-30 | Ph | H | H | H | X5 and X6 form a fused ring. | Ph | | | | Ph |
| D-31 | 4-biphenyl | H | H | H | H | 4-biphenyl | | | | Ph |
| D-32 | CH3 | H | H | H | X5 and X6 form a fused ring. | CH3 | | | | Ph |

-continued

| Compound No. | X15 | X16 | X17 | X18 |
|---|---|---|---|---|
| D-1 | 4-methylbiphenyl | H | H | H |
| D-2 | H | | | H |
| D-3 | H | | | H |
| D-4 | H | | | H |
| D-5 | H | | | H |
| D-6 | H | | | H |
| D-7 | H | | | H |
| D-8 | Ph | | | Ph |
| D-9 | H | | | H |
| D-10 | CH3 | | | CH3 |
| D-11 | H | | | H |
| D-12 | H | | | H |
| D-13 | H | H, Ph (4-methylbiphenyl) | H | H |
| D-14 | H | CH3 | H | H |
| D-15 | H | H | H | H |
| D-16 | H | H | H | H |
| D-17 | H | H | H | H |
| D-18 | H | H | H | H |
| D-19 | H | H | H | H |
| D-20 | H | H | H | H |
| D-21 | H | H | H | H |
| D-22 | H | H | H | H |
| D-23 | H | H | H | H |
| D-24 | H | Ph | H | Ph |
| D-25 | 4-methylbiphenyl CH3 H | H | H | H |
| D-26 | | | H, Ph (4-methylbiphenyl) | 4-methylbiphenyl |
| D-27 | | | CH3 | CH3 |
| D-28 | | | H | H |
| D-29 | | | H | H |
| D-30 | | | H | H |
| D-31 | | | H | H |
| D-32 | | | H | H |

-continued
"A and B form a fused ring" in 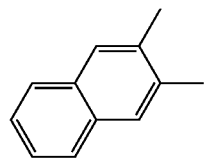 means 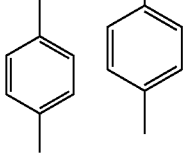
| Compound No. | X1 | X2 | X3 | X4 | X5 | X6 | X7 | X8 | X11 |
|---|---|---|---|---|---|---|---|---|---|
| D-33 | H | H | H | H | H | H | H | H | H |
| D-34 | H | H | H | H | H | H | H | H | Ph |
| D-35 | H | H | H | H | H | H | H | H | 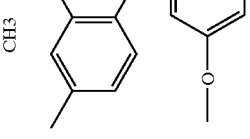 |
| D-36 | H | H | H | H | H | H | H | H |  |
| D-37 | H | H | H | H | H | H | H | H | CH3 |
| D-38 | H | H | H | H | H | H | H | H | 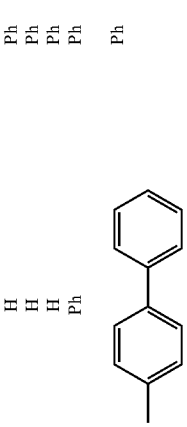 |
| D-39 | H | H | H | H | H | H | H | H | 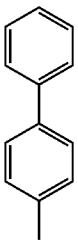 |
| D-40 | H | H | H | H | H | H | H | H | Ph |
| D-41 | H | H | H | H | H | H | H | H | Ph |
| D-42 | H | H | H | H | H | H | H | Ph | Ph |
| D-43 | Ph | H | H | H | H | H | H | H | |
| D-44 | 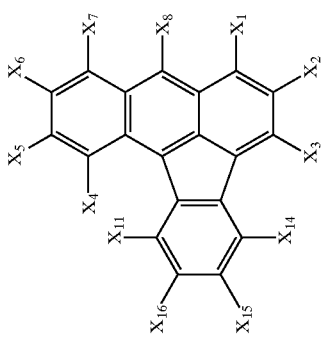 | H | H | H | H | H | H | H | Ph |

US 6,613,454 B2

-continued

| ID | | | | | | | |
|---|---|---|---|---|---|---|---|
| D-45 | CH3 | H | H | H | H | H | CH3 |
| D-46 | H | H | H | X5 and X6 form a fused ring. | H | Ph |
| D-47 | H | H | H | X5 and X6 form a fused ring. | H | Ph |
| D-48 | H | H | H | X5 and X6 form a fused ring. | H | 4-methylphenyl |
| D-49 | H | H | H | X5 and X6 form a fused ring. | H | 4-methylphenyl (CH3) |
| D-50 | H | H | H | X5 and X6 form a fused ring. | H | 6-methylnaphth-2-yl |
| D-51 | H | H | H | X5 and X6 form a fused ring. | H | 4-methoxyphenyl |
| D-52 | H | H | H | X5 and X6 form a fused ring. | H | Ph |
| D-53 | H | H | H | X5 and X6 form a fused ring. | H | Ph |
| D-54 | H | H | H | X5 and X6 form a fused ring. | H | Ph |
| D-55 | H | H | H | X5 and X6 form a fused ring. | H | Ph |
| D-56 | Ph | H | H | X5 and X6 form a fused ring. | Ph | — |
| D-57 | H | H | H | X5 and X6 form a fused ring. | H | 4-methyl-4'-biphenylyl |
| D-58 | CH3 | H | X2 and X3 form a fused ring. | H | X5 and X6 form a fused ring. | H | Ph |
| D-59 | H | H | X2 and X3 form a fused ring. | H | H | H | H |
| D-60 | H | H | X2 and X3 form a fused ring. | H | H | H | Ph |
| D-61 | H | X2 and X3 form a fused ring. | H | H | H | biphenyl |
| D-62 | H | X2 and X3 form a fused ring. | H | H | H | 4-methylphenyl |
| D-63 | H | X2 and X3 form a fused ring. | H | H | H | CH3 |

| Compound | | | | | | | | | | |
|---|---|---|---|---|---|---|---|---|---|---|
| D-64 | [4-methylbiphenyl] | H | H | H | H | H | H | X2 and X3 form a fused ring. | H | [2-methylnaphthyl] |
| D-65 | H | H | H | H | H | H | H | X2 and X3 form a fused ring. | H | [methoxyphenyl] |
| D-66 | H | H | H | H | H | H | H | X2 and X3 form a fused ring. | H | Ph |
| D-67 | H | H | H | H | H | H | H | X2 and X3 form a fused ring. | H | Ph |
| D-68 | H | H | H | H | H | H | H | X2 and X3 form a fused ring. | H | Ph |
| D-69 | Ph | H | H | H | H | H | Ph | X2 and X3 form a fused ring. | H | Ph |
| D-70 | [4-methylbiphenyl] | H | H | H | H | H | H | X2 and X3 form a fused ring. | H | Ph |
| D-71 | CH3 | H | H | H | H | H | H | X2 and X3 form a fused ring. | CH3 | Ph |

| Compound No. | X14 | X15 | X16 |
|---|---|---|---|
| D-33 | H | H | H |
| D-34 | Ph | H | H |
| D-35 | [4-methylbiphenyl] | H | H |
| D-36 | [4-methylphenyl (tolyl)] | H | H |
| D-37 | CH3 | H | H |
| D-38 | [2-methylnaphthyl] | H | H |
| D-39 | [methoxyphenyl] | H | H |
| D-40 | Ph | Ph | Ph |

-continued
| | | | | |
|---|---|---|---|---|
| D-41 |  |  | | |
| D-42 | Ph | CH3 | H | H |
| D-43 | Ph | H | | |
| D-44 | Ph | H | | |
| D-45 | Ph | H | | |
| D-46 | H | H | | |
| D-47 | Ph | H | | |
| D-48 |  | H | H | H |
| D-49 |  | | | |
| D-50 | CH3 | H | H | H |
| D-51 |  | | | |
| D-52 |  | H | H | H |
| D-53 | Ph | Ph | CH3 | H |
| D-54 | Ph | Ph | H | H |
| D-55 | Ph | Ph | | |
| D-56 | Ph | H | | |
| D-57 | Ph | H | | |
| D-58 | Ph | H | | |
| D-59 | H | H | | |
| D-60 | Ph | H | | |
| D-61 |  | | | |

-continued

| Compound | | | | | |
|---|---|---|---|---|---|
| D-62 | 4-methylphenyl | H | H | H | H |
| D-63 | CH3 | | | | |
| D-64 | 2-naphthyl | H | H | H | H |
| D-65 | phenoxy | | | | |
| D-66 | Ph | Ph | | | |
| D-67 | Ph | Ph | | | |
| D-68 | Ph | 4-biphenyl | CH3 | H | H |
| D-69 | Ph | | H | H | H |
| D-70 | Ph | | H | H | H |
| D-71 | Ph | 4'-methyl-4-biphenyl | CH3 | H | H |

"A and B form a fused ring" in

[structure: A and B on dimethylbenzene ring]

means

[structure: naphthalene fused]

| Compound No. | X1 | X2 | X3 | X4 | X5 | X6 | X7 | X8 | X11 | X14 |
|---|---|---|---|---|---|---|---|---|---|---|
| D-72 | H | X2 and X3 form a fused ring. | | H | H | H | H | H | H | H |
| D-73 | H | X2 and X3 form a fused ring. | | H | H | H | H | H | Ph | Ph |

-continued

| No. | | | | | | | |
|---|---|---|---|---|---|---|---|
| D-74 | H | X2 and X3 form a fused ring. | H | H | H | 4-biphenyl | 4-biphenyl |
| D-75 | H | X2 and X3 form a fused ring. | H | H | H | 4-tolyl (CH3) | 4-tolyl (CH3) |
| | | | | | | CH3 | CH3 |
| D-76 | H | X2 and X3 form a fused ring. | H | H | H | 2-naphthyl | 2-naphthyl |
| D-77 | H | X2 and X3 form a fused ring. | H | H | H | phenoxy (PhO) | phenoxy (PhO) |
| D-78 | H | X2 and X3 form a fused ring. | H | H | H | Ph | Ph |
| D-79 | H | X2 and X3 form a fused ring. | H | H | H | Ph | Ph |
| D-80 | H | X2 and X3 form a fused ring. | H | H | H | Ph | Ph |
| D-81 | H | X2 and X3 form a fused ring. | H | H | H | Ph | Ph |
| D-82 | H | X2 and X3 form a fused ring. | H | H | H | Ph | Ph |
| D-83 | H | X2 and X3 form a fused ring. | H | H | H | Ph | Ph |
| D-84 | H | X2 and X3 form a fused ring. | H | H | H | Ph | Ph |
| D-85 | Ph | X2 and X3 form a fused ring. | H | H | H | Ph | Ph |
| D-86 | 4-biphenyl | X2 and X3 form a fused ring. | H | H | 4-biphenyl | Ph | Ph |
| D-87 | CH3 | X2 and X3 form a fused ring. | H | H | CH3 | Ph | Ph |
| D-88 | H | X2 and X3 form a fused ring. | H | H | H | H | H |
| D-89 | H | X2 and X3 form a fused ring. | H | H | H | Ph | Ph |
| D-90 | H | X2 and X3 form a fused ring. | H | H | H | 4-biphenyl | 4-biphenyl |
| D-91 | H | X2 and X3 form a fused ring. | H | H | H | 4-tolyl (CH3) | 4-tolyl (CH3) |
| | | | | | | CH3 | CH3 |
| D-92 | H | X2 and X3 form a fused ring. | H | H | H | | |

-continued

| | | | | | | | |
|---|---|---|---|---|---|---|---|
| D-93 | H | X2 and X3 form a fused ring. | H | H | H | [2-naphthyl] | [2-naphthyl] |
| D-94 | H | X2 and X3 form a fused ring. | H | H | H | [phenoxy] | [phenoxy] |
| D-95 | Ph | X2 and X3 form a fused ring. | H | H | H | Ph | Ph |
| D-96 | [4-biphenyl] | X2 and X3 form a fused ring. | H | H | H | Ph | Ph |
| D-97 | CH3 | X2 and X3 form a fused ring. | H | H | H | Ph | Ph |

| Compound No. | X15 | | | X16 | X17 | X18 |
|---|---|---|---|---|---|---|
| D-72 | H | | | H | H | H |
| D-73 | H | | | H | H | H |
| D-74 | H | | | H | H | H |
| D-75 | H | | | H | H | H |
| D-76 | H | | | H | H | H |
| D-77 | H | | | H | H | H |
| D-78 | Ph | | | H | H | Ph |
| D-79 | | | | | | |
| D-80 | [4-biphenyl] | | | H | H | [4-biphenyl] |
| D-81 | CH3 | | | CH3 | H | CH3 |
| D-82 | H | | | Ph | Ph | H |

-continued

| | | | | |
|---|---|---|---|---|
| D-83 | | ![biphenyl] | ![biphenyl] | H |
| D-84 | H | CH3 | CH3 | H |
| D-85 | H | H | H | H |
| D-86 | H | H | H | H |
| D-87 | H | H | H | H |
| D-88 | X15 and X16 form a fused ring. | | X17 and X18 form a fused ring. | |
| D-89 | X15 and X16 form a fused ring. | | X17 and X18 form a fused ring. | |
| D-90 | X15 and X16 form a fused ring. | | X17 and X18 form a fused ring. | |
| D-91 | X15 and X16 form a fused ring. | | X17 and X18 form a fused ring. | |
| D-92 | X15 and X16 form a fused ring. | | X17 and X18 form a fused ring. | |
| D-93 | X15 and X16 form a fused ring. | | X17 and X18 form a fused ring. | |
| D-94 | X15 and X16 form a fused ring. | | X17 and X18 form a fused ring. | |
| D-95 | X15 and X16 form a fused ring. | | X17 and X18 form a fused ring. | |
| D-96 | X15 and X16 form a fused ring. | | X17 and X18 form a fused ring. | |
| D-97 | X15 and X16 form a fused ring. | | X17 and X18 form a fused ring. | |

"A and B form a fused ring" in

| Compound No. | X2 | X3 | X6 | X7 | X11 = X21 | X12 = X22 | X13 = X23 | X14 = X24 |
|---|---|---|---|---|---|---|---|---|
| E-1 | H | H | H | H | H | H | H | H |
| E-2 | H | H | H | H | Ph | H | H | Ph |
| E-3 | H | H | H | H | 4-biphenyl | H | H | 4-biphenyl |
| E-4 | H | H | H | H | p-tolyl | H | H | p-tolyl |
| E-5 | H | H | H | H | 2-naphthyl | H | H | 2-naphthyl |
| E-6 | H | H | H | H | CH3 | H | H | CH3 |
| E-7 | H | H | H | H | 4-methoxyphenyl | H | H | 4-methoxyphenyl |
| E-8 | H | H | H | H | Ph | Ph | Ph | Ph |
| E-9 | H | H | H | H | Ph | CH3 | CH3 | Ph |
| E-10 | H | H | H | H | Ph | H | H | Ph |
| E-11 | Ph | H | Ph | H | Ph | H | H | Ph |

-continued

| Compound No. | | | | | | | | | | | |
|---|---|---|---|---|---|---|---|---|---|---|---|
| E-12 | CH3 | ![biphenyl] | H | H | CH3 | ![biphenyl] | H | Ph | H | H | Ph |
| E-13 | ![biphenyl] | H | CH3 | H | ![biphenyl] | H | H | H | H | H | Ph |

| Compound No. | X2 | X3 | X6 | X7 | X11 = 21 | X12 = X22 | X13 | X14 | X23 | X24 |
|---|---|---|---|---|---|---|---|---|---|---|
| E-14 | H | H | H | H | H | H | X13 and X14, X23 and X24 form fused rings. | | | |
| E-15 | H | H | H | H | Ph | H | X13 and X14, X23 and X24 form fused rings. | | | |
| E-16 | H | H | H | H | ![biphenyl] | H | X13 and X14, X23 and X24 form fused rings. | | | |
| E-17 | H | H | H | H | ![p-tolyl with CH3] | H | X13 and X14, X23 and X24 form fused rings. | | | |
| E-18 | H | H | H | H | ![methylnaphthalene] | H | X13 and X14, X23 and X24 form fused rings. | | | |
| E-19 | H | H | H | H | CH3 | H | X13 and X14, X23 and X24 form fused rings. | | | |
| E-20 | H | H | H | H | ![anisole (PhOCH3)] | H | X13 and X14, X23 and X24 form fused rings. | | | |
| E-21 | H | H | H | H | Ph | Ph | X13 and X14, X23 and X24 form fused rings. | | | |
| E-22 | H | H | H | H | Ph | ![biphenyl] | X13 and X14, X23 and X24 form fused rings. | | | |
| E-23 | H | H | H | H | Ph | CH3 | X13 and X14, X23 and X24 form fused rings. | | | |
| E-24 | Ph | H | H | Ph | Ph | H | X13 and X14, X23 and X24 form fused rings. | | | |
| E-25 | ![biphenyl-CH3] | H | CH3 | ![biphenyl-CH3] | Ph | H | X13 and X14, X23 and X24 form fused rings. | | | |
| E-26 | CH3 | H | H | CH3 | H | H | X13 and X14, X23 and X24 form fused rings. | | | |

-continued

| Compound No. | X2 | X3 | X6 | X7 | X11 = X21 | X12 = X22 | X13 = X23 | X14 = X24 |
|---|---|---|---|---|---|---|---|---|
| E-27 | 4-biphenylyl | H | H | H | X11 and X12, X21 and X22 form fused rings. | | X13 and X14, X23 and X24 form fused rings. | |
| E-28 | Ph | H | Ph | H | X11 and X12, X21 and X22 form fused rings. | | X13 and X14, X23 and X24 form fused rings. | |
| E-29 | H | H | 4-biphenylyl | H | X11 and X12, X21 and X22 form fused rings. | | X13 and X14, X23 and X24 form fused rings. | |
| E-30 | CH3 | H | CH3 | H | X11 and X12, X21 and X22 form fused rings. | | X13 and X14, X23 and X24 form fused rings. | |

| Compound No. | X2 | X3 | X6 | X7 | X11 = X21 | X12 = X22 | X13 = X23 | X14 = X22 |
|---|---|---|---|---|---|---|---|---|
| E-31 | H | H | H | H | H | H | H | H |
| E-32 | H | H | H | H | H | Ph | H | H |
| E-33 | H | H | H | H | H | 4-methylbiphenyl | H | H |
| E-34 | H | H | H | H | H | p-tolyl (with CH3) | H | H |
| E-35 | H | H | H | H | H | 6-methyl-2-naphthyl | H | H |
| E-36 | H | H | H | H | H | 4-methoxyphenyl (with CH3) | H | H |
| E-37 | H | H | H | H | H | Ph | H | H |
| E-38 | H | H | H | H | H | Ph | H | H |
| E-39 | H | H | Ph | H | H | Ph | H | H |
| E-40 | H | H | H | H | H | Ph | 4-phenylphenyl | H |
| E-41 | Ph | H | Ph | H | H | Ph | CH3 | H |

-continued

| | | | | | | |
|---|---|---|---|---|---|---|
| E-42 | ![biphenyl-CH3] | H | ![biphenyl-CH3] | Ph | H | H |
| E-43 | CH3 | H | CH3 | Ph | H | H |

| Compound No. | X13 | X14 | X23 | X24 |
|---|---|---|---|---|
| E-31 | X13 and X14 form a fused ring. | | H | H |
| E-32 | X13 and X14 form a fused ring. | | H | Ph |
| E-33 | X13 and X14 form a fused ring. | | H | 4-methylbiphenyl |
| E-34 | X13 and X14 form a fused ring. | | H | 4-methylphenyl (CH3-C6H4) |
| E-35 | X13 and X14 form a fused ring. | | H | 2-methylnaphthyl |
| E-36 | X13 and X14 form a fused ring. | | H | CH3 |
| E-37 | X13 and X14 form a fused ring. | | H | methoxyphenyl (PhO-) |
| E-38 | X13 and X14 form a fused ring. | | Ph | Ph |
| E-39 | X13 and X14 form a fused ring. | | 4-methylbiphenyl | Ph |
| E-40 | X13 and X14 form a fused ring. | | CH3 | Ph |
| E-41 | X13 and X14 form a fused ring. | | H | Ph |
| E-42 | X13 and X14 form a fused ring. | | H | Ph |
| E-43 | X13 and X14 form a fused ring. | | H | Ph |

| Compound No. | X2 | X3 | X6 | X7 | X11 | X12 | X13 | X14 |
|---|---|---|---|---|---|---|---|---|
| E-44 | H | H | H | H | X11 and X12 form a fused ring. | | X13 and X14 form a fused ring. | |
| E-45 | H | H | H | H | X11 and X12 form a fused ring. | | X13 and X14 form a fused ring. | |
| E-46 | H | H | H | H | X11 and X12 form a fused ring. | | X13 and X14 form a fused ring. | |
| E-47 | H | H | H | H | X11 and X12 form a fused ring. | | X13 and X14 form a fused ring. | |

-continued

| Compound No. | | | | X11–X12 | X13–X14 |
|---|---|---|---|---|---|
| E-48 | H | H | H | H | X11 and X12 form a fused ring. | X13 and X14 form a fused ring. |
| E-49 | H | H | H | H | X11 and X12 form a fused ring. | X13 and X14 form a fused ring. |
| E-50 | H | H | H | H | X11 and X12 form a fused ring. | X13 and X14 form a fused ring. |
| E-51 | H | H | H | H | X11 and X12 form a fused ring. | X13 and X14 form a fused ring. |
| E-52 | H | H | H | H | X11 and X12 form a fused ring. | X13 and X14 form a fused ring. |
| E-53 | Ph | Ph | Ph | Ph | X11 and X12 form a fused ring. | X13 and X14 form a fused ring. |
| E-54 | 4-biphenylyl | 4-biphenylyl | 4-biphenylyl | 4-biphenylyl | X11 and X12 form a fused ring. | X13 and X14 form a fused ring. |
| E-55 | CH3 | CH3 | CH3 | CH3 | X11 and X12 form a fused ring. | X13 and X14 form a fused ring. |
| E-56 | H | H | H | H | X11 and X12 form a fused ring. | X13 and X14 form a fused ring. |

| Compound No. | X21 | X22 | X23 | X24 |
|---|---|---|---|---|
| E-44 | H | H | H | H |
| E-45 | Ph | H | H | Ph |
| E-46 | 4-biphenylyl |  |  | 4-biphenylyl |
| E-47 | p-tolyl |  |  | p-tolyl |
| E-48 | 2-methylnaphth-6-yl |  |  | 2-methylnaphth-6-yl |
| E-49 | CH3 |  |  | CH3 |
| E-50 | 4-methoxyphenyl |  |  | 4-methoxyphenyl |
| E-51 | Ph | Ph | Ph | Ph |
| E-52 | 4-biphenylyl | 4-biphenylyl | 4-biphenylyl | 4-biphenylyl |
| E-53 | Ph | CH3 | CH3 | Ph |
| E-54 | Ph | H | H | Ph |
| E-55 | Ph | H | H | Ph |
| E-56 | Ph | H | H | Ph |

-continued

| Compound No. | X2 | X3 | X6 | X7 | X11 = 21 | X12 |
|---|---|---|---|---|---|---|
| E-57 | H | H | H | H | H | H |
| E-58 | H | H | H | H | Ph | H |
| E-59 | H | H | H | H | 4-methyl-biphenyl-4'-yl | |
| E-60 | H | H | H | H | 4-methylphenyl (p-tolyl) | |
| E-61 | H | H | H | H | 6-methylnaphthalen-2-yl | |
| E-62 | H | H | H | H | 4-methoxyphenyl (CH3O-Ph) | |
| E-63 | H | H | H | H | Ph | H |
| E-64 | H | H | H | H | Ph | H |
| E-65 | H | H | H | H | Ph | H |
| E-66 | H | H | H | H | Ph | Ph |
| E-67 | Ph | H | Ph | H | Ph | 4-methyl-biphenyl-4'-yl |
| E-68 | 4-methyl-biphenyl-4'-yl | H | 4-methyl-biphenyl-4'-yl | H | CH3 | H |
| E-69 | CH3 | H | CH3 | H | Ph | H |

| Compound No. | X13 | X14 | X22 | X23 | X24 |
|---|---|---|---|---|---|
| E-57 | X13 and X14 form a fused ring. | | X22 and X23 form a fused ring. | | H |
| E-58 | X13 and X14 form a fused ring. | | X22 and X23 form a fused ring. | | Ph |

-continued

| Compound No. | Substituent | Note |
|---|---|---|
| E-59 | 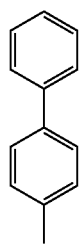 (biphenyl) | X13 and X14 form a fused ring. X22 and X23 form a fused ring. |
| E-60 | 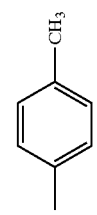 (4-methylphenyl, CH3) | X13 and X14 form a fused ring. X22 and X23 form a fused ring. |
| E-61 | 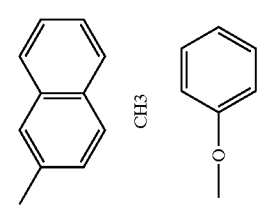 (methylnaphthyl) | X13 and X14 form a fused ring. X22 and X23 form a fused ring. |
| E-62 | CH3 | X13 and X14 form a fused ring. X22 and X23 form a fused ring. |
| E-63 |  (phenoxy/methoxyphenyl) | X13 and X14 form a fused ring. X22 and X23 form a fused ring. |
| E-64 | Ph | X13 and X14 form a fused ring. X22 and X23 form a fused ring. |
| E-65 | Ph | X13 and X14 form a fused ring. X22 and X23 form a fused ring. |
| E-66 | Ph | X13 and X14 form a fused ring. X22 and X23 form a fused ring. |
| E-67 | Ph | X13 and X14 form a fused ring. X22 and X23 form a fused ring. |
| E-68 | Ph | X13 and X14 form a fused ring. X22 and X23 form a fused ring. |
| E-69 | Ph | X13 and X14 form a fused ring. X22 and X23 form a fused ring. |

| Compound No. | X2 | X3 | X6 | X7 | X11 = 24 | X12 = X23 |
|---|---|---|---|---|---|---|
| E-70 | H | H | H | H | H | H |
| E-71 | H | H | H | H | Ph | H |
| E-72 | H | H | H | H | 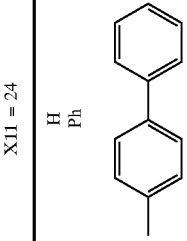 (biphenyl) | H |
| E-73 | H | H | H | H |  (4-methylphenyl, CH3) | H |
| E-74 | H | H | H | H |  (methylnaphthyl) | H |
| E-75 | H | H | H | H | CH3 | H |

| Compound No. | X2 | X3 | X6 | X7 | | |
|---|---|---|---|---|---|---|
| E-76 | H | H | H | H | | |
| E-77 | H | H | H | H | | |
| E-78 | H | H | H | H | | |
| E-79 | H | H | H | H | | |
| E-80 | Ph | H | Ph | H | | |
| E-81 | H | H | Ph | H | | |
| E-82 | CH3 | H | CH3 | H | | |

(Substituents in E-76 to E-82 include biphenyl and methoxyphenyl groups as drawn)

| Compound No. | X11 | X12 | X13 | X14 |
|---|---|---|---|---|
| E-70 | X11 and X12 form a fused ring. | | X13 and X14 form a fused ring. | |
| E-71 | X11 and X12 form a fused ring. | | X13 and X14 form a fused ring. | |
| E-72 | X11 and X12 form a fused ring. | | X13 and X14 form a fused ring. | |
| E-73 | X11 and X12 form a fused ring. | | X13 and X14 form a fused ring. | |
| E-74 | X11 and X12 form a fused ring. | | X13 and X14 form a fused ring. | |
| E-75 | X11 and X12 form a fused ring. | | X13 and X14 form a fused ring. | |
| E-76 | X11 and X12 form a fused ring. | | X13 and X14 form a fused ring. | |
| E-77 | X11 and X12 form a fused ring. | | X13 and X14 form a fused ring. | |
| E-78 | X11 and X12 form a fused ring. | | X13 and X14 form a fused ring. | |
| E-79 | X11 and X12 form a fused ring. | | X13 and X14 form a fused ring. | |
| E-80 | X11 and X12 form a fused ring. | | X13 and X14 form a fused ring. | |
| E-81 | X11 and X12 form a fused ring. | | X13 and X14 form a fused ring. | |
| E-82 | X11 and X12 form a fused ring. | | X13 and X14 form a fused ring. | |

| Compound No. | X13 | X14 | X21 | X22 |
|---|---|---|---|---|
| E-70 | | | X21 and X22 form a fused ring. | H |
| E-71 | | | X21 and X22 form a fused ring. | Ph |
| E-72 | | | X21 and X22 form a fused ring. | Ph |
| E-73 | Ph | | X21 and X22 form a fused ring. | Ph |
| E-74 | Ph | | X21 and X22 form a fused ring. | Ph |
| E-75 | Ph | | X21 and X22 form a fused ring. | Ph |
| E-76 | Ph | | X21 and X22 form a fused ring. | Ph |
| E-77 | Ph | | X21 and X22 form a fused ring. | Ph |
| E-78 | Ph | | X21 and X22 form a fused ring. | Ph |
| E-79 | Ph | | X21 and X22 form a fused ring. | CH3 |
| E-80 | Ph | | X21 and X22 form a fused ring. | H |
| E-81 | Ph | | X21 and X22 form a fused ring. | H |
| E-82 | Ph | | X21 and X22 form a fused ring. | H |

| Compound No. | X2 | X3 | X6 | X7 |
|---|---|---|---|---|
| E-83 | H | H | H | H |
| E-84 | H | H | H | H |
| E-85 | H | H | H | H |
| E-86 | H | H | H | H |
| E-87 | H | H | H | H |
| E-88 | H | H | H | H |
| E-89 | H | H | Ph | H |
| E-90 | Ph | H | H | H |
| E-91 | Ph | H | Ph | H |
| E-92 | CH3 | H | CH3 | H |

-continued

| Compound No. | X21 | X22 | X23 | X24 |
|---|---|---|---|---|
| E-83 | H | X22 and X23 form a fused ring. | X22 and X23 form a fused ring. | H |
| E-84 | Ph | X22 and X23 form a fused ring. | X22 and X23 form a fused ring. | Ph |
| E-85 | 4-methylphenyl | X22 and X23 form a fused ring. | X22 and X23 form a fused ring. | 4-methylphenyl |
| E-86 | 4-methylphenyl (CH3) | X22 and X23 form a fused ring. | X22 and X23 form a fused ring. | 4-methylphenyl (CH3) |
| E-87 | 2-methylnaphthyl | X22 and X23 form a fused ring. | X22 and X23 form a fused ring. | 2-methylnaphthyl |
| E-88 | CH3 | X22 and X23 form a fused ring. | X22 and X23 form a fused ring. | CH3 |
| E-89 | phenoxyphenyl | X22 and X23 form a fused ring. | X22 and X23 form a fused ring. | phenoxyphenyl |
| E-90 | Ph | X22 and X23 form a fused ring. | X22 and X23 form a fused ring. | Ph |
| E-91 | Ph | X22 and X23 form a fused ring. | X22 and X23 form a fused ring. | Ph |
| E-92 | Ph | X22 and X23 form a fused ring. | X22 and X23 form a fused ring. | Ph |

| Compound No. | X2 | X3 | X6 | X7 | X11 | X12 | X13 | X14 |
|---|---|---|---|---|---|---|---|---|
| E-93 | X2 and X3 form a fused ring. | X2 and X3 form a fused ring. | H | H | H | H | X13 and X14 form a fused ring. | X13 and X14 form a fused ring. |
| E-94 | X2 and X3 form a fused ring. | X2 and X3 form a fused ring. | H | H | Ph | H | X13 and X14 form a fused ring. | X13 and X14 form a fused ring. |
| E-95 | X2 and X3 form a fused ring. | X2 and X3 form a fused ring. | H | H | 4-methylphenyl | H | X13 and X14 form a fused ring. | X13 and X14 form a fused ring. |
| E-96 | X2 and X3 form a fused ring. | X2 and X3 form a fused ring. | H | H | 4-methylphenyl (CH3) | H | X13 and X14 form a fused ring. | X13 and X14 form a fused ring. |
| E-97 | X2 and X3 form a fused ring. | X2 and X3 form a fused ring. | H | H | 2-methylnaphthyl | H | X13 and X14 form a fused ring. | X13 and X14 form a fused ring. |

-continued

| Compound No. | | | | | |
|---|---|---|---|---|---|
| E-98 | X2 and X3 form a fused ring. | H | CH3 | H | X13 and X14 form a fused ring. |
| E-99 | X2 and X3 form a fused ring. | H |  | H | X13 and X14 form a fused ring. |
| E-100 | X2 and X3 form a fused ring. | H | Ph | H | X13 and X14 form a fused ring. |
| E-101 | X2 and X3 form a fused ring. | H | Ph | Ph | X13 and X14 form a fused ring. |
| E-102 | X2 and X3 form a fused ring. | H | Ph | H | X13 and X14 form a fused ring. |
| E-103 | X2 and X3 form a fused ring. | H | Ph | Ph | X13 and X14 form a fused ring. |
| E-104 | X2 and X3 form a fused ring. | H |  | H | X13 and X14 form a fused ring. |
| E-105 | X2 and X3 form a fused ring. | CH3 |  | CH3 | X13 and X14 form a fused ring. |

| Compound No. | X21 | X22 | X23 | X24 |
|---|---|---|---|---|
| E-93 | X21 and X22 form a fused ring. | X21 and X22 form a fused ring. | H | H |
| E-94 | X21 and X22 form a fused ring. | X21 and X22 form a fused ring. | H | Ph |
| E-95 | X21 and X22 form a fused ring. | X21 and X22 form a fused ring. | H |  |
| E-96 | X21 and X22 form a fused ring. | X21 and X22 form a fused ring. | H |  |
| E-97 | X21 and X22 form a fused ring. | X21 and X22 form a fused ring. | H |  |
| E-98 | X21 and X22 form a fused ring. | X21 and X22 form a fused ring. | H |  |
| E-99 | X21 and X22 form a fused ring. | X21 and X22 form a fused ring. | H | CH3 |
| E-100 | X21 and X22 form a fused ring. | X21 and X22 form a fused ring. | Ph | Ph |

-continued

| Compound No. | X2 | X3 | X6 | X7 | X11 = 21 | X12 = X22 | X13 = X23 | X14 = X24 |
|---|---|---|---|---|---|---|---|---|
| E-101 | | | | | | X21 and X22 form a fused ring. | | Ph |
| E-102 | | | | | | X21 and X22 form a fused ring. | CH3 | Ph |
| E-103 | | | | | | X21 and X22 form a fused ring. | H | Ph |
| E-104 | | | | | | X21 and X22 form a fused ring. | H | Ph |
| E-105 | | | | | | X21 and X22 form a fused ring. | H | Ph |
| E-106 | X2 and X3 form a fused ring. | | H | H | H | H | H | H |
| E-107 | X2 and X3 form a fused ring. | | H | H | Ph | H | H | Ph |
| E-108 | X2 and X3 form a fused ring. | | H | H | 4-biphenylyl | H | H | 4-biphenylyl |
| E-109 | X2 and X3 form a fused ring. | | H | H | p-tolyl | H | H | p-tolyl |
| E-110 | X2 and X3 form a fused ring. | | H | H | 2-methylnaphthyl | H | H | 2-methylnaphthyl |
| E-111 | X2 and X3 form a fused ring. | | H | H | p-methoxyphenyl | H | H | p-methoxyphenyl |
| E-112 | X2 and X3 form a fused ring. | | H | H | Ph | H | H | Ph |
| E-113 | X2 and X3 form a fused ring. | | H | H | Ph | Ph | Ph | Ph |
| E-114 | X2 and X3 form a fused ring. | | H | H | Ph | 4-biphenylyl | 4-biphenylyl | Ph |
| E-115 | X2 and X3 form a fused ring. | | H | H | Ph | CH3 | CH3 | Ph |
| E-116 | X2 and X3 form a fused ring. | | Ph | H | Ph | H | H | Ph |

-continued

| Compound No. | X2 | X3 | X6 | X7 | X11 = 21 | X12 |
|---|---|---|---|---|---|---|
| E-117 | X2 and X3 form a fused ring. | (4-methylbiphenyl) | Ph | H | H | Ph |
| E-118 | X2 and X3 form a fused ring. | CH3 | Ph | H | H | Ph |

| Compound No. | X2 | X3 | X6 | X7 | X11 = 21 | X12 |
|---|---|---|---|---|---|---|
| E-119 | X2 and X3 form a fused ring. | X2 and X3 form a fused ring. | H | H | H | H |
| E-120 | X2 and X3 form a fused ring. | X2 and X3 form a fused ring. | H | H | Ph | H |
| E-121 | X2 and X3 form a fused ring. | | H | H | (4-methylbiphenyl) | H |
| E-122 | X2 and X3 form a fused ring. | | H | H | (p-tolyl, CH3) | H |
| E-123 | X2 and X3 form a fused ring. | | H | H | (6-methylnaphthalen-2-yl) | H |
| E-124 | X2 and X3 form a fused ring. | | H | H | CH3 | H |
| E-125 | X2 and X3 form a fused ring. | | H | H | (4-methoxyphenyl) | H |
| E-126 | X2 and X3 form a fused ring. | | H | H | Ph | Ph |
| E-127 | X2 and X3 form a fused ring. | | H | H | Ph | Ph |
| E-128 | X2 and X3 form a fused ring. | | H | H | Ph | CH3 |
| E-129 | X2 and X3 form a fused ring. | | Ph | H | Ph | H |
| E-130 | X2 and X3 form a fused ring. | | (4-methylbiphenyl) | H | Ph | H |
| E-131 | X2 and X3 form a fused ring. | | CH3 | H | Ph | H |

-continued

| Compound No. | X13 | X22 | X23 | X14 = X24 |
|---|---|---|---|---|
| E-119 | H | X22 and X23 form a fused ring. | X22 and X23 form a fused ring. | H |
| E-120 | H | X22 and X23 form a fused ring. | X22 and X23 form a fused ring. | Ph |
| E-121 | H | X22 and X23 form a fused ring. | X22 and X23 form a fused ring. | 4-methylphenyl (p-tolyl) |
| E-122 | H | X22 and X23 form a fused ring. | X22 and X23 form a fused ring. | 2-methylnaphthyl |
| E-123 | H | X22 and X23 form a fused ring. | X22 and X23 form a fused ring. | CH3 |
| E-124 | H | X22 and X23 form a fused ring. | X22 and X23 form a fused ring. | phenoxyphenyl (OMe-Ph) |
| E-125 | H | X22 and X23 form a fused ring. | X22 and X23 form a fused ring. | Ph |
| E-126 | 4-methylbiphenyl (Ph-substituted) | X22 and X23 form a fused ring. | X22 and X23 form a fused ring. | Ph |
| E-127 | CH3 | X22 and X23 form a fused ring. | X22 and X23 form a fused ring. | Ph |
| E-128 | H | X22 and X23 form a fused ring. | X22 and X23 form a fused ring. | Ph |
| E-129 | H | X22 and X23 form a fused ring. | X22 and X23 form a fused ring. | Ph |
| E-130 | H | X22 and X23 form a fused ring. | X22 and X23 form a fused ring. | Ph |
| E-131 | H | X22 and X23 form a fused ring. | X22 and X23 form a fused ring. | Ph |

| Compound No. | X12 = X22 | X13 = X23 | X11 = 21 | X14 = X24 |
|---|---|---|---|---|
| E-132 | H | H | H | H |
| E-133 | H | H | Ph | Ph |
| E-134 | H | H | 4-methylbiphenyl | 4-methylbiphenyl |
| E-135 | H | H | 4-methylphenyl (p-tolyl) | 4-methylphenyl (p-tolyl) |

| Compound No. | X2 | X3 | X6 | X7 |
|---|---|---|---|---|
| E-132 | X2 and X3 form a fused ring. | X2 and X3 form a fused ring. | X6 and X7 form a fused ring. | X6 and X7 form a fused ring. |
| E-133 | X2 and X3 form a fused ring. | X2 and X3 form a fused ring. | X6 and X7 form a fused ring. | X6 and X7 form a fused ring. |
| E-134 | X2 and X3 form a fused ring. | X2 and X3 form a fused ring. | X6 and X7 form a fused ring. | X6 and X7 form a fused ring. |
| E-135 | X2 and X3 form a fused ring. | X2 and X3 form a fused ring. | X6 and X7 form a fused ring. | X6 and X7 form a fused ring. |

-continued

| Compound No. | X2 | X3 | X6 | X7 | | | |
|---|---|---|---|---|---|---|---|
| E-136 | X2 and X3 form a fused ring. | X6 and X7 form a fused ring. | 2-methylnaphthyl | CH3 | H | H | |
| E-137 | X2 and X3 form a fused ring. | X6 and X7 form a fused ring. | CH3 | H | H | | |
| E-138 | X2 and X3 form a fused ring. | X6 and X7 form a fused ring. | 4-methoxyphenyl | H | H | | |
| E-139 | X2 and X3 form a fused ring. | X6 and X7 form a fused ring. | Ph | 4-phenylbenzyl (biphenyl-CH2) | Ph | | |
| E-140 | X2 and X3 form a fused ring. | X6 and X7 form a fused ring. | Ph | biphenyl | Ph | | |
| E-141 | X2 and X3 form a fused ring. | X6 and X7 form a fused ring. | Ph | CH3 | Ph | | |

| Compound No. | X2 | X3 | X6 | X7 | X11 = 21 | X12 |
|---|---|---|---|---|---|---|
| E-142 | X2 and X3 form a fused ring. | X6 and X7 form a fused ring. | | | H | H |
| E-143 | X2 and X3 form a fused ring. | X6 and X7 form a fused ring. | | | Ph | H |
| E-144 | X2 and X3 form a fused ring. | X6 and X7 form a fused ring. | | | 4-methylbiphenyl | H |
| E-145 | X2 and X3 form a fused ring. | X6 and X7 form a fused ring. | | | p-tolyl (4-methylphenyl) | H |
| E-146 | X2 and X3 form a fused ring. | X6 and X7 form a fused ring. | | | 2-methylnaphthyl | H |
| E-147 | X2 and X3 form a fused ring. | X6 and X7 form a fused ring. | | | CH3 | H |
| E-148 | X2 and X3 form a fused ring. | X6 and X7 form a fused ring. | | | 4-methoxyphenyl | H |
| E-149 | X2 and X3 form a fused ring. | X6 and X7 form a fused ring. | | | Ph | Ph |

-continued

| Compound No. | X2 | X3 | X6 | X7 |
|---|---|---|---|---|
| E-150 | X2 and X3 form a fused ring. | | X6 and X7 form a fused ring. | |
| E-151 | X2 and X3 form a fused ring. | | X6 and X7 form a fused ring. | |

| Compound No. | X13 | X22 | X23 | X14 = X24 |
|---|---|---|---|---|
| E-142 | H | X22 and X23 form a fused ring. | | H |
| E-143 | H | X22 and X23 form a fused ring. | | Ph |
| E-144 | H | X22 and X23 form a fused ring. | | 4-biphenylyl |
| E-145 | H | X22 and X23 form a fused ring. | | 4-methylphenyl (p-tolyl) |
| E-146 | H | X22 and X23 form a fused ring. | | 2-methylnaphthyl |
| E-147 | H | X22 and X23 form a fused ring. | | CH3 |
| E-148 | H | X22 and X23 form a fused ring. | | phenoxyphenyl |
| E-149 | Ph | X22 and X23 form a fused ring. | | Ph |
| E-150 | CH3 | X22 and X23 form a fused ring. | | Ph |
| E-151 | | X22 and X23 form a fused ring. | | Ph |

| Compound No. | X2 | X3 | X6 | X7 | X11 = 21 | X12 = 22 |
|---|---|---|---|---|---|---|
| E-152 | X2 and X3 form a fused ring. | | X6 and X7 form a fused ring. | | H | H |
| E-153 | X2 and X3 form a fused ring. | | X6 and X7 form a fused ring. | | Ph | H |
| E-154 | X2 and X3 form a fused ring. | | X6 and X7 form a fused ring. | | 4-methylbiphenylyl | H |

-continued

| Compound No. | | | |
|---|---|---|---|
| E-155 | X2 and X3 form a fused ring. | X6 and X7 form a fused ring. | 4-methylphenyl (p-tolyl), H |
| E-156 | X2 and X3 form a fused ring. | X6 and X7 form a fused ring. | 2-methylnaphthyl, H |
| E-157 | X2 and X3 form a fused ring. | X6 and X7 form a fused ring. | CH3, H |
| E-158 | X2 and X3 form a fused ring. | X6 and X7 form a fused ring. | methoxyphenyl (-OCH3), H |
| E-159 | X2 and X3 form a fused ring. | X6 and X7 form a fused ring. | Ph, Ph |
| E-160 | X2 and X3 form a fused ring. | X6 and X7 form a fused ring. | biphenyl-methyl, Ph |
| E-161 | X2 and X3 forms fused ring. | X6 and X7 form a fused ring. | Ph, CH3 |

| Compound No. | X13 | X14 | X23 | X24 |
|---|---|---|---|---|
| E-152 | X13 and X14 form a fused ring. | | H | H |
| E-153 | X13 and X14 form a fused ring. | | H | Ph |
| E-154 | X13 and X14 form a fused ring. | | H | biphenyl |
| E-155 | X13 and X14 form a fused ring. | | H | 4-methylphenyl (p-tolyl) |
| E-156 | X13 and X14 form a fused ring. | | H | 2-methylnaphthyl |
| E-157 | X13 and X14 form a fused ring. | | H | CH3 |

-continued

| Compound No. | X2 | X3 | X6 | X7 | X11 = X21 | X12 = X22 | X13 | X14 | X23 | X24 |
|---|---|---|---|---|---|---|---|---|---|---|
| E-158 | | | | | | | X13 and X14 form a fused ring. | H | | *(phenyl-OMe)* |
| E-159 | | | | | | | X13 and X14 form a fused ring. | Ph | | Ph |
| E-160 | | | | | | | X13 and X14 form a fused ring. | Ph | | *(4-methylbiphenyl)* |
| E-161 | | | | | | | X13 and X14 form a fused ring. | CH3 | | Ph |
| E-162 | X2 and X3 form a fused ring. | | X6 and X7 form a fused ring. | | H | H | X13 and X14 form a fused ring. | | X23 and X24 form a fused ring. | |
| E-163 | X2 and X3 form a fused ring. | | X6 and X7 form a fused ring. | | Ph | H | X13 and X14 form a fused ring. | | X23 and X24 form a fused ring. | |
| E-164 | X2 and X3 form a fused ring. | | X6 and X7 form a fused ring. | | *(4-methylbiphenyl)* | H | X13 and X14 form a fused ring. | | X23 and X24 form a fused ring. | |
| E-165 | X2 and X3 form a fused ring. | | X6 and X7 form a fused ring. | | *(p-tolyl, CH3)* | H | X13 and X14 form a fused ring. | | X23 and X24 form a fused ring. | |
| E-166 | X2 and X3 form a fused ring. | | X6 and X7 form a fused ring. | | *(2-methylnaphthyl)* | H | X13 and X14 form a fused ring. | | X23 and X24 form a fused ring. | |
| E-167 | X2 and X3 form a fused ring. | | X6 and X7 form a fused ring. | | CH3 | H | X13 and X14 form a fused ring. | | X23 and X24 form a fused ring. | |
| E-168 | X2 and X3 form a fused ring. | | X6 and X7 form a fused ring. | | *(phenyl-OMe)* | H | X13 and X14 form a fused ring. | | X23 and X24 form a fused ring. | |
| E-169 | X2 and X3 form a fused ring. | | X6 and X7 form a fused ring. | | Ph | Ph | X13 and X14 form a fused ring. | | X23 and X24 form a fused ring. | |
| E-170 | X2 and X3 form a fused ring. | | X6 and X7 form a fused ring. | | Ph | *(4-methylbiphenyl)* | X13 and X14 form a fused ring. | | X23 and X24 form a fused ring. | |
| E-171 | X2 and X3 form a fused ring. | | X6 and X7 form a fused ring. | | Ph | CH3 | X13 and X14 form a fused ring. | | X23 and X24 form a fused ring. | |

-continued

| Compound No. | X2 | X3 | X6 | X7 | X11 | X12 | X13 | X14 |
|---|---|---|---|---|---|---|---|---|
| E-172 | X2 and X3 form a fused ring. | | X6 and X7 form a fused ring. | | H | H | X13 and X14 form a fused ring. | |
| E-173 | X2 and X3 form a fused ring. | | X6 and X7 form a fused ring. | | Ph | H | X13 and X14 form a fused ring. | |
| E-174 | X2 and X3 form a fused ring. | | X6 and X7 form a fused ring. | | 4-methylbiphenyl | H | X13 and X14 form a fused ring. | |
| E-175 | X2 and X3 form a fused ring. | | X6 and X7 form a fused ring. | | p-tolyl (CH$_3$-C$_6$H$_4$-) | H | X13 and X14 form a fused ring. | |
| E-176 | X2 and X3 form a fused ring. | | X6 and X7 form a fused ring. | | 6-methyl-2-naphthyl | H | X13 and X14 form a fused ring. | |
| E-177 | X2 and X3 form a fused ring. | | X6 and X7 form a fused ring. | | CH$_3$ | H | X13 and X14 form a fused ring. | |
| E-178 | X2 and X3 form a fused ring. | | X6 and X7 form a fused ring. | | 4-methoxyphenyl | H | X13 and X14 form a fused ring. | |
| E-179 | X2 and X3 form a fused ring. | | X6 and X7 form a fused ring. | | Ph | Ph | X13 and X14 form a fused ring. | |
| E-180 | X2 and X3 form a fused ring. | | X6 and X7 form a fused ring. | | Ph | 4-methylbiphenyl | X13 and X14 form a fused ring. | |
| E-181 | X2 and X3 form a fused ring. | | X6 and X7 form a fused ring. | | Ph | CH$_3$ | X13 and X14 form a fused ring. | |

| Compound No. | X21 | X22 | X23 | X24 |
|---|---|---|---|---|
| E-172 | X21 and X22 form a fused ring. | | H | H |
| E-173 | X21 and X22 form a fused ring. | | H | Ph |
| E-174 | X21 and X22 form a fused ring. | | H | 4-methylbiphenyl |
| E-175 | X21 and X22 form a fused ring. | | H | p-tolyl (CH$_3$-C$_6$H$_4$-) |

-continued

| Compound No. | | | | | |
|---|---|---|---|---|---|
| E-176 | | X21 and X22 form a fused ring. | 2-methylnaphthyl | H | |
| E-177 | | X21 and X22 form a fused ring. | CH3 | H | |
| E-178 | | X21 and X22 form a fused ring. | 4-methoxyphenyl | H | |
| E-179 | | X21 and X22 form a fused ring. | Ph | Ph | |
| E-180 | | X21 and X22 form a fused ring. | 4'-methylbiphenyl | Ph | |
| E-181 | | X21 and X22 form a fused ring. | CH3 | Ph | |

| Compound No. | X2 | X3 | X6 | X7 | X11 = 21 | X12 |
|---|---|---|---|---|---|---|
| E-182 | X2 and X3 form a fused ring. | | X6 and X7 form a fused ring. | | H | H |
| E-183 | X2 and X3 form a fused ring. | | X6 and X7 form a fused ring. | | Ph | H |
| E-184 | X2 and X3 form a fused ring. | | X6 and X7 form a fused ring. | | biphenyl | H |
| E-185 | X2 and X3 form a fused ring. | | X6 and X7 form a fused ring. | | 4-methylphenyl | H |
| E-186 | X2 and X3 form a fused ring. | | X6 and X7 form a fused ring. | | 2-methylnaphthyl | H |
| E-187 | X2 and X3 form a fused ring. | | X6 and X7 form a fused ring. | | CH3 | H |
| E-188 | X2 and X3 form a fused ring. | | X6 and X7 form a fused ring. | | 4-methoxyphenyl | H |
| E-189 | X2 and X3 form a fused ring. | | X6 and X7 form a fused ring. | | Ph | Ph |

-continued

| | | | |
|---|---|---|---|
| E-190 | X2 and X3 form a fused ring. | X6 and X7 form a fused ring. | Ph |
| E-191 | X2 and X3 form a fused ring. | X6 and X7 form a fused ring. | Ph |

| Compound No. | X13 | X14 | X22 | X23 | X24 |
|---|---|---|---|---|---|
| E-182 | X13 and X14 form a fused ring. | X13 and X14 form a fused ring. | X22 and X23 form a fused ring. | X22 and X23 form a fused ring. | H |
| E-183 | X13 and X14 form a fused ring. | X13 and X14 form a fused ring. | X22 and X23 form a fused ring. | X22 and X23 form a fused ring. | Ph |
| E-184 | X13 and X14 form a fused ring. | X13 and X14 form a fused ring. | X22 and X23 form a fused ring. | X22 and X23 form a fused ring. | 4-biphenylyl |
| E-185 | X13 and X14 form a fused ring. | X13 and X14 form a fused ring. | X22 and X23 form a fused ring. | X22 and X23 form a fused ring. | p-tolyl |
| E-186 | X13 and X14 form a fused ring. | X13 and X14 form a fused ring. | X22 and X23 form a fused ring. | X22 and X23 form a fused ring. | 2-methylnaphthyl |
| E-187 | X13 and X14 form a fused ring. | X13 and X14 form a fused ring. | X22 and X23 form a fused ring. | X22 and X23 form a fused ring. | CH3 |
| E-188 | X13 and X14 form a fused ring. | X13 and X14 form a fused ring. | X22 and X23 form a fused ring. | X22 and X23 form a fused ring. | OPh |
| E-189 | X13 and X14 form a fused ring. | X13 and X14 form a fused ring. | X22 and X23 form a fused ring. | X22 and X23 form a fused ring. | Ph |
| E-190 | X13 and X14 form a fused ring. | X13 and X14 form a fused ring. | X22 and X23 form a fused ring. | X22 and X23 form a fused ring. | Ph |
| E-191 | X13 and X14 form a fused ring. | X13 and X14 form a fused ring. | X22 and X23 form a fused ring. | X22 and X23 form a fused ring. | Ph |

| Compound No. | [structure with X2-X28] | X2 | X3 | X6 | X7 | X11 = X21 | X14 = X24 | X15 = X25 |
|---|---|---|---|---|---|---|---|---|
| F-1 | | H | H | H | H | H | H | H |
| F-2 | | H | H | H | H | Ph | Ph | H |
| F-3 | | H | H | H | H | 4-biphenyl | 4-biphenyl | H |
| F-4 | | H | H | H | H | p-tolyl | p-tolyl | H |
| F-5 | | H | H | H | H | 2-naphthyl | 2-naphthyl | H |
| F-6 | | H | H | H | H | CH3 | CH3 | H |
| F-7 | | H | H | H | H | PhO | PhO | H |
| F-8 | | H | H | H | H | Ph | Ph | Ph |
| F-9 | | H | H | H | H | Ph | Ph | 4-biphenyl |
| F-10 | | H | H | H | H | Ph | Ph | CH3 |
| F-11 | | H | H | H | H | Ph | Ph | H |
| F-12 | | H | H | H | H | Ph | Ph | H |
| F-13 | | H | H | H | H | Ph | Ph | H |

"A and B form a fused ring" in A[benzene]B means [naphthalene]

-continued

| | | | | | |
|---|---|---|---|---|---|
| F-14 | X2 and X3 form a fused ring. | H | H | H | H |
| F-15 | X2 and X3 form a fused ring. | H | H | 4-Ph-C6H4- | Ph |
| F-16 | X2 and X3 form a fused ring. | H | H | 4-CH3-C6H4- | H |
| F-17 | X2 and X3 form a fused ring. | H | H | 2-naphthyl | H |
| F-18 | X2 and X3 form a fused ring. | H | H | CH3 | H |
| F-19 | X2 and X3 form a fused ring. | H | H | 2-MeO-C6H4- | H |
| F-20 | X2 and X3 form a fused ring. | H | H | 2-MeO-C6H4- | H |
| F-21 | X2 and X3 form a fused ring. | H | H | Ph | Ph |
| F-22 | X2 and X3 form a fused ring. | H | H | Ph | 4-Ph-C6H4- |
| F-23 | X2 and X3 form a fused ring. | H | H | Ph | CH3 |
| F-24 | X2 and X3 form a fused ring. | H | H | Ph | H |
| F-25 | X2 and X3 form a fused ring. | H | H | Ph | H |
| F-26 | X2 and X4 form a fused ring. | H | H | | |

| Compound No. | X16 = X26 | X17 = X27 | X18 = X28 |
|---|---|---|---|
| F-1 | H | H | H |
| F-2 | H | H | H |
| F-3 | H | H | H |
| F-4 | H | H | H |
| F-5 | H | H | H |
| F-6 | H | H | H |
| F-7 | H | H | H |
| F-8 | H | H | Ph |
| F-9 | H | H | 4-CH3-C6H4- |

-continued

| Compound No. | X2 | X3 | X6 | X7 | X11 = X21 | X14 = X24 | X15 = X25 | X16 | X17 |
|---|---|---|---|---|---|---|---|---|---|
| F-10 | | | | | H | H | | CH3 | H |
| F-11 | | | | | Ph | Ph | | H | H |
| F-12 | | | | | 4-biphenyl | 4-biphenyl | | | |
| F-13 | | | | | CH3 | CH3 | | | |
| F-14 | | | | | H | H | | | |
| F-15 | | | | | H | H | | | |
| F-16 | | | | | H | H | | | |
| F-17 | | | | | H | H | | | |
| F-18 | | | | | H | H | | | |
| F-19 | | | | | H | H | | | |
| F-20 | | | | | H | H | | | |
| F-21 | | | | | H | H | | | Ph |
| F-22 | | | | | 4-biphenyl | 4-biphenyl | | 4-biphenyl | |
| F-23 | | | | | H | H | | CH3 | H |
| F-24 | | | | | Ph | Ph | | H | H |
| F-25 | | | | | 4-biphenyl | 4-biphenyl | | | |
| F-26 | | | | | CH3 | CH3 | | H | |
| F-27 | H | H | H | H | H | H | H | X16 and X17 form a fused ring. | |
| F-28 | H | H | H | H | Ph | Ph | H | X16 and X17 form a fused ring. | |
| F-29 | H | H | H | H | 4-biphenyl | 4-biphenyl | H | X16 and X17 form a fused ring. | |
| F-30 | H | H | H | H | 2,5-dimethylphenyl | 2,5-dimethylphenyl | H | X16 and X17 form a fused ring. | |
| F-31 | H | H | H | H | 2-naphthyl | 2-naphthyl | H | X16 and X17 form a fused ring. | |

-continued

| Compound No. | X2 | X3 | X6 | X7 | X11 = X21 | X14 = X24 | X15 = X25 | X18 = X28 | X26 | X27 |
|---|---|---|---|---|---|---|---|---|---|---|
| F-32 | H | H | H | H | CH3 | CH3 | | H | | X16 and X17 form a fused ring. |
| F-33 | H | H | H | H | 4-methoxyphenyl | 4-methoxyphenyl | | H | | X16 and X17 form a fused ring. |
| F-34 | H | H | H | H | Ph | Ph | | Ph | | X16 and X17 form a fused ring. |
| F-35 | H | H | H | H | Ph | Ph | | 4-methylbiphenyl | | X16 and X17 form a fused ring. |
| F-36 | H | H | H | H | Ph | Ph | | CH3 | | X16 and X17 form a fused ring. |
| F-37 | H | H | H | H | Ph | Ph | | H | | X16 and X17 form a fused ring. |
| F-38 | H | H | H | H | Ph | Ph | | H | | X16 and X17 form a fused ring. |
| F-39 | H | H | H | H | Ph | Ph | | H | | X16 and X17 form a fused ring. |

| Compound No. | X18 = X28 | X26 | X27 |
|---|---|---|---|
| F-27 | H | H | H |
| F-28 | H | H | H |
| F-29 | H | H | H |
| F-30 | H | H | H |
| F-31 | H | H | H |
| F-32 | H | H | H |
| F-33 | H | H | H |
| F-34 | Ph | H | H |
| F-35 | H | H | H |
| F-36 | CH3 | H | H |
| F-37 | H | Ph | H |
| F-38 | H | H | H |
| F-39 | H | H | H |

| Compound No. | X2 | X3 | X6 | X7 | X11 = X21 | X14 = X24 | X15 = X25 | X16 | X17 |
|---|---|---|---|---|---|---|---|---|---|
| F-40 | H | H | H | H | H | H | H | CH3 | 4-methylbiphenyl |
| F-41 | H | H | H | H | Ph | Ph | H | X16 and X17 form a fused ring. | X16 and X17 form a fused ring. |

| Compound No. | X2 | X3 | X6 | X7 | | |
|---|---|---|---|---|---|---|
| F-42 | H | H | ![biphenyl] | ![biphenyl] | H | X16 and X17 form a fused ring. |
| F-43 | H | H | ![tolyl-CH3] | ![tolyl-CH3] | H | X16 and X17 form a fused ring. |
| F-44 | H | H | ![naphthyl-CH3] | ![naphthyl-CH3] | H | X16 and X17 form a fused ring. |
| F-45 | H | H | CH3 | CH3 | H | X16 and X17 form a fused ring. |
| F-46 | H | H | ![anisyl-OMe] | ![anisyl-OMe] | H | X16 and X17 form a fused ring. |
| F-47 | H | H | Ph | Ph | Ph | X16 and X17 form a fused ring. |
| F-48 | H | H | Ph | Ph | Ph | X16 and X17 form a fused ring. |
| F-49 | H | H | Ph | Ph | CH3 | CH3 |

| Compound No. | X11 = X21 | X14 = X24 | X18 = X28 | X26 | X27 |
|---|---|---|---|---|---|
| F-40 | H | H | H | X26 and X27 form a fused ring. | X26 and X27 form a fused ring. |
| F-41 | Ph | H | H | X26 and X27 form a fused ring. | X26 and X27 form a fused ring. |
| F-42 | | | H | X26 and X27 form a fused ring. | X26 and X27 form a fused ring. |
| F-43 | | | H | X26 and X27 form a fused ring. | X26 and X27 form a fused ring. |
| F-44 | | | H | X26 and X27 form a fused ring. | X26 and X27 form a fused ring. |
| F-45 | | | H | X26 and X27 form a fused ring. | X26 and X27 form a fused ring. |
| F-46 | | | H | X26 and X27 form a fused ring. | X26 and X27 form a fused ring. |
| F-47 | | | Ph | X26 and X27 form a fused ring. | X26 and X27 form a fused ring. |
| F-48 | | | | | |
| F-49 | | | CH3 | X26 and X27 form a fused ring. | X26 and X27 form a fused ring. |

| Compound No. | X2 | X3 | X6 | X7 | X14 = X24 | X15 = X25 |
|---|---|---|---|---|---|---|
| F-50 | X2 and X3 form a fused ring. | | X6 and X7 form a fused ring. | | H | H |
| F-51 | X2 and X3 form a fused ring. | | X6 and X7 form a fused ring. | | Ph | H |

-continued

| Compound No. | Substituent 1 | Substituent 2 | X2/X3 | X6/X7 | Other |
|---|---|---|---|---|---|
| F-52 | 4-biphenyl | 4-biphenyl | X2 and X3 form a fused ring. | X6 and X7 form a fused ring. | H |
| F-53 | 4-methylphenyl (CH3) | 4-methylphenyl (CH3) | X2 and X3 form a fused ring. | X6 and X7 form a fused ring. | H |
| F-54 | 2-methylnaphthyl | 2-methylnaphthyl | X2 and X3 form a fused ring. | X6 and X7 form a fused ring. | H |
| F-55 | CH3 | CH3 | X2 and X3 form a fused ring. | X6 and X7 form a fused ring. | H |
| F-56 | phenoxy (OPh) | phenoxy (OPh) | X2 and X3 form a fused ring. | X6 and X7 form a fused ring. | H |
| F-57 | Ph | Ph | X2 and X3 form a fused ring. | X6 and X7 form a fused ring. | Ph |
| F-58 | Ph | Ph | X2 and X3 form a fused ring. | X6 and X7 form a fused ring. | 4-methylbiphenyl, CH3 |
| F-59 | Ph | Ph | X2 and X3 form a fused ring. | X6 and X7 form a fused ring. | H |
| F-60 | Ph | Ph | X2 and X3 form a fused ring. | X6 and X7 form a fused ring. | H |
| F-61 | Ph | Ph | X2 and X3 form a fused ring. | X6 and X7 form a fused ring. | H |
| F-62 | Ph | Ph | X2 and X3 form a fused ring. | X6 and X7 form a fused ring. | H |

| Compound No. | X16 = X26 | X17 = X27 | X18 = X28 |
|---|---|---|---|
| F-50 | H | H | H |
| F-51 | H | H | H |
| F-52 | H | H | H |
| F-53 | H | H | H |
| F-54 | H | H | H |
| F-55 | H | H | H |
| F-56 | H | H | H |
| F-57 | H | H | Ph |
| F-58 | H | H | 4-methylbiphenyl, CH3 |
| F-59 | H | H | H |
| F-60 | Ph | Ph | H |

-continued

| Compound No. | X2 | X3 | X6 | X7 | X11 = X21 | X15 | X16 | X14 = X24 | X25 |
|---|---|---|---|---|---|---|---|---|---|
| F-63 | X2 and X3 form a fused ring. | X2 and X3 form a fused ring. | X6 and X7 form a fused ring. | X6 and X7 form a fused ring. | H | X15 and X16 form a fused ring. | X15 and X16 form a fused ring. | CH3 (4-methylphenyl) | H |
| F-64 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | Ph | H |
| F-65 | X2 and X3 form a fused ring. | X2 and X3 form a fused ring. | X6 and X7 form a fused ring. | X6 and X7 form a fused ring. | 4-biphenylyl | X15 and X16 form a fused ring. | X15 and X16 form a fused ring. | 4-biphenylyl | H |
| F-66 | X2 and X3 form a fused ring. | X2 and X3 form a fused ring. | X6 and X7 form a fused ring. | X6 and X7 form a fused ring. | o-tolyl | X15 and X16 form a fused ring. | X15 and X16 form a fused ring. | p-tolyl | H |
| F-67 | X2 and X3 form a fused ring. | X2 and X3 form a fused ring. | X6 and X7 form a fused ring. | X6 and X7 form a fused ring. | 2-naphthyl | X15 and X16 form a fused ring. | X15 and X16 form a fused ring. | 2-naphthyl | H |
| F-68 | X2 and X3 form a fused ring. | X2 and X3 form a fused ring. | X6 and X7 form a fused ring. | X6 and X7 form a fused ring. | CH3 | X15 and X16 form a fused ring. | X15 and X16 form a fused ring. | CH3 | H |
| F-69 | X2 and X3 form a fused ring. | X2 and X3 form a fused ring. | X6 and X7 form a fused ring. | X6 and X7 form a fused ring. | 2-methoxyphenyl | X15 and X16 form a fused ring. | X15 and X16 form a fused ring. | 2-methoxyphenyl | H |
| F-70 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | Ph | H |
| F-71 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | Ph | 4'-methylbiphenyl-4-yl |
| F-72 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | Ph | CH3 |
| F-73 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | Ph | H |
| F-74 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | Ph | H |
| F-75 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | Ph | H |

| Compound No. | X17 = X27 | X26 | X18 = X28 |
|---|---|---|---|
| F-63 | H | H | H |
| F-64 | H | H | H |
| F-65 | H | H | H |
| F-66 | H | H | H |

-continued

| Compound No. | X2 | X3 | X6 | X7 | X11 = X21 | X15 | X16 | X17 | X18 | X14 = X24 |
|---|---|---|---|---|---|---|---|---|---|---|
| F-67 | | | | | | | | | | H |
| F-68 | | | | | | | | | | H |
| F-69 | | | | | | | | | | H |
| F-70 | | | | | | | | | | Ph |
| F-71 | | | | | | | | | | |
| F-72 | | | | | | | | | | H |
| F-73 | | | | | | | | | | Ph |
| F-74 | | | | | | | | | | |
| F-75 | | | | | | CH3 | | CH3 | | |
| F-76 | X2 and X3 form a fused ring. | X2 and X3 form a fused ring. | X6 and X7 form a fused ring. | X6 and X7 form a fused ring. | H | X15 and X16 form a fused ring. | X15 and X16 form a fused ring. | X17 and X18 form a fused ring. | X17 and X18 form a fused ring. | H |
| F-77 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | X17 and X18 form a fused ring. | X17 and X18 form a fused ring. | Ph |
| F-78 | X2 and X3 form a fused ring. | X2 and X3 form a fused ring. | X6 and X7 form a fused ring. | X6 and X7 form a fused ring. | (4-biphenylyl) | X15 and X16 form a fused ring. | X15 and X16 form a fused ring. | X17 and X18 form a fused ring. | X17 and X18 form a fused ring. | (4-biphenylyl) |
| F-79 | X2 and X3 form a fused ring. | X2 and X3 form a fused ring. | X6 and X7 form a fused ring. | X6 and X7 form a fused ring. | (p-tolyl) | X15 and X16 form a fused ring. | X15 and X16 form a fused ring. | X17 and X18 form a fused ring. | X17 and X18 form a fused ring. | (p-tolyl) |
| F-80 | X2 and X3 form a fused ring. | X2 and X3 form a fused ring. | X6 and X7 form a fused ring. | X6 and X7 form a fused ring. | (2-methylnaphthyl) | X15 and X16 form a fused ring. | X15 and X16 form a fused ring. | X17 and X18 form a fused ring. | X17 and X18 form a fused ring. | (2-methylnaphthyl) |
| F-81 | X2 and X3 form a fused ring. | X2 and X3 form a fused ring. | X6 and X7 form a fused ring. | X6 and X7 form a fused ring. | CH3 | X15 and X16 form a fused ring. | X15 and X16 form a fused ring. | X17 and X18 form a fused ring. | X17 and X18 form a fused ring. | CH3 |
| F-82 | X2 and X3 form a fused ring. | X2 and X3 form a fused ring. | X6 and X7 form a fused ring. | X6 and X7 form a fused ring. | (anisyl) | X15 and X16 form a fused ring. | X15 and X16 form a fused ring. | X17 and X18 form a fused ring. | X17 and X18 form a fused ring. | (anisyl) |
| F-83 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | X17 and X18 form a fused ring. | X17 and X18 form a fused ring. | Ph |
| F-84 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | X17 and X18 form a fused ring. | X17 and X18 form a fused ring. | Ph |
| F-85 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | X17 and X18 form a fused ring. | X17 and X18 form a fused ring. | Ph |
| F-86 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | X17 and X18 form a fused ring. | X17 and X18 form a fused ring. | Ph |
| F-87 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | X17 and X18 form a fused ring. | X17 and X18 form a fused ring. | Ph |
| F-88 | X2 and X3 form a fused ring. | X2 and X3 form a fused ring. | X6 and X7 form a fused ring. | X6 and X7 form a fused ring. | Ph | X15 and X16 form a fused ring. | X15 and X16 form a fused ring. | X17 and X18 form a fused ring. | X17 and X18 form a fused ring. | Ph |

-continued

| Compound No. | X25 | X26 | X27 | X28 |
|---|---|---|---|---|
| F-76 | (4-phenylphenyl)methyl | H | H | H |
| F-77 | H | (4-phenylphenyl)methyl | H | H |
| F-78 | H | H | (4-phenylphenyl)methyl | H |
| F-79 | H | H | H | (4-phenylphenyl)methyl |
| F-80 | H | H | H | H |
| F-81 | H | H | H | H |
| F-82 | H | H | H | H |
| F-83 | Ph | H | H | Ph |
| F-84 | CH3 | CH3 | CH3 | CH3 |
| F-85 | H | H | H | H |
| F-86 | H | Ph | Ph | H |
| F-87 | H | H | H | H |

| Compound No. | X2 | X3 | X6 | X7 | X11 = X21 | X15 | X16 | X17 | X18 |
|---|---|---|---|---|---|---|---|---|---|
| F-88 | X2 and X3 form a fused ring. | | X6 and X7 form a fused ring. | | H | X15 and X16 form a fused ring. | | CH3 | H |
| F-89 | X2 and X3 form a fused ring. | | X6 and X7 form a fused ring. | | H | X15 and X16 form a fused ring. | | H | H |
| F-90 | X2 and X3 form a fused ring. | | X6 and X7 form a fused ring. | | Ph | X15 and X16 form a fused ring. | | H | H |
| F-91 | X2 and X3 form a fused ring. | | X6 and X7 form a fused ring. | | 4-methylbiphenyl | X15 and X16 form a fused ring. | | H | H |
| F-92 | X2 and X3 form a fused ring. | | X6 and X7 form a fused ring. | | p-tolyl | X15 and X16 form a fused ring. | | H | H |
| F-93 | X2 and X3 form a fused ring. | | X6 and X7 form a fused ring. | | 2-naphthyl | X15 and X16 form a fused ring. | | H | H |
| F-94 | X2 and X3 form a fused ring. | | X6 and X7 form a fused ring. | | CH3 | X15 and X16 form a fused ring. | | H | H |
| F-95 | X2 and X3 form a fused ring. | | X6 and X7 form a fused ring. | | phenoxy (PhO-) | X15 and X16 form a fused ring. | | H | H |

-continued

| Compound No. | | | | | | | |
|---|---|---|---|---|---|---|---|
| F-96 | X2 and X3 form a fused ring. | X6 and X7 form a fused ring. | Ph | X15 and X16 form a fused ring. | H | H | H |
| F-97 | X2 and X3 form a fused ring. | X6 and X7 form a fused ring. | Ph | X15 and X16 form a fused ring. | 4-biphenyl | H | H |
| F-98 | X2 and X3 form a fused ring. | X6 and X7 form a fused ring. | Ph | X15 and X16 form a fused ring. | 4-biphenyl | CH3 | H |
| F-99 | X2 and X3 form a fused ring. | X6 and X7 form a fused ring. | Ph | X15 and X16 form a fused ring. | 4-biphenyl | H | Ph |
| F-100 | X2 and X3 form a fused ring. | X6 and X7 form a fused ring. | Ph | X15 and X16 form a fused ring. | H | H | — |
| F-101 | X2 and X3 form a fused ring. | X6 and X7 form a fused ring. | Ph | X15 and X16 form a fused ring. | 4-methyl-4′-biphenyl | CH3 | — |

| Compound No. | X14 = X24 | X25 | X26 | X27 | X28 |
|---|---|---|---|---|---|
| F-89 | H | X25 and X26 form a fused ring. | X25 and X26 form a fused ring. | H | H |
| F-90 | Ph | X25 and X26 form a fused ring. | X25 and X26 form a fused ring. | H | H |
| F-91 | 4-biphenyl | X25 and X26 form a fused ring. | X25 and X26 form a fused ring. | H | H |
| F-92 | 4-methylphenyl | X25 and X26 form a fused ring. | X25 and X26 form a fused ring. | H | H |
| F-93 | 2-naphthyl | X25 and X26 form a fused ring. | X25 and X26 form a fused ring. | H | H |
| F-94 | CH3 | X25 and X26 form a fused ring. | X25 and X26 form a fused ring. | H | H |
| F-95 | 4-methoxyphenyl | X25 and X26 form a fused ring. | X25 and X26 form a fused ring. | H | H |
| F-96 | Ph | X25 and X26 form a fused ring. | X25 and X26 form a fused ring. | H | H |
| F-97 | Ph | X25 and X26 form a fused ring. | X25 and X26 form a fused ring. | H | 4-biphenyl-Ph |
| F-98 | Ph | X25 and X26 form a fused ring. | X25 and X26 form a fused ring. | H | 4-methyl-4′-biphenyl-CH3 |

-continued

| Compound No. | X2 | X3 | X6 | X7 | | | X11 = X21 | X14 = X24 | X15 = X25 | |
|---|---|---|---|---|---|---|---|---|---|---|
| F-99 | | | | | | | | Ph | Ph | H |
| F-100 | | | | | | | | Ph | Ph | H |
| | | | | | | | | | | X25 and X26 form a fused ring. |
| | | | | | | | | | | X25 and X26 form a fused ring. |
| F-101 | | | | | | | | Ph | CH3 | H |

| Compound No. | X2 | X3 | X6 | X7 | | X11 = X21 | X14 = X24 | X15 = X25 |
|---|---|---|---|---|---|---|---|---|
| F-102 | X2 and X3 form a fused ring. | | X6 and X7 form a fused ring. | | | H | H | H |
| F-103 | X2 and X3 form a fused ring. | | X6 and X7 form a fused ring. | | | Ph | Ph | H |
| F-104 | X2 and X3 form a fused ring. | | X6 and X7 form a fused ring. | | | 4-biphenyl | 4-biphenyl | H |
| F-105 | X2 and X3 form a fused ring. | | X6 and X7 form a fused ring. | | | 4-tolyl | 4-tolyl | H |
| F-106 | X2 and X3 form a fused ring. | | X6 and X7 form a fused ring. | | | 2-naphthyl | 2-naphthyl | H |
| F-107 | X2 and X3 form a fused ring. | | X6 and X7 form a fused ring. | | | CH3 | CH3 | H |
| F-108 | X2 and X3 form a fused ring. | | X6 and X7 form a fused ring. | | | 4-methoxyphenyl | 4-methoxyphenyl | H |
| F-109 | X2 and X3 form a fused ring. | | X6 and X7 form a fused ring. | | | Ph | Ph | H |
| F-110 | X2 and X3 form a fused ring. | | X6 and X7 form a fused ring. | | | Ph | Ph | H |
| F-111 | X2 and X3 form a fused ring. | | X6 and X7 form a fused ring. | | | Ph | Ph | 4-biphenyl |

| Compound No. | X16 = X26 | X17 = X27 | X18 = X28 |
|---|---|---|---|
| F-102 | X16 and X17, X26 and X27 form fused rings. | | H |
| F-103 | X16 and X17, X26 and X27 form fused rings. | | H |
| F-104 | X16 and X17, X26 and X27 form fused rings. | | H |
| F-105 | X16 and X17, X26 and X27 form fused rings. | | H |
| F-106 | X16 and X17, X26 and X27 form fused rings. | | H |

-continued
| | |
|---|---|
| F-107 | X16 and X17, X26 and X27 form fused rings. H |
| F-108 | X16 and X17, X26 and X27 form fused rings. H |
| F-109 | X16 and X17, X26 and X27 form fused rings. Ph |
| F-110 | X16 and X17, X26 and X27 form fused rings. CH3 |
| F-111 | X16 and X17, X26 and X27 form fused rings. 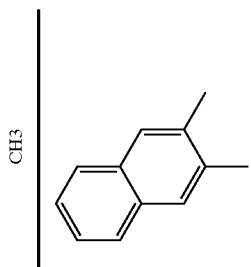 |
"A and B form a fused ring" in 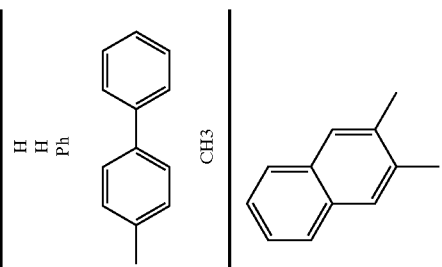 means 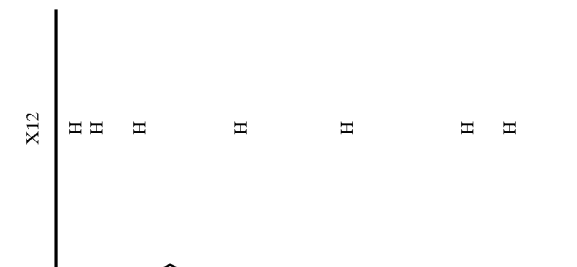
| Compound No. | X2 | X3 | X6 | X7 | X32 | X33 | X36 | X37 | X11 | X12 |
|---|---|---|---|---|---|---|---|---|---|---|
| F-112 | H | H | H | H | H | H | H | H | H | H |
| F-113 | H | H | H | H | H | H | H | H | Ph | H |
| F-114 | H | H | H | H | H | H | H | H | biphenyl | H |
| F-115 | H | H | H | H | H | H | H | H | p-tolyl | H |
| F-116 | H | H | H | H | H | H | H | H | 3-methylnaphthyl | H |
| F-117 | H | H | H | H | H | H | H | H | CH3 | H |
| F-118 | H | H | H | H | H | H | H | H | OPh | H |

-continued

| Compound No. | X13 | X14 | X21 | X22 | X23 | X24 |
|---|---|---|---|---|---|---|
| F-119 | 4-methylbiphenyl | H | H | H | Ph | H |
| F-120 | Ph | H | H | H | Ph | H |
| F-121 | CH3 | H | H | H | Ph | H |
| F-122 | H | H | H | H | Ph | Ph |
| F-123 | H | H | 4-methylbiphenyl | H | Ph | H |
| F-124 | H | H | CH3 | H | Ph | H |
| F-125 | H | H | H | H | Ph | Ph |
| F-126 | H | H | H | H | Ph | H |
| F-127 | H | H | H | H | Ph | CH3 |

| Compound No. | X13 | X14 | X21 | X22 | X23 | X24 |
|---|---|---|---|---|---|---|
| F-112 | H | H | H | H | H | H |
| F-113 | H | Ph | 4-methylbiphenyl | H | H | Ph |
| F-114 | H | 4-methylbiphenyl | 4-methylphenyl (CH3) | H | H | 4-methylphenyl (CH3) |
| F-115 | H | 4-methylphenyl (CH3) | 2-methylnaphthyl | H | H | 2-methylnaphthyl |
| F-116 | H | 2-methylnaphthyl | CH3 | H | H | CH3 |
| F-117 | H | CH3 | H | H | H | CH3 |

-continued

| Compound No. | | | | | | | | | |
|---|---|---|---|---|---|---|---|---|---|
| F-118 | H | H | H | H | H | H | H | H | H |
| F-119 | H | Ph | H | Ph | H | H | H | H | Ph |
| F-120 | H | Ph | H | Ph | H | H | H | H | Ph |
| F-121 | H | Ph | H | Ph | H | H | H | H | Ph |
| F-122 | H | Ph | H | Ph | H | H | H | H | Ph |
| F-123 | H | Ph | H | Ph | H | H | H | H | Ph |
| F-124 | H | Ph | H | Ph | H | H | H | H | Ph |
| F-125 | Ph | Ph | H | Ph | H | Ph | Ph | H | Ph |
| F-126 | CH3 | Ph | H | Ph | H | | | | Ph |
| F-127 | CH3 | Ph | H | Ph | H | CH3 | CH3 | H | Ph |

| Compound No. | X2 | X3 | X6 | X7 | X11 | X32 | X33 | X36 | X37 |
|---|---|---|---|---|---|---|---|---|---|
| F-128 | H | H | H | H | H | H | H | H | H |
| F-129 | H | H | H | H | Ph | H | H | H | H |
| F-130 | H | H | H | H | H | H | H | H | H |
| F-131 | H | H | H | H | H | H | H | H | H |
| F-132 | H | H | H | H | H | H | H | H | H |
| F-133 | H | H | H | H | H | H | H | H | H |
| F-134 | H | H | H | H | H | H | H | H | H |
| F-135 | Ph | H | H | H | Ph | Ph | H | H | H |

-continued

| Compound No. | | | | | | | |
|---|---|---|---|---|---|---|---|
| F-136 | 4-methylbiphenyl | CH3 | H | | | | Ph |
| F-137 | | H | | H | | H | Ph |
| F-138 | | | Ph | H | Ph | H | Ph |
| F-139 | | H | | H | | H | Ph |
| F-140 | | H | CH3 | H | CH3 | H | Ph |
| F-141 | | H | H | H | H | H | Ph |
| F-142 | | H | H | H | H | H | Ph |
| F-143 | | H | H | H | H | H | Ph |

| Compound No. | X12 | X13 | X14 | X21 | X22 | X23 | X24 |
|---|---|---|---|---|---|---|---|
| F-128 | X12 and X13 form a fused ring. | | | H | H | H | H |
| F-129 | X12 and X13 form a fused ring. | | | Ph | | | Ph |
| F-130 | X12 and X13 form a fused ring. | | 4-methylbiphenyl | 4-methylbiphenyl | H | H | 4-methylbiphenyl |
| F-131 | X12 and X13 form a fused ring. | | p-tolyl (CH3) | p-tolyl (CH3) | H | H | p-tolyl (CH3) |
| F-132 | X12 and X13 form a fused ring. | | 2-methylnaphthyl | 2-methylnaphthyl | H | H | 2-methylnaphthyl |
| F-133 | X12 and X13 form a fused ring. | | CH3 / methoxyphenyl | CH3 / methoxyphenyl | H | H | CH3 / methoxyphenyl |
| F-134 | X12 and X13 form a fused ring. | | methoxyphenyl | methoxyphenyl | H | H | methoxyphenyl |
| F-135 | X12 and X13 form a fused ring. | | Ph | Ph | H | H | Ph |
| F-136 | X12 and X13 form a fused ring. | | Ph | Ph | H | H | Ph |
| F-137 | X12 and X13 form a fused ring. | | Ph | Ph | H | H | Ph |
| F-138 | X12 and X13 form a fused ring. | | Ph | Ph | H | H | Ph |
| F-139 | X12 and X13 form a fused ring. | | Ph | Ph | H | H | Ph |
| F-140 | X12 and X13 form a fused ring. | | Ph | Ph | H | H | Ph |
| F-141 | X12 and X13 form a fused ring. | | Ph | Ph | Ph | Ph | Ph |

-continued

| Compound No. | X2 | X3 | X6 | X7 | X32 | X33 | X36 | X37 | X11 |
|---|---|---|---|---|---|---|---|---|---|
| F-142 | X12 and X13 form a fused ring. | Ph | | | | | CH3 | | Ph |
| F-143 | X12 and X13 form a fused ring. | Ph | | | | | | | Ph |
| F-144 | H | H | H | H | H | H | H | H | H |
| F-145 | H | H | H | H | H | H | H | H | Ph |
| F-146 | H | H | H | H | H | H | H | H | 4-methylphenyl (CH3) |
| F-147 | H | H | H | H | H | H | H | H | 6-methyl-2-naphthyl |
| F-148 | H | H | H | H | H | H | H | H | CH3 |
| F-149 | H | H | H | H | H | H | H | H | 4-methoxyphenyl (—O—Ph) |
| F-150 | H | H | H | H | H | H | H | H | Ph |
| F-151 | 4′-phenyl-4-biphenyl (Ph-C6H4-) | H | H | H | Ph-biphenyl | H | H | H | Ph |
| F-152 | CH3 | H | H | H | CH3 | H | H | H | Ph |
| F-153 | H | H | H | H | H | H | H | H | Ph |
| F-154 | H | H | H | H | H | 4′-phenylbiphenyl | H | H | Ph |
| F-155 | H | H | H | H | H | CH3 | H | H | Ph |
| F-156 | H | H | H | H | H | H | H | H | Ph |
| F-157 | H | H | H | H | H | H | H | H | Ph |
| F-158 | H | H | H | H | H | H | H | H | Ph |
| F-159 | H | H | H | H | H | H | H | H | Ph |

-continued

| Compound No. | X12 | X13 | X14 | X21 | X22 | X23 | X24 |
|---|---|---|---|---|---|---|---|
| F-144 | H | H | H | X21 and X22 form a fused ring. | X21 and X22 form a fused ring. | X23 and X24 form a fused ring. | X23 and X24 form a fused ring. |
| F-145 | H | H | Ph | X21 and X22 form a fused ring. | X21 and X22 form a fused ring. | X23 and X24 form a fused ring. | X23 and X24 form a fused ring. |
| F-146 | H | H | 4-biphenylyl | X21 and X22 form a fused ring. | X21 and X22 form a fused ring. | X23 and X24 form a fused ring. | X23 and X24 form a fused ring. |
| F-147 | H | H | 4-methylphenyl (CH3) | X21 and X22 form a fused ring. | X21 and X22 form a fused ring. | X23 and X24 form a fused ring. | X23 and X24 form a fused ring. |
| F-148 | H | H | 2-methylnaphthyl | X21 and X22 form a fused ring. | X21 and X22 form a fused ring. | X23 and X24 form a fused ring. | X23 and X24 form a fused ring. |
| F-149 | H | H | CH3 | X21 and X22 form a fused ring. | X21 and X22 form a fused ring. | X23 and X24 form a fused ring. | X23 and X24 form a fused ring. |
| F-150 | H | H | 4-methoxyphenyl | X21 and X22 form a fused ring. | X21 and X22 form a fused ring. | X23 and X24 form a fused ring. | X23 and X24 form a fused ring. |
| F-151 | H | H | Ph | X21 and X22 form a fused ring. | X21 and X22 form a fused ring. | X23 and X24 form a fused ring. | X23 and X24 form a fused ring. |
| F-152 | H | H | Ph | X21 and X22 form a fused ring. | X21 and X22 form a fused ring. | X23 and X24 form a fused ring. | X23 and X24 form a fused ring. |
| F-153 | H | H | Ph | X21 and X22 form a fused ring. | X21 and X22 form a fused ring. | X23 and X24 form a fused ring. | X23 and X24 form a fused ring. |
| F-154 | H | H | Ph | X21 and X22 form a fused ring. | X21 and X22 form a fused ring. | X23 and X24 form a fused ring. | X23 and X24 form a fused ring. |
| F-155 | H | H | Ph | X21 and X22 form a fused ring. | X21 and X22 form a fused ring. | X23 and X24 form a fused ring. | X23 and X24 form a fused ring. |
| F-156 | H | H | Ph | X21 and X22 form a fused ring. | X21 and X22 form a fused ring. | X23 and X24 form a fused ring. | X23 and X24 form a fused ring. |
| F-157 | Ph | Ph | Ph | X21 and X22 form a fused ring. | X21 and X22 form a fused ring. | X23 and X24 form a fused ring. | X23 and X24 form a fused ring. |
| F-158 | H | 4-biphenylyl | Ph | X21 and X22 form a fused ring. | X21 and X22 form a fused ring. | X23 and X24 form a fused ring. | X23 and X24 form a fused ring. |
| F-159 | CH3 | CH3 | Ph | X21 and X22 form a fused ring. | X21 and X22 form a fused ring. | X23 and X24 form a fused ring. | X23 and X24 form a fused ring. |

| Compound No. | X2 | X3 | X6 | X7 | X32 | X33 | X36 | X37 | X11 | X12 |
|---|---|---|---|---|---|---|---|---|---|---|
| F-160 | H | H | H | H | H | H | H | H | X11 and X12 form a fused ring. | X11 and X12 form a fused ring. |
| F-161 | Ph | H | H | H | Ph | H | H | H | X11 and X12 form a fused ring. | X11 and X12 form a fused ring. |
| F-162 | 4-biphenylyl | H | H | H | 4-biphenylyl | H | H | H | X11 and X12 form a fused ring. | X11 and X12 form a fused ring. |

-continued

| Compound No. | X2 | X3 | | X6 | X7 | | X13 | X14 | X21 | X22 | X23 | X24 |
|---|---|---|---|---|---|---|---|---|---|---|---|---|
| F-163 | CH3 | | CH3 | H | H | | | | H | H | H | X11 and X12 form a fused ring. |
| F-164 | H | | H | H | H | | | | Ph | H | H | X11 and X12 form a fused ring. |
| F-165 | H | | H | H | H | | | | H | H | H | X11 and X12 form a fused ring. |
| F-166 | H | | H | H | H | | | | CH3 | H | H | X11 and X12 form a fused ring. |

| Compound No. | X13 | X14 | X21 | X22 | X23 | X24 |
|---|---|---|---|---|---|---|
| F-160 | X13 and X14 form a fused ring. | | X21 and X22 form a fused ring. | | X23 and X24 form a fused ring. | |
| F-161 | X13 and X14 form a fused ring. | | X21 and X22 form a fused ring. | | X23 and X24 form a fused ring. | |
| F-162 | X13 and X14 form a fused ring. | | X21 and X22 form a fused ring. | | X23 and X24 form a fused ring. | |
| F-163 | X13 and X14 form a fused ring. | | X21 and X22 form a fused ring. | | X23 and X24 form a fused ring. | |
| F-164 | X13 and X14 form a fused ring. | | X21 and X22 form a fused ring. | | X23 and X24 form a fused ring. | |
| F-165 | X13 and X14 form a fused ring. | | X21 and X22 form a fused ring. | | X23 and X24 form a fused ring. | |
| F-166 | X13 and X14 form a fused ring. | | X21 and X22 form a fused ring. | | X23 and X24 form a fused ring. | |

| Compound No. | X2 | X3 | X6 | X7 | X32 | X33 | X36 | X37 | X11 |
|---|---|---|---|---|---|---|---|---|---|
| F-167 | H | H | H | H | H | H | H | H | H |
| F-168 | H | H | H | H | H | H | H | H | Ph |
| F-169 | H | H | H | H | H | H | H | H | (4-methylbiphenyl) |
| F-170 | H | H | H | H | H | H | H | H | (p-tolyl) |
| F-171 | H | H | H | H | H | H | H | H | (3-methylnaphthyl) |
| F-172 | H | H | H | H | H | H | H | H | CH3 |
| F-173 | H | H | H | H | H | H | H | H | (methoxyphenyl) |
| F-174 | Ph | H | H | H | Ph | H | H | H | Ph |

-continued

| Compound No. | | | | | | | |
|---|---|---|---|---|---|---|---|
| F-175 | [4-phenylphenyl] | H | H | H | H | H | Ph |
| F-176 | CH3 | H | [4-phenylphenyl] | H | H | H | Ph |
| F-177 | H | Ph | H | H | Ph | H | Ph |
| F-178 | H | H | H | CH3 | H | H | Ph |
| F-179 | CH3 | H | H | CH3 | H | H | Ph |
| F-180 | H | H | H | H | [4-phenylphenyl] | H | Ph |
| F-181 | H | H | H | H | H | H | Ph |
| F-182 | H | H | H | H | H | H | Ph |

| Compound No. | X12 | X13 | X14 | X21 | X22 | X23 | X24 |
|---|---|---|---|---|---|---|---|
| F-167 | H | X13 and X14 form a fused ring. | | X21 and X22 form a fused ring. | | H | [4-biphenyl] |
| F-168 | H | X13 and X14 form a fused ring. | | X21 and X22 form a fused ring. | | H | Ph |
| F-169 | H | X13 and X14 form a fused ring. | | X21 and X22 form a fused ring. | | H | [p-tolyl (CH3)] |
| F-170 | H | X13 and X14 form a fused ring. | | X21 and X22 form a fused ring. | | H | [6-methyl-2-naphthyl] |
| F-171 | H | X13 and X14 form a fused ring. | | X21 and X22 form a fused ring. | | H | CH3 |
| F-172 | H | X13 and X14 form a fused ring. | | X21 and X22 form a fused ring. | | H | [4-methoxyphenyl] |
| F-173 | H | X13 and X14 form a fused ring. | | X21 and X22 form a fused ring. | | H | Ph |
| F-174 | H | X13 and X14 form a fused ring. | | X21 and X22 form a fused ring. | | H | Ph |
| F-175 | H | X13 and X14 form a fused ring. | | X21 and X22 form a fused ring. | | H | Ph |
| F-176 | H | X13 and X14 form a fused ring. | | X21 and X22 form a fused ring. | | H | Ph |
| F-177 | H | X13 and X14 form a fused ring. | | X21 and X22 form a fused ring. | | H | Ph |
| F-178 | H | X13 and X14 form a fused ring. | | X21 and X22 form a fused ring. | | H | Ph |
| F-179 | H | X13 and X14 form a fused ring. | | X21 and X22 form a fused ring. | | Ph | Ph |
| F-180 | Ph | X13 and X14 form a fused ring. | | X21 and X22 form a fused ring. | | H | Ph |

-continued

| Compound No. | X2 | X3 | X6 | X7 | X32 | X33 | X36 | X37 | X11 |
|---|---|---|---|---|---|---|---|---|---|
| F-181 | 4'-methylbiphenyl-4-yl | CH3 | X13 and X14 form a fused ring. | | X21 and X22 form a fused ring. | | | 4'-methylbiphenyl-4-yl | Ph |
| F-182 | | | X13 and X14 form a fused ring. | | X21 and X22 form a fused ring. | | | CH3 | Ph |

| Compound No. | X2 | X3 | X6 | X7 | X32 | X33 | X36 | X37 | X11 |
|---|---|---|---|---|---|---|---|---|---|
| F-183 | H | H | H | H | H | H | H | H | H |
| F-184 | H | H | H | H | H | H | H | H | Ph |
| F-185 | H | H | H | H | H | H | H | H | 4-biphenylyl |
| F-186 | H | H | H | H | H | H | H | H | p-tolyl |
| F-187 | H | H | H | H | H | H | H | H | 2-methylnaphthyl |
| F-188 | H | H | H | H | H | H | H | H | 4-methoxyphenyl |
| F-189 | H | H | H | H | H | H | H | H | Ph |
| F-190 | Ph | H | H | H | Ph | H | H | H | Ph |
| F-191 | 4'-methylbiphenyl-4-yl | H | H | H | 4'-methylbiphenyl-4-yl | H | H | H | Ph |
| F-192 | CH3 | CH3 | H | H | CH3 | CH3 | H | H | Ph |
| F-193 | H | H | H | H | H | H | H | H | Ph |
| F-194 | H | H | H | H | H | 4'-methylbiphenyl-4-yl | H | H | Ph |
| F-195 | H | H | H | H | H | H | H | H | Ph |
| F-196 | H | H | H | H | H | H | H | H | Ph |

-continued

| Compound No. | X12 | X13 | X14 | X21 | X22 | X23 | X24 |
|---|---|---|---|---|---|---|---|
| F-183 | H | X13 and X14 form a fused ring. | | H | H | H | H |
| F-184 | H | X13 and X14 form a fused ring. | | Ph | H | X23 and X24 form a fused ring. | |
| F-185 | H | X13 and X14 form a fused ring. | | 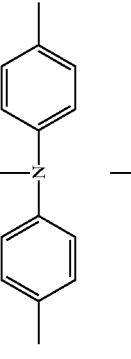 | H | X23 and X24 form a fused ring. | |
| F-186 | H | X13 and X14 form a fused ring. | | 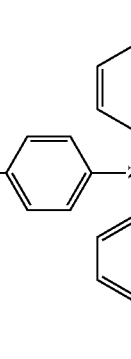 | H | X23 and X24 form a fused ring. | |
| F-187 | H | X13 and X14 form a fused ring. | | 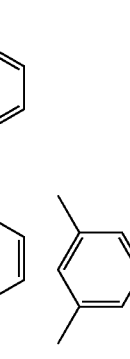 | H | X23 and X24 form a fused ring. | |
| F-188 | H | X13 and X14 form a fused ring. | | CH3 | H | X23 and X24 form a fused ring. | |
| F-189 | H | X13 and X14 form a fused ring. | |  | H | X23 and X24 form a fused ring. | |
| F-190 | H | X13 and X14 form a fused ring. | | Ph | H | X23 and X24 form a fused ring. | |
| F-191 | H | X13 and X14 form a fused ring. | | Ph | H | X23 and X24 form a fused ring. | |
| F-192 | H | X13 and X14 form a fused ring. | | Ph | H | X23 and X24 form a fused ring. | |
| F-193 | H | X13 and X14 form a fused ring. | | Ph | H | X23 and X24 form a fused ring. | |
| F-194 | H | X13 and X14 form a fused ring. | | Ph | H | X23 and X24 form a fused ring. | |
| F-195 | H | X13 and X14 form a fused ring. | | Ph | H | X23 and X24 form a fused ring. | |
| F-196 | Ph | X13 and X14 form a fused ring. | | Ph | Ph | X23 and X24 form a fused ring. | |
| F-197 |  | X13 and X14 form a fused ring. | | Ph |  | X23 and X24 form a fused ring. | |
| F-198 | CH3 | X13 and X14 form a fused ring. | | Ph | CH3 | X23 and X24 form a fused ring. | |

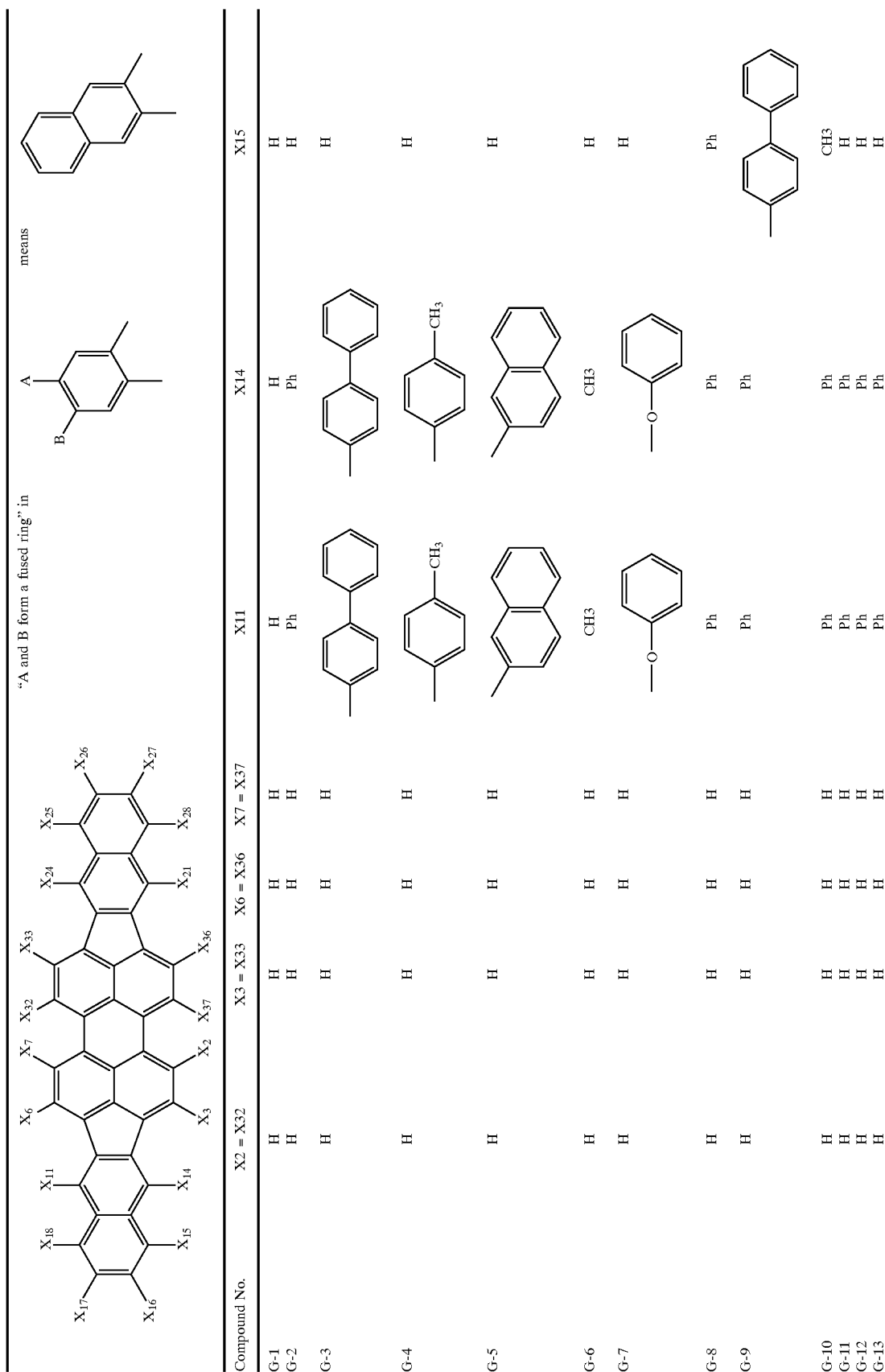

-continued

| Compound No. | X16 | X17 | X18 | X21 | X24 |
|---|---|---|---|---|---|
| G-14 | Ph | H | Ph | Ph | H |
| G-15 | Ph | H | Ph | Ph | H |
| G-16 | 4-MeC6H4 (4-methylphenyl) | H | Ph | Ph | H |

| Compound No. | X16 | X17 | X18 | X21 | X24 |
|---|---|---|---|---|---|
| G-1 | H | H | H | H | H |
| G-2 | H | H | H | Ph | Ph |
| G-3 | H | H | H | 4-biphenylyl | 4-biphenylyl |
| G-4 | H | H | H | 4-methylphenyl | 4-methylphenyl |
| G-5 | H | H | H | 2-naphthyl | 2-naphthyl |
| G-6 | H | H | H | CH3 | CH3 |
| G-7 | H | H | H | 2-methoxyphenyl | 2-methoxyphenyl |
| G-8 | H | H | H | Ph | Ph |
| G-9 | H | H | H | Ph | Ph |
| G-10 | H | H | Ph | Ph | Ph |
| G-11 | Ph | Ph | | Ph | Ph |
| G-12 | 4-biphenylyl | 4-biphenylyl | CH3 | Ph | Ph |
| G-13 | CH3 | CH3 | H | Ph | Ph |

-continued

| Compound No. | X2 = X32 | X3 = X33 | X6 = X36 X7 = X37 | X25 | X26 | X27 | X28 |
|---|---|---|---|---|---|---|---|
| G-14 | H | H | H | | | | Ph |
| G-15 | H | H | H | | | | Ph |
| G-16 | H | H | H | | | | Ph |
| G-1 | | | | H | H | H | H |
| G-2 | | | | H | H | H | H |
| G-3 | | | | H | H | H | H |
| G-4 | | | | H | H | H | H |
| G-5 | | | | H | H | H | H |
| G-6 | | | | H | H | H | H |
| G-7 | | | | H | H | H | H |
| G-8 | | | | Ph | Ph | H | Ph |
| G-9 | | | | H | H | H | H (biphenyl substituent) |
| G-10 | | | | CH3 | H | H | CH3 |
| G-11 | | | | H | Ph | H | H |
| G-12 | | | | H | H | H | H (biphenyl substituent) |
| G-13 | | | | H | CH3 | CH3 | H |
| G-14 | | | | H | H | H | H |
| G-15 | | | | H | H | H | H |
| G-16 | | | | H | H | H | H |

| Compound No. | X2 = X32 | X3 = X33 | X6 = X36 X7 = X37 | X11 | X14 | X15 | X16 | X17 |
|---|---|---|---|---|---|---|---|---|
| G-17 | H | H | H | H | H | H | X16 and X17 form a fused ring. | |
| G-18 | H | H | H | Ph | Ph | H | X16 and X17 form a fused ring. | |
| G-19 | H | H | H | (p-tolyl-phenyl) | (p-tolyl-phenyl) | H | X16 and X17 form a fused ring. | |
| G-20 | H | H | H | (p-tolyl) | (p-tolyl) | H | X16 and X17 form a fused ring. | |

| Compound No. | | | | | | | |
|---|---|---|---|---|---|---|---|
| G-21 | H | H | H | — | 2-naphthyl-CH3 | H | X16 and X17 form a fused ring. |
| G-22 | H | H | H | 2-naphthyl-CH3 | 2-naphthyl-CH3 | H | X16 and X17 form a fused ring. |
| G-23 | H | H | H | 2-methoxyphenyl | 2-methoxyphenyl | H | X16 and X17 form a fused ring. |
| G-24 | H | H | H | Ph | Ph | Ph | X16 and X17 form a fused ring. |
| G-25 | H | H | H | Ph | Ph | Ph | X16 and X17 form a fused ring. |
| G-26 | H | H | H | Ph | Ph | CH3 | X16 and X17 form a fused ring. |
| G-27 | Ph | H | H | Ph | Ph | H | X16 and X17 form a fused ring. |
| G-28 | 4-biphenyl | H | H | Ph | Ph | H | X16 and X17 form a fused ring. |
| G-29 | CH3 | H | H | Ph | Ph | H | X16 and X17 form a fused ring. |

| Compound No. | X18 | X21 | X24 | X25 | X26 | X27 | X28 |
|---|---|---|---|---|---|---|---|
| G-17 | H | H | H | H | X26 and X27 form a fused ring | X26 and X27 form a fused ring | H |
| G-18 | H | Ph | Ph | H | X26 and X27 form a fused ring | X26 and X27 form a fused ring | H |
| G-19 | H | 4-biphenyl | 4-biphenyl | H | X26 and X27 form a fused ring | X26 and X27 form a fused ring | H |
| G-20 | H | 4-methylphenyl | 4-methylphenyl | H | X26 and X27 form a fused ring | X26 and X27 form a fused ring | H |
| G-21 | H | 2-naphthyl | 2-naphthyl | H | X26 and X27 form a fused ring | X26 and X27 form a fused ring | H |
| G-22 | H | CH3 | CH3 | H | X26 and X27 form a fused ring | X26 and X27 form a fused ring | H |

-continued

| Compound No. | | | | | | | |
|---|---|---|---|---|---|---|---|
| G-23 | phenoxy | phenoxy | biphenyl (4-methyl) | H | phenoxy | X26 and X27 form a fused ring | H |
| G-24 | | | biphenyl-Ph | Ph | Ph | X26 and X27 form a fused ring | H |
| G-25 | | | CH3 | Ph | Ph | X26 and X27 form a fused ring | H |
| G-26 | | | H | Ph | Ph | X26 and X27 form a fused ring | H |
| G-27 | | | H | Ph | Ph | X26 and X27 form a fused ring | H |
| G-28 | | | H | Ph | Ph | X26 and X27 form a fused ring | H |
| G-29 | | | H | Ph | Ph | X26 and X27 form a fused ring | H |

| Compound No. | X2 = X32 | X3 = X33 | X6 = X36 | X7 = X37 | X11 | X14 | X15 |
|---|---|---|---|---|---|---|---|
| G-30 | H | H | H | H | H | H | H |
| G-31 | H | H | H | H | Ph | Ph | H |
| G-32 | H | H | H | H | biphenyl (4-methyl) | biphenyl (4-methyl) | H |
| G-33 | H | H | H | H | 4-methylphenyl (CH3) | 4-methylphenyl (CH3) | H |
| G-34 | H | H | H | H | naphthyl | naphthyl | H |
| G-35 | H | H | H | H | CH3 | CH3 | H |
| G-36 | H | H | H | H | methoxyphenyl | methoxyphenyl | H |
| G-37 | H | H | H | H | Ph | Ph | H |
| G-38 | H | H | H | H | Ph | Ph | biphenyl-Ph |
| G-39 | H | H | H | H | Ph | Ph | CH3 |
| G-40 | H | H | H | H | Ph | Ph | H |

-continued

| Compound No. | X16 | X17 | X18 | X21 | X24 | X25 |
|---|---|---|---|---|---|---|
| G-41 | 4-phenylphenyl | | H | H | Ph | H |
| G-42 | | | H | H | Ph | H |
| G-43 | | | H | Ph | Ph | H |
| G-44 | | | H | H | Ph | H |
| G-45 | CH3 | | H | H | Ph | H |

| Compound No. | X16 | X17 | X18 | X21 | X24 | X25 |
|---|---|---|---|---|---|---|
| G-30 | X16 and X17 form a fused ring. | X16 and X17 form a fused ring. | H | H | H | H |
| G-31 | X16 and X17 form a fused ring. | X16 and X17 form a fused ring. | H | Ph | Ph | H |
| G-32 | X16 and X17 form a fused ring. | | H | 4-phenylphenyl | 4-phenylphenyl | H |
| G-33 | X16 and X17 form a fused ring. | | H | 4-methylphenyl | 4-methylphenyl | H |
| G-34 | X16 and X17 form a fused ring. | | H | 2-methylnaphthyl | 2-methylnaphthyl | H |
| G-35 | X16 and X17 form a fused ring. | | H | 2-methoxyphenyl | 2-methoxyphenyl | H |
| G-36 | X16 and X17 form a fused ring. | | H | Ph | Ph | H |
| G-37 | X16 and X17 form a fused ring. | | Ph | Ph | Ph | Ph |
| G-38 | X16 and X17 form a fused ring. | | 4-phenylphenyl | Ph | Ph | 4-phenylphenyl |
| G-39 | X16 and X17 form a fused ring. | | CH3 | Ph | Ph | CH3 |
| G-40 | X16 and X17 form a fused ring. | | H | Ph | Ph | H |
| G-41 | X16 and X17 form a fused ring. | | H | Ph | Ph | H |
| G-42 | X16 and X17 form a fused ring. | | H | Ph | Ph | H |
| G-43 | X16 and X17 form a fused ring. | | H | Ph | Ph | H |
| G-44 | X16 and X17 form a fused ring. | | H | Ph | Ph | H |
| G-45 | X16 and X17 form a fused ring. | | H | Ph | Ph | H |

-continued

| Compound No. | X26 | X27 | X28 |
|---|---|---|---|
| G-30 | H | H | H |
| G-31 | H | H | H |
| G-32 | H | H | H |
| G-33 | H | H | H |
| G-34 | H | H | H |
| G-35 | H | H | H |
| G-36 | H | H | H |
| G-37 | H | H | Ph |
| G-38 | H (-C6H4-C6H5) | H | CH3 |
| G-39 | H | H | H |
| G-40 | Ph | Ph | H |
| G-41 | CH3 | CH3 | H |
| G-42 | CH3 | CH3 | H |
| G-43 | H | H | H |
| G-44 | H | H | H |
| G-45 | H | H | H |

| Compound No. | X2 = X32 | X3 = X33 | X6 = X36 | X7 = X37 | X11 | X14 | X15 | X16 | X17 |
|---|---|---|---|---|---|---|---|---|---|
| G-46 | H | H | H | H | H | H | X15 and X16 form a fused ring. | | H |
| G-47 | H | H | H | H | Ph | Ph | X15 and X16 form a fused ring. | | H |
| G-48 | H | H | H | H | (-C6H4-C6H5) | (-C6H4-C6H5) | X15 and X16 form a fused ring. | | H |
| G-49 | H | H | H | H | (p-CH3-C6H4) | (p-CH3-C6H4) | X15 and X16 form a fused ring. | | H |
| G-50 | H | H | H | H | (naphthyl) | (naphthyl) | X15 and X16 form a fused ring. | | H |
| G-51 | H | H | H | H | CH3 | CH3 | X15 and X16 form a fused ring. | | H |

-continued

| Compound No. | | | | | | |
|---|---|---|---|---|---|---|
| G-52 | H | H | H | H (phenoxy) | Ph (phenyl) | X15 and X16 form a fused ring. H |
| G-53 | H | H | H | Ph | Ph | X15 and X16 form a fused ring. H |
| G-54 | H | H | H | Ph | Ph | X15 and X16 form a fused ring. H |
| G-55 | H | H | H | Ph | Ph | X15 and X16 form a fused ring. H |
| G-56 | H | H | H | Ph | Ph | X15 and X16 form a fused ring. Ph |
| G-57 | H | H | H | Ph | Ph | X15 and X16 form a fused ring. |
| G-58 | H | H | H | Ph | Ph | X15 and X16 form a fused ring. H |
| G-59 | Ph | H | H | Ph | Ph | X15 and X16 form a fused ring. H |
| G-60 | (biphenyl) | H | H | Ph | Ph | X15 and X16 form a fused ring. |
| G-61 | CH3 | H | H | Ph | Ph | X15 and X16 form a fused ring. CH3 (p-tolyl) |

| Compound No. | X18 | X21 | X24 | X25 | X26 | X27 | X28 |
|---|---|---|---|---|---|---|---|
| G-46 | H | H | H | H | H | X27 and X28 form a fused ring. | X27 and X28 form a fused ring. |
| G-47 | H | Ph | Ph | H | H | X27 and X28 form a fused ring. | X27 and X28 form a fused ring. |
| G-48 | H | biphenyl | biphenyl | H | H | X27 and X28 form a fused ring. | X27 and X28 form a fused ring. |
| G-49 | H | p-tolyl (CH3) | p-tolyl (CH3) | H | H | X27 and X28 form a fused ring. | X27 and X28 form a fused ring. |
| G-50 | H | methylnaphthyl | methylnaphthyl | H | H | X27 and X28 form a fused ring. | X27 and X28 form a fused ring. |
| G-51 | H | OMe (methoxyphenyl) | OMe (methoxyphenyl) | H | H | X27 and X28 form a fused ring. | X27 and X28 form a fused ring. |
| G-52 | H | | | H | H | X27 and X28 form a fused ring. | X27 and X28 form a fused ring. |

-continued

| | X2 = X32 | X3 = X33 | X6 = X36 | X7 = X37 | X11 | X14 | | |
|---|---|---|---|---|---|---|---|---|
| G-53 | H | Ph | H | H | Ph | Ph | Ph | X27 and X28 form a fused ring. |
| G-54 | H | Ph | H | H | Ph | Ph | H | X27 and X28 form a fused ring. |
| G-55 | H | CH3 | H | H | Ph | Ph | CH3 | X27 and X28 form a fused ring. |
| G-56 | H | H | H | H | Ph | Ph | H | X27 and X28 form a fused ring. |
| G-57 | H | H | H | H | Ph | Ph | Ph (biphenyl) | X27 and X28 form a fused ring. |
| G-58 | H | H | H | H | Ph | Ph | H | X27 and X28 form a fused ring. |
| G-59 | H | H | H | H | Ph | Ph | H | X27 and X28 form a fused ring. |
| G-60 | H | H | H | H | Ph | Ph | H | X27 and X28 form a fused ring. |
| G-61 | H | H | H | H | Ph | Ph | CH3 (tolyl) | X27 and X28 form a fused ring. |

| Compound No. | | | X11 | X14 | X15 | X16 | X17 | X18 |
|---|---|---|---|---|---|---|---|---|
| G-62 | H | H | H | H | X15 and X16 form a fused ring. | X15 and X16 form a fused ring. | X17 and X18 form a fused ring. | X17 and X18 form a fused ring. |
| G-63 | H | H | H | Ph | Ph | X15 and X16 form a fused ring. | X15 and X16 form a fused ring. | X17 and X18 form a fused ring. | X17 and X18 form a fused ring. |
| G-64 | H | H | H | biphenyl | biphenyl | X15 and X16 form a fused ring. | X17 and X18 form a fused ring. |
| G-65 | H | H | H | tolyl (CH3) | tolyl (CH3) | X15 and X16 form a fused ring. | X17 and X18 form a fused ring. |
| G-66 | H | H | H | naphthyl | naphthyl | X15 and X16 form a fused ring. | X17 and X18 form a fused ring. |
| G-67 | H | H | H | CH3 | CH3 | X15 and X16 form a fused ring. | X17 and X18 form a fused ring. |
| G-68 | H | H | H | OPh | OPh | X15 and X16 form a fused ring. | X17 and X18 form a fused ring. |
| G-69 | Ph | H | H | Ph | Ph | X15 and X16 form a fused ring. | X17 and X18 form a fused ring. |

-continued

| Compound No. | X2 | X3 | X6 | X7 | | | | | | |
|---|---|---|---|---|---|---|---|---|---|---|
| G-70 | (4-methylbiphenyl structure) | H | H | H | Ph | Ph | X15 and X16 form a fused ring. | X17 and X18 form a fused ring. |
| G-71 | CH3 | H | H | H | | | | |

| Compound No. | X21 | X24 | X25 | X26 | X27 | X28 |
|---|---|---|---|---|---|---|
| G-62 | H | H | X25 and X26 form a fused ring. | | X27 and X28 form a fused ring. | |
| G-63 | Ph | Ph | X25 and X26 form a fused ring. | | X27 and X28 form a fused ring. | |
| G-64 | (4-methylbiphenyl) | (4-methylbiphenyl) | X25 and X26 form a fused ring. | | X27 and X28 form a fused ring. | |
| G-65 | (p-tolyl, CH3) | (p-tolyl, CH3) | X25 and X26 form a fused ring. | | X27 and X28 form a fused ring. | |
| G-66 | (methylnaphthyl) | (methylnaphthyl) | X25 and X26 form a fused ring. | | X27 and X28 form a fused ring. | |
| G-67 | CH3 | CH3 | X25 and X26 form a fused ring. | | X27 and X28 form a fused ring. | |
| G-68 | (methoxyphenyl) | (methoxyphenyl) | X25 and X26 form a fused ring. | | X27 and X28 form a fused ring. | |
| G-69 | Ph | Ph | X25 and X26 form a fused ring. | | X27 and X28 form a fused ring. | |
| G-70 | Ph | Ph | X25 and X26 form a fused ring. | | X27 and X28 form a fused ring. | |
| G-71 | Ph | Ph | X25 and X26 form a fused ring. | | X27 and X28 form a fused ring. | |

| Compound No. | X2 | X32 | X33 | X36 | X37 | X11 = X21 | X14 = X24 |
|---|---|---|---|---|---|---|---|
| G-72 | X2 and X3 form a fused ring. | H | H | H | H | H | H |
| G-73 | X2 and X3 form a fused ring. | H | H | H | H | Ph | Ph |
| G-74 | X2 and X3 form a fused ring. | H | H | H | H | (4-methylbiphenyl) | (4-methylbiphenyl) |

-continued

| Compound No. | | | | | | |
|---|---|---|---|---|---|---|
| G-75 | X2 and X3 form a fused ring. | H | H | H | 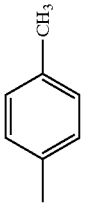 (p-tolyl) | 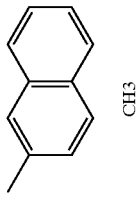 (p-tolyl) |
| G-76 | X2 and X3 form a fused ring. | H | H | H | 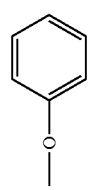 (2-methylnaphthyl) | 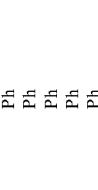 (2-methylnaphthyl) |
| G-77 | X2 and X3 form a fused ring. | H | H | H | CH3 | CH3 |
| G-78 | X2 and X3 form a fused ring. | H | H | H | 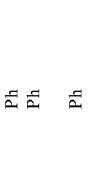 (OPh) | 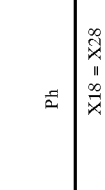 (OPh) |
| G-79 | X2 and X3 form a fused ring. | H | H | H | Ph | Ph |
| G-80 | X2 and X3 form a fused ring. | H | H | H | Ph | Ph |
| G-81 | X2 and X3 form a fused ring. | H | H | H | Ph | Ph |
| G-82 | X2 and X3 form a fused ring. | H | H | H | Ph | Ph |
| G-83 | X2 and X3 form a fused ring. | H | H | H | Ph | Ph |
| G-84 | X2 and X3 form a fused ring. | H | H | H | Ph | Ph |
| G-85 | X2 and X3 form a fused ring. | H | H | Ph | Ph | Ph |
| G-86 | X2 and X3 form a fused ring. | H | H | 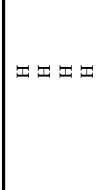 (4-methylbiphenyl) | Ph | Ph |
| G-87 | X2 and X3 form a fused ring. | H | H | CH3 | Ph | Ph |

| Compound No. | X15 = X25 | X16 = X26 | X17 = X27 | X18 = X28 |
|---|---|---|---|---|
| G-72 | H | H | H | H |
| G-73 | H | H | H | H |
| G-74 | H | H | H | H |
| G-75 | H | H | H | H |
| G-76 | H | H | H | H |
| G-77 | H | H | H | H |
| G-78 | H | H | H | Ph |
| G-79 | H | H | H | H |
| G-80 | 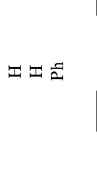 (4-methylbiphenyl) | H | H | 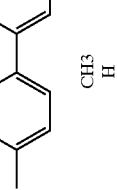 (4-methylbiphenyl) |
| G-81 | CH3 | H | H | CH3 |
| G-82 | H | Ph | Ph | H |

-continued

| Compound No. | X2 | X3 | X6 | X7 | X32 | X33 | X36 | X37 | X11 = X21 | X14 = X24 |
|---|---|---|---|---|---|---|---|---|---|---|
| G-83 | | | | | | | | | *biphenyl-CH3* | *biphenyl-CH3* |
| G-84 | | | | | | | | | H | H |
| G-85 | | | | | | | | | Ph | Ph |
| G-86 | | | | | | | | | | H |
| G-87 | | | | | | | | | | H |
| G-88 | X2 and X3 form a fused ring. | | H | H | X32 and X33 form a fused ring. | H | H | H | | |
| G-89 | X2 and X3 form a fused ring. | | H | H | X32 and X33 form a fused ring. | H | H | H | | |
| G-90 | X2 and X3 form a fused ring. | | H | H | X32 and X33 form a fused ring. | | H | H | *biphenyl* | *biphenyl* |
| G-91 | X2 and X3 form a fused ring. | | H | H | X32 and X33 form a fused ring. | | H | H | *p-tolyl (CH3)* | *p-tolyl (CH3)* |
| G-92 | X2 and X3 form a fused ring. | | H | H | X32 and X33 form a fused ring. | | H | H | *2-methylnaphthyl* | *2-methylnaphthyl* |
| G-93 | X2 and X3 form a fused ring. | | H | H | X32 and X33 form a fused ring. | | H | H | *CH3* | *CH3* |
| G-94 | X2 and X3 form a fused ring. | | H | H | X32 and X33 form a fused ring. | | H | H | *anisyl (OCH3)* | *anisyl (OCH3)* |
| G-95 | X2 and X3 form a fused ring. | | H | H | X32 and X33 form a fused ring. | | H | H | Ph | Ph |
| G-96 | X2 and X3 form a fused ring. | | H | H | X32 and X33 form a fused ring. | | H | H | Ph | Ph |
| G-97 | X2 and X3 form a fused ring. | | H | H | X32 and X33 form a fused ring. | | H | H | Ph | Ph |
| G-98 | X2 and X3 form a fused ring. | | H | H | X32 and X33 form a fused ring. | | H | H | Ph | Ph |
| G-99 | X2 and X3 form a fused ring. | | H | H | X32 and X33 form a fused ring. | | H | H | Ph | Ph |
| G-100 | X2 and X3 form a fused ring. | | H | H | X32 and X33 form a fused ring. | | H | H | Ph | Ph |

-continued
| Compound No. | X15 = X25 | X16 = X26 | X17 = X27 | X18 = X28 |
|---|---|---|---|---|
| G-88 | H | H | H | H |
| G-89 | H | H | H | H |
| G-90 | H | H | H | H |
| G-91 | H | H | H | H |
| G-92 | H | H | H | H |
| G-93 | H | H | H | H |
| G-94 | H | H | H | H |
| G-95 | Ph | H | H | Ph |
| G-96 | 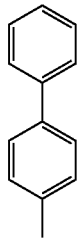 | H | H |  |
| G-97 | CH3 | H | H | CH3 |
| G-98 | H | Ph | Ph | H |
| G-99 | H | 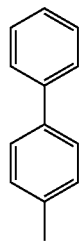 | 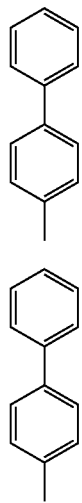 | H |
| G-100 | H | CH3 | CH3 | H |
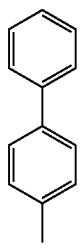
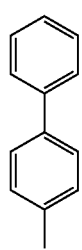

| Compound No. | X2 | X3 | X6 | X7 | X32 | X33 | X36 | X37 | X34 = X35 | X11 | X14 |
|---|---|---|---|---|---|---|---|---|---|---|---|
| H-1 | H | H | H | H | X2 and X3 form a fused ring. | X2 and X3 form a fused ring. | H | H | H | H | H |
| H-2 | H | H | H | H | X2 and X3 form a fused ring. | X2 and X3 form a fused ring. | H | H | H | Ph | Ph |
| H-3 | | H | H | H | X2 and X3 form a fused ring. | X2 and X3 form a fused ring. | H | H | H | 4-biphenyl | 4-biphenyl |
| H-4 | | H | H | H | X2 and X3 form a fused ring. | X2 and X3 form a fused ring. | H | H | H | p-tolyl | p-tolyl |
| H-5 | H | H | H | H | X2 and X3 form a fused ring. | X2 and X3 form a fused ring. | H | H | H | 2-naphthyl | 2-naphthyl |
| H-6 | H | H | H | H | X2 and X3 form a fused ring. | X2 and X3 form a fused ring. | H | H | H | CH3 | CH3 |
| H-7 | H | H | H | H | X2 and X3 form a fused ring. | X2 and X3 form a fused ring. | H | H | H | OPh | OPh |
| H-8 | H | H | H | H | X2 and X3 form a fused ring. | X2 and X3 form a fused ring. | H | H | H | Ph | Ph |
| H-9 | H | H | H | H | X2 and X3 form a fused ring. | X2 and X3 form a fused ring. | H | H | H | Ph | Ph |
| H-10 | H | H | H | H | X2 and X3 form a fused ring. | X2 and X3 form a fused ring. | H | H | H | Ph | Ph |
| H-11 | H | H | H | H | X2 and X3 form a fused ring. | X2 and X3 form a fused ring. | H | H | H | Ph | Ph |
| H-12 | H | H | H | H | X2 and X3 form a fused ring. | X2 and X3 form a fused ring. | H | H | H | Ph | Ph |
| H-13 | H | H | H | H | X2 and X3 form a fused ring. | X2 and X3 form a fused ring. | H | H | H | Ph | Ph |
| H-14 | Ph | H | H | H | X2 and X3 form a fused ring. | X2 and X3 form a fused ring. | H | H | H | Ph | Ph |

"A and B form a fused ring" in means

-continued

| Compound No. | | | | | | | |
|---|---|---|---|---|---|---|---|
| H-15 | ![biphenyl] | H | H | H | X2 and X3 form a fused ring. | H | Ph |
| H-16 | CH3 | H | H | H | X2 and X3 form a fused ring. | H | Ph |

| Compound No. | X15 | X16 | X17 | X18 |
|---|---|---|---|---|
| H-1 | H | H | H | H |
| H-2 | H | H | H | H |
| H-3 | H | H | H | H |
| H-4 | H | H | H | H |
| H-5 | H | H | H | H |
| H-6 | H | H | H | H |
| H-7 | H | H | H | H |
| H-8 | Ph | H | H | Ph |
| H-9 | ![4-methylbiphenyl] | H | ![4-methylbiphenyl] | ![biphenyl] |
| H-10 | CH3 | CH3 | CH3 | CH3 |
| H-11 | H | H | H | H |
| H-12 | H | H | H | H |
| H-13 | H | H | H | H |
| H-14 | H | H | H | H |
| H-15 | H | H | H | H |
| H-16 | Ph | Ph | Ph | Ph |

| Compound No. | X2 = X32 | X3 = X33 | X6 = X36 | X7 = X37 | X34 = X35 | X11 | X14 | X15 |
|---|---|---|---|---|---|---|---|---|
| H-17 | H | H | H | H | H | H | H | H |
| H-18 | H | H | H | H | H | Ph | Ph | H |
| H-19 | H | ![4-methylbiphenyl] | H | H | H | ![4-methylbiphenyl] | ![4-methylbiphenyl] | H |
| H-20 | H | ![p-tolyl-CH3] | H | H | H | ![p-tolyl-CH3] | ![p-tolyl-CH3] | H |

-continued

| Compound No. | | | | | | | | | |
|---|---|---|---|---|---|---|---|---|---|
| H-21 | H | H | H | H | H | H | H | [naphthyl] | H |
| H-22 | H | H | H | H | H | H | CH3 | CH3 | H |
| H-23 | H | H | H | H | H | H | [PhO-] | [PhO-] | H |
| H-24 | H | H | H | H | H | H | Ph | Ph | Ph |
| H-25 | H | H | H | H | H | H | Ph | Ph | Ph |
| H-26 | H | H | H | H | H | H | Ph | Ph | Ph |
| H-27 | H | H | H | H | H | H | Ph | Ph | Ph |
| H-28 | H | H | H | H | H | H | Ph | Ph | Ph |
| H-29 | H | H | H | H | H | H | Ph | Ph | Ph |
| H-30 | H | H | H | Ph | Ph | H | Ph | Ph | Ph |
| H-31 | H | H | H | H | H | H | Ph | Ph | Ph |
| H-32 | [biphenyl] | CH3 | H | H | H | H | Ph | Ph | Ph |

| Compound No. | X16 | X17 | X18 |
|---|---|---|---|
| H-17 | H | H | H |
| H-18 | H | H | H |
| H-19 | H | H | H |
| H-20 | H | H | H |
| H-21 | H | H | H |
| H-22 | H | H | Ph |
| H-23 | H | H | H |
| H-24 | H | H | H |
| H-25 | Ph | Ph | [biphenyl-methyl] |
| H-26 | H | H | CH3 |
| H-27 | Ph | Ph | H |

-continued

| Compound No. | X2 = X32 | X3 = X33 | X6 = X36 | X7 = X37 | X34 = X35 | X11 | X14 |
|---|---|---|---|---|---|---|---|
| H-33 | H | H | H | H | CH3 | 4-methylbiphenyl | 4-methylbiphenyl |
| H-34 | H | H | H | H | H | H | H |
| H-35 | H | H | H | H | H | Ph | H |
| H-36 | H | H | H | H | H | 4-methylphenyl | 4-methylphenyl |
| H-37 | H | H | H | H | H | 4-methylphenyl (p-tolyl) | 4-methylphenyl (p-tolyl) |
| H-38 | H | H | H | H | H | 2-methylnaphthyl | 2-methylnaphthyl |
| H-39 | H | H | H | H | H | 2-methoxyphenyl | 2-methoxyphenyl |
| H-40 | H | H | H | H | H | Ph | Ph |
| H-41 | H | H | H | H | H | Ph | Ph |
| H-42 | H | H | H | H | H | Ph | Ph |
| H-43 | H | H | H | H | H | Ph | Ph |
| H-44 | H | H | H | H | H | Ph | Ph |
| H-45 | H | H | H | H | H | Ph | Ph |
| H-46 | Ph | H | H | H | H | | |
| H-47 | 4-methylbiphenyl | H | H | H | H | Ph | Ph |
| H-48 | CH3 | H | H | H | H | Ph | Ph |

H-28

H-29  CH3
H-30  H
H-31  H
H-32  H

-continued

| Compound No. | X15 | X16 | X17 | X18 |
|---|---|---|---|---|
| H-33 | X15 and X16 form a fused ring. | | H | H |
| H-34 | X15 and X16 form a fused ring. | | H | H |
| H-35 | X15 and X16 form a fused ring. | | H | H |
| H-36 | X15 and X16 form a fused ring. | | H | H |
| H-37 | X15 and X16 form a fused ring. | | H | H |
| H-38 | X15 and X16 form a fused ring. | | H | H |
| H-39 | X15 and X16 form a fused ring. | | H | H |
| H-40 | X15 and X16 form a fused ring. | | H | Ph |
| H-41 | X15 and X16 form a fused ring. | | H | 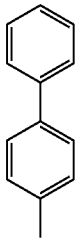 |
| H-42 | X15 and X16 form a fused ring. | | H | CH3 |
| H-43 | X15 and X16 form a fused ring. | | Ph | H |
| H-44 | X15 and X16 form a fused ring. | |  | H |
| H-45 | X15 and X16 form a fused ring. | | CH3 | H |
| H-46 | X15 and X16 form a fused ring. | | H | H |
| H-47 | X15 and X16 form a fused ring. | | H | H |
| H-48 | X15 and X16 form a fused ring. | | H | H |

| Compound No. | X2 = X32 | X3 = X33 | X6 = X36 | X7 = X37 | X34 = X35 | X11 | X14 |
|---|---|---|---|---|---|---|---|
| H-49 | H | H | H | H | H | H | H |
| H-50 | H | H | H | H | H | Ph | Ph |
| H-51 | H | H | H | H | H | 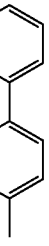 |  |
| H-52 | H | H | H | H | H |  | 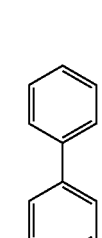 |
| H-53 | H | H | H | H | H | 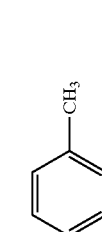 | 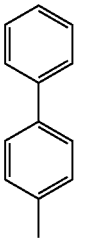 |
| H-54 | H | H | H | H | H | CH3 | CH3 |

-continued

| Compound No. | X2 = X32 | X3 = X33 | X6 = X36 | X7 = X37 | X15 | X16 | X17 | X18 |
|---|---|---|---|---|---|---|---|---|
| H-55 | H | H | H | H | H | Ph | Ph | H |
| H-56 | H | H | H | H | H | Ph | Ph | Ph |
| H-57 | H | H | H | H | H | Ph | Ph | Ph |
| H-58 | H | H | H | H | H | Ph | Ph | Ph |
| H-59 | H | H | H | H | H | Ph | Ph | Ph |
| H-60 | H | H | H | H | H | Ph | Ph | Ph |
| H-61 | H | H | H | H | H | Ph | Ph | Ph |
| H-62 | Ph | H | H | H | H | Ph | Ph | Ph |
| H-63 | H | H | H | H | H | Ph | Ph | Ph |
| H-64 | CH3 | H | H | H | H | Ph | Ph | Ph |

| Compound No. | X15 | X16 | X17 | X18 |
|---|---|---|---|---|
| H-49 | H | X16 and X17 form a fused ring. | | H |
| H-50 | H | X16 and X17 form a fused ring. | | H |
| H-51 | H | X16 and X17 form a fused ring. | | H |
| H-52 | H | X16 and X17 form a fused ring. | | H |
| H-53 | H | X16 and X17 form a fused ring. | | H |
| H-54 | H | X16 and X17 form a fused ring. | | H |
| H-55 | Ph | X16 and X17 form a fused ring. | | Ph |
| H-56 | H | X16 and X17 form a fused ring. | | H |
| H-57 | H | X16 and X17 form a fused ring. | | H |
| H-58 | CH3 | X16 and X17 form a fused ring. | | CH3 |
| H-59 | H | X16 and X17 form a fused ring. | | H |
| H-60 | H | X16 and X17 form a fused ring. | | H |
| H-61 | H | X16 and X17 form a fused ring. | | H |
| H-62 | H | X16 and X17 form a fused ring. | | H |
| H-63 | H | X16 and X17 form a fused ring. | | H |
| H-64 | H | X16 and X17 form a fused ring. | | Ph |

| Compound No. | X2 = X32 | X3 = X33 | X6 = X36 | X7 = X37 | X34 = X35 | X11 | X14 |
|---|---|---|---|---|---|---|---|
| H-65 | H | H | H | H | H | H | H |
| H-66 | H | H | H | H | H | Ph | Ph |
| H-67 | H | H | H | H | H | | |

| Compound No. | X15 | X16 | X17 | X18 |
|---|---|---|---|---|
| H-65 | X15 and X16 form a fused ring. | | X17 and X18 form a fused ring. | |
| H-66 | X15 and X16 form a fused ring. | | X17 and X18 form a fused ring. | |
| H-67 | X15 and X16 form a fused ring. | | X17 and X18 form a fused ring. | |
| H-68 | X15 and X16 form a fused ring. | | X17 and X18 form a fused ring. | |
| H-69 | X15 and X16 form a fused ring. | | X17 and X18 form a fused ring. | |
| H-70 | X15 and X16 form a fused ring. | | X17 and X18 form a fused ring. | |
| H-71 | X15 and X16 form a fused ring. | | X17 and X18 form a fused ring. | |
| H-72 | X15 and X16 form a fused ring. | | X17 and X18 form a fused ring. | |
| H-73 | X15 and X16 form a fused ring. | | X17 and X18 form a fused ring. | |
| H-74 | X15 and X16 form a fused ring. | | X17 and X18 form a fused ring. | |

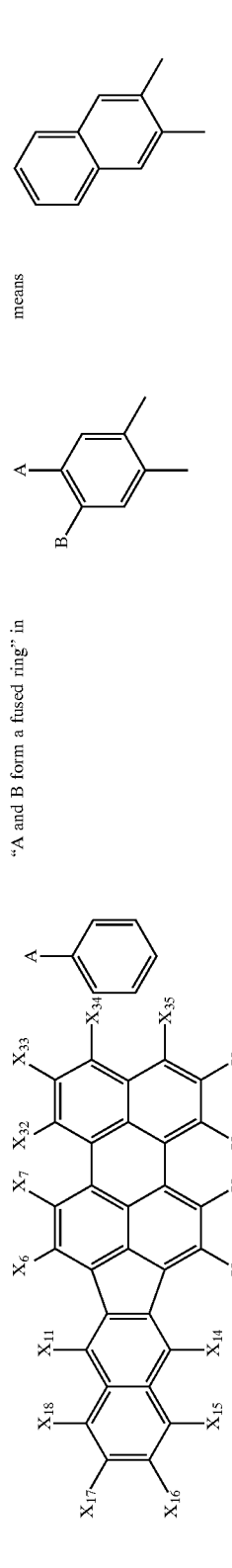

-continued

"A and B form a fused ring" means

| Compound No. | X2 | X3 | X6 | X7 | X32 | X33 | X36 | X37 | X34 = X35 | X11 | X14 |
|---|---|---|---|---|---|---|---|---|---|---|---|
| H-75 | X2 and X3 form a fused ring. | X2 and X3 form a fused ring. | H | H | X32 and X33 form a fused ring. | X32 and X33 form a fused ring. | H | H | H | H | H |
| H-76 | X2 and X4 form a fused ring. | X2 and X4 form a fused ring. | H | H | X32 and X33 form a fused ring. | X32 and X33 form a fused ring. | H | H | H | Ph | Ph |
| H-77 | X2 and X5 form a fused ring. | | H | H | X32 and X33 form a fused ring. | | H | H | H | biphenyl | biphenyl |
| H-78 | X2 and X6 form a fused ring. | | H | H | X32 and X33 form a fused ring. | | H | H | H | p-tolyl | p-tolyl |
| H-79 | X2 and X7 form a fused ring. | | H | H | X32 and X33 form a fused ring. | | H | H | H | naphthyl | naphthyl |
| H-80 | X2 and X8 form a fused ring. | | H | H | X32 and X33 form a fused ring. | | H | H | H | CH3 | CH3 |
| H-81 | X2 and X9 form a fused ring. | | H | H | X32 and X33 form a fused ring. | | H | H | H | OPh | OPh |
| H-82 | X2 and X10 form a fused ring. | | H | H | X32 and X33 form a fused ring. | | H | H | H | Ph | Ph |
| H-83 | X2 and X11 form a fused ring. | | H | H | X32 and X33 form a fused ring. | | H | H | H | Ph | Ph |
| H-84 | X2 and X12 form a fused ring. | | H | H | X32 and X33 form a fused ring. | | H | H | H | Ph | Ph |
| H-85 | X2 and X13 form a fused ring. | | H | H | X32 and X33 form a fused ring. | | H | H | H | Ph | Ph |
| H-86 | X2 and X14 form a fused ring. | | H | H | X32 and X33 form a fused ring. | | H | H | H | Ph | Ph |
| H-87 | X2 and X15 form a fused ring. | | H | H | X32 and X33 form a fused ring. | | H | H | H | Ph | Ph |

| Compound No. | X15 | X16 | X17 | X18 |
|---|---|---|---|---|
| H-75 | H | H | H | H |
| H-76 | H | H | H | H |
| H-77 | H | H | H | H |

-continued

| | | | | | |
|---|---|---|---|---|---|
| H-78 | | | | H | H |
| H-79 | | | | H | H |
| H-80 | | | | H | H |
| H-81 | | | | H | Ph |
| H-82 | | | | | |
| H-83 | CH3 | | | CH3 | H |
| H-84 | | | | H | H |
| H-85 | | | | Ph | Ph |
| H-86 | H | H | H | H | H |
| H-87 | H | CH3 | CH3 | H | H |

"A and B form a fused ring" in means

| Compound No. | X2 | X3 | X6 | X7 | X32 | X33 | X36 | X37 | X34 = X35 | X11 | X14 |
|---|---|---|---|---|---|---|---|---|---|---|---|
| H-88 | X2 and X3 form a fused ring. | | H | H | H | H | H | H | H | H | H |
| H-89 | X2 and X4 form a fused ring. | | H | H | H | H | H | H | H | Ph | Ph |
| H-90 | X2 and X5 form a fused ring. | | H | H | H | H | H | H | H | H | H |
| H-91 | X2 and X6 form a fused ring. | | H | H | H | H | H | H | H | H | H |

-continued

| Compound No. | | | | | | | | Notes |
|---|---|---|---|---|---|---|---|---|
| H-92 | H | H | H | H | H | 2-methylnaphthyl | 2-methylnaphthyl | X2 and X7 form a fused ring. |
| H-93 | H | H | H | H | H | methoxyphenyl | methoxyphenyl | X2 and X8 form a fused ring. |
| H-94 | H | H | H | H | H | Ph | Ph | X2 and X9 form a fused ring. |
| H-95 | H | H | H | H | H | Ph | Ph | X2 and X10 form a fused ring. |
| H-96 | H | H | H | H | H | Ph | Ph | X2 and X11 form a fused ring. |
| H-97 | H | H | H | H | H | Ph | Ph | X2 and X12 form a fused ring. |
| H-98 | H | H | H | H | H | Ph | Ph | X2 and X13 form a fused ring. |
| H-99 | H | H | H | H | H | Ph | Ph | X2 and X14 form a fused ring. |
| H-100 | H | H | H | H | Ph | Ph | Ph | X2 and X15 form a fused ring. |
| H-101 | H | H | H | H | 4-methylbiphenyl | Ph | Ph | X2 and X16 form a fused ring. |
| H-102 | H | H | H | H | CH3 | Ph | Ph | X2 and X17 form a fused ring. |
| H-103 | H | H | H | H | H | Ph | Ph | X2 and X18 form a fused ring. |

| Compound No. | X15 | X16 | X17 | X18 |
|---|---|---|---|---|
| H-88 | H | H | H | H |
| H-89 | H | H | H | H |
| H-90 | H | H | H | H |
| H-91 | H | H | H | H |
| H-92 | H | H | H | H |
| H-93 | H | H | H | H |
| H-94 | Ph | H | H | Ph |
| H-95 | H | H | H | H |
| H-96 | 4-methylbiphenyl | H | H | H |
| H-97 | CH3 | H | H | CH3 |
| H-98 | H | Ph | Ph | H |
| H-99 | H | 4-methylbiphenyl | 4-methylbiphenyl | 4-methylbiphenyl |
| H-100 | H | CH3 | CH3 | H |
| H-101 | H | H | H | H |
| H-102 | H | H | H | H |
| H-103 | H | H | H | H |

| Compound No. | X2 | X3 | X6 | X7 | X32 | X33 | X34=X35 | X36 | X37 |
|---|---|---|---|---|---|---|---|---|---|
| I-1 | H | H | H | H | H | H | H | H | H |
| I-2 | H | H | H | H | H | H | H | H | H |
| I-3 | H | H | H | H | H | H | H | H | H |
| I-4 | H | H | H | H | H | H | H | H | H |
| I-5 | H | H | H | H | H | H | H | H | H |
| I-6 | H | H | H | H | H | H | H | H | H |
| I-7 | Ph | H | H | H | H | H | H | H | H |
| I-8 | Ph | Ph | H | H | Ph | Ph | H | H | H |
| I-9 | H | H | H | H | H | H | H | H | H |
| I-10 | CH₃ | CH₃ | H | H | CH₃ | CH₃ | H | H | H |
| I-11 | H | H | H | H | H | H | H | H | H |
| I-12 | H | H | H | H | H | H | H | H | H |
| I-13 | H | H | H | H | H | H | H | H | H |
| I-14 | H | H | H | H | H | H | H | H | H |
| I-15 | H | H | H | H | H | H | H | H | H |
| I-16 | H | H | H | H | H | H | H | H | H |
| I-17 | H | H | H | H | H | H | H | H | H |
| I-18 | H | H | H | H | H | H | H | H | H |
| I-19 | H | H | H | H | H | H | H | H | H |
| I-20 | H | H | H | H | H | H | H | H | H |
| I-21 | H | H | H | H | H | H | H | H | H |
| I-22 | H | H | H | H | H | H | H | H | H |
| I-23 | H | H | H | H | H | H | H | H | H |
| I-24 | Ph | Ph | H | H | Ph | Ph | H | H | H |

Note: Certain rows (e.g., I-9, I-11) contain 4'-methylbiphenyl-4-yl (tolylphenyl) substituents at positions X2, X3, X32, X33 as depicted in the original figure.

"A and B form a fused ring" means the fused naphthalene ring structure.

-continued

| | | | | | | |
|---|---|---|---|---|---|---|
| I-25 | 4-methylbiphenyl | | H | | | H H H |
| I-26 | | CH3 | H | 4-methylbiphenyl | H Ph | H H |
| I-27 | | H | | | | H |
| I-28 | | | H | | CH3 | H H H |
| I-29 | | H | | 4-methylbiphenyl | H | H H H |
| I-30 | | H | | | H | H H |
| I-31 | | H | | | H | H H |
| I-32 | | H | | | H | H H |

| Compound No. | X11 | X12 | X13 | X14 |
|---|---|---|---|---|
| I-1 | H | H | H | H |
| I-2 | Ph | H | H | Ph |
| I-3 | biphenyl | H | H | biphenyl |
| I-4 | p-tolyl | H | H | p-tolyl |
| I-5 | 2-methylnaphthyl | H | H | 2-methylnaphthyl |
| I-6 | CH3 | H | H | CH3 |
| I-7 | methoxyphenyl | H | H | methoxyphenyl |
| I-8 | Ph | H | H | Ph |
| I-9 | Ph | H | H | Ph |
| I-11 | Ph | H | H | Ph |
| I-12 | Ph | H | H | Ph |
| I-13 | Ph | H | H | Ph |
| I-14 | Ph | Ph | Ph | Ph |

-continued

| Compound No. | X2 | X3 | | | | | | |
|---|---|---|---|---|---|---|---|---|
| I-15 | | | Ph | | |  | | Ph |
| I-16 | | | Ph | | | CH3 | CH3 | |
| I-17 | | | H | | | H | X13 and X14 form a fused ring. | |
| I-18 | | | Ph | | | H | X13 and X14 form a fused ring. | |
| I-19 | | | 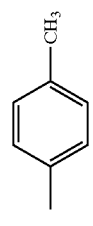 | | | H | X13 and X14 form a fused ring. | |
| I-20 | | | 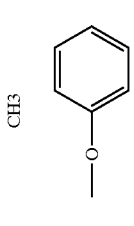 | | | H | X13 and X14 form a fused ring. | |
| I-21 | | | 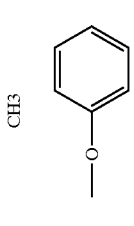 | | | H | X13 and X14 form a fused ring. | |
| I-22 | | | CH3 | | | H | X13 and X14 form a fused ring. | |
| I-23 | | | 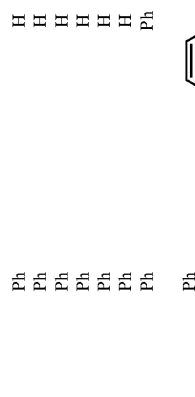 | | | H | X13 and X14 form a fused ring. | |
| I-24 | | | Ph | | | H | X13 and X14 form a fused ring. | |
| I-25 | | | Ph | | | H | X13 and X14 form a fused ring. | |
| I-26 | | | Ph | | | H | X13 and X14 form a fused ring. | |
| I-27 | | | Ph | | | H | X13 and X14 form a fused ring. | |
| I-28 | | | Ph | | | H | X13 and X14 form a fused ring. | |
| I-29 | | | Ph | | | H | X13 and X14 form a fused ring. | |
| I-30 | | | Ph | | | Ph | X13 and X14 form a fused ring. | |
| I-31 | | | Ph | | | 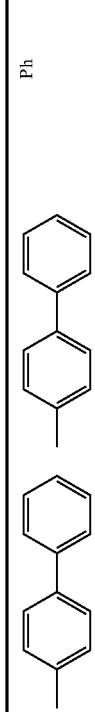 | X13 and X14 form a fused ring. | |
| I-32 | | | Ph | | | CH3 | | |

| Compound No. | X2 | X3 | X6 | X7 | X32 | X33 | X36 | X37 |
|---|---|---|---|---|---|---|---|---|
| I-33 | H | H | H | H | H | H | H | H |
| I-34 | Ph | H | H | H | Ph | H | H | H |

-continued

| Compound No. | X2 | X3 | X6 | X7 | X32 | | | | |
|---|---|---|---|---|---|---|---|---|---|
| I-35 | ![4-methylbiphenyl] | | H | H | H | H | H | H | H |
| I-36 | CH3 | H | H | H | H | H | CH3 | H | H |
| I-37 | H | H | H | H | Ph | H | H | Ph | H |
| I-38 | H | | H | H | ![4-methylbiphenyl] | | ![4-methylbiphenyl] | | H |
| I-39 | H | | H | H | CH3 | | CH3 | | H |

| Compound No. | X11 | X12 | X13 | X14 |
|---|---|---|---|---|
| I-33 | X11 and X12 form a fused ring. | | X13 and X14 form a fused ring. | |
| I-34 | X11 and X12 form a fused ring. | | X13 and X14 form a fused ring. | |
| I-35 | X11 and X12 form a fused ring. | | X13 and X14 form a fused ring. | |
| I-36 | X11 and X12 form a fused ring. | | X13 and X14 form a fused ring. | |
| I-37 | X11 and X12 form a fused ring. | | X13 and X14 form a fused ring. | |
| I-38 | X11 and X12 form a fused ring. | | X13 and X14 form a fused ring. | |
| I-39 | X11 and X12 form a fused ring. | | X13 and X14 form a fused ring. | |

| Compound No. | X2 | X3 | X33 | X34 = X35 | X36 | X37 | X11 |
|---|---|---|---|---|---|---|---|
| I-40 | X2 and X3 form a fused ring. | | H | H | H | H | H |
| I-41 | X2 and X3 form a fused ring. | | H | H | H | H | Ph |
| I-42 | X2 and X3 form a fused ring. | | H | H | H | H | ![biphenyl] |
| I-43 | X2 and X3 form a fused ring. | | H | H | H | H | ![p-tolyl] |
| I-44 | X2 and X3 form a fused ring. | | H | H | H | H | ![methylnaphthyl] |
| I-45 | X2 and X3 form a fused ring. | | H | H | H | H | CH3 |
| I-46 | X2 and X3 form a fused ring. | | H | H | H | H | ![methoxyphenyl] |

-continued

| Compound No. | | | | | | | |
|---|---|---|---|---|---|---|---|
| I-47 | X2 and X3 form a fused ring. | H | H | 4-methylbiphenyl | H | H | Ph |
| I-48 | X2 and X3 form a fused ring. | H | H | Ph | H | H | Ph |
| I-49 | X2 and X3 form a fused ring. | H | H | CH3 | H | H | Ph |
| I-50 | X2 and X3 form a fused ring. | H | H | H | Ph | H | Ph |
| I-51 | X2 and X3 form a fused ring. | H | H | H | 4-methylbiphenyl | H | Ph |
| I-52 | X2 and X3 form a fused ring. | H | H | H | CH3 | H | Ph |
| I-53 | X2 and X3 form a fused ring. | H | H | H | H | H | Ph |
| I-54 | X2 and X3 form a fused ring. | H | H | H | H | H | Ph |
| I-55 | X2 and X3 form a fused ring. | H | H | H | H | H | Ph |

| Compound No. | X12 | X13 | X14 |
|---|---|---|---|
| I-40 | H | H | H |
| I-41 | H | H | Ph |
| I-42 | H | H | 4-biphenylyl |
| I-43 | H | H | p-tolyl |
| I-44 | H | H | 6-methyl-2-naphthyl |
| I-45 | H | H | CH3 |
| I-46 | H | H | 4-methoxyphenyl |
| I-47 | H | H | Ph |
| I-48 | H | H | Ph |
| I-49 | H | H | Ph |
| I-50 | H | H | Ph |
| I-51 | H | H | Ph |

-continued

| Compound No. | X2 | X3 | X6 | X7 | X32 | X33 | X34 = X35 | X36 | X37 | X11 |
|---|---|---|---|---|---|---|---|---|---|---|
| I-56 | H | H | H | H | X32 and X33 form a fused ring. | | H | H | H | Ph |
| I-57 | H | H | H | H | X32 and X33 form a fused ring. | | H | H | H | Ph |
| I-58 | H | H | H | H | X32 and X33 form a fused ring. | | H | H | H | Ph (biphenyl) |
| I-59 | H | H | H | H | X32 and X33 form a fused ring. | | H | H | H | tolyl |
| I-60 | H | H | H | H | X32 and X33 form a fused ring. | | H | H | H | naphthyl |
| I-61 | H | H | H | H | X32 and X33 form a fused ring. | | H | H | H | CH3 |
| I-62 | H | H | H | H | X32 and X33 form a fused ring. | | H | H | H | anisyl (OMe-Ph) |
| I-63 | Ph | H | H | H | X32 and X33 form a fused ring. | | H | H | H | Ph |
| I-64 | (4-methylbiphenyl) | H | H | H | X32 and X33 form a fused ring. | | H | H | H | Ph |
| I-65 | CH3 | H | H | H | X32 and X33 form a fused ring. | | H | H | H | Ph |
| I-66 | H | H | H | H | X32 and X33 form a fused ring. | | H | H | H | Ph |
| I-67 | H | H | H | H | X32 and X33 form a fused ring. | | H | H | H | Ph |
| I-68 | H | H | H | H | X32 and X33 form a fused ring. | | H | H | H | Ph |

| | X32 | X33 | X36 | X37 | X11 |
|---|---|---|---|---|---|
| I-52 | | | H | H | H |
| I-53 | | | Ph | Ph | Ph |
| I-54 | (4-methylbiphenyl) | H | | | Ph |
| I-55 | CH3 | CH3 | | | CH3 |

-continued

| Compound No. | X12 | X13 | X14 |
|---|---|---|---|
| I-56 | H | H | H |
| I-57 | H | H | Ph |
| I-58 | H | H | 4-biphenyl |
| I-59 | H | H | 4-methylphenyl (p-tolyl) |
| I-60 | H | H | 2-methylnaphthyl |
| I-61 | H | H | CH3 |
| I-62 | H | H | 4-methoxyphenyl |
| I-63 | H | H | Ph |
| I-64 | H | H | Ph |
| I-65 | H | H | Ph |
| I-66 | Ph | Ph | Ph |
| I-67 | 4-biphenyl | 4-methylbiphenyl | Ph |
| I-68 | CH3 | CH3 | Ph |

| Compound No. | X2 | X3 | X6 | X7 | X32 | X33 | X34 = X35 | X36 | X37 | X11 |
|---|---|---|---|---|---|---|---|---|---|---|
| I-69 | X2 and X3 form a fused ring. | | H | H | X32 and X33 form a fused ring. | | H | H | H | H |
| I-70 | X2 and X3 form a fused ring. | | H | H | X32 and X33 form a fused ring. | | H | H | H | Ph |
| I-71 | X2 and X3 form a fused ring. | | H | H | X32 and X33 form a fused ring. | | H | H | H | 4-biphenyl |
| I-72 | X2 and X3 form a fused ring. | | H | H | X32 and X33 form a fused ring. | | H | H | H | 4-methylphenyl |

-continued

| | | | | | | |
|---|---|---|---|---|---|---|
| I-73 | X2 and X3 form a fused ring. | H | H | X32 and X33 form a fused ring. | H | H | 2-methylnaphthyl |
| I-74 | X2 and X3 form a fused ring. | H | H | X32 and X33 form a fused ring. | H | H | CH3 |
| I-75 | X2 and X3 form a fused ring. | H | H | X32 and X33 form a fused ring. | H | H | methoxyphenyl |
| I-76 | X2 and X3 form a fused ring. | H | H | X32 and X33 form a fused ring. | H | H | Ph |
| I-77 | X2 and X3 form a fused ring. | H | H | X32 and X33 form a fused ring. | H | H | Ph |
| I-78 | X2 and X3 form a fused ring. | H | H | X32 and X33 form a fused ring. | H | H | Ph |

| Compound No. | X12 | X13 | X14 |
|---|---|---|---|
| I-69 | H | H | H |
| I-70 | H | H | Ph |
| I-71 | H | H | 4-methylbiphenyl |
| I-72 | H | H | 4-methylphenyl (CH3) |
| I-73 | H | H | 2-methylnaphthyl |
| I-74 | H | H | CH3 |
| I-75 | H | H | methoxyphenyl |
| I-76 | H | H | Ph |
| I-77 | Ph | Ph | Ph |
| I-78 | 4-methylbiphenyl (CH3) | 4-methylbiphenyl (CH3) | Ph |

-continued

| Compound No. | X2 | X3 | X6 | X7 | X32 | X33 | X34 = X35 | X36 | X37 |
|---|---|---|---|---|---|---|---|---|---|
| I-79 | X2 and X3 form a fused ring. | | H | H | H | H | H | H | H |
| I-80 | X2 and X3 form a fused ring. | | H | H | H | H | H | H | H |
| I-81 | X2 and X3 form a fused ring. | | H | H | H | H | H | H | H |
| I-82 | X2 and X3 form a fused ring. | | H | H | H | H | H | H | H |
| I-83 | X2 and X3 form a fused ring. | | H | H | H | H | H | H | H |
| I-84 | X2 and X3 form a fused ring. | | H | H | H | H | H | H | H |
| I-85 | X2 and X3 form a fused ring. | | H | H | H | H | H | H | H |
| I-86 | X2 and X3 form a fused ring. | | H | H | Ph | H | H | H | H |
| I-87 | X2 and X3 form a fused ring. | | H | H | 4-methylbiphenyl | H | H | H | H |
| I-88 | X2 and X3 form a fused ring. | | H | H | CH3 | H | H | H | H |
| I-89 | X2 and X3 form a fused ring. | | H | H | H | Ph | H | H | H |
| I-90 | X2 and X3 form a fused ring. | | H | H | H | 4-methylbiphenyl | H | H | H |
| I-91 | X2 and X3 form a fused ring. | | H | H | H | CH3 | H | H | H |
| I-92 | X2 and X3 form a fused ring. | | H | H | H | H | H | H | H |
| I-93 | X2 and X3 form a fused ring. | | H | H | H | H | H | H | H |
| I-94 | X2 and X3 form a fused ring. | | H | H | H | H | H | H | H |

| Compound No. | X11 | X12 | X13 | X14 |
|---|---|---|---|---|
| I-79 | H | H | X13 and X14 form a fused ring. | |
| I-80 | Ph | H | X13 and X14 form a fused ring. | |
| I-81 | biphenyl | H | X13 and X14 form a fused ring. | |
| I-82 | 4-methylphenyl (CH3) | H | X13 and X14 form a fused ring. | |
| I-83 | methylnaphthalene | H | X13 and X14 form a fused ring. | |
| I-84 | CH3 | H | X13 and X14 form a fused ring. | |

-continued

| Compound No. | | |
|---|---|---|
| I-85 | | X13 and X14 form a fused ring. |
| I-86 | Ph | H |
| I-87 | Ph | H |
| I-88 | Ph | H |
| I-89 | Ph | H |
| I-90 | Ph | H |
| I-91 | Ph | H |
| I-92 | Ph | Ph |
| I-93 | Ph | X13 and X14 form a fused ring. |
| I-94 | Ph | X13 and X14 form a fused ring. |

"A and B form a fused ring" in I-94 means 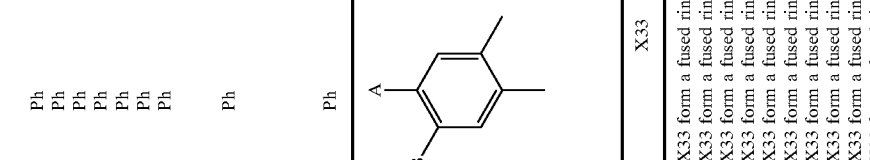 CH3  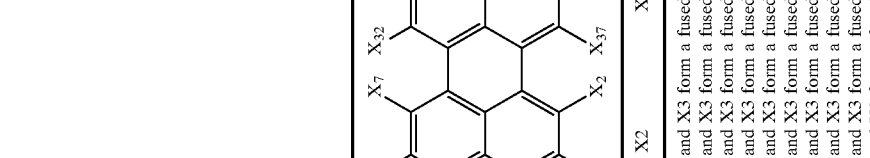

| Compound No. | X2 | X3 | X6 | X7 | X32 | X33 | X34 = X35 | X36 | X37 |
|---|---|---|---|---|---|---|---|---|---|
| I-95 | X2 and X3 form a fused ring. | | H | H | X32 and X33 form a fused ring. | | H | H | H |
| I-96 | X2 and X3 form a fused ring. | | H | H | X32 and X33 form a fused ring. | | H | H | H |
| I-97 | X2 and X3 form a fused ring. | | H | H | X32 and X33 form a fused ring. | | H | H | H |
| I-98 | X2 and X3 form a fused ring. | | H | H | X32 and X33 form a fused ring. | | H | H | H |
| I-99 | X2 and X3 form a fused ring. | | H | H | X32 and X33 form a fused ring. | | H | H | H |
| I-100 | X2 and X3 form a fused ring. | | H | H | X32 and X33 form a fused ring. | | H | H | H |
| I-101 | X2 and X3 form a fused ring. | | H | H | X32 and X33 form a fused ring. | | H | H | H |
| I-102 | X2 and X3 form a fused ring. | | H | H | X32 and X33 form a fused ring. | | H | H | H |
| I-103 | X2 and X3 form a fused ring. | | H | H | X32 and X33 form a fused ring. | | H | H | H |
| I-104 | X2 and X3 form a fused ring. | | H | H | X32 and X33 form a fused ring. | | H | H | H |

| Compound No. | X11 | X12 | X13 | X14 |
|---|---|---|---|---|
| I-95 | X11 and X12 form a fused ring. | | H | H |
| I-96 | X11 and X12 form a fused ring. | | H | Ph |

-continued

| | | |
|---|---|---|
| I-97 | 4-methylbiphenyl | X11 and X12 form a fused ring. |
| I-98 | p-tolyl (CH₃-C₆H₄-) | X11 and X12 form a fused ring. |
| I-99 | 6-methyl-2-naphthyl | X11 and X12 form a fused ring. |
| I-100 | 4-methoxyphenyl | X11 and X12 form a fused ring. |
| I-101 | Ph | X11 and X12 form a fused ring. |
| I-102 | Ph, 4'-methylbiphenyl | X11 and X12 form a fused ring. |
| I-103 | Ph | X11 and X12 form a fused ring. |
| I-104 | CH4 | X11 and X12 form a fused ring. |

"A and B form a fused ring" in

[structure: A and B substituents on a dimethylbenzene ring]

means

[structure showing fused ring formed from A and B positions]

[Core polycyclic structure with positions X2, X3, X6, X7, X11, X12, X13, X14, X32, X33, X34, X35, X36, X37]

| Compound No. | X2 | X3 | X6 | X7 | X32 | X33 | X34 = X35 | X36 | X37 |
|---|---|---|---|---|---|---|---|---|---|
| I-105 | H | H | H | H | X32 and X33 form a fused ring. | | H | X36 and X37 form a fused ring. | |
| I-106 | H | H | H | H | X32 and X33 form a fused ring. | | H | X36 and X37 form a fused ring. | |

(with X11 substituents: I-105: H; I-106: Ph — 2,3-dimethylnaphthyl fused group shown)

-continued

| | | | | | |
|---|---|---|---|---|---|
| I-107 | H | H | H | X32 and X33 form a fused ring. | H | X36 and X37 form a fused ring. | 4-biphenyl |
| I-108 | H | H | H | X32 and X33 form a fused ring. | H | X36 and X37 form a fused ring. | 4-methylphenyl |
| I-109 | H | H | H | X32 and X33 form a fused ring. | H | X36 and X37 form a fused ring. | 2-methylnaphthyl |
| I-110 | H | H | H | X32 and X33 form a fused ring. | H | X36 and X37 form a fused ring. | 4-methoxyphenyl |
| I-111 | H | H | H | X32 and X33 form a fused ring. | H | X36 and X37 form a fused ring. | Ph |
| I-112 | H | H | Ph | X32 and X33 form a fused ring. | H | X36 and X37 form a fused ring. | Ph |
| I-113 | H | H | 4-methylbiphenyl | X32 and X33 form a fused ring. | H | X36 and X37 form a fused ring. | Ph |
| I-114 | H | H | CH3 | X32 and X33 form a fused ring. | H | X36 and X37 form a fused ring. | Ph |
| I-115 | H | H | H | X32 and X33 form a fused ring. | H | X36 and X37 form a fused ring. | Ph |
| I-116 | H | H | H | X32 and X33 form a fused ring. | H | X36 and X37 form a fused ring. | Ph |
| I-117 | H | H | H | X32 and X33 forms fused ring. | H | X36 and X37 form a fused ring. | Ph |

| Compound No. | X12 | X13 | X14 |
|---|---|---|---|
| I-105 | H | H | H |
| I-106 | H | H | Ph |
| I-107 | H | H | 4-biphenyl |
| I-108 | H | H | 4-methylphenyl |

-continued

| Compound No. | | | | |
|---|---|---|---|---|
| I-109 | 6-methylnaphthalen-2-yl | H | H | |
| I-110 | CH3 | H | H | |
| I-111 | 4-methoxyphenyl | H | H | |
| I-112 | Ph | 4-phenylphenyl | H | |
| I-113 | Ph | 4-phenylphenyl | H | |
| I-114 | Ph | 4-phenylphenyl, Ph | H, Ph | |
| I-115 | Ph | 4-phenylphenyl, Ph | H, Ph | |
| I-116 | Ph | 4-phenylphenyl | H | |
| I-117 | Ph | CH3 | CH3 | |

| Compound No. | X2 | X3 | X6 | X7 | X32 | X33 | X34 = X35 | X36 | X37 |
|---|---|---|---|---|---|---|---|---|---|
| I-118 | X2 and X3 form a fused ring. | | X6 and X7 form a fused ring. | | H | H | H | H | H |
| I-119 | X2 and X3 form a fused ring. | | X6 and X7 form a fused ring. | | H | H | H | H | H |
| I-120 | X2 and X3 form a fused ring. | | X6 and X7 form a fused ring. | | H | H | H | H | H |
| I-121 | X2 and X3 form a fused ring. | | X6 and X7 form a fused ring. | | H | H | H | H | H |
| I-122 | X2 and X3 form a fused ring. | | X6 and X7 form a fused ring. | | H | H | H | H | H |
| I-123 | X2 and X3 form a fused ring. | | X6 and X7 form a fused ring. | | H | H | H | H | H |
| I-124 | X2 and X3 form a fused ring. | | X6 and X7 form a fused ring. | | H | H | H | H | H |
| I-125 | X2 and X3 form a fused ring. | | X6 and X7 form a fused ring. | | Ph | Ph | H | H | H |
| I-126 | X2 and X3 form a fused ring. | | X6 and X7 form a fused ring. | | H | H | H | H | H |
| I-127 | X2 and X3 form a fused ring. | | X6 and X7 form a fused ring. | | CH3 | H | H | H | H |
| I-128 | X2 and X3 form a fused ring. | | X6 and X7 form a fused ring. | | H | Ph | H | H | H |
| I-129 | X2 and X3 form a fused ring. | | X6 and X7 form a fused ring. | | H | H | H | H | H |
| I-130 | X2 and X3 form a fused ring. | | X6 and X7 form a fused ring. | | H | CH3 | H | H | H |
| I-131 | X2 and X3 form a fused ring. | | X6 and X7 form a fused ring. | | H | H | H | H | H |

-continued

| | | | | | |
|---|---|---|---|---|---|
| I-132 | X2 and X3 form a fused ring. | X6 and X7 form a fused ring. | H | H | H |
| I-133 | X2 and X3 form a fused ring. | X6 and X7 form a fused ring. | H | H | H |

| Compound No. | X11 | X12 | X13 | X14 |
|---|---|---|---|---|
| I-118 | H | H | H | H |
| I-119 | Ph | H | H | Ph |
| I-120 | 4-biphenyl | H | H | 4-biphenyl |
| I-121 | p-tolyl | H | H | p-tolyl |
| I-122 | 2-methylnaphthyl | H | H | 2-methylnaphthyl |
| I-123 | CH3 | H | H | CH3 |
| I-124 | phenoxy | H | H | phenoxy |
| I-125 | Ph | H | H | Ph |
| I-126 | Ph | H | H | Ph |
| I-127 | Ph | H | H | Ph |
| I-128 | Ph | H | H | Ph |
| I-129 | Ph | H | H | Ph |
| I-130 | Ph | H | H | Ph |
| I-131 | Ph | Ph | Ph | Ph |
| I-132 | Ph | 4-biphenylmethyl (CH3) | 4-biphenylmethyl (CH3) | Ph |
| I-133 | Ph | | | Ph |

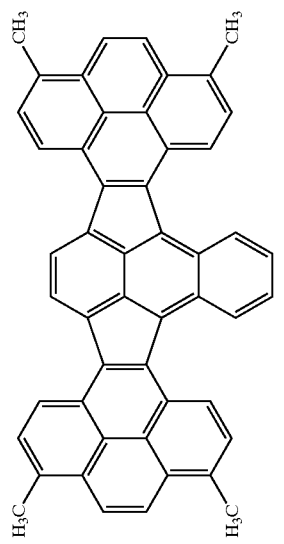
J-4
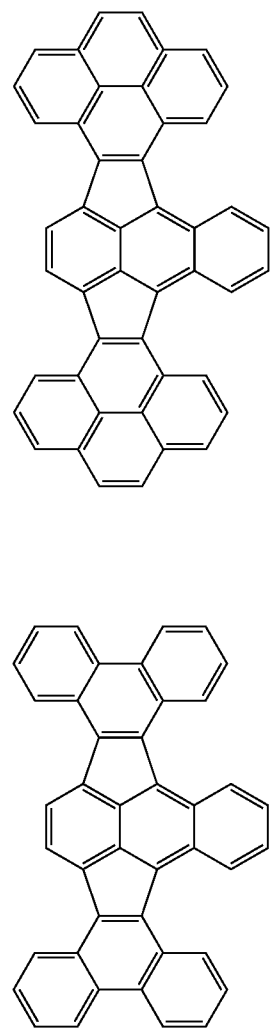
J-2
J-1
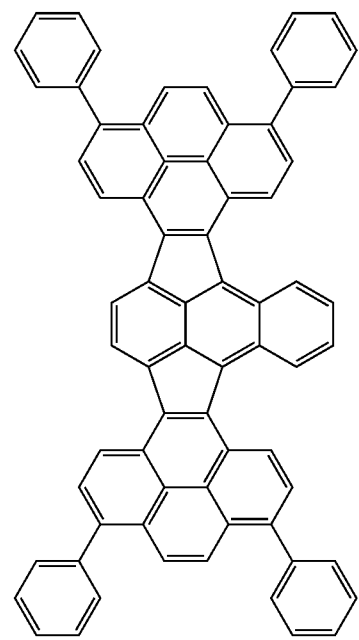
J-3

-continued
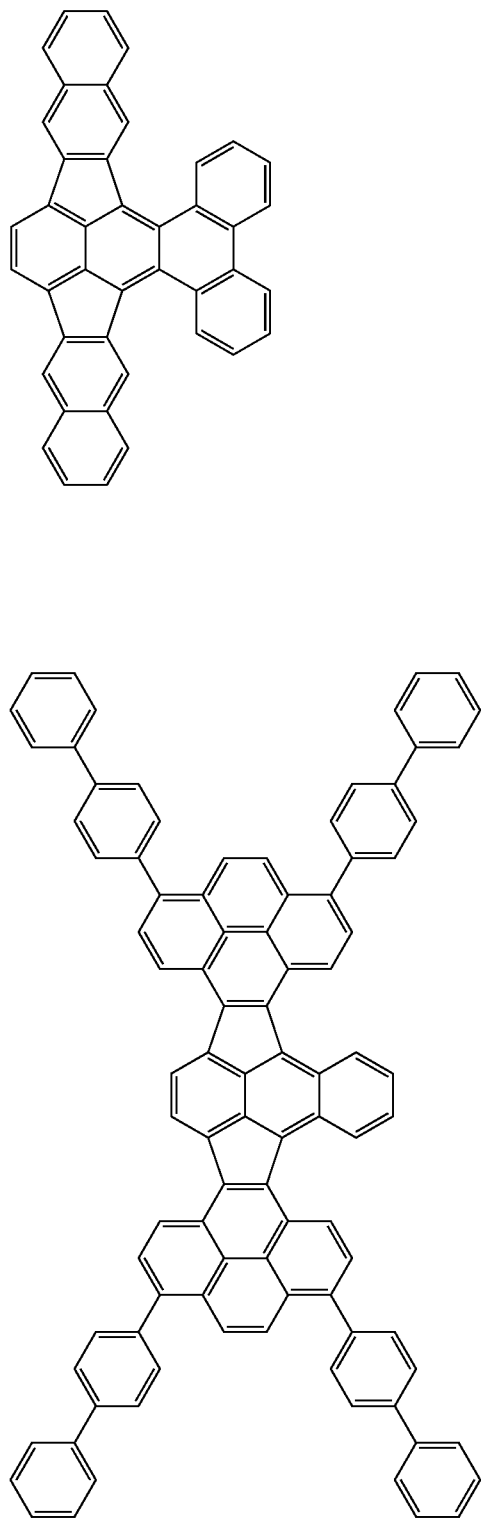
J-6
J-5
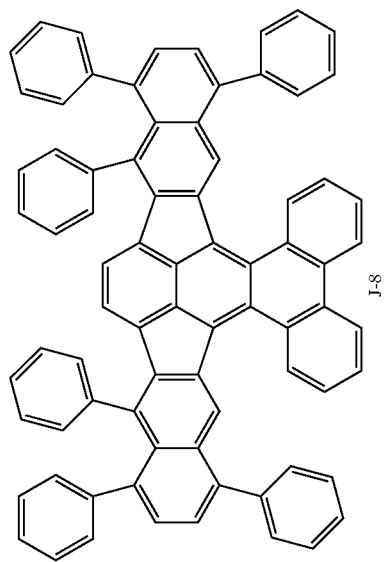
J-8
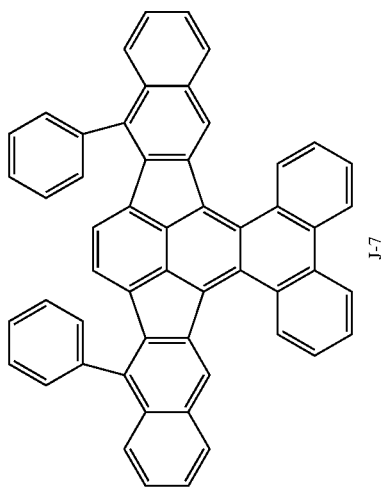
J-7

-continued
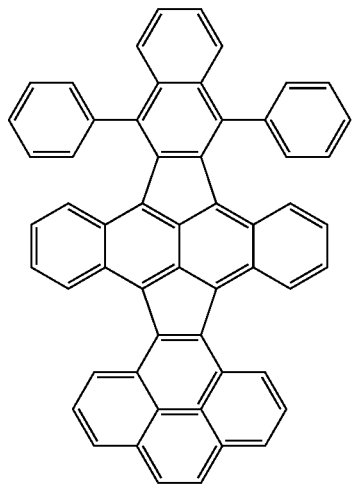
J-11
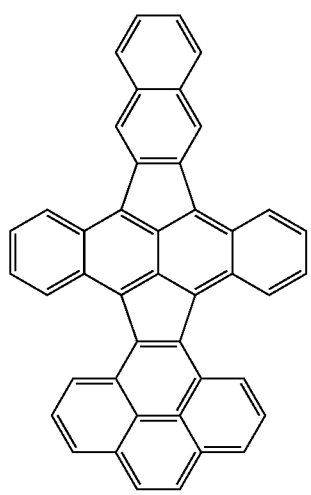
J-10
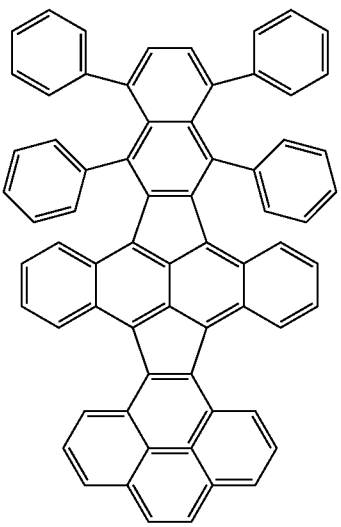
J-13
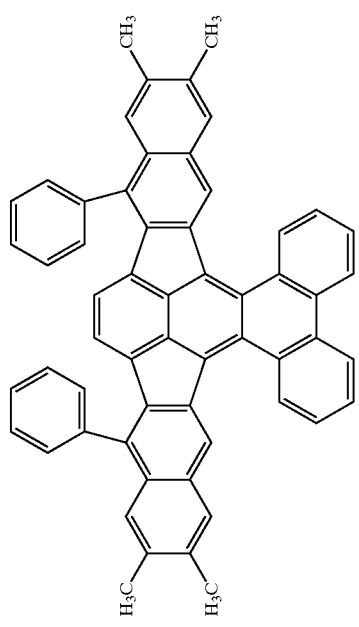
J-9
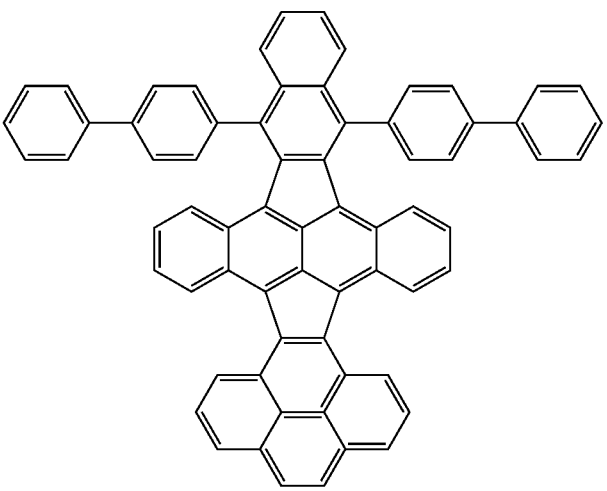
J-12

813
814
-continued
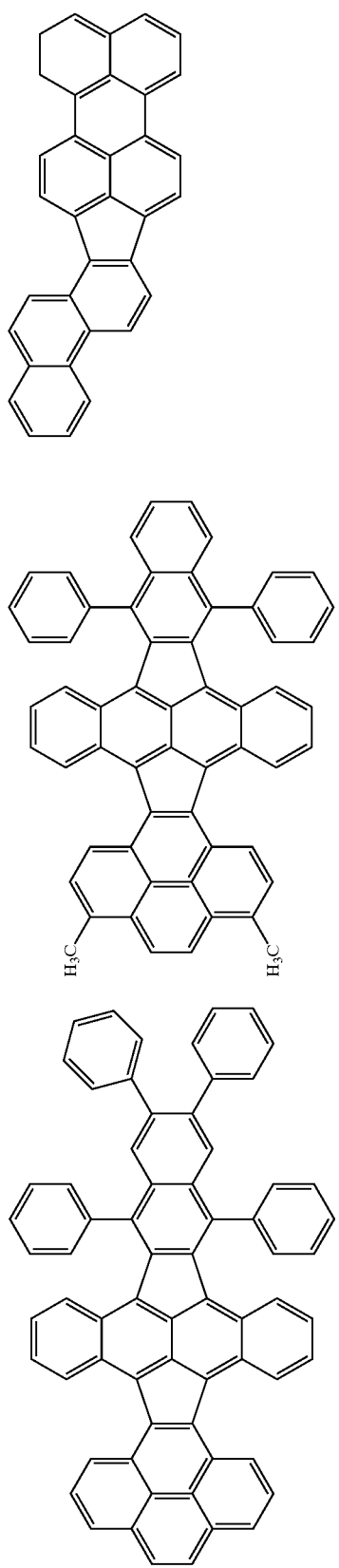
J-16
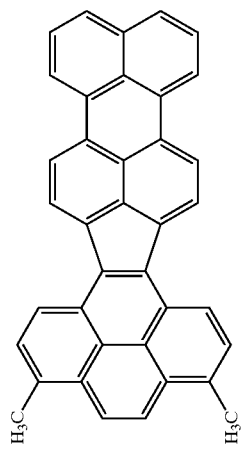
J-19
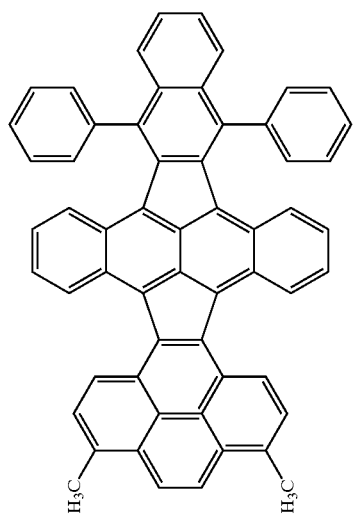
J-15
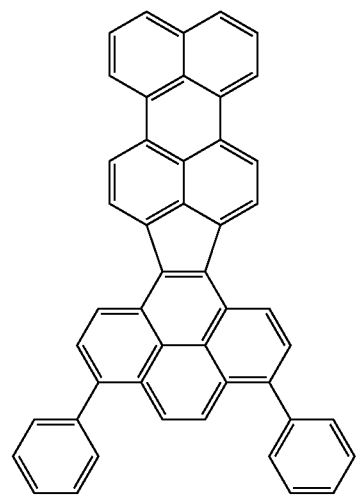
J-18
J-14
J-17
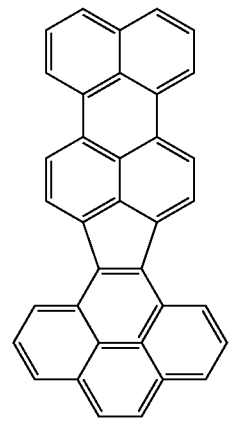

-continued
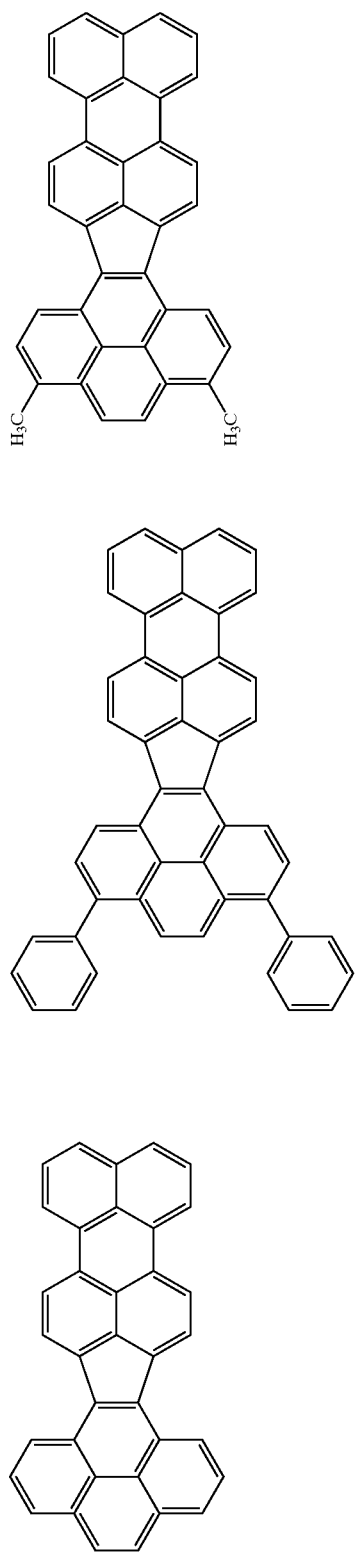
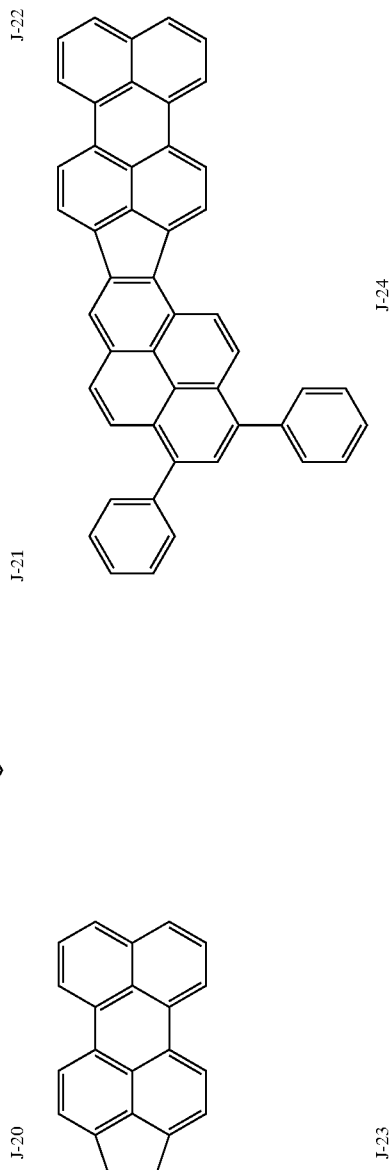
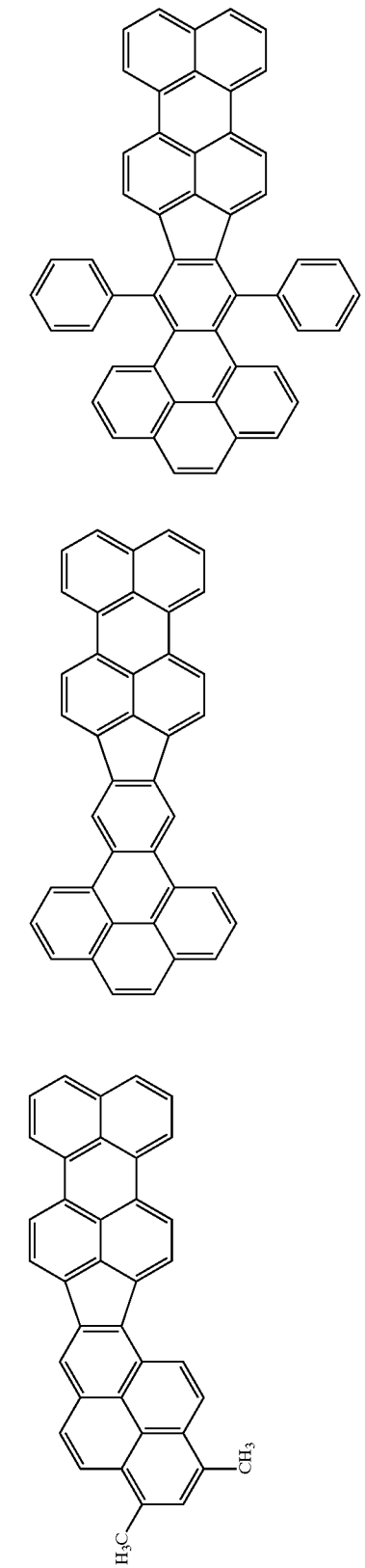

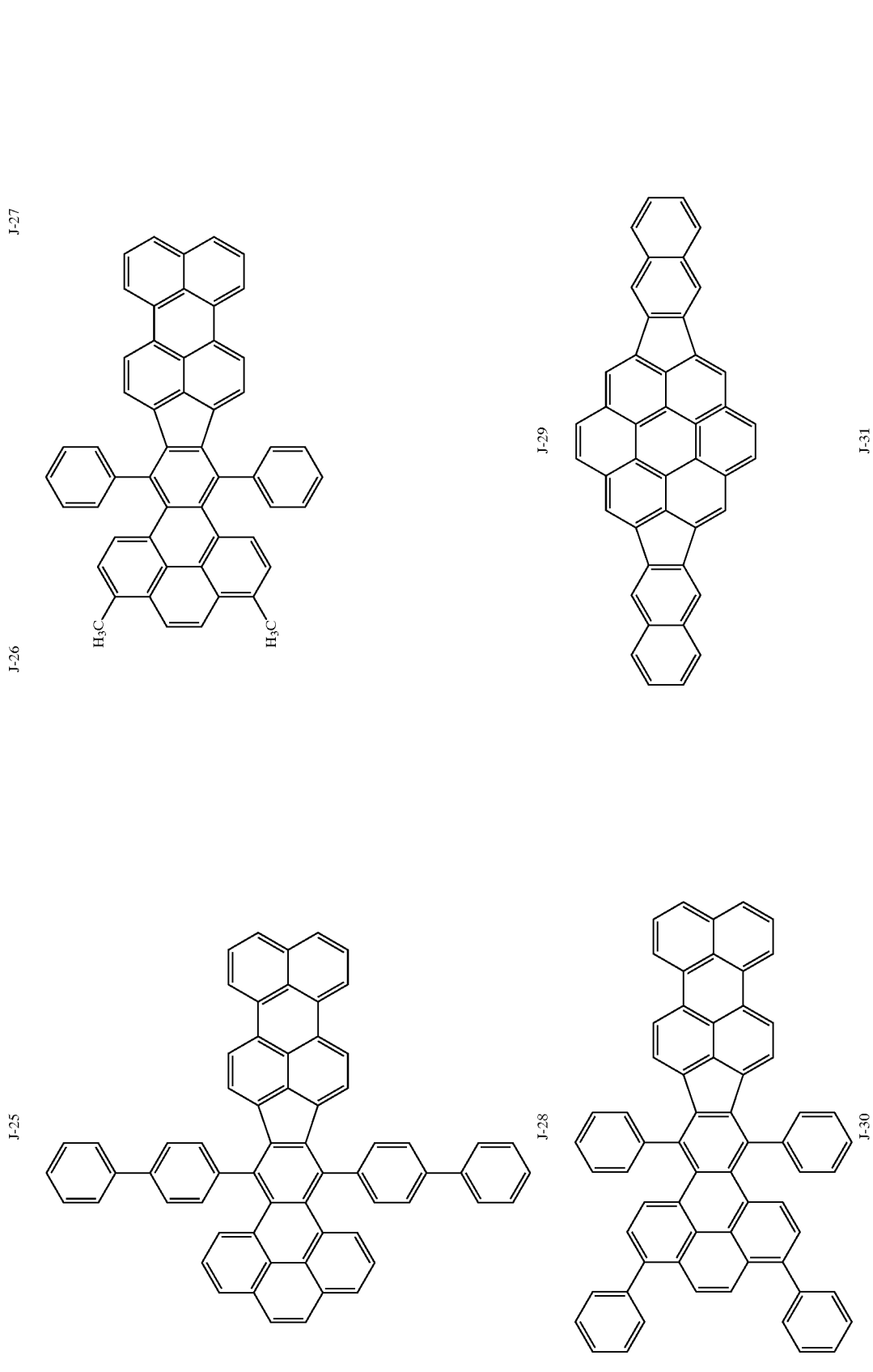

-continued
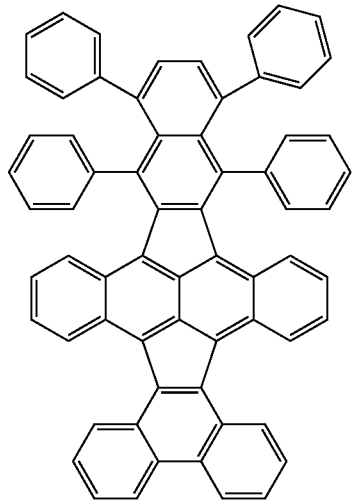
J-34
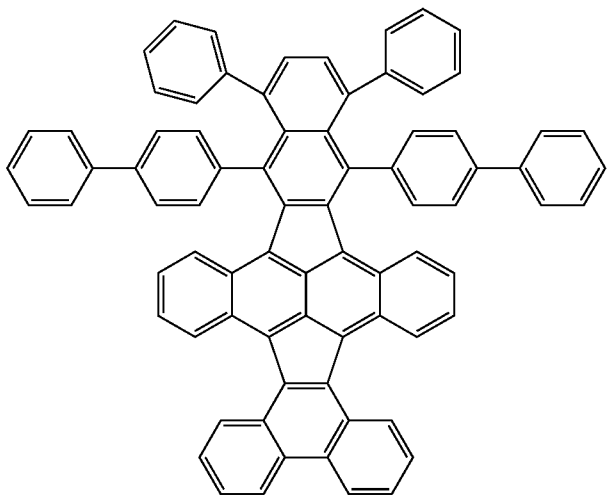
J-37
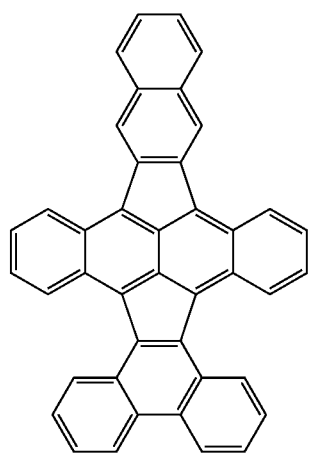
J-33
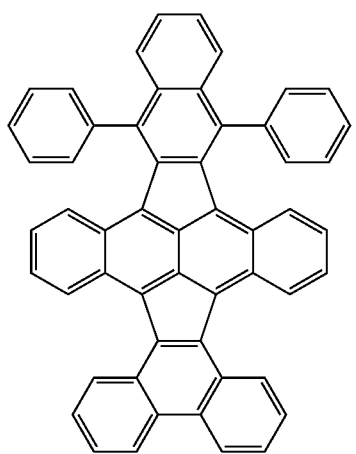
J-36
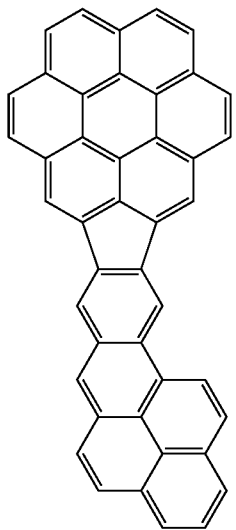
J-32
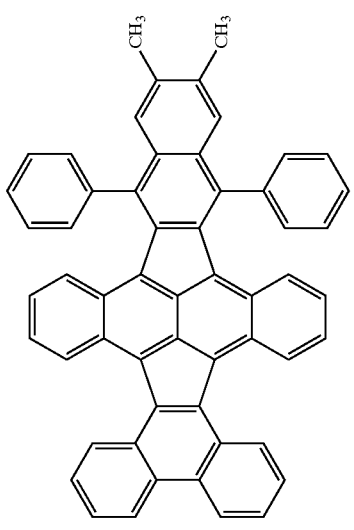
J-35

-continued
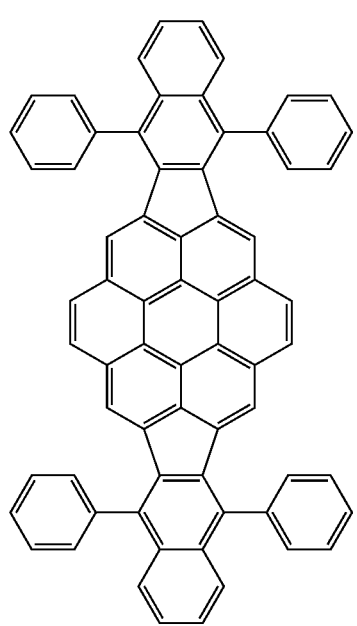
J-39
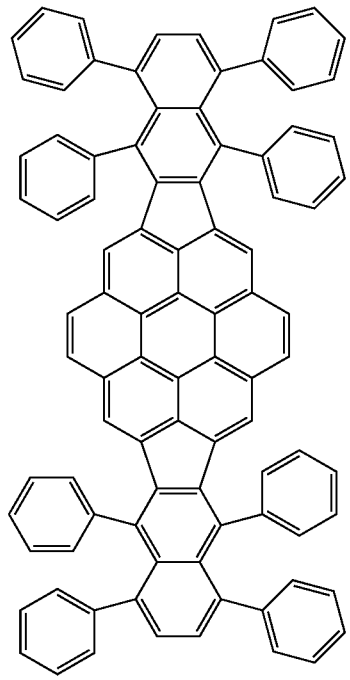
J-41
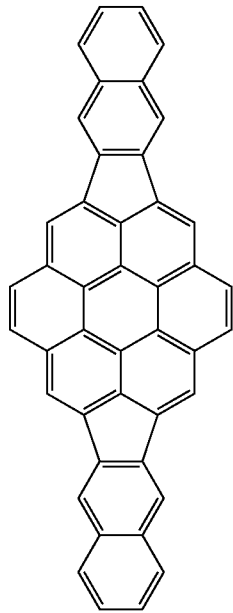
J-38
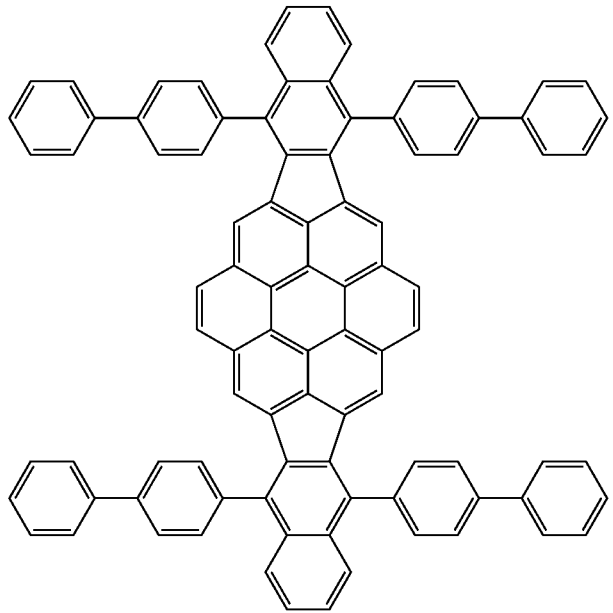
J-40

-continued
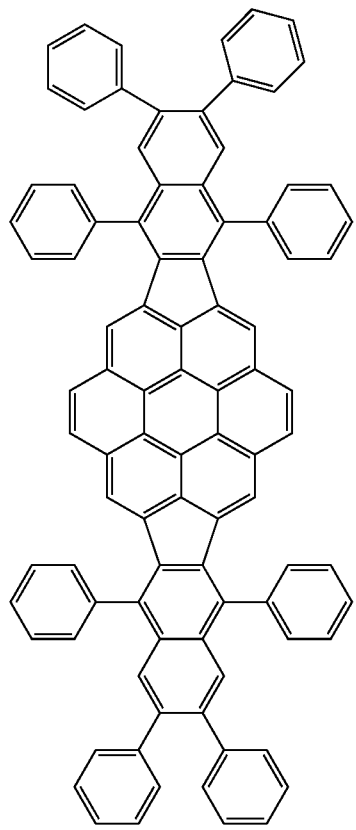
J-42
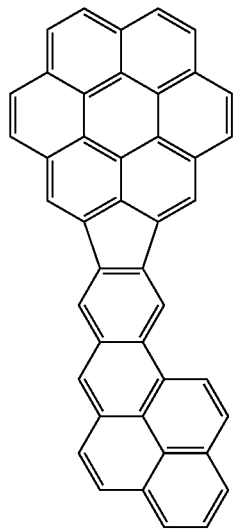
J-43
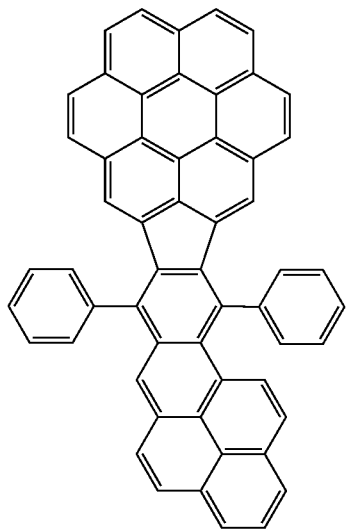
J-44
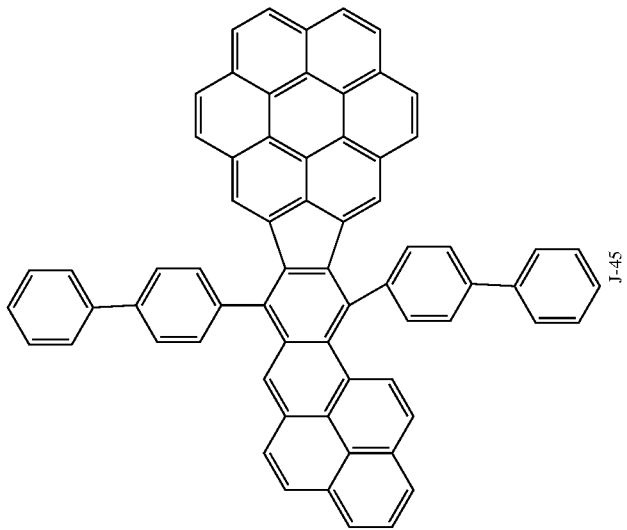
J-45

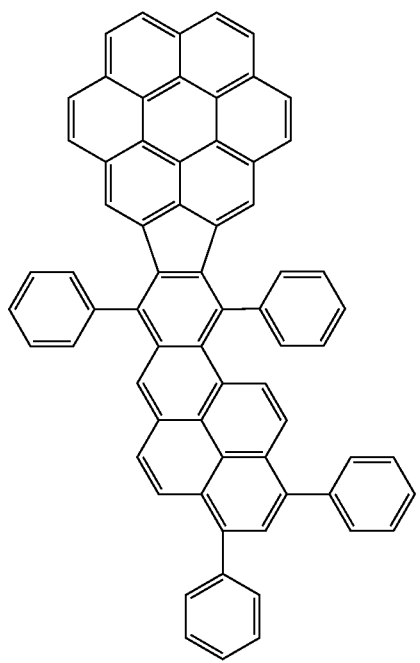
J-46

The above dopants, for example, the compounds of formula (VI) can be produced, for example, by the method described in J. Amer. Chem. Soc., 118, 2374 (1996). Specifically, as shown by the following scheme, the end compound can be produced by reacting a compound of formula (2) with a compound of formula (3) in the presence of aluminum chloride/sodium chloride, cobalt fluoride or thallium trifluoroacetate.

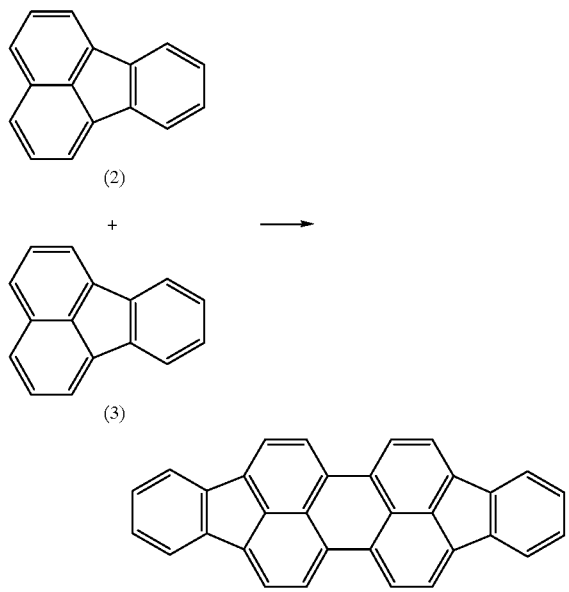

It is noted that the fluoranthene derivatives of formulas (V), (2) and (3), can be produced, for example, by the method described in J. Amer. Chem. Soc., 118, 2374 (1996). Specifically, as shown by the following scheme, the end compound can be produced by reacting a compound of formula (4) with a compound of formula (5).

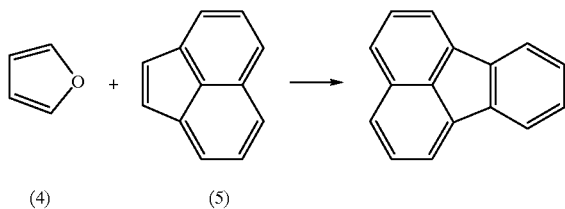

Once the skeleton of formula (VI) is formed, exchange of substituents is effected by a conventional method, obtaining a compound having the desired substituent(s).

The compounds of formula (VI) are preferably compounds, dibenzo[f,f']diindeno[1,2,3-cd:1',2',3'-lm]perylene derivatives in the following formula (VI').

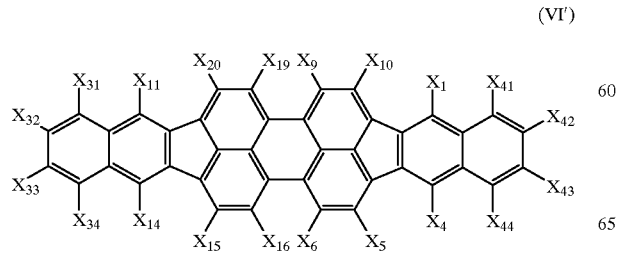

(VI')

In formula (VI'), $X_1$ to $X_{44}$ are as defined for $X_1$ to $X_{20}$ in formula (VI).

Preferably, $X_1$ to $X_{20}$ in formula (VI) and $X_1$ to $X_{44}$ in formula (VI') are independently selected from among substituted or unsubstituted aryl, alkyl, alkenyl, alkoxy and aryloxy radicals.

Further preferably, at least one of $X_1$ to $X_{20}$ in formula (VI) and $X_1$ to $X_{44}$ in formula (VI') is an ortho-substituted phenyl radical. Even more preferably, in formula (VI) or (VI'), either one or both of $X_1$ and $X_4$ and/or either one or both of $X_{11}$ and $X_{14}$ are ortho-substituted phenyl radicals. The introduction of a substituent at the ortho-position holds down the propensity for the compound to decompose upon sublimation purification and improves fluorescence.

The use of the ortho-substituted compound is effective for increasing the fluorescent luminance and holding down the concentration quenching of the EL device, thereby spreading the margin of the EL dopant and improving the freedom of design.

The introduction of an ortho-substituted phenyl group has several advantages. The ortho-substituted phenyl group introduced makes it possible to control the association of the perylene skeleton by virtue of its steric hindrance, to improve the solubility in solvents and to purify the compound to a high purity. For the same reason, sublimation purification becomes possible at a lower temperature and entails little decomposition. This is also advantageous in obtaining a high purity material. Using such a pure material, an organic EL device having a high emission efficiency is obtainable because the deactivation of excitons by impurities is minimized. Another reason accounting for the high efficiency is that the association between similar or distinct molecules in the light emitting layer is suppressed whereby concentration quenching is restrained.

Preferred examples of the compound of formula (VI') are given below.

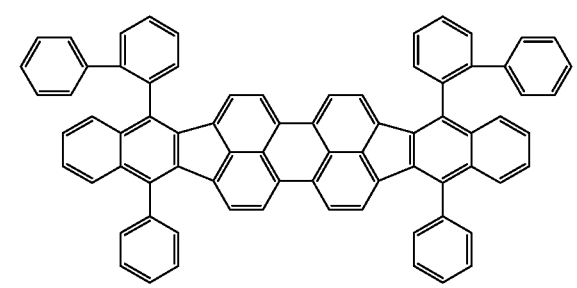

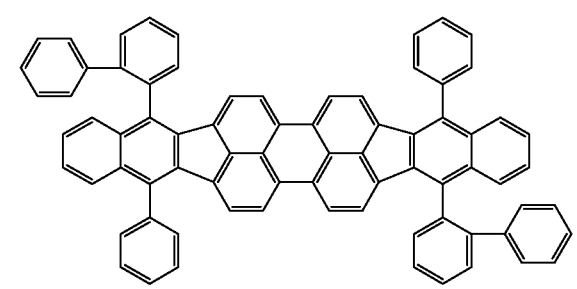

829
-continued
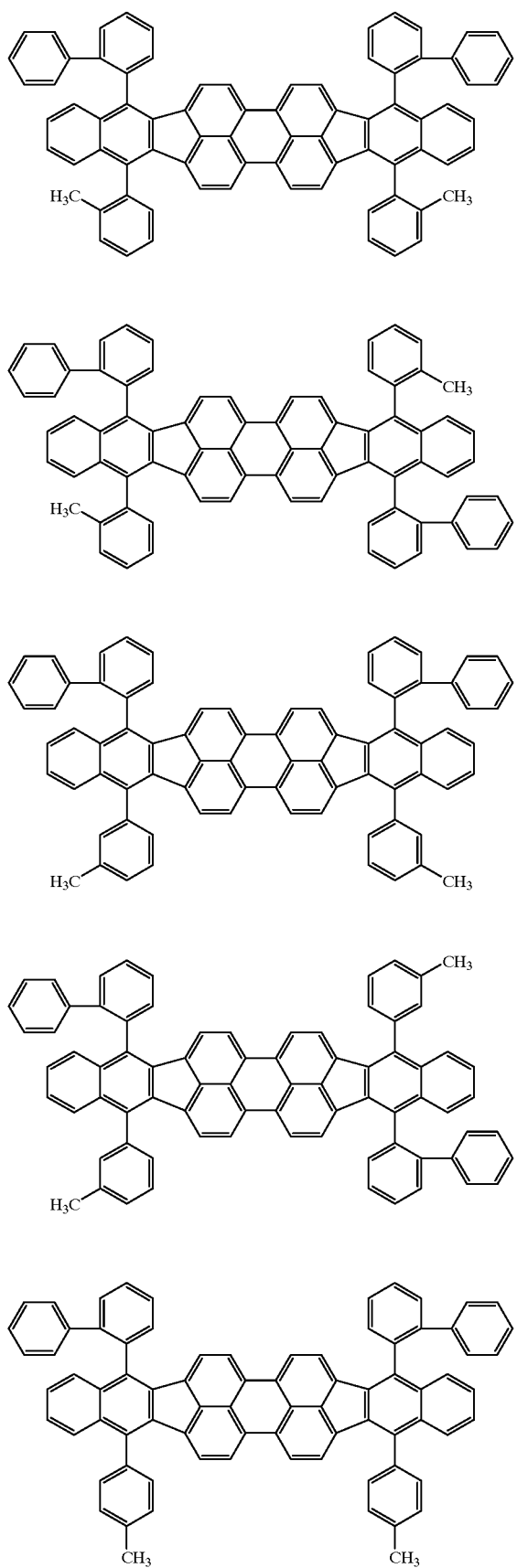
830
-continued
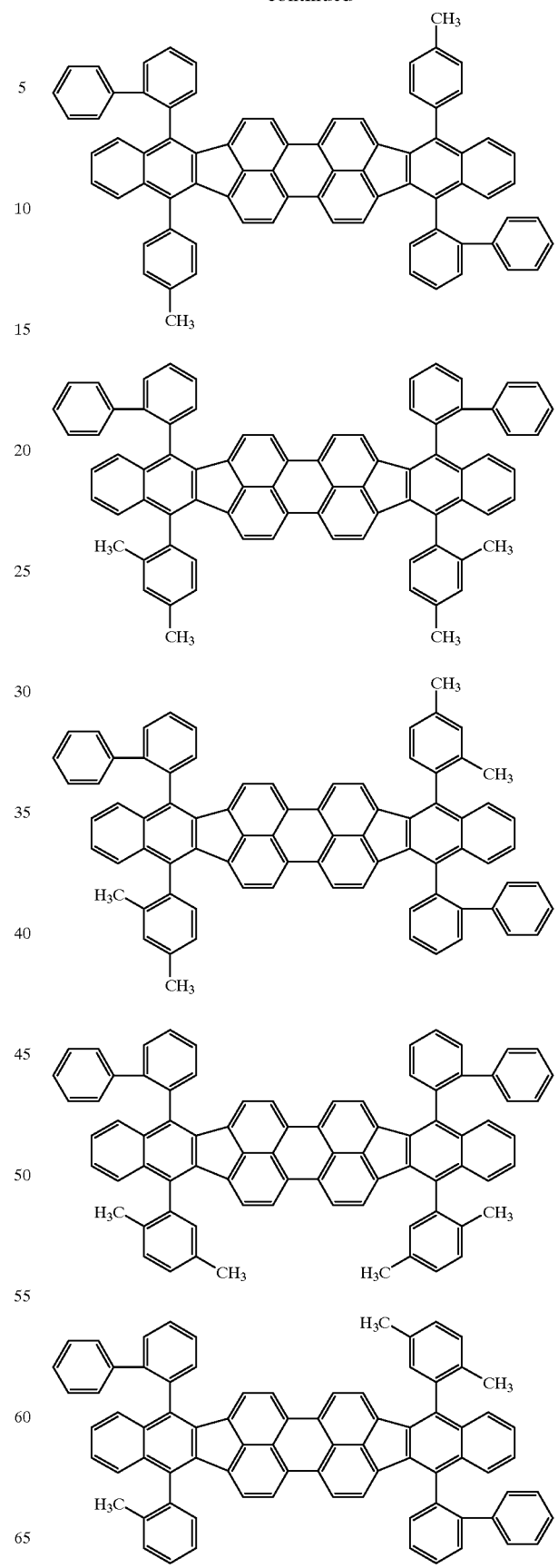

831
-continued
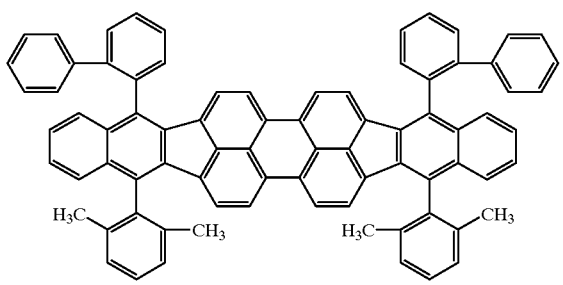
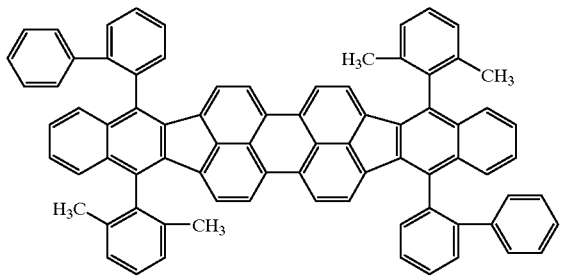
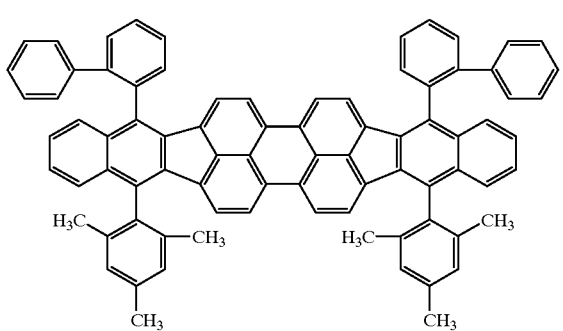
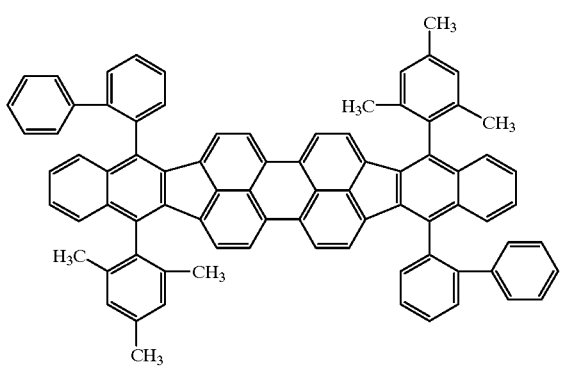
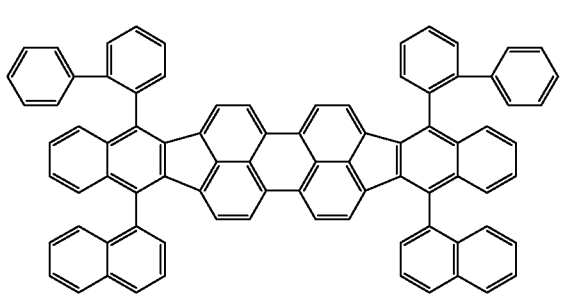
832
-continued
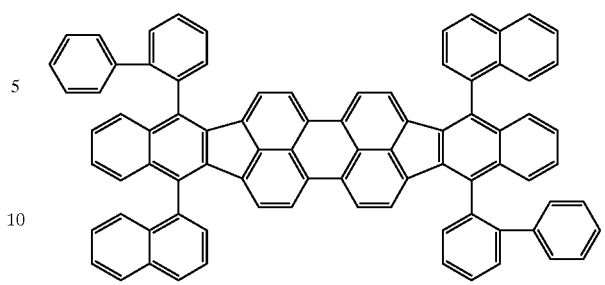
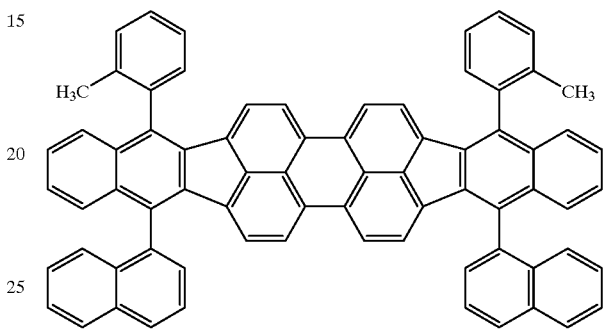
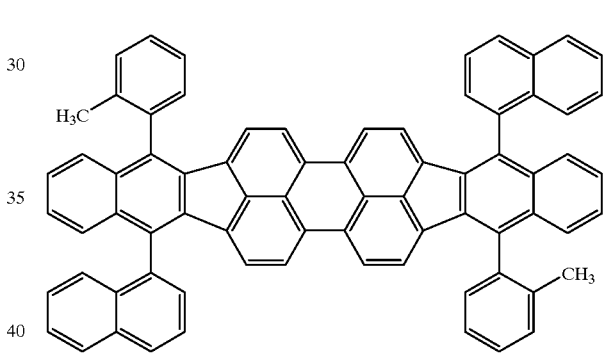
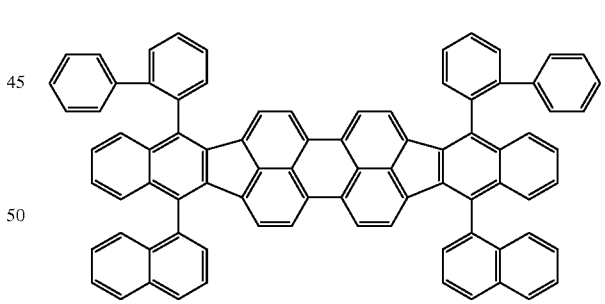
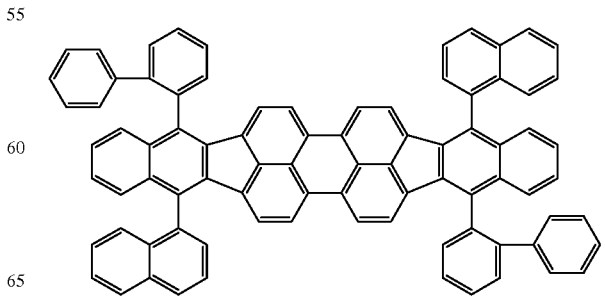

833
-continued
834
-continued
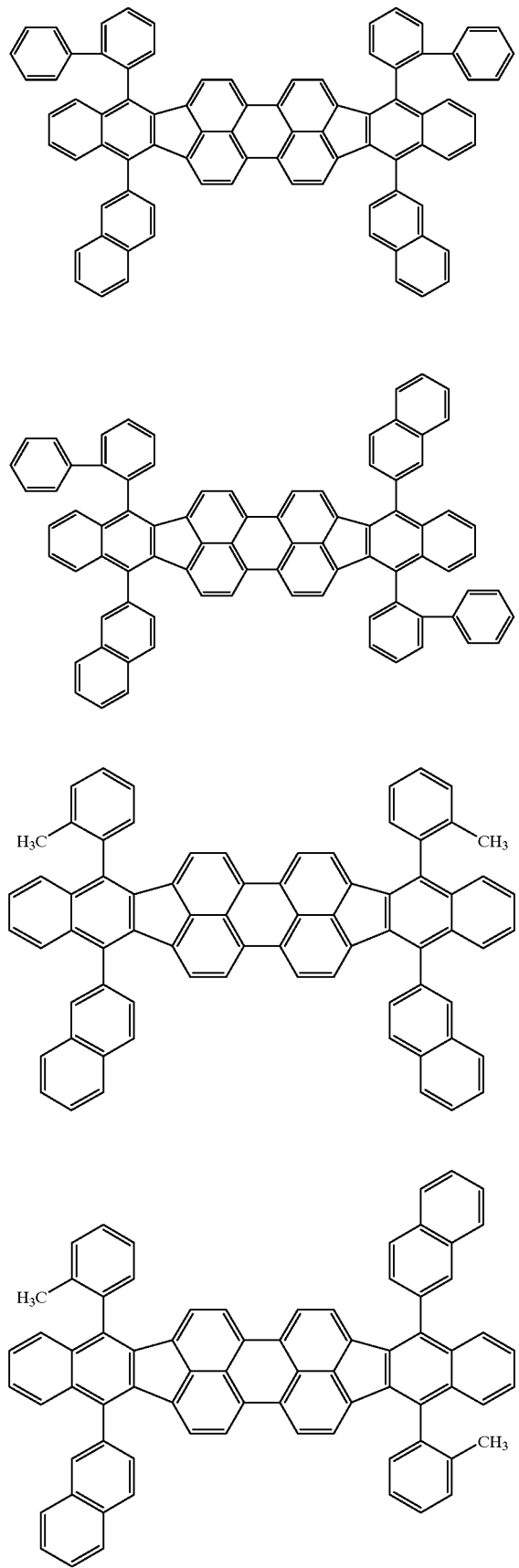

-continued

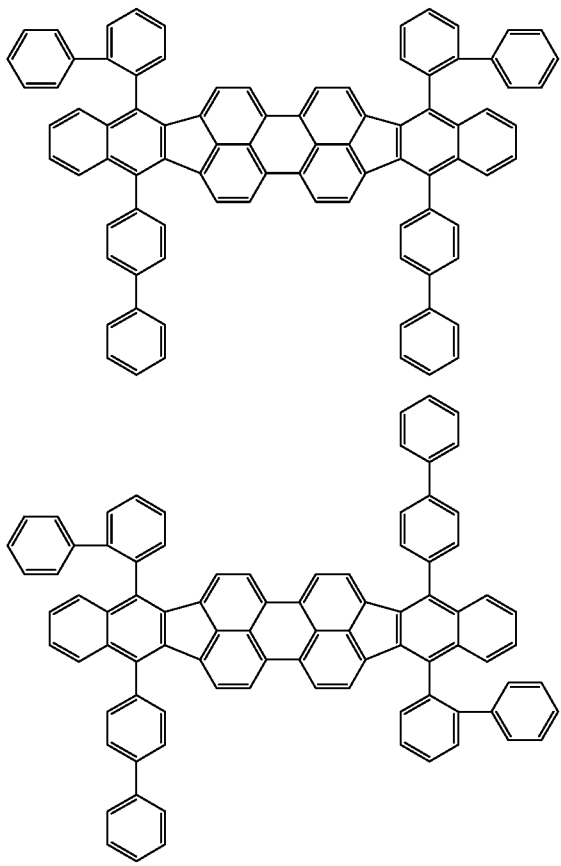

The diindeno[1,2,3-cd:1',2',3'-lm]perylene derivative should preferably have a vibration structure in both an excitation spectrum and a fluorescence spectrum. The presence of such a vibration structure is ascertainable by the appearance of two or more peaks in each of the spectra.

More preferably, a host material obtained by doping the indenoperylene derivative has such a vibration structure.

The possession of a vibration structure leads to the manufacture of an organic EL device having improved temperature characteristics.

It is believed that a drop of EL luminous efficiency by temperature is due to thermal relaxation entailing a change of conformation in the excited state. Once a change of conformation in the excited state occurs, the overlap of molecular orbital function between the ground state and the excited state changes so that the fluorescence spectrum does not become a mirror image of the absorption spectrum. The fluorescence spectrum of a compound which can take a plurality of conformations in the excited state is the total of various vibration structures and thus becomes a broad spectrum apparently free of a vibration structure.

Accordingly, an organic compound which exhibits a vibration structure in the fluorescence spectrum and specifically, a compound whose vibration structure is a mirror image of the absorption spectrum experiences a minimal change of conformation in the excited state and therefore, when used as a luminescent material in an organic EL device, enables to produce a device having improved temperature characteristics as demonstrated by a minimal drop of EL luminous efficiency by temperature during driving.

For the same reason as above, the organic compound should preferably have a Stokes shift of up to 0.1 eV, especially up to 0.05 eV. The lower limit of Stokes shift is not critical although it is usually about 0.01 eV.

Another factor that governs the temperature characteristics of an organic EL device is the thermal excitation of carriers from the trap level. Especially in a doped light emitting layer, the dopant creates a trap level. Upon a temperature change, the hopping probability of carriers by thermal excitation changes. This sometimes results in changes of the carrier balance in the light emitting layer, leading to temperature dependent characteristics with a high efficiency. In contrast, the device of the invention has a minimized thermal change of the trapping of the light emitting layer, that is, minimized temperature dependence with a high efficiency.

In a preferred embodiment, the host material, especially at least one of the organic compounds of formulas (I) to (IV), in a light emitting layer has a greater electron affinity than an electron transporting layer and/or a hole transporting layer. If the host material in a light emitting layer has a greater electron affinity than an electron transporting layer and/or a hole transporting layer, the injection efficiency of electrons into the light emitting layer increases and electrons are blocked at the hole transporting layer interface, leading to an improvement in luminous efficiency and hence, device lifetime.

Others

The light emitting layer containing the host material and the dopant according to the invention has functions of injecting holes and electrons, transporting them, and recombining holes and electrons to create excitons. The use of relatively electronically neutral compounds in the light emitting layer in addition to the compounds of the invention enables easy and well-balanced injection and transportation of electrons and holes.

The host material may be used alone or in admixture of two or more. When a mixture of two or more host materials is used, the mix ratio is not critical. In a preferred embodiment, the light emitting layer contains 80 to 99.9%, more preferably 90 to 99.9%, even more preferably 95.0 to 99.5% by weight of the host material.

The thickness of the light emitting layer preferably ranges from the thickness corresponding to a single molecule layer to less than the thickness of an organic compound layer, for example, preferably from 1 to 85 nm, more preferably 5 to 60 nm, most preferably 5 to 50 nm.

Preferably the mix layer is formed by a co-deposition process of evaporating the compounds from distinct sources. If both the compounds have equal or very close vapor pressure or evaporation temperature, they may be pre-mixed in a common evaporation boat, from which they are evaporated together. The mix layer is preferably a uniform mixture of both the compounds although the compounds can be present in island form. The light emitting layer is generally formed to a predetermined thickness by evaporating an organic fluorescent material or coating a dispersion thereof in a resin binder.

One exemplary construction of the organic EL light emitting device fabricated using the inventive compounds has on a substrate, a hole injecting electrode, a hole injecting and transporting layer, a light emitting and electron injecting and transporting layer, and an electron injecting electrode in the described order. If desired, a protective electrode, an auxiliary electrode and a sealing layer are provided on the electron injecting electrode.

The organic EL device of the invention is not limited to the above exemplary construction and may have various other constructions. In another exemplary construction, the light emitting layer is provided singly and an electron injecting and transporting layer is interposed between the light emitting layer and the electron injecting electrode. Also, the light emitting layer may be mixed with the hole injecting and transporting layer, if desired.

The thicknesses of the light emitting layer, hole injecting and transporting layer, and electron injecting and transporting layer are not critical and vary with a particular formation technique. Usually a single layer is about 5 to 500 nm thick, especially about 10 to 300 nm thick.

The thicknesses of the hole injecting and transporting layer and electron injecting and transporting layer are equal to or range from 1/10 to 10 times the thickness of the light emitting layer although they depend on the design of a recombination/light emitting region. When the electron or hole injecting and transporting layer is divided into an injecting layer and a transporting layer, preferably the injecting layer is at least 1 nm thick and the transporting layer is at least 1 nm thick. The upper limit of thickness is generally about 500 nm for the injecting layer and about 500 nm for the transporting layer. The same applies when two injecting and transporting layers are provided.

The hole injecting and transporting layer has functions of facilitating injection of holes from the hole injecting electrode, transporting them stably, and blocking electrons. The electron injecting and transporting layer has functions of facilitating injection of electrons from the electron injecting electrode, transporting them stably, and blocking holes. These layers are effective for increasing the number of holes and electrons injected into the light emitting layer and confining holes and electrons therein for optimizing the recombination region to improve light emission efficiency.

In the hole injecting and transporting layer, there may be used various organic compounds as described, for example, in JP-A 63-295695, 2-191694, 3-792, 5-234681, 5-239455, 5-299174, 7-126225, 7-126226, and 8-100172, and EPO 650955A1. Exemplary are tetraarylbenzidine compounds (triaryldiamines or triphenyldiamines: TPD), aromatic tertiary amines, hydrazone derivatives, carbazole derivatives, triazole derivatives, imidazole derivatives, oxadiazole derivatives having an amino group, and polythiophenes. Two or more of these compounds may be used, and on such combined use, they may be formed as separate layers or mixed.

Where the hole injecting and transporting layer is formed separately as a hole injecting layer and a hole transporting layer, two or more compounds are selected in a proper combination from the compounds commonly used in hole injecting and transporting layers. In this regard, it is preferred to laminate layers in such an order that a layer of a compound having a lower ionization potential may be disposed adjacent the hole injecting electrode (ITO). It is also preferred to use a compound having good thin film forming ability at the hole injecting electrode surface. The order of lamination also applies where a plurality of hole injecting and transporting layers are provided. Such an order of lamination is effective for lowering the drive voltage and preventing current leakage and the development and growth of dark spots. Since evaporation is utilized in the manufacture of devices, films as thin as about 1 to 10 nm can be formed uniform and pinhole-free, which restrains any change in color tone of light emission and a drop of efficiency by re-absorption even if a compound having a low ionization potential and absorption in the visible range is used in the hole injecting layer. Like the light emitting layer, the hole injecting and transporting layer may be formed by evaporating the above-mentioned compounds.

In the electron injecting and transporting layer, there may be used quinoline derivatives including organic metal complexes having 8-quinolinol or a derivative thereof as a ligand such as tris(8-quinolinolato)aluminum (Alq3), oxadiazole derivatives, perylene derivatives, pyridine derivatives, pyrimidine derivatives, quinoxaline derivatives, diphenylquinone derivatives, and nitro-substituted fluorene derivatives. The electron injecting and transporting layer can also serve as the light emitting layer. Like the light emitting layer, the electron injecting and transporting layer may be formed by evaporation or the like.

Where the electron injecting and transporting layer is formed separately as an electron injecting layer and an electron transporting layer, two or more compounds are selected in a proper combination from the compounds commonly used in electron injecting and transporting layers. In this regard, it is preferred to stack layers in such an order that a layer of a compound having a greater electron affinity may be disposed adjacent the electron injecting electrode. The order of stacking also applies where a plurality of electron injecting and transporting layers are provided.

In forming the hole injecting and transporting layer, the light emitting layer, and the electron injecting and transporting layer, vacuum evaporation is preferably used because homogeneous thin films are available. By utilizing vacuum evaporation, there is obtained a homogeneous thin film which is amorphous or has a crystal grain size of less than 0.1 $\mu$m. If the grain size is more than 0.1 $\mu$m, uneven light emission would take place and the drive voltage of the device must be increased with a substantial drop of hole injection efficiency.

The conditions for vacuum evaporation are not critical although a vacuum of $10^{-4}$ Pa or lower and a deposition rate of about 0.01 to 1 nm/sec are preferred. It is preferred to successively form layers in vacuum because the successive formation in vacuum can avoid adsorption of impurities on the interface between the layers, thus ensuring better performance. Also, the drive voltage of a device can be reduced and the development and growth of dark spots be restrained.

In the embodiment wherein the respective layers are formed by vacuum evaporation, where it is desired for a single layer to contain two or more compounds, preferably boats having the compounds received therein are individually temperature controlled to achieve co-deposition.

The electron injecting electrode is preferably made of metals, alloys or intermetallic compounds having a work function of up to 4 eV. With a work function of more than 4 eV, the electron injecting efficiency lowers and consequently, the light emission efficiency lowers. Examples of the metal having a work function of up to 4 eV of which the electron injecting electrode film is constructed include alkali metals such as Li, Na and K, alkaline earth metals such as Mg, Ca, Sr and Ba, rare earth metals such as La and Ce, and Al, In, Ag, Sn, Zn, and Zr. Examples of the film-forming alloy having a work function of up to 4 eV include Ag—Mg (Ag: 0.1 to 50 at %), Al—Li (Li: 0.01 to 12 at %), In—Mg (Mg: 50 to 80 at %), and Al—Ca (Ca: 0.01 to 20 at %). These materials may be present alone or in combination of two or more. Where two or more materials are combined, their mixing ratio is arbitrary. It is also acceptable that an oxide or halide of an alkali metal, alkaline earth metal or rare earth metal is thinly deposited and a supporting electrode (auxiliary electrode or wiring electrode) of aluminum etc. is used.

The electron injecting electrode may be formed by evaporation or sputtering.

The electron injecting electrode may have at least a sufficient thickness to effect electron injection, for example, a thickness of at least 0.1 nm. Although the upper limit is not critical, the electrode thickness is typically about 0.1 to about 500 nm.

The hole injecting electrode is preferably formed of such a material to such a thickness that the electrode may have a transmittance of at least 80% of emitted light. Illustratively, oxide transparent conductive thin films are preferred. For example, materials based on tin-doped indium oxide (ITO), zinc-doped indium oxide (IZO), indium oxide ($In_2O_3$), tin oxide ($SnO_2$) or zinc oxide (ZnO) are preferable. These oxides may deviate somewhat from their stoichiometry. An appropriate proportion of $SnO_2$ mixed with $In_2O_3$ is about 1 to 20% by weight, more preferably about 5 to 12% by weight. An appropriate proportion of $ZnO_2$ mixed with $In_2O_3$ is about 12 to 32% by weight.

The hole injecting electrode should preferably have a light transmittance of at least 80%, especially at least 90% in the light emission band, typically from 350 to 800 nm, and especially at each light emission. Since the emitted light is generally taken out through the hole injecting electrode, with a lower transmittance, the light emitted by the light emitting layer would be attenuated through the electrode, failing to provide a luminance necessary as a light emitting device. It is noted that only the side from which the emitted light exits has a transmittance of at least 80%.

The hole injecting electrode has at least a sufficient thickness to effect hole injection, preferably a thickness of 50 to 500 nm, especially 50 to 300 nm. Although the upper limit of the electrode thickness is not critical, a too thick electrode would have the risk of separation. Too thin an electrode would have problems with respect to film strength during fabrication, hole transporting ability, and resistance value.

In depositing the hole injecting electrode, a sputtering process is preferred. The sputtering process may be a high-frequency sputtering process using an RF power supply although a dc sputtering process is preferably used when the ease of control of physical properties of the hole injecting electrode being deposited and the flatness of the deposited film are taken into account.

A protective film may be formed if necessary. The protective film may be formed using an inorganic material such as SiOx or an organic material such as Teflon. The protective film may be either transparent or opaque and have a thickness of about 50 to 1,200 nm. Apart from the reactive sputtering process mentioned above, the protective film may also be formed by an ordinary sputtering or evaporation process.

Further, a sealing layer is provided on the device in order to prevent the organic layers and electrodes from oxidation. In order to prevent the ingress of moisture, the sealing layer is formed by attaching a sealing plate such as a glass plate to the substrate with an adhesive resin layer such as a commercially available low moisture absorption photo-curable adhesive, epoxy base adhesive, silicone base adhesive, or crosslinking ethylene-vinyl acetate copolymer adhesive sheet. Metal plates and plastic plates may also be used instead of the glass plate.

Transparent or translucent materials such as glass, quartz and resins are used as the substrate when the emitted light exits from the substrate side. The substrate may be provided with a color filter film, a fluorescent material-containing color conversion film or a dielectric reflecting film for controlling the color of light emission. In the case of the inversely stacked layer structure, the substrate may be either transparent or opaque. For the opaque substrate, ceramic and other materials may be used.

The color filter film used herein may be a color filter as used in liquid crystal displays and the like. The properties of a color filter may be adjusted in accordance with the light emission of the organic EL device so as to optimize the extraction efficiency and chromatic purity.

It is also preferred to use a color filter capable of cutting external light of short wavelength which is otherwise absorbed by the EL device materials and fluorescence conversion layer, because the light resistance and display contrast of the device are improved.

An optical thin film such as a dielectric multilayer film may be used instead of the color filter.

Referring to FIG. 1, there is illustrated one exemplary construction of the organic EL device fabricated according to the invention. The organic EL device is shown in FIG. 1 as having on a substrate 1, a hole injecting electrode (or anode) 2, a hole injecting layer 3, a hole transporting layer 4, a light emitting layer 5, an electron injecting and transporting layer 6, an electron injecting electrode (or cathode) 7, and optionally, a protective electrode 8 in the described order. The organic EL device of the invention is not limited to the illustrated construction, and various other constructions are possible depending on the desired device function. For example, the order of lamination may be inverse to the above-described order. The hole injecting 3, the hole transporting layer 4 and the electron injecting and transporting layer 6 may be omitted or either one of them may be a common layer to the light emitting layer 5.

The organic EL device of the invention is generally of the dc or pulse drive type while it can be of the ac drive type. The applied voltage is generally about 2 to 30 volts.

EXAMPLE

Examples of the present invention are given below together with Comparative Examples for further illustrating the invention.

Example 1

On a glass substrate, a transparent ITO electrode thin film was deposited to a thickness of 100 nm by RF sputtering and patterned. The glass substrate having the transparent ITO electrode was subjected to ultrasonic washing with neutral detergent, acetone, and ethanol, pulled up from boiling ethanol, and dried. The transparent electrode surface was further cleaned with UV/ozone. Thereafter, the substrate was secured by a holder in a vacuum evaporation chamber, which was evacuated to a vacuum of $1\times10^{-5}$ Pa or lower.

With the vacuum kept, N,N'-diphenyl-N,N'-bis[N-(4-methylphenyl)-N-phenyl-(4-aminophenyl)]-1,1'-biphenyl-4,4'-diamine was evaporated at a deposition rate of 0.1 nm/sec. to a thickness of 50 nm, forming a hole injecting layer.

Then, N,N,N',N'-tetrakis(m-biphenyl)-1,1'-biphenyl-4,4'-diamine (TPD) was evaporated at a deposition rate of 0.1 nm/sec to a thickness of 20 nm, forming a hole transporting layer.

With the vacuum kept, the host material and dopant of the following structural formulas were evaporated in a weight ratio of 99:1 and at an overall deposition rate of 0.1 nm/sec to a thickness of 40 nm, forming a light emitting layer.

HOST

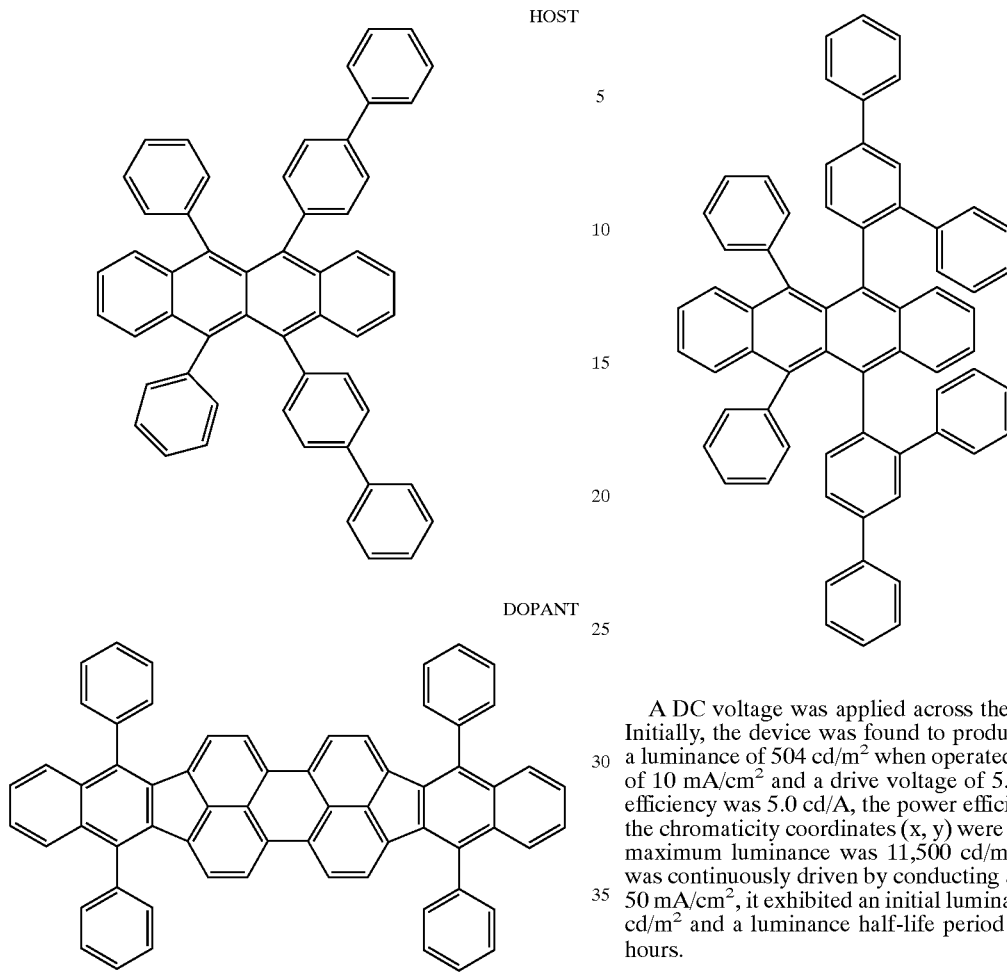

DOPANT

Next, with the vacuum kept, tris(8-quinolinolato) aluminum was evaporated at a deposition rate of 0.1 nm/sec to a thickness of 20 nm, forming an electron transporting layer.

With the vacuum kept, LiF was evaporated at a deposition rate of 0.01 nm/sec to a thickness of 0.3 nm, forming an electron injecting electrode. Finally, aluminum was evaporated to a thickness of 150 nm to form a protective electrode, completing an organic EL device.

A DC voltage was applied across the organic EL device. Initially, the device was found to produce light emission to a luminance of 614 cd/m² when operated at a current density of 10 mA/cm² and a drive voltage of 5.9 volts. The current efficiency was 6.1 cd/A, the power efficiency was 3.3 lm/W, the chromaticity coordinates (x, y) were (0.65, 0.35), and the maximum luminance was 19,600 cd/m². When the device was continuously driven by conducting a constant current of 50 mA/cm², it exhibited an initial luminance of at least 3,200 cd/m² and a luminance half-life period of more than 600 hours.

Example 2

An organic EL device was prepared as in Example 1 except that the host material in the light emitting layer was changed to the following compound.

A DC voltage was applied across the organic EL device. Initially, the device was found to produce light emission to a luminance of 504 cd/m² when operated at a current density of 10 mA/cm² and a drive voltage of 5.9 volts. The current efficiency was 5.0 cd/A, the power efficiency was 2.7 lm/W, the chromaticity coordinates (x, y) were (0.64, 0.36), and the maximum luminance was 11,500 cd/m². When the device was continuously driven by conducting a constant current of 50 mA/cm², it exhibited an initial luminance of at least 2,170 cd/m² and a luminance half-life period of more than 1,500 hours.

Example 3

An organic EL device was prepared as in Example 1 except that the host material in the light emitting layer was changed to the following compound.

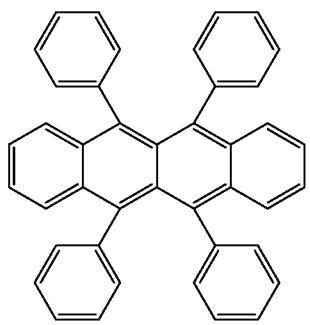

A DC voltage was applied across the organic EL device. Initially, the device was found to produce light emission to a luminance of 449 cd/m² when operated at a current density of 10 mA/cm² and a drive voltage of 5.9 volts. The current efficiency was 4.5 cd/A, the power efficiency was 2.4 lm/W, the chromaticity coordinates (x, y) were (0.66, 0.34), and the maximum luminance was 17,200 cd/m². When the device was continuously driven by conducting a constant current of 50 mA/cm², it exhibited an initial luminance of at least 2,440 cd/m² and a luminance half-life period of more than 1,500 hours.

Example 4

An organic EL device was prepared as in Example 1 except that the host material in the light emitting layer was changed to the following compound.

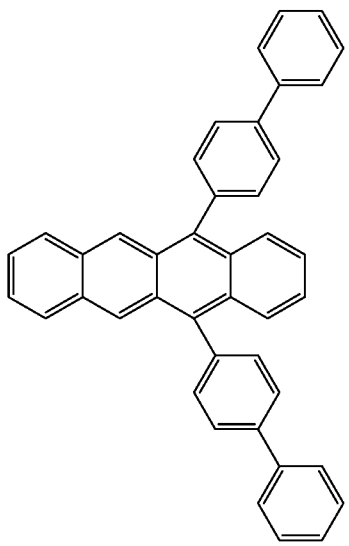

A DC voltage was applied across the organic EL device. Initially, the device was found to produce light emission to a luminance of 441 cd/m² when operated at a current density of 10 mA/cm² and a drive voltage of 5.9 volts. The current efficiency was 4.4 cd/A, the power efficiency was 2.3 lm/W, the chromaticity coordinates (x, y) were (0.65, 0.34), and the maximum luminance was 35,200 cd/m². When the device was continuously driven by conducting a constant current of 50 mA/cm², it exhibited an initial luminance of at least 2,400 cd/m² and a luminance attenuation of up to 10% after 1,000 hours and up to 15% after 4,500 hours.

Figure 2:
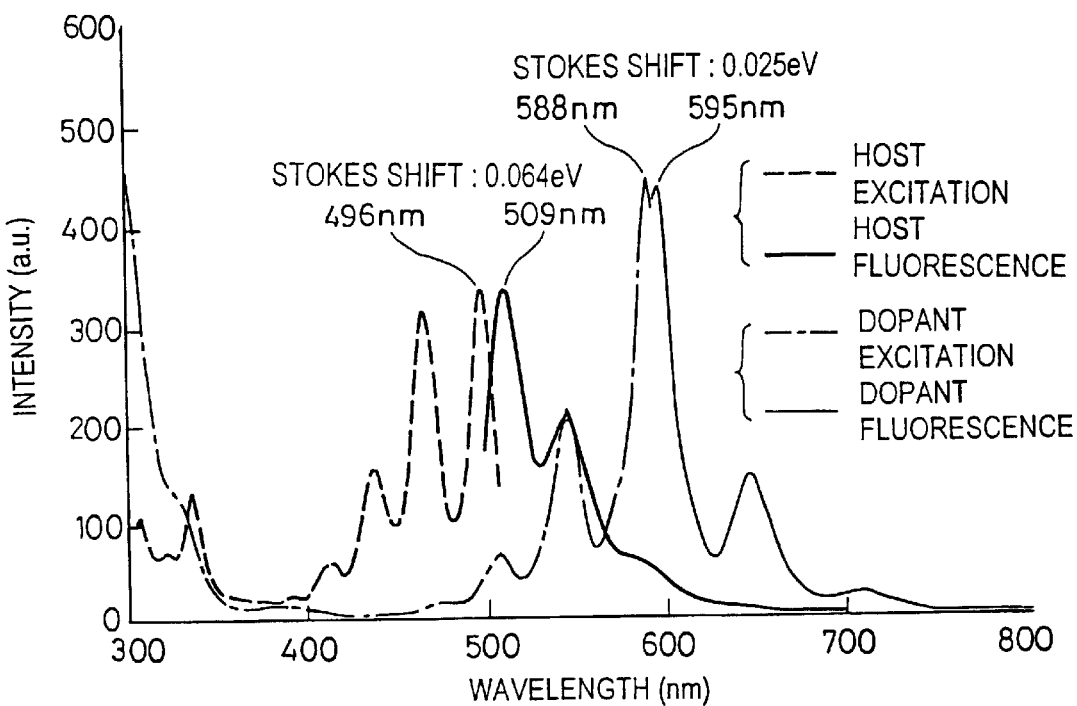
FIG. 2 is a diagram showing the excitation and fluorescence spectra of the host material and dopant used in Example.

The host material and dopant used in this device were assessed for excitation and fluorescence spectra, from which a Stokes shift was computed. The host material and dopant had a Stokes shift of 0.06 eV and 0.03 eV, respectively. FIG. 2 shows excitation and fluorescence spectra of the host material and dopant. It is seen from these spectral curves that both the host material and dopant have vibration structures.

The temperature characteristics of the device were examined to find the following luminance change on 10 mA/cm² constant current driving in various temperature ranges:

−40° C. to 20° C.: ≦10%

20° C. to 60° C.: ≦3%

−40° C. to 60° C.: ≦13%.

After 500 hours of continuous driving at 85° C., the device exhibited a luminance change of up to 10% and a drive voltage change of less than 2 V.

Example 5

An organic EL device was prepared as in Example 1 except that the host material in the light emitting layer was changed to the following compound.

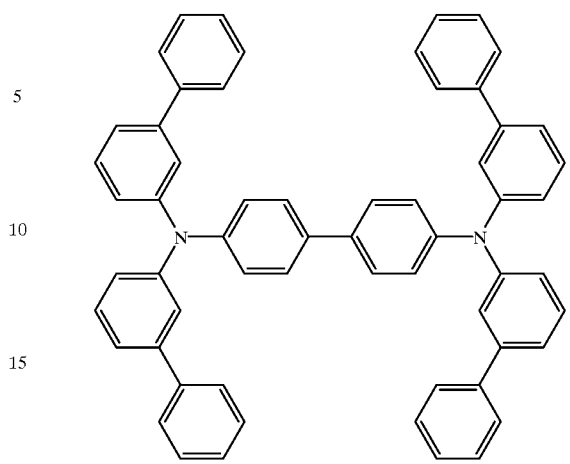

A DC voltage was applied across the organic EL device. Initially, the device was found to produce light emission to a luminance of 296 cd/m² when operated at a current density of 10 mA/cm² and a drive voltage of 6.7 volts. The current efficiency was 3.0 cd/A, the power efficiency was 1.4 lm/W, the chromaticity coordinates (x, y) were (0.60, 0.38), and the maximum luminance was 16,500 cd/m². When the device was continuously driven by conducting a constant current of 79 mA/cm², it exhibited an initial luminance of at least 2,400 cd/m² and a luminance half-life period of more than 300 hours.

Example 6

An organic EL device was prepared as in Example 1 except that the host material in the light emitting layer was changed to the following compound.

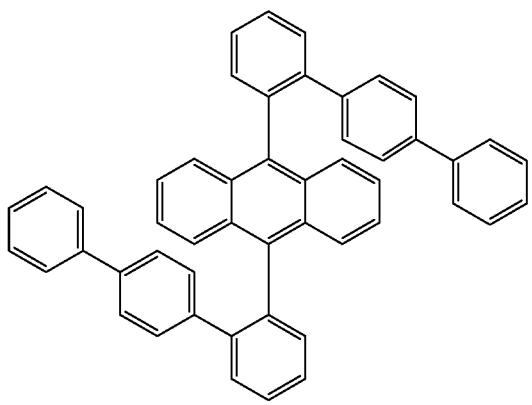

A DC voltage was applied across the organic EL device. Initially, the device was found to produce light emission to a luminance of 267 cd/m² when operated at a current density of 10 mA/cm² and a drive voltage of 6.6 volts. The current efficiency was 2.7 cd/A, the power efficiency was 1.3 lm/W, the chromaticity coordinates (x, y) were (0.55, 0.37), and the maximum luminance was 12,860 cd/m². When the device was continuously driven by conducting a constant current of 97 mA/cm², it exhibited an initial luminance of at least 2,400 cd/m² and a luminance half-life period of more than 300 hours.

Example 7

An organic EL device was prepared as in Example 1 except that the host material in the light emitting layer was changed to the following compound.

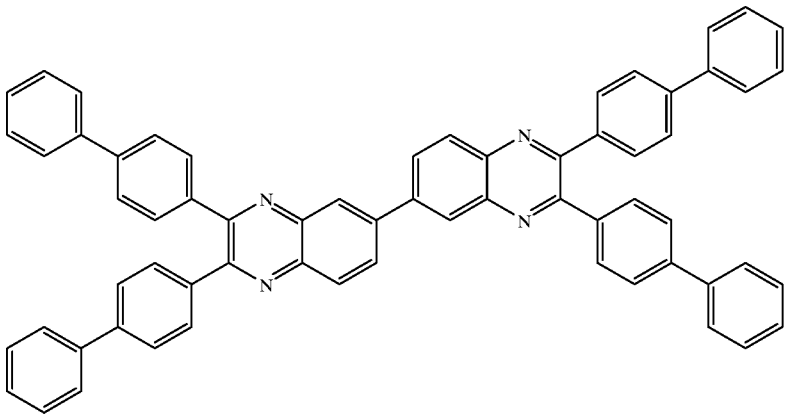

A DC voltage was applied across the organic EL device. Initially, the device was found to produce light emission to a luminance of 260 cd/m² when operated at a current density of 10 mA/cm² and a drive voltage of 6.7 volts. The current efficiency was 2.6 cd/A, the power efficiency was 1.2 lm/W, the chromaticity coordinates (x, y) were (0.64, 0.36), and the maximum luminance was 8,780 cd/m². When the device was continuously driven by conducting a constant current of 95 mA/cm², it exhibited an initial luminance of at least 2,400 cd/m² and a luminance half-life period of more than 300 hours.

Example 8

An organic EL device was prepared as in Example 1 except that the host material in the light emitting layer was changed to a mixture of the following compounds in a weight ratio of 9:1 (the former compound is the same as used in Example 4).

HOST

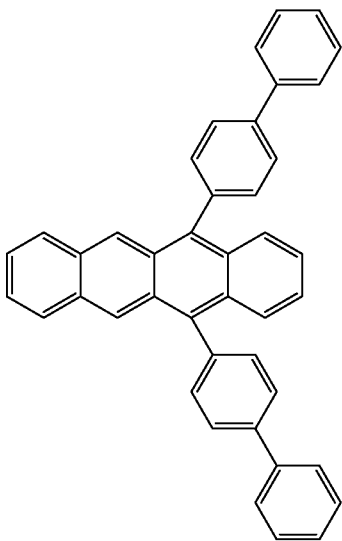

-continued

DOPANT

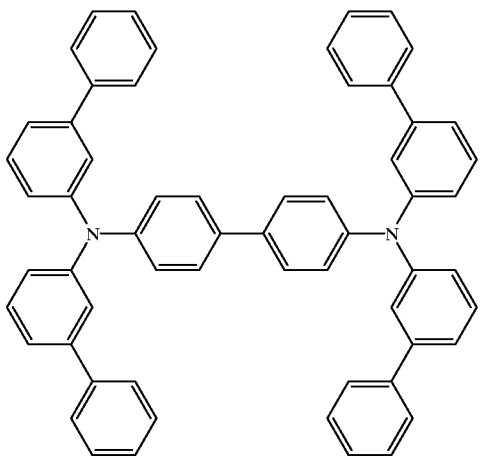

The host material (mixture) and the dopant were evaporated in a weight ratio of 99:1 and at an overall deposition rate of 0.1 nm/sec to a thickness of 40 nm, forming a light emitting layer.

A DC voltage was applied across the organic EL device. Initially, the device was found to produce light emission to a luminance of 494 cd/m² when operated at a current density of 10 mA/cm² and a drive voltage of 5.9 volts. The current efficiency was 4.9 cd/A, the power efficiency was 2.6 lm/W, and the chromaticity coordinates (x, y) were (0.65, 0.34). When the device was continuously driven by conducting a constant current of 50 mA/cm², it exhibited an initial luminance of at least 2,640 cd/m² and a luminance attenuation of up to 10% after 2,000 hours.

Example 9

An organic EL device was prepared as in Example 8 except that the weight ratio of the host compounds in the light emitting layer was changed to 7.5:2.5.

A DC voltage was applied across the organic EL device. Initially, the device was found to produce light emission to a luminance of 510 cd/m² when operated at a current density of 10 mA/cm² and a drive voltage of 6 volts. The current efficiency was 5.1 cd/A, the power efficiency was 2.8 lm/W, and the chromaticity coordinates (x, y) were (0.65, 0.34). When the device was continuously driven by conducting a constant current of 50 mA/cm², it exhibited an initial luminance of at least 2,330 cd/m² and a luminance attenuation of up to 10% after 2,000 hours.

Example 10

An organic EL device was prepared as in Example 8 except that the weight ratio of the host compounds in the light emitting layer was changed to 5:5.

A DC voltage was applied across the organic EL device. Initially, the device was found to produce light emission to a luminance of 534 cd/m² when operated at a current density of 10 mA/cm² and a drive voltage of 5.9 volts. The current efficiency was 5.3 cd/A, the power efficiency was 2.8 lm/W, and the chromaticity coordinates (x, y) were (0.65, 0.35). When the device was continuously driven by conducting a constant current of 50 mA/cm², it exhibited an initial luminance of at least 2,391 cd/m² and a luminance attenuation of up to 10% after 2,000 hours.

Example 11

An organic EL device was prepared as in Example 1 except that the host material and the dopant in the light emitting layer were changed to the following compounds.

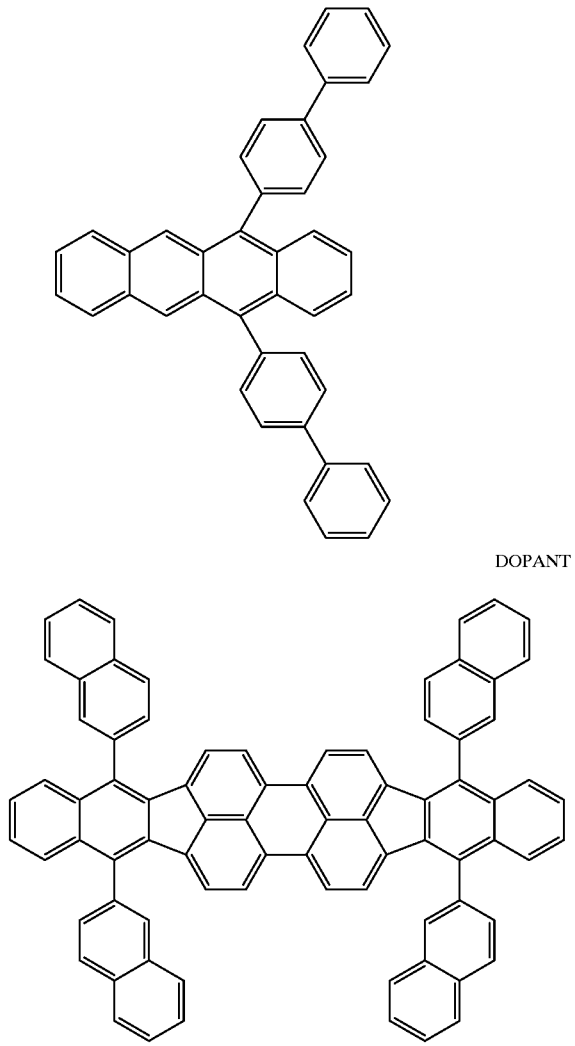

HOST

DOPANT

The host material and the dopant were evaporated in a weight ratio of 99:1 and at an overall deposition rate of 0.1 nm/sec to a thickness of 40 nm, forming a light emitting layer. The dopant material had to be heated at 460° C. or higher for purification by sublimation.

A DC voltage was applied across the organic EL device. Initially, the device was found to produce light emission to a luminance of 505 cd/m² when operated at a current density of 10 mA/cm² and a drive voltage of 5.7 volts. The current efficiency was 5.1 cd/A, the power efficiency was 2.8 lm/W, and the chromaticity coordinates (x, y) were (0.65, 0.35). When the device was continuously driven by conducting a constant current of 50 mA/cm², it exhibited an initial luminance of at least 2,330 cd/m² and a luminance attenuation of up to 30% after 1,700 hours.

Example 12

An organic EL device was prepared as in Example 1 except that the host material and the dopant in the light emitting layer were changed to the following compounds.

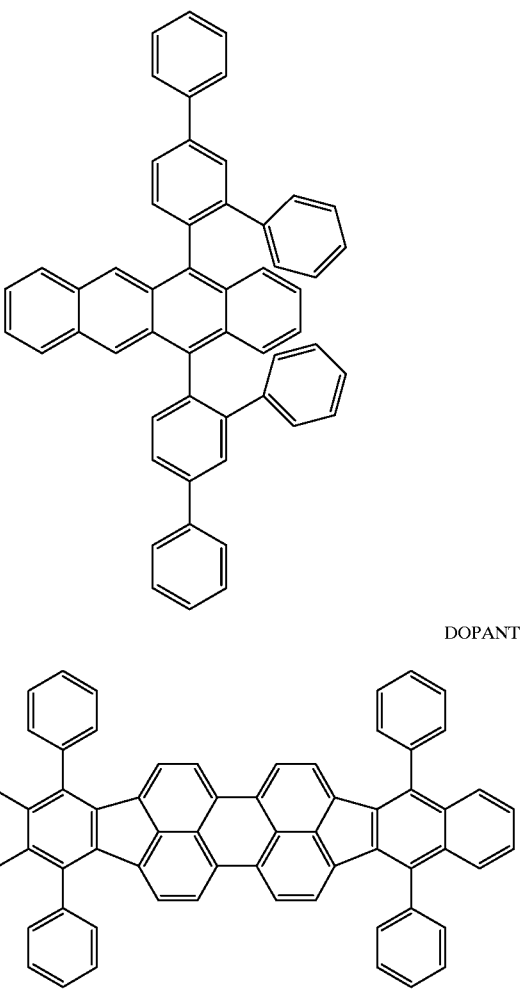

HOST

DOPANT

The host material and the dopant were evaporated in a weight ratio of 99:1 and at an overall deposition rate of 0.1 nm/sec to a thickness of 40 nm, forming a light emitting layer.

A DC voltage was applied across the organic EL device. Initially, the device was found to produce light emission to a luminance of 438 cd/m² when operated at a current density of 10 mA/cm² and a drive voltage of 6 volts. The current efficiency was 4.4 cd/A, the power efficiency was 2.3 lm/W, and the chromaticity coordinates (x, y) were (0.65, 0.35). When the device was continuously driven by conducting a constant current of 50 mA/cm², it exhibited an initial luminance of at least 2,650 cd/m² and a luminance attenuation of up to 10% after 2,300 hours.

Example 13

An organic EL device was prepared as in Example 1 except that the host material and the dopant in the light emitting layer were changed to the following compounds.

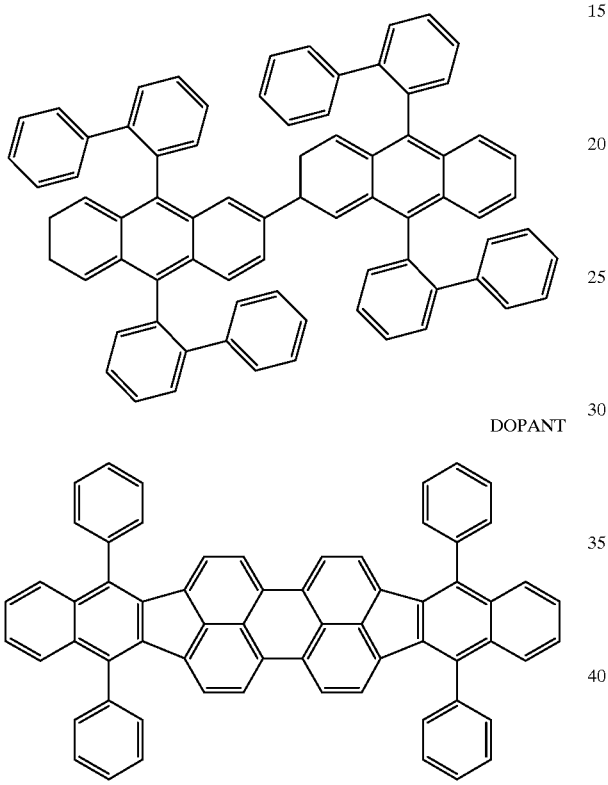

The host material and the dopant were evaporated in a weight ratio of 99:1 and at an overall deposition rate of 0.1 nm/sec to a thickness of 40 nm, forming a light emitting layer.

The host material and dopant used in this device were assessed for excitation and fluorescence spectra, from which a Stokes shift was computed. The host material had a Stokes shift of 0.24 eV. It is seen from the spectral curves that both the host material and dopant have vibration structures.

The temperature characteristics of the device were examined to find the following luminance change in various temperature ranges:

−40° C. to 20° C.: ≦−4%
20° C. to 60° C.: ≦−3%
−40° C. to 60° C.: ≦−7%.

Example 14

An organic EL device was prepared as in Example 1 except that the host material and the dopant in the light emitting layer were changed to the following compounds.

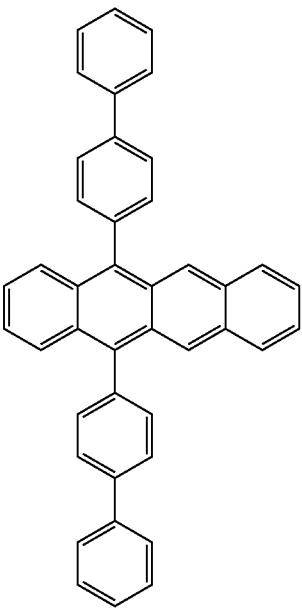

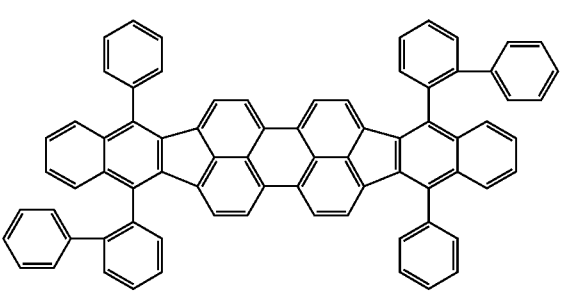

The host material and the dopant were evaporated in a weight ratio of 99:1 and at an overall deposition rate of 0.1 nm/sec to a thickness of 40 nm, forming a light emitting layer. It is noted that the dopant material could be purified by sublimation at a temperature below 360° C.

A DC voltage was applied across the organic EL device. Initially, the device was found to produce light emission to a luminance of 660 cd/m² when operated at a current density of 10 mA/cm² and a drive voltage of 5.6 volts. The current efficiency was 6.6 cd/A, the power efficiency was 3.7 lm/W, and the chromaticity coordinates (x, y) were (0.65, 0.35). The maximum luminance was 55,000 cd/m². When the device was continuously driven by conducting a constant current of 50 mA/cm², it exhibited an initial luminance of at least 3,530 cd/m² and a luminance attenuation of up to 10% after 500 hours.

Example 15

An organic EL device was prepared as in Example 1 except that the host material and the dopant in the light emitting layer were changed to the following compounds.

HOST

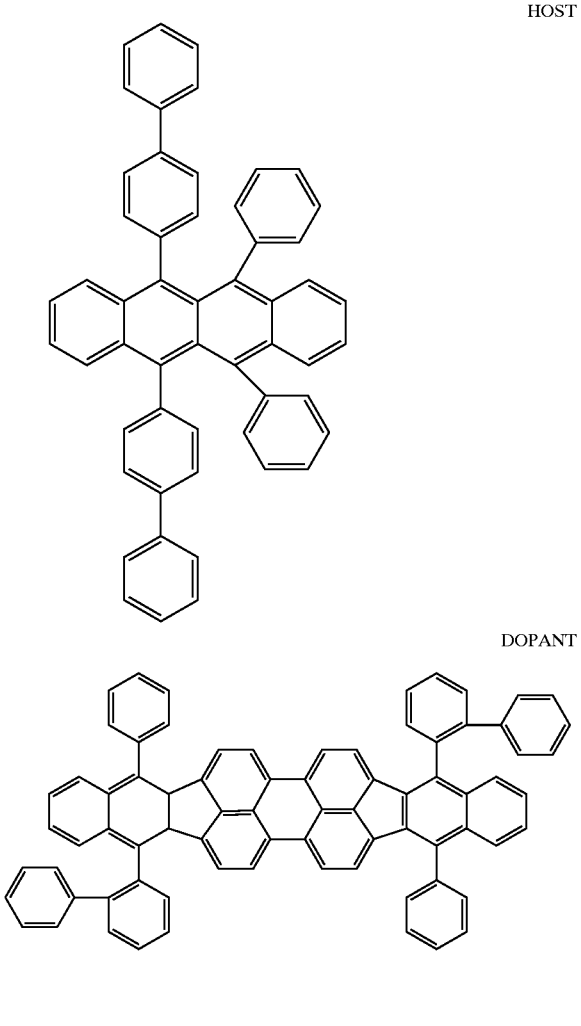

DOPANT

The host material and the dopant were evaporated in a weight ratio of 99:1 and at an overall deposition rate of 0.1 nm/sec to a thickness of 40 nm, forming a light emitting layer. It is noted that the dopant material could be purified by sublimation at a temperature below 360° C.

A DC voltage was applied across the organic EL device. Initially, the device was found to produce light emission to a luminance of 764 cd/m² when operated at a current density of 10 mA/cm² and a drive voltage of 6 volts. The current efficiency was 7.6 cd/A, the power efficiency was 4.0 lm/W, and the chromaticity coordinates (x, y) were (0.65, 0.35). The maximum luminance was 24,500 cd/m². When the device was continuously driven by conducting a constant current of 50 mA/cm², it exhibited an initial luminance of at least 4,200 cd/m² and a luminance attenuation of up to 10% after 500 hours.

Comparative Example 1

An organic EL device was prepared as in Example 1 except that the host material in the light emitting layer was changed to the following compound.

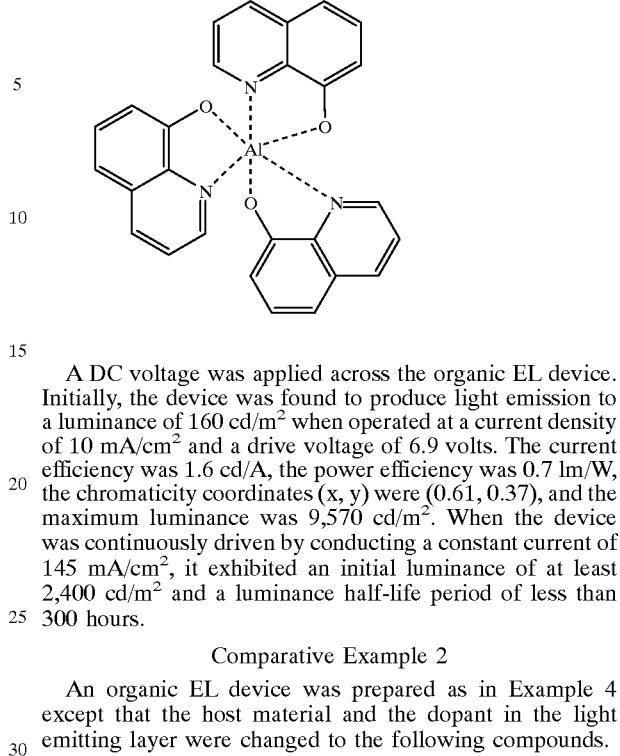

A DC voltage was applied across the organic EL device. Initially, the device was found to produce light emission to a luminance of 160 cd/m² when operated at a current density of 10 mA/cm² and a drive voltage of 6.9 volts. The current efficiency was 1.6 cd/A, the power efficiency was 0.7 lm/W, the chromaticity coordinates (x, y) were (0.61, 0.37), and the maximum luminance was 9,570 cd/m². When the device was continuously driven by conducting a constant current of 145 mA/cm², it exhibited an initial luminance of at least 2,400 cd/m² and a luminance half-life period of less than 300 hours.

Comparative Example 2

An organic EL device was prepared as in Example 4 except that the host material and the dopant in the light emitting layer were changed to the following compounds.

HOST

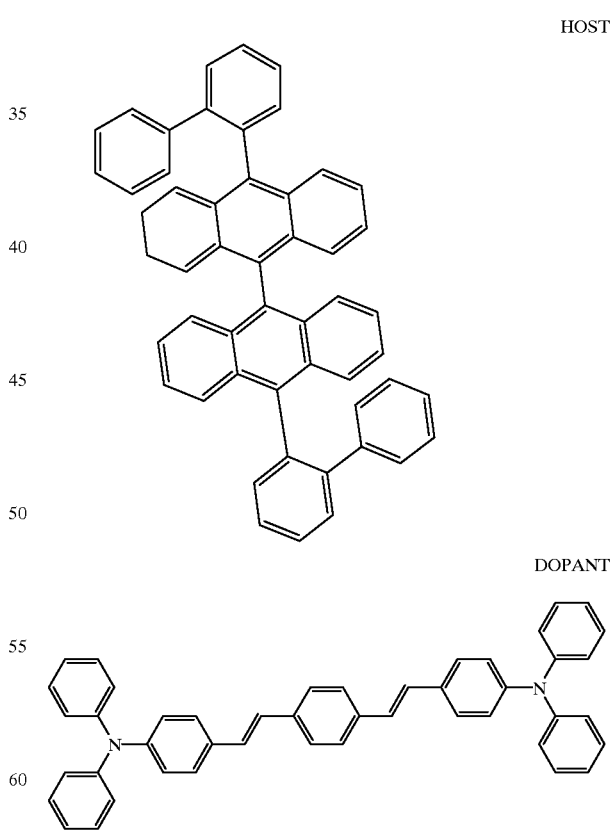

DOPANT

The host material and the dopant were evaporated in a weight ratio of 97:3 and at an overall deposition rate of 0.1 nm/sec to a thickness of 40 nm, forming a light emitting layer.

Figure 3:
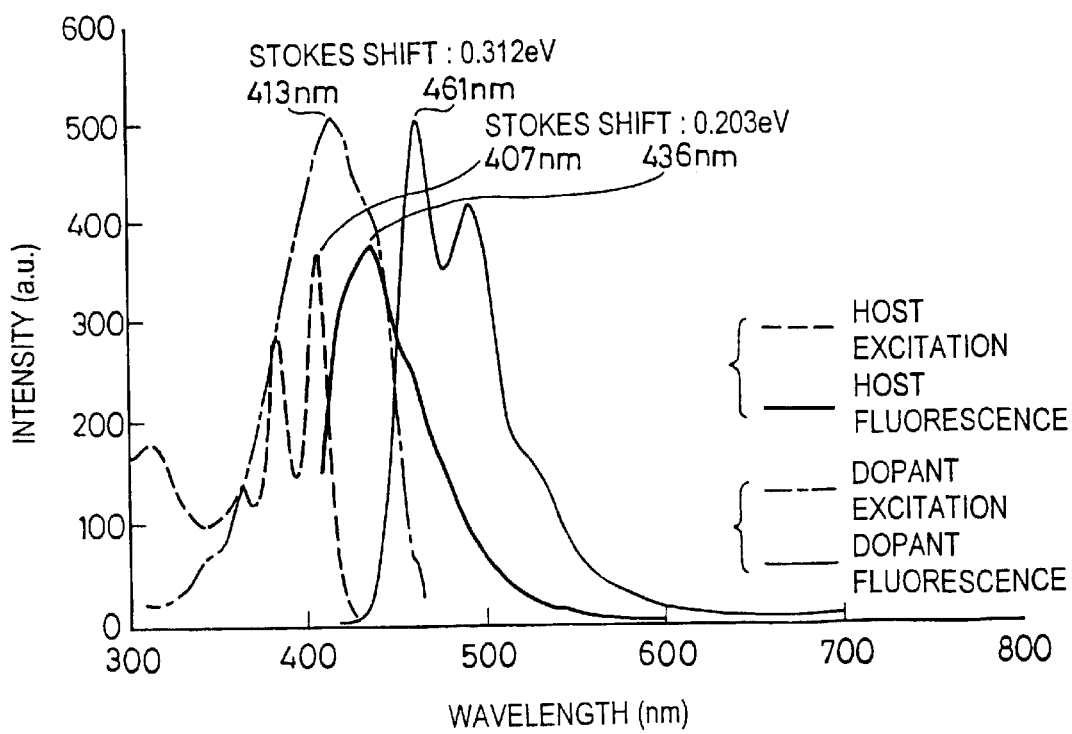
FIG. 3 is a diagram showing the excitation and fluorescence spectra of the host material and dopant used in Comparative Example.

The host material and dopant used in this device were assessed for excitation and fluorescence spectra, from which a Stokes shift was computed. The host material and dopant had a Stokes shift of 0.2 eV and 0.31 eV, respectively. FIG. 3 shows excitation and fluorescence spectra of the host material and dopant. It is seen from the spectral curves that the dopant does not have a vibration structure in the excitation spectrum, and the host material does not have a vibration structure in the fluorescence spectrum.

The temperature characteristics of the device were examined to find the following luminance change on 10 mA/cm$^2$ constant current driving in various temperature ranges:

−40° C. to 20° C.: ≧−12%
20° C. to 60° C.: ≧−9%
−40° C. to 60° C.: ≧−21%.

Comparative Example 3

An organic EL device was prepared as in Example 4 except that the host material and the dopant in the light emitting layer were changed to the following compounds.

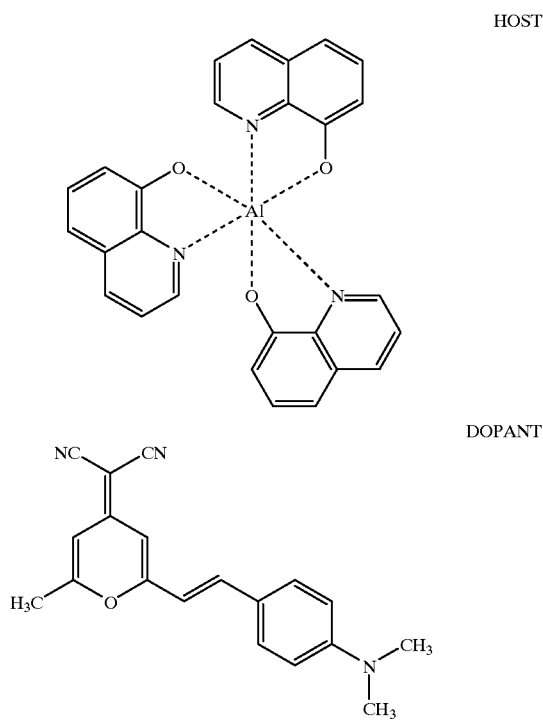

The host material and the dopant were evaporated in a weight ratio of 99:1 and at an overall deposition rate of 0.1 nm/sec to a thickness of 40 nm, forming a light emitting layer.

The host material and dopant used in this device were assessed for excitation and fluorescence spectra, from which a Stokes shift was computed. The host material and dopant had a Stokes shift of 0.2 eV and 0.31 eV, respectively. It is seen from the spectral curves that neither the host material nor the dopant has a vibration structure.

The temperature characteristics of the device were examined to find the following luminance change in various temperature ranges:

−40° C. to 20° C.: ≧31%
20° C. to 60° C.: ≧18%
−40° C. to 60° C.: ≧49%.

There has been described an organic EL device which emits light to a satisfactory luminance, especially in a long wavelength region, is operated at a constant voltage, and has a sufficient durability to maintain satisfactory light emission performance over a long period of time, experience a minimal voltage rise during continuous operation, and undergo a minimal degradation on driving at elevated temperature. Especially when a red light emitting device is fabricated, it has a high chromatic purity because the host produces little light emission. Over a wide temperature region, the device produces a consistent luminance with minimal changes of efficiency. The device can produce linear luminance characteristics in proportion to current flow over a wide current region covering from the low current region for use in TFT driving to the high current region for use in simple matrix driving and thus provide a satisfactory tone display.

Although some preferred embodiments have been described, many modifications and variations may be made thereto in light of the above teachings. It is therefore to be understood that the invention may be practiced otherwise than as specifically described without departing from the scope of the appended claims.

This application is based on Japanese patent applications JP 2000-121724, filed Apr. 21, 2000, and JP 2001-121664, filed Apr. 19, 2001, the entire contents of each of which are hereby incorporated by reference, the same as if set forth at length.

What is claimed is:

1. An organic EL device comprising one or more organic layers between a pair of electrodes participating in at least a light emitting function, at least one of the organic layers containing at least one of organic compounds having basic skeletons of the following formulas (I) to (IV) and at least one organic compound having a skeleton of the following formula (V) at the same time:

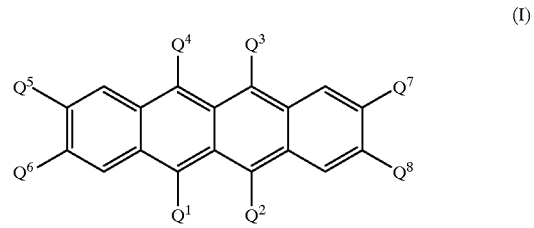

(I)

wherein $Q^1$ to $Q^8$ are independently hydrogen or substituted or unsubstituted alkyl, aryl, amino, heterocyclic or alkenyl radicals,

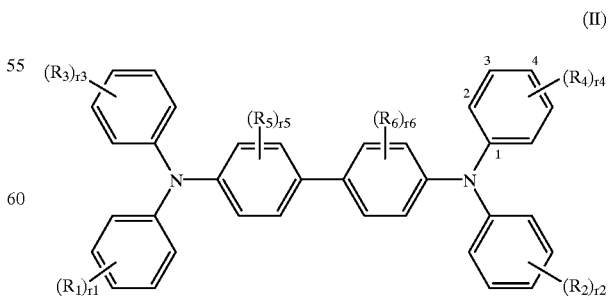

(II)

wherein $R^1$, $R^2$, $R^3$ and $R^4$ are in dependently aryl, fluorene, carbazolyl, alkyl, alkoxy, aryloxy, amino or halogen radicals, at least one of $R_1$, $R_2$, $R_3$ and $R_4$ is aryl, r1, r2, r3 and r4 each are 0 or an integer of 1 to 5, with the proviso that r1, r2, r3 and r4 are not 0 at the same time, $R_5$ and $R_6$ are independently alkyl, alkoxy, amino, aryl or halogen radicals and may be the same or different, r5 and r6 each are 0 or an integer of 1 to 4, $$(A_{101})_n\text{—L} \tag{III}$$

wherein $A_{101}$ is a monophenylanthryl or diphenylanthryl radical and may be the same or different, L is hydrogen, a single bond or an n-valent linkage, and n is an integer of 1 to 4, $$Q_n\text{-}L_{101} \tag{IV}$$

wherein Q is a pyrazinyl radical having fused thereto a six-membered aromatic ring containing 0 to 2 nitrogen atoms and may be the same or different, n is 2 or 3, and $L_{101}$ is a single bond or n-valent radical,

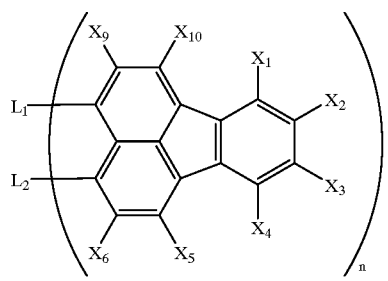

(V)

wherein $X_1$ to $X_{10}$, $L_1$ and $L_2$ are independently hydrogen, halogen atoms, straight, branched or cyclic alkyl radicals which may have substituents, straight, branched or cyclic alkoxy radicals which may have substituents, straight, branched or cyclic alkylthio radicals which may have substituents, straight, branched or cyclic alkenyl radicals which may have substituents, straight, branched or cyclic alkenyloxy radicals which may have substituents, straight, branched or cyclic alkenylthio radicals which may have substituents, substituted or unsubstituted aralkyl radicals, substituted or unsubstituted aralkyloxy radicals, substituted or unsubstituted aralkylthio radicals, substituted or unsubstituted aryl radicals, substituted or unsubstituted aryloxy radicals, substituted or unsubstituted arylthio radicals, substituted or unsubstituted amino radicals, cyano, hydroxyl, —COOR$^2$ radicals (wherein R$^2$ is hydrogen, a substituted or unsubstituted straight, branched or cyclic alkyl radical, a substituted or unsubstituted straight, branched or cyclic alkenyl radical, a substituted or unsubstituted aralkyl radical or a substituted or unsubstituted aryl radical), —COR$^2$ radicals (wherein R$^2$ is hydrogen, a substituted or unsubstituted straight, branched or cyclic alkyl radical, a substituted or unsubstituted straight, branched or cyclic alkenyl radical, a substituted or unsubstituted aralkyl radical, a substituted or unsubstituted aryl radical or an amino radical), or —OCOR$^3$ radicals (wherein R$^3$ is a substituted or unsubstituted straight, branched or cyclic alkyl radical, a substituted or unsubstituted straight, branched or cyclic alkenyl radical, a substituted or unsubstituted aralkyl radical, or a substituted or unsubstituted aryl radical), or at least two adjoining radicals selected from $X_1$ to $X_{10}$, $L_1$ and $L_2$ may bond or fuse together to form a substituted or unsubstituted carbocyclic aliphatic ring, aromatic ring or fused aromatic ring with the carbon atoms to which they are attached, or $L_1$ and $L_2$ each may be a single bond, and n is 1 or 2.

2. The organic EL device of claim 1 wherein the at least one of the organic layers contains a host material and a dopant,
said host material comprises at least one compound selected from the organic compounds having basic skeletons of the formulas (I) to (IV) and
said dopant comprises at least one compound selected from the organic compounds having a skeleton of the formula (V).

3. The organic EL device of claim 2 wherein the at least one of the organic layers contains 80 to 99.9% by weight of the host material.

4. The organic EL device of claim 2 wherein in formula (V), at least two adjoining radicals selected from $X_1$ to $X_{10}$, $L_1$ and $L_2$ bond or fuse together to form a substituted or unsubstituted carbocyclic aliphatic ring, aromatic ring or fused aromatic ring with the carbon atoms to which they are attached.

5. The organic EL device of claim 1 wherein in formula (V), at least two adjoining radicals selected from $X_1$ to $X_{10}$, $L_1$ and $L_2$ bond or fuse together to form a substituted or unsubstituted carbocyclic aliphatic ring, aromatic ring or fused aromatic ring with the carbon atoms to which they are attached.

6. The organic EL device of claim 1 wherein the compound of formula (V) is a compound of the following formula (VI):

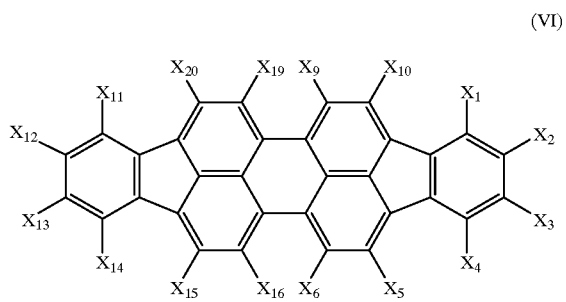

(VI)

wherein $X_1$ to $X_6$, $X_9$, $X_{10}$, $X_{11}$ to $X_{16}$, $X_{19}$ and $X_{20}$ are independently hydrogen, halogen atoms, straight, branched or cyclic alkyl radicals which may have substituents, straight, branched or cyclic alkoxy radicals which may have substituents, straight, branched or cyclic alkylthio radicals which may have substituents, straight, branched or cyclic alkenyl radicals which may have substituents, straight, branched or cyclic alkenyloxy radicals which may have substituents, straight, branched or cyclic alkenylthio radicals which may have substituents, substituted or unsubstituted aralkyl radicals, substituted or unsubstituted aralkyloxy radicals, substituted or unsubstituted aralkylthio radicals, substituted or unsubstituted aryl radicals, substituted or unsubstituted aryloxy radicals, substituted or unsubstituted arylthio radicals, substituted or unsubstituted arylalkenyl radicals, substituted or unsubstituted alkenylaryl radicals, substituted or unsubstituted amino radicals, cyano, hydroxyl, —COOR$^1$ radicals (wherein R$^1$ is hydrogen, a substituted or unsubstituted straight, branched or cyclic alkyl radical, a substituted or unsubstituted straight, branched or cyclic alkenyl radical, a substituted or unsubstituted aralkyl radical or a substituted or unsubstituted aryl radical), —COR² radicals (wherein R² is hydrogen, a substituted or unsubstituted straight, branched or cyclic alkyl radical, a substituted or unsubstituted straight, branched or cyclic alkenyl radical, a substituted or unsubstituted aralkyl radical, a substituted or unsubstituted aryl radical or an amino radical), or —OCOR³ radicals (wherein R³ is a substituted or unsubstituted straight, branched or cyclic alkyl radical, a substituted or unsubstituted straight, branched or cyclic alkenyl radical, a substituted or unsubstituted aralkyl radical, or a substituted or unsubstituted aryl radical), or at least two adjoining radicals selected from $X_1$ to $X_{20}$ may bond together to form a substituted or unsubstituted carbocyclic aliphatic ring, aromatic ring or fused aromatic ring with the carbon atoms to which they are attached.

7. The organic EL device of claim 4 wherein the compound of formula (VI) is a compound of the following formula (VI'):

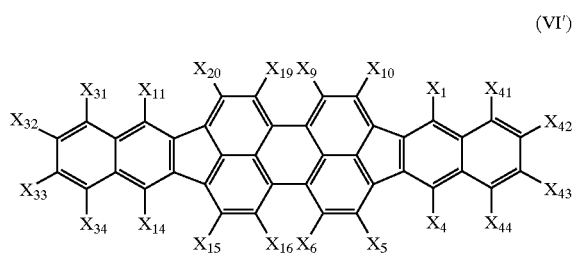

(VI')

wherein $X_1$ to $X_{44}$ are as defined for $X_1$ to $X_{20}$ in formula (VI).

8. The organic EL device of claim 7 wherein $X_1$ to $X_{20}$ in formula (VI') are independently substituted or unsubstituted aryl, alkyl, alkenyl, alkoxy or aryloxy radicals.

9. The organic EL device of claim 7 wherein at least one of $X_1$ to $X_{20}$ in formula (VI') is an ortho-substituted phenyl radical.

10. The organic EL device of claim 6 wherein $X_1$ to $X_{20}$ in formula (VI) are independently substituted or unsubstituted aryl, alkyl, alkenyl, alkoxy or aryloxy radicals.

11. The organic EL device of claim 6 wherein at least one of $X_1$ to $X_{20}$ in formula (VI) is an ortho-substituted phenyl radical.

12. The organic EL device of claim 6 wherein in formula (VI), at least one of $X_1$, $X_4$, $X_{11}$ and $X_{14}$ are ortho-substituted phenyl radicals.

13. The organic EL device of claim 6 wherein at least one of the organic compounds has a vibration structure in both an excitation spectrum and a fluorescence spectrum.

14. The organic EL device of claim 6 wherein at least one of the organic compounds has a Stokes shift of up to 0.1 eV.

15. The organic EL device of claim 1 wherein said at least one of the organic layers contains at least one organic compound having a basic skeleton of the formula (I).

16. The organic EL device of claim 1 wherein said at least one of the organic layers contains at least one organic compound having a basic skeleton of the formula (I) and at least one organic compound having a basic skeleton of the formula (II) at the same time.

17. The organic EL device of claim 1 wherein the host material in a light emitting layer has a greater electron affinity than an electron transporting layer and/or a hole transporting layer.

18. The organic EL device of claim 1 wherein the organic compound having a basic skeleton of the formula (I) is one wherein at least two of $Q^1$ to $Q^8$ are substituted or unsubstituted aryl radicals.

19. The organic EL device of claim 18 wherein the organic compound having a basic skeleton of the formula (I) is one wherein at least two of $Q^1$, $Q^2$, $Q^3$ and $Q^4$ are substituted or unsubstituted aryl radicals.

20. The organic EL device of claim 18 wherein the organic compound having a basic skeleton of the formula (I) is one wherein at least four of $Q^1$, $Q^2$, $Q^3$ and $Q^4$ are substituted or unsubstituted aryl radicals.

21. The organic EL device of claim 18 wherein at least two of the aryl radicals represented by $Q^1$, $Q^2$, $Q^3$ and $Q^4$ have aryl radicals substituted thereon.

22. The organic EL device of claim 18 wherein the organic compound having a basic skeleton of the formula (I) is one wherein at least six of $Q^1$ to $Q^8$ are substituted or unsubstituted aryl radicals.

23. The organic EL device of claim 1, further comprising at least one hole injecting and transporting layer.

24. The organic EL device of claim 1, further comprising at least one electron injecting and transporting layer.

25. An organic EL device wherein at least one of organic layers contains at least one organic compound having a basic skeleton of the formula (I) as set forth in claim 16 and at least one organic compound having a basic skeleton of the formula VI':

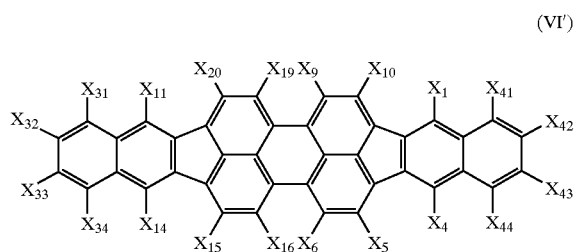

(VI')

wherein $X_1$, $X_4$ to $X_6$, $X_9$ to $X_{11}$, $X_{14}$ to $X_{16}$, $X_{19}$, $X_{20}$, $X_{31}$ to $X_{34}$ and $X_{41}$ to $X_{44}$ are independently hydrogen, halogen atoms, straight, branched or cyclic alkyl radicals which may have substituents, straight, branched or cyclic alkoxy radicals which may have substituents, straight, branched or cyclic alkylthio radicals which may have substituents, straight, branched or cyclic alkenyl radicals which may have substituents, straight, branched or cyclic alkenyloxy radicals which may have substituents, straight, branched or cyclic alkenylthio radicals which may have substituents, substituted or unsubstituted aralkyl radicals, substituted or unsubstituted aralkyloxy radicals, substituted or unsubstituted aralkylthio radicals, substituted or unsubstituted aryl radicals, substituted or unsubstituted aryloxy radicals, substituted or unsubstituted arylthio radicals, substituted or unsubstituted arylalkenyl radicals, substituted or unsubstituted alkenylaryl radicals, substituted or unsubstituted amino radicals, cyano, hydroxyl, —COOR¹ radicals (wherein R¹ is hydrogen, a substituted or unsubstituted straight, branched or cyclic alkyl radical, a substituted or unsubstituted straight, branched or cyclic alkenyl radical, a substituted or unsubstituted aralkyl radical or a substituted or unsubstituted aryl radical), —COR² radicals (wherein R² is hydrogen, a substituted or unsubstituted straight, branched or cyclic alkyl radical, a substituted or unsubstituted straight, branched or cyclic alkenyl radical, a substituted or unsubstituted aralkyl radical, a substituted or unsubstituted aryl radical or an amino radical), or —OCOR³ radicals (wherein R³ is a substituted or unsubstituted straight, branched or cyclic alkyl radical, a substituted or unsubstituted straight, branched or cyclic alkenyl radical, a substituted or unsubstituted aralkyl radical, or a substituted or unsubstituted aryl radical), or at least two adjoining radicals selected from $X_1$, $X_4$ to $X_6$, $X_9$ to $X_{11}$, $X_{14}$ to $X_{16}$, $X_{19}$ and $X_{20}$ may bond together to form a substituted or unsubstituted carbocyclic aliphatic ring, aromatic ring or fused aromatic ring with the carbon atoms to which they are attached.

26. An organic EL device comprising one or more organic layers between a pair of electrodes participating in at least a light emitting function of a light emitting layer, wherein the one or more organic layers contain organic compounds, at least one of which has a Stokes shift of up to 0.1 eV.

27. The organic EL device of claim 26 wherein a host material in a light emitting layer has a greater electron affinity than an electron transporting layer or a hole transporting layer or mixtures thereof.

* * * * *

UNITED STATES PATENT AND TRADEMARK OFFICE
CERTIFICATE OF CORRECTION

PATENT NO. : 6,613,454 B2
DATED : September 2, 2003
INVENTOR(S) : Kensuke Ara et al.

It is certified that error appears in the above-identified patent and that said Letters Patent is hereby corrected as shown below:

Column 854,
Line 66, "in dependently" should read -- independently --.

Column 857,
Line 16, "claim 4" should read -- claim 6 --.

Column 858,
Line 22, "claim 16" should read -- claim 19 --.

Signed and Sealed this

Seventeenth Day of February, 2004

JON W. DUDAS
*Acting Director of the United States Patent and Trademark Office*